United States Patent [19]
Bauer et al.

[11] Patent Number: 6,093,395
[45] Date of Patent: *Jul. 25, 2000

[54] CO-ADMINISTRATION OF INTERLEUKIN-3 MUTANT POLYPEPTIDES WITH CSF'S FOR MULTI-LINEAGE HEMATOPOIETIC CELL PRODUCTION

[75] Inventors: S. Christopher Bauer, New Haven; Mark Allen Abrams; Sarah Ruth Braford-Goldberg, both of St. Louis; Maire Helena Caparon, Chesterfield; Alan Michael Easton, Maryland Heights; Barbara Kure Klein, St. Louis; John P. McKearn; Peter O. Olins, both of Glencoe; Kumnan Paik, Ballwin; John W. Thomas, Town & Country, all of Mo.

[73] Assignee: G. D. Searle & Co., Chicago, Ill.

[*] Notice: This patent is subject to a terminal disclaimer.

[21] Appl. No.: 08/469,712

[22] Filed: Jun. 6, 1995

Related U.S. Application Data

[60] Division of application No. PCT/US95/01184, Feb. 2, 1995, which is a continuation-in-part of application No. 08/193,373, Feb. 4, 1994, which is a continuation-in-part of application No. PCT/US93/11197, Nov. 22, 1993, which is a continuation-in-part of application No. 07/981,044, Nov. 24, 1992, abandoned, which is a continuation-in-part of application No. 08/411,795, Apr. 6, 1995, Pat. No. 5,604,116.

[51] Int. Cl.$^7$ ............................. C12N 15/24; A61K 38/20

[52] U.S. Cl. .................... 424/93.71; 424/85.2; 424/85.1; 424/93.7; 435/69.52; 604/4

[58] Field of Search ........................ 435/69.52; 424/85.1, 424/85.2, 93.7, 93.71; 604/4

[56] References Cited

U.S. PATENT DOCUMENTS

| | | |
|---|---|---|
| 4,810,643 | 3/1989 | Souza . |
| 4,877,729 | 10/1989 | Clark et al. . |
| 4,959,455 | 9/1990 | Clark et al. . |
| 4,999,291 | 3/1991 | Souza . |
| 5,032,395 | 7/1991 | Clark et al. . |
| 5,199,942 | 4/1993 | Gillis ............................................ 604/4 |
| 5,516,512 | 5/1996 | Dorssers et al. ........................ 424/85.2 |
| 5,604,116 | 2/1997 | Bauer et al. ........................... 435/69.52 |

FOREIGN PATENT DOCUMENTS

| | | |
|---|---|---|
| 0275598 | 7/1988 | European Pat. Off. . |
| 413383 | 2/1991 | European Pat. Off. . |
| 4-63595 | 2/1992 | Japan . |
| WO 86/00639 | 1/1986 | WIPO . |
| WO 88/00598 | 1/1988 | WIPO . |
| WO 88/06161 | 8/1988 | WIPO . |
| WO 91/07988 | 12/1989 | WIPO . |
| WO 90/12874 | 11/1990 | WIPO . |
| WO 91/00350 | 6/1991 | WIPO . |
| WO 93/07171 | 4/1993 | WIPO . |
| WO 88/05469 | 7/1998 | WIPO . |

OTHER PUBLICATIONS

Ihle et al., *J. Immunol.* 126:2184 (1981).
Fung et al., *Nature* 307:233 (1984).
Yokota et al., *Proc.Natl.Acad.Sci. USA* 81:1070 (1984).
Yang et al., *Cell* 47:3 (1986).
Dorssers et al., *Gene* 55:115 (1987).
Clark–Lewis et al., *Science* 231:134 (1986).
Clark–Lewis et al., *Proc.Natl.Acad.Sci. USA* 85:7897 (1988).
Curtis et al., *Proc.Natl.Acad.Sci. USA* 88:5809 (1991).
Williams et al., *Cancer* 67:2705–2707 (1991).
Lokker et al., *The EM80 Journal* 10:2125 (1991).
Aglietta, M., et al., *Stem Cells Dayt* 2(83):83–7 (1993).
Appelbaum, F.R. *Cancer* 72(11 Suppl):3387–92 (1993).
Bodine, D.M.et al., *Blood* 78(4):914–20 (1991).
Brandt, J., et al. *Blood* 79(3):634–641 (1992).
Brandt, J.E., et al., *Blood* 83(6):1507–1514 (1994).
Briddell, R.A et al., *Blood* 76(3):516–522 (1990).
Broxmeyer, H.E., et al. *J. Immun* 141:3852–3862 (1988).
Broxmeyer, H.E., et al. *Blood* 77 (10):2142–2149 (1991).
Brugger, W., et al., *Blood* 81 (10):2679–2584 (1993).
Bruno, E., et al., *Blood* 73 (3):671–677 (1989).
Bruno, E., et al., *Blood* 77 (11):2339–2346 (1991).
Donahue, R.E., et al., *Science* 241:1820–1823 (1988).
Donahue, R.E., et al., *Annals N. Y. Acad. of Sci* 511:10–16 (1987).
Emerson, S.G., et al., *J. Clin. Invest.* 82:1282–1287 (1988).
Farese, A.M., et al., *Blood* 82(10): 3012–3018 (1993).
Ganser, A.,et al., *Blood* 79(10):2583–2591 (1992).
Gordon, M.S. et al., *Blood* 80(2):302–307 (1992).
Grosh, W.W. et al., *Clin Immunol Immunopathol* 62(1 Pt 2):s25–38 (1992).
Heyworth, C.M., et al., *Growth Factors* 2(2–3):197–211 (1990).
Iscova, N.N., et al., *J. Immun* 142:2332–2337 (1989).
Ikebuchi, K., et al., *Proc. Natl. Acad. Sci. USA* 84:9035–9039 (1987).
Jacobsen, S.E.W.et al., *Blood* 80(3):678–687 (1992).
Jacobsen, F.W., et al., *Blood* 84(3):775–779 (1994).
Jacobsen, S.E.W., et al., *J. Exp. Med.* 181:1357–1363 (1995).
Kaushansky, K., et al., *Proc. Natl. Acad. Sci. USA* 92:3234–3238 (1995).
Kawano, Y., et al., *Blood* 77(10):2118–2121 (1991).
Kawano, Y., et al., *Stem Cells* 12:514–520 (1994).
Krumwieh, D., et al., *Int J Cell Cloning* 1(229):229–47 (1990).
Lopez, A.F., et al., *Proc. Natl. Acad. Sci. USA* 89:11842–11846 (1992).
Mayani, H., et al., *Blood* 81 (12):3252–3258 (1993).

(List continued on next page.)

*Primary Examiner*—David L. Fitzgerald
*Attorney, Agent, or Firm*—Dennis A. Bennett

[57] ABSTRACT

The present invention relates to human interleukin-3 (hIL-3) variant or mutant proteins (muteins) functionally co-administered with other colony stimulating factors (CSF's), cytokines, lymphokines, interleukins, hematopoietic growth factors or IL-3 variants.

56 Claims, 4 Drawing Sheets

OTHER PUBLICATIONS

MacVittie, T.J., et al., *Blood* 84(8):2515–2522 (1994).
Metcalf, D. et al., *Blood* 79(11):2861–2866 (1992).
Metcalf, D. *Stem Cells Dayt* 2(1):1–11 (1993).
Metcalf, D. *Blood* 82(12):3515–3523 (1993).
Moore, M.A. *Cancer* 65(3 Suppl):836–44 (1990).
Moore, M.A. *Blood* 78(1):1–19 (1991).
Nand, S., et al., *Blood* 83(2):357–360 (1994).
Neidhart, J.A. *Cancer Supplement* 72(11):3381–3386 (1993).
Ogawa, M. *Blood* 81(11):2844–53 (1993).
Pietsch, T.,et al., *Blood* 80(5):1199–206 (1992).
Ploemacher, R.E., et al., *Leukemia* 7(9):1381–1388 (1993).
Rennick, D., et al., *Experimental Hematology* 22:136–141):(1994).

Robinson, B.E., et al., *J. Clin. Invest.* 79:1648–1652 (1987).
Sekhsaria, S. et al., *Blood* 81(8):2152–2130 (1993).
Sieff, C.A.,et al., *Blood* 73(3):688–693 (1989).
Smith, S.L., et al., *Exp. Hem.* 21(7):870–7 (1993).
Sonoda, Y., et al., *Proc. Natl. Acd. Sci. USA* 85:4360–4364 (1988).
Stahl, C.P., et al., *Blood* 80(10):1479–2485 (1992).
Sutherland, H.J., et al., *Blood* 81(6):1465–1470 (1993).
Takaue, Y., et al., *Blood* 76(2):330–5 (1990).
Tsuji, K., et al., *Blood* 79(11):2855–60 (1992).
Warren, D.J. et al., *J. of Immunology* 140:94–99 (1988).

FIG. 1

```
       1                        5                              10
ATG   GCT   CCA   ATG   ACT   CAG   ACT   ACT   TCT   CTT   AAG   ACT   TCT
Met   Ala   Pro   Met   Thr   Gln   Thr   Thr   Ser   Leu   Lys   Thr   Ser
            15                      20                                  25
TGG   GTT   AAC   TGC   TCT   AAC   ATG   ATC   GAT   GAA   ATT   ATA   ACA
Trp   Val   Asn   Cys   Ser   Asn   Met   Ile   Asp   Glu   Ile   Ile   Thr
                        30                      35
CAC   TTA   AAG   CAG   CCA   CCT   TTG   CCT   TTG   CTG   GAC   TTC   AAC
His   Leu   Lys   Gln   Pro   Pro   Leu   Pro   Leu   Leu   Asp   Phe   Asn
            40                      45                      50
AAC   CTC   AAT   GGG   GAA   GAC   CAA   GAC   ATT   CTG   ATG   GAA   AAT
Asn   Leu   Asn   Gly   Glu   Asp   Gln   Asp   Ile   Leu   Met   Glu   Asn
                        55                      60
AAC   CTT   CGA   AGG   CCA   AAC   CTG   GAG   GCA   TTC   AAC   AGG   GCT
Asn   Leu   Arg   Arg   Pro   Asn   Leu   Glu   Ala   Phe   Asn   Arg   Ala
65                                  70                      75
GTC   AAG   AGT   TTA   CAG   AAT   GCA   TCA   GCA   ATT   GAG   AGC   ATT
Val   Lys   Ser   Leu   Gln   Asn   Ala   Ser   Ala   Ile   Glu   Ser   Ile
                  80                            85                      90
CTT   AAA   AAT   CTC   CTG   CCA   TGT   CTG   CCC   CTG   GCC   ACG   GCC
Leu   Lys   Asn   Leu   Leu   Pro   Cys   Leu   Pro   Leu   Ala   Thr   Ala
                        95                            100
GCA   CCC   ACG   CGA   CAT   CCA   ATC   CAT   ATC   AAG   GAC   GGT   GAC
Ala   Pro   Thr   Arg   His   Pro   Ile   His   Ile   Lys   Asp   Gly   Asp
      105                           110                           115
TGG   AAT   GAA   TTC   CGT   CGT   AAA   CTG   ACC   TTC   TAT   CTG   AAA
Trp   Asn   Glu   Phe   Arg   Arg   Lys   Leu   Thr   Phe   Tyr   Leu   Lys
                        120                           125
ACC   TTG   GAG   AAC   GCG   CAG   GCT   CAA   CAG   ACC   ACT   CTG   TCG
Thr   Leu   Glu   Asn   Ala   Gln   Ala   Gln   Gln   Thr   Thr   Leu   Ser
130
CTA   GCG   ATC   TTT   TAA   TAA          (SEQ ID NO: 58)
Leu   Ala   Ile   Phe   END   END          (SEQ ID NO: 49)
```

CO-ADMINISTRATION OF INTERLEUKIN-3 MUTANT POLYPEPTIDES WITH CSF'S FOR MULTI-LINEAGE HEMATOPOIETIC CELL PRODUCTION

This is a divisional of international application PCT/US/95/01184 filed on Feb. 02, 1995 (and which entered the U.S. National stage under 35 U.S.C. §371 as Ser. No. 08/446,871 on Jun. 06, 1995); which is a continuation-in-part of Ser. No. 08/193,373 which was filed Feb. 04, 1994; which is a continuation-in-part of international application PCT/US93/11197, filed on Nov. 22, 1993 (and which entered the U.S. National stage under 35 U.S.C. §371 as Ser. No. 08/411,795 on Apr. 06, 1995, now U.S. Pat. No. 5,604,116) which is a continuation-in-part of U.S. Ser. No. 07/981,044; filed Nov. 24, 1992, which is now abandoned. The noted applications are incorporated herein by reference.

FIELD OF THE INVENTION

The present invention relates to the coadministration or sequential treatment using mutants or variants of human interleukin-3 (hIL-3) and other colony stimulating factors (CSFs), cytokines, lymphokines, interleukins, hematopoietic growth factors or IL-3 variants.

BACKGROUND OF THE INVENTION

Colony stimulating factors (CSFs) which stimulate the differentiation and/or proliferation of bone marrow cells have generated much interest because of their therapeutic potential for restoring depressed levels of hematopoietic stem cell-derived cells. CSFs in both human and murine systems have been identified and distinguished according to their activities. For example, granulocyte-CSF (G-CSF) and macrophage-CSF (M-CSF) stimulate the in vitro formation of neutrophilic granulocyte and macrophage colonies, respectively while GM-CSF and interleukin-3 (IL-3) have broader activities and stimulate the formation of both macrophage, neutrophilic and eosinophilic granulocyte colonies. IL-3 also stimulates the formation of mast, megakaryocyte and pure and mixed erythroid colonies (when erythropoietin is added).

Because of its ability to stimulate the proliferation of a number of different cell types and to support the growth and proliferation of progenitor cells, IL-3 has potential for therapeutic use in restoring hematopoietic cells to normal amounts in those cases where the number of cells has been reduced due to diseases or to therapeutic treatments such as radiation and/or chemotherapy.

Interleukin-3 (IL-3) is a hematopoietic growth factor which has the property of being able to promote the survival, growth and differentiation of hematopoietic cells. Among the biological properties of IL-3 are the ability (a) to support the growth and differentiation of progenitor cells committed to all, or virtually all, blood cell lineages; (b) to interact with early multipotential stem cells; (c) to sustain the growth of pluripotent precursor cells; (d) to stimulate proliferation of chronic myelogenous leukemia (CML) cells; (e) to stimulate proliferation of mast cells, eosinophils and basophils; (f) to stimulate DNA synthesis by human acute myelogenous leukemia (AML) cells; (g) to prime cells for production of leukotrienes and histamines; (h) to induce leukocyte chemotaxis; and (i) to induce cell surface molecules needed for leukocyte adhesion.

Mature human interleukin-3 (hIL-3) consists of 133 amino acids. It has one disulfide bridge and two potential glycosylation sites (Yang, et al., CELL 47:3 (1986)).

Murine IL-3 (mIL-3) was first identified by Ihle, et al., J. IMMUNOL. 126:2184 (1981) as a factor which induced expression of a T cell associated enzyme, 20-hydroxysteroid dehydrogenase. The factor was purified to homogeneity and shown to regulate the growth and differentiation of numerous subclasses of early hematopoietic and lymphoid progenitor cells.

In 1984, cDNA clones coding for murine IL-3 were isolated (Fung, et al., NATURE 307:233 (1984) and Yokota, et al., PROC. NATL. ACAD. SCI. USA 31:1070 (1984)). The murine DNA sequence coded for a polypeptide of 166 amino acids including a putative signal peptide.

The gibbon IL-3 sequence was obtained using a gibbon cDNA expression library. The gibbon IL-3 sequence was then used as a probe against a human genomic library to obtain a human IL-3 sequence.

Gibbon and human genomic DNA homologues of the murine IL-3 sequence were disclosed by Yang, et al., CELL 47:3 (1986). The human sequence reported by Yang, et al. included a serine residue at position 8 of the mature protein sequence. Following this finding, others reported isolation of $Pro^8$ hIL-3 cDNAs having proline at position 8 of the protein sequence. Thus it appears that there may be two allelic forms of hIL-3.

Dorssers, et al., GENE 55:115 (1987), found a clone from a human cDNA library which hybridized with mIL-3. This hybridization was the result of the high degree of homology between the 3' noncoding regions of mIL-3 and hIL-3. This cDNA coded for an hIL-3 ($Pro^8$) sequence.

U.S. Pat. No. 4,877,729 and U.S. Pat. No. 4,959,454 disclose human IL-3 and gibbon IL-3 cDNAs and the protein sequences for which they code. The hIL-3 disclosed has serine rather than proline at position 8 in the protein sequence.

Clark-Lewis, et al., SCIENCE 231:134 (1986) performed a functional analysis of murine IL-3 analogs synthesized with an automated peptide synthesizer. The authors concluded that the stable tertiary structure of the complete molecule was required for full activity. A study on the role of the disulfide bridges showed that replacement of all four cysteines by alanine gave a molecule with 1/500th the activity as the native molecule. Replacement of two of the four Cys residues by Ala($Cys^{79}$, $Cys^{140} \rightarrow Ala^{79}$, $Ala^{140}$) resulted in an increased activity. The authors concluded that in murine IL-3 a single disulfide bridge is required between cysteines 17 and 80 to get biological activity that approximates physiological levels and that this structure probably stabilizes the tertiary structure of the protein to give a conformation that is optimal for function. (Clark-Lewis, et al., PROC. NATL. ACAD. SCI. USA 85:7897 (1988)).

International Patent Application (PCT) WO 88/00598 discloses gibbon- and human-like IL-3. The hIL-3 contains a $Ser^8 \rightarrow Pro^8$ replacement. Suggestions are made to replace Cys by Ser, thereby breaking the disulfide bridge, and to replace one or more amino acids at the glycosylation sites.

EP-A-0275598 (WO 88/04691) illustrates that $Ala^1$ can be deleted while retaining biological activity. Some mutant hIL-3 sequences are provided, e.g., two double mutants, $Ala^1 \rightarrow Asp^1$, $Trp^{13} \rightarrow Arg^{13}$ (pGB/IL-302) and $Ala^1 \rightarrow Asp^1$, $Met^3 \rightarrow Thr^3$ (pGB/IL-304) and one triple mutant $Ala^1 \rightarrow Asp^1$, $Leu^9 \rightarrow Pro^9$, $Trp^{13} \rightarrow Arg^{13}$ (pGB/IL-303).

WO 88/05469 describes how deglycosylation mutants can be obtained and suggests mutants of $Arg^{54}Arg^{55}$ and $Arg^{108}Arg^{109}Lys^{110}$ might avoid proteolysis upon expression in Saccharomyces cerevisiae by KEX2 protease. No mutated proteins are disclosed. Glycosylation and the KEX2 protease activity are only important, in this context, upon expression in yeast.

WO 88/06161 mentions various mutants which theoretically may be conformationally and antigenically neutral. The only actually performed mutations are Met$^2$→Ile$^2$ and Ile$^{131}$→Leu$^{131}$. It is not disclosed whether the contemplated neutralities were obtained for these two mutations.

WO 91/00350 discloses nonglycosylated hIL-3 analog proteins, for example, hIL-3 (Pro$^8$Asp$^{15}$Asp$^{70}$), Met$^3$ rhuIL-3 (Pro$^8$Asp$^{15}$Asp$^{70}$); Thr$^4$ rhuIL-3 (Pro$^8$Asp$^{15}$Asp$^{70}$) and Thr$^6$ rhuIL-3 (Pro$^8$Asp$^{15}$Asp$^{70}$). It is said that these protein compositions do not exhibit certain adverse side effects associated with native hIL-3 such as urticaria resulting from infiltration of mast cells and lymphocytes into the dermis. The disclosed analog hIL-3 proteins may have N termini at Met$^3$, Thr$^4$, or Thr$^6$.

WO 91/12874 discloses cysteine added variants (CAVs) of IL-3 which have at least one Cys residue substituted for a naturally occurring amino acid residue.

U.S. Pat. No. 4,810,643 discloses the DNA sequence encoding human G-CSF.

WO 91/07988 discloses a method to increase megakaryocyte production comprised of administration of G-CSF with IL-3 or GM-CSF. Also disclosed is a method for increasing platelet production comprised of administration of IL-6 with IL-3, G-CSF or GM-CSF.

SUMMARY OF THE INVENTION

The present invention encompasses recombinant human interleukin-3 (hIL-3) variant or mutant proteins (muteins) These hIL-3 muteins contain amino acid substitutions and may also have amino acid deletions at either/or both the N- and C- termini. This invention encompasses coadministration or sequential treatment using IL-3 variants of the present invention with other colony stimulating factors (CSFs), cytokines, lymphokines, interleukins, hematopoietic growth factors (herein after collectively referred to as "colony stimulating factors") which may have the potential for therapeutic use in restoring hematopoietic cells to normal amounts in those cases where the number of cells has been reduced due to diseases or to therapeutic treatments such as radiation and/or chemotherapy. Coadministration or sequential treatment using IL-3 variants of the present invention with other colony stimulating factors may enhance therapeutic value due to the synergistic effects of the proteins that make up the treatment. The use of multiple factors may also have the potential advantage by lowering the demands placed on factor-producing cells and their induction systems. If there are limitations in the ability of a cell to produce a factor then by lowering the required concentrations of each of the factors by using them in combination may usefully reduce demands on the factor-producing cells. The use of multiple factors may lower the amount of the factors that would be needed, probably reducing the likelihood of adverse responses.

Coadministration or sequential treatment may have the usual activity of the peptides forming the mixture or it may be further characterized by having a biological or physiological activity greater than simply the additive function of the presence of IL-3 or the other growth factors alone. Coadministration or sequential treatment may also unexpectedly provide an enhanced effect on the activity or an activity different from that expected by the presence of IL-3 or the other growth factors. The IL-3 variants of the present invention may also have an improved activity profile which may include reduction of undesirable biological activities associated with native hIL-3.

The present invention includes mutants of hIL-3 in which from 1 to 14 amino acids have been deleted from the N-terminus and/or from 1 to 15 amino acids have been deleted from the C-terminus, containing multiple amino acid substitutions, which are used with other growth factors or IL-3 variant. Preferred IL-3 variants of the present invention include variants in which amino acids 1 to 14 have been deleted from the N-terminus, amino acids 126 to 133 have been deleted from the C-terminus and contain from about four to about twenty-six amino acid substitutions in the polypeptide sequence.

The present invention also provides IL-3 variants which may function as IL-3 antagonists or as discrete antigenic fragments for the production of antibodies useful in immunoassay and immunotherapy protocols. Antagonists of hIL-3 would be particularly useful in blocking the growth of certain cancer cells like AML, CML and certain types of B lymphoid cancers. Other conditions where antagonists would be useful include those in which certain blood cells are produced at abnormally high numbers or are being activated by endogenous ligands. Antagonists would effectively compete for ligands, presumably naturally occurring hemopoietins including and not limited to IL-3, GM-CSF and IL-5, which might trigger or augment the growth of cancer cells by virtue of their ability to bind to the IL-3 receptor complex while intrinsic activation properties of the ligand are diminished. IL-3, GM-CSF and/or IL-5 also play a role in certain asthmatic responses. An antagonist of the IL-3 receptor may have the utility in this disease by blocking receptor-mediated activation and recruitment of inflammatory cells.

In addition to the use of the IL-3 variants of the present invention with other colony stimulating factors in vivo, it is envisioned that in vitro uses would include the ability to stimulate bone marrow and blood cell activation and growth before infusion into patients.

BRIEF DESCRIPTION OF THE DRAWINGS

FIG. 1 is the human IL-3 gene for *E. coli* expression (pMON5873), encoding the polypeptide sequence of natural (wild type) human IL-3 [SEQ ID NO:58], plus an initiator methionine, as expressed in *E. coli*, with the amino acids numbered from the N-terminus of the natural hIL-3.

Figure 2:
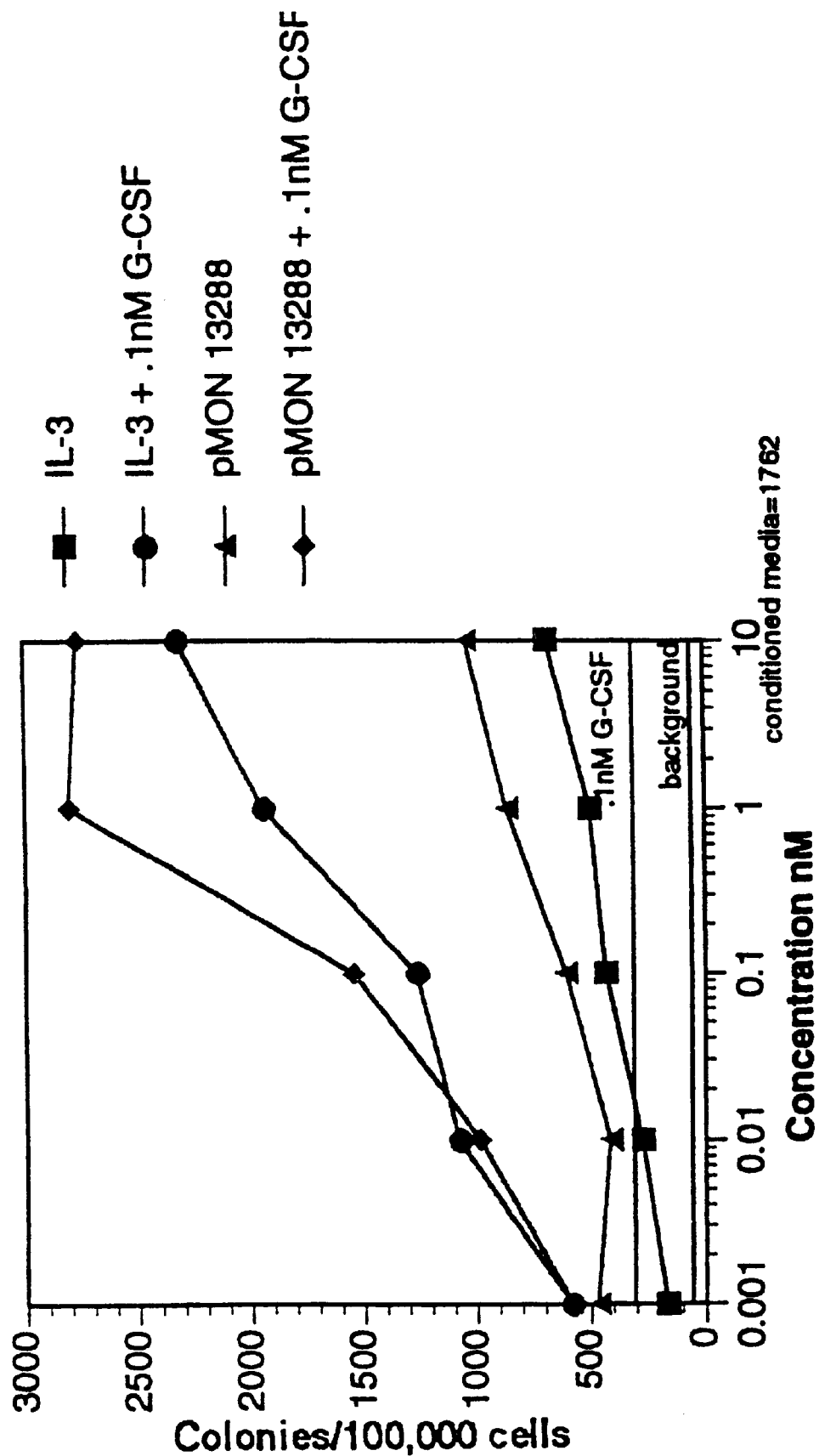
FIG. 2 shows the synergistic effects, in the methylcellulose assay, of the IL-3 variant, pMON13288, with G-CSF compared to the synergy of native IL-3 with G-CSF. Also shown are the effects of native IL-3 and the IL-3 variant, pMON13288, alone. The concentration of IL-3 is plotted versus the colony counts per 100,000 starting CD34+ cells.

(PMON5873) with stem cell factor (SCF). Also shown are the effects of native IL-3 (PMON5873) and the IL-3 variant, pMON13288, alone. The concentration of IL-3 is plotted versus the colony counts (CFU) per 10,000 starting CD34+ cells.

DETAILED DESCRIPTION OF THE INVENTION

The present invention encompasses the coadministration or sequential treatment with recombinant human interleukin-3 (hIL-3) variant or mutant proteins (muteins) with other colony stimulating factors (CSFs), cytokines, lymphokines, interleukins, hematopoietic growth factors and variants thereof (herein after collectively referred to as "colony stimulating factors"). This invention encompasses the coadministration or sequential treatment using IL-3 variants and other colony stimulating factors colony stimulating factors, each of which may act through a different and specific cell receptor to initiate complementary biological activities. Hematopoiesis requires a complex series of cellular events in which stem cells generate continuously into large populations of maturing cells in all major lineages. There are currently at least 20 known regulators with hematopoietic proliferative activity. Most of these proliferative regulators can stimulate one or another type of colony formation in vitro, the precise pattern of colony formation stimulated by each regulator is quite distinctive. No two regulators stimulate exactly the same pattern of colony formation, as evaluated by colony numbers or, more importantly, by the lineage and maturation pattern of the cells making up the developing colonies. Proliferative responses can most readily be analyzed in simplified in vitro culture systems. Three quite different parameters can be distinguished: alteration in colony size, alteration in colony numbers and cell lineage. Two or more factors may act on the progenitor cell, inducing the formation of larger number of progeny thereby increasing the colony size. Two or more factors may allow increased number of progenitor cells to proliferate either because distinct subsets of progenitors cells exist that respond exclusively to one factor or because some progenitors require stimulation by two or more factors before being able to respond. Activation of additional receptors on a cell by the use of two or more factors is likely to enhance the mitotic signal because of coalescence of initially differing signal pathways into a common final pathway reaching the nucleus (Metcalf, 1989). Other mechanism could explain synergy. For example, if one signaling pathway is limited by an intermediate activation of an additional signaling pathway by a second factor may result in a superadditive response. In some cases, activation of one receptor type can induce an enhanced expression of other receptors (Metcalf, 1993). Two or more factors may result in a different pattern of cell lineages then from a single factor. The use of the IL-3 variants of the present invention with other colony stimulating factors may have the potential clinical advantage resulting from a proliferative response that is not possible by any single factor.

Hematopoietic and other growth factors can be grouped in to two distinct families of related receptors: (1) tyrosine kinase receptors, including those for epidermal growth factor, M-CSF (Sherr, 1990) and SCF (Yarden et al., 1987): and (2) hematopoietic receptors, not containing a tyrosine kinase domain, but exhibiting obvious homology in their extracellular domain (Bazan, 1990). Included in the later group are erythropoietin (D'Andrea et al., 1989), GM-CSF (Gearing et al., 1989), IL-3 (Kitamura et al., 1991), G-CSF (Fukunaga et al., 1990), IL-4 (Harada et al., 1990), IL-5 (Takaki et al., 1990), IL-6 (Yamasaki et al., 1988), IL-7 (Goodwin et al., 1990), LIF (Gearing et al., 1991) and IL-2 (Cosman et al., 1987). Most of the later group of receptors exists in high-affinity form as a heterodimers. After ligand binding, the specific α-chains become associated with at least one other receptor chain (β-chain, γ-chain). Many of these factors share a common receptor subunit. The α-chains for GM-CSF, IL-3 and IL-5 share the same β-chain (Kitamura et al., 1991) and receptor complexes for IL-6, LIF and IL-11 share a common β-chain (gp130) (Taga et al., 1989; Gearing et al., 1992). The receptor complexes of IL-2, IL-4 and IL-7 share a common γ-chain (Kondo et al., 1993; Russell et al., 1993; Noguchi et al., 1993).

GM-CSF accelerates recovery of neutrophils and maintains functional capacity, yet has little demonstrable effect on platelet recovery. In contrast IL-3 promotes a slower increase recovery in neutrophils and monocytes while accelerating the recovery of platelets.

Recent studies in normal primates indicate that when IL-3 was administered before GM-CSF that the combination of IL-3 and GM-CSF promoted a synergistic rise in peripheral white blood cells and platelets (Donahue R. E. et al., 1988; Krumwieh D. et al., 1988; and Stahl C. P. et al., 1992). The synergistic effect observed in the sequential combination of IL-3 before GM-CSF may result from the expansion of GM-CSF sensitive cells by IL-3 resulting in a more efficient production of neutrophils. The coadministration of GM-CSF and IL-3 resulted in diminished neutrophils production relative to GM-CSF alone (Farese et al., 1993). The coadministration of IL-3 and GM-CSF, may result in down regulation of GM-CSF receptors by IL-3 thereby dampening the GM-CSF induced increase in neutrophils. However the coadministration of IL-3 and GM-CSF in a marrow-ablated rhesus monkeys promoted accelerated platelets and neutrophil recovery relative to sequential cytokine treatment or with either IL-3 or GM-CSF alone (Farese et al., 1993).

The in vitro activity of both IL-3 and GM-CSF has been shown to be additive with respect to stimulating larger colonies than either cytokine alone (Robinson et al., 1987; Bruno et al., 1989; Metcalf et al., 1992; Bruno et al., 1991; Bridell et al., 1990). Recently IL-12 has been shown to synergize with IL-3 and c-kit (stem cell factor) to enhance the recovery of hemopoietic stem cells in liquid culture (Ploemacher et al., 1993).

Recent in vitro (Emerson et al., 1988: Sonodo et al., 1988) and in vivo (Ganser et al., 1992; Donahue R. E. et al., 1988; Krumwieh D. et al., 1988; and Stahl C. P. et al., 1992) results of combined IL-3 and GM-CSF treatment suggests an increased clinical efficacy in cytokine combination treatment.

As mentioned earlier some of the factors that are involved in hematopoiesis are limited to a specific cell lineage and others have much broader effects and may result in the proliferation and support of multi-lineages and there may be considerable overlap between these factors but that the proliferative profiles are distinct. This suggests that the coadministration or sequential treatment with multiple factors may have a clinical advantage. IL-3 variants of the present invention that have an increased therapeutic index, compared to native IL-3, may have a distinct clinical advantage when coadministered or used sequentially in treatment.

The use of multiple factors may also have potential advantage by lowering the demands placed on factor-producing cells and their induction systems. If there are limitations in the ability of a cell to produce a factor then by lowering the required concentrations of each of the factors by using them in combination may usefully reduce demands on the factor-producing cells. The use of multiple factors may lower the amount of the factors that would be needed, probably reducing the likelihood of adverse responses.

A non-exclusive list of growth factors, colony stimulating factors (CSFs) including; cytokines, lymphokines, interleukins, hematopoietic growth factors, which can be used in coadministration or sequential treatment with the hIL-3 variant of the present invention include GM-CSF, CSF-1, G-CSF, Meg-CSF (more recently referred to as c-mpl ligand), M-CSF, erythropoietin (EPO), IL-1, IL-4, IL-2, IL-5, IL-6, IL-7, IL-8, IL-9, IL-10, IL-11, IL-12, IL-13, LIF, flt3/flk2, human growth hormone, B-cell growth factor, B-cell differentiation factor, eosinophil differentiation factor and stem cell factor (SCF) also known as steel factor or c-kit ligand and variants thereof.

The present invention relates to novel variants of human interleukin-3 (hIL-3) in which amino acid substitutions have been made at four or more positions in amino acid sequence of the polypeptide used in sequential treatment or coadministration with other colony stimulating factors. Preferred IL-3 variants of the present invention which have deletions of amino acids 1 to 14 at the N-terminus and 126 to 133 at the C-terminus and which also have four or more amino acid substitutions in the polypeptide used in coadministered or sequential treatment with other colony stimulating factors or IL-3 variants. Among the preferred IL-3 variants are those having twenty-six amino acid substitutions. The present invention includes mutant polypeptides comprising minimally amino acids 15 to 118 of hIL-3 with or without additional amino acid extensions to the N-terminus and/or C-terminus which further contain four or more amino acid substitutions in the amino acid sequence of the polypeptide.

As used herein human interleukin-3 corresponds to the amino acid sequence (1–133) as depicted in FIG. 1 and (15–125) hIL-3 corresponds to the 15 to 125 amino acid sequence of the hIL-3 polypeptide. Naturally occurring variants of hIL-3 polypeptide amino acids are also included in the present invention (for example, the allele in which proline rather than serine is at position 8 in the hIL-3 polypeptide sequence) as are variant hIL-3 molecules which are modified post-translationally (e.g. glycosylation).

"Mutant amino acid sequence," "mutant protein" or "mutant polypeptide" refers to a polypeptide having an amino acid sequence which varies from a native sequence or is encoded by a nucleotide sequence intentionally made variant from a native sequence. "Mutant protein," "variant protein" or "mutein" means a protein comprising a mutant amino acid sequence and includes polypeptides which differ from the amino acid sequence of native hIL-3 due to amino acid deletions, substitutions, or both. "Native sequence" refers to an amino acid or nucleic acid sequence which is identical to a wild-type or native form of a gene or protein.

Human IL-3 can be characterized by its ability to stimulate colony formation by human hematopoietic progenitor cells. The colonies formed include erythroid, granulocyte, megakaryocyte, granulocytic macrophages and mixtures thereof. Human IL-3 has demonstrated an ability to restore bone marrow function and peripheral blood cell populations to therapeutically beneficial levels in studies performed initially in primates and subsequently in humans (Gillio, A. P., et al. (1990); Ganser, A, et al. (1990); Falk, S., et al. (1991). Additional activities of hIL-3 include the ability to stimulate leukocyte migration and chemotaxis; the ability to prime human leukocytes to produce high levels of inflammatory mediators like leukotrienes and histamine; the ability to induce cell surface expression of molecules needed for leukocyte adhesion; and the ability to trigger dermal inflammatory responses and fever. Many or all of these biological activities of hIL-3 involve signal transduction and high affinity receptor binding. Coadministration or sequential treatment using the IL-3 variants of the present invention with other colony stimulating factors may exhibit useful properties such as having similar or greater biological activity when compared to native hIL-3 or by having improved half-life or decreased adverse side effects, or a combination of these properties. The IL-3 variants of the present invention may also be useful as antagonists. IL-3 variants which have little or no activity when compared to native hIL-3 may still be useful as antagonists, as antigens for the production of antibodies for use in immunology or immunotherapy, as genetic probes or as intermediates used to construct other useful hIL-3 muteins.

The use of IL-3 variants of the present invention when coadministered or as part of sequential treatment will preferably have at least one biological property of human IL-3. Coadministration or sequential treatment may also have more than one IL-3-like biological property, or an improved property, or a reduction in an undesirable biological property of human IL-3. Some mutant polypeptides of the present invention may also exhibit an improved side effect profile. For example, they may exhibit a decrease in leukotriene release or histamine release when compared to native hIL-3 or (15A–125) hIL-3. Such hIL-3 or hIL-3-like biological properties may include one or more of the following biological characteristics and in vivo and in vitro activities.

One such property is the support of the growth and differentiation of progenitor cells committed to erythroid, lymphoid, and myeloid lineages. For example, in a standard human bone marrow assay, an IL-3-like biological property is the stimulation of granulocytic type colonies, megakaryocytic type colonies, monocyte/macrophage type colonies, and erythroid bursts. Other IL-3-like properties are the interaction with early multipotential stem cells, the sustaining of the growth of pluripotent precursor cells, the ability to stimulate chronic myelogenous leukemia (CML) cell proliferation, the stimulation of proliferation of mast cells, the ability to support the growth of various factor-dependent cell lines, and the ability to trigger immature bone marrow cell progenitors. Other biological properties of IL-3 have been disclosed in the art. Human IL-3 also has some biological activities which may in some cases be undesirable, for example the ability to stimulate leukotriene release and the ability to stimulate increased histamine synthesis in spleen and bone marrow cultures and in vivo.

Biological activity of hIL-3 and hIL-3 variant proteins of the present invention is determined by DNA synthesis by human acute myelogenous leukemia cells (AML). The factor-dependent cell line AML 193 was adapted for use in testing biological activity. The biological activity of hIL-3 and hIL-3 variant proteins of the present invention is also determined by counting the colony forming units in a bone marrow assay.

Other in vitro cell based assays may also be useful to determine the synergistic effect of multiple colony stimulating factors that comprise the mixture. The following are examples of other useful assays.

TF-1 proliferation assay: The TF-1 cell line was derived from bone marrow of a patient with erythroleukemia (Kitamura et al., 1989). TF-1 cells respond to IL-3, GM-CSF, EPO and IL-5. 32D proliferation assay: 32D is a murine IL-3 dependent cell line which does not respond to human IL-3 but does respond to human G-CSF which is not species restricted.

T1165 proliferation assay: T1165 cells are a IL-6 dependent murine cell line (Nordan et al., 1986) which respond to IL-6 and IL-11. Human Plasma Clot meg-CSF Assay: Used to assay megakaryocyte colony formation activity (Mazur et al., 1981).

One object of the present invention is to provide hIL-3 variant with four or more amino acid substitutions in the polypeptide sequence used in coadministration or sequential treatment with other colony stimulating factors or IL-3 variants, which have similar or improved biological activity in relation to native hIL-3 or the other colony stimulating factors or IL-3 variant.

The hIL-3 variants of the present invention may have hIL-3 or hIL-3-like activity. For example, they may possess one or more of the biological activities of native hIL-3 and may be useful in stimulating the production of hematopoietic cells by human or primate progenitor cells. The IL-3 variants of the present invention and pharmaceutical compositions containing them may be useful in the treatment of conditions in which hematopoietic cell populations have been reduced or destroyed due to disease or to treatments such as radiation or chemotherapy. Pharmaceutical compositions containing IL-3 variants of the present invention can be administered parenterally, intravenously, or subcutaneously.

Native hIL-3 possesses considerable inflammatory activity and has been shown to stimulate synthesis of the arachidonic acid metabolites LTC4, LTD4, and LTE4; histamine synthesis and histamine release. Human clinical trials with native hIL-3 have documented inflammatory responses (Biesma, et al., BLOOD, 80:1141–1148 (1992) and Postmus, et al., J. CLIN. ONCOL., 10:1131–1140 (1992)). A recent study indicates that leukotrienes were involved in IL-3 actions in vivo and may contribute significantly to the biological effects of IL-3 treatment (Denzlinger, C., et al., BLOOD, 81:2466–2470 (1993))

Some IL-3 variants of the present invention, when co-administered with other CSFs, cytokines, lymphokines, interleukins, hematopoietic growth factors or IL-3 variants, may have an improved therapeutic profile as compared to native hIL-3 or (15–125)hIL-3. For example, some IL-3 variants of the present invention may have a similar or more potent growth factor activity relative to native hIL-3 or (15–125)hIL-3 without having a similar or corresponding increase in the stimulation of leukotriene or histamine. These IL-3 variants would be expected to have a more favorable therapeutic profile since the amount of polypeptide which needs to be given to achieve the desired growth factor activity (e.g. cell proliferation) would have a diminished leukotriene or histamine stimulating effect. In studies with native hIL-3, the stimulation of inflammatory factors has been an undesirable side effect of the treatment. Reduction or elimination of the stimulation of mediators of inflammation would provide an advantage over the use of native hIL-3.

Novel IL-3 variants of the present invention may also be useful as antagonists which block the hIL-3 receptor by binding specifically to it and preventing binding of the agonist.

One potential advantage of the novel IL-3 variants of the present invention, particularly those which retain activity similar to or better than that of native hIL-3, is that it may be possible to use a smaller amount of the biologically active mutein to produce the desired therapeutic effect. This may make it possible to reduce the number of treatments necessary to produce the desired therapeutic effect. The use of smaller amounts may also reduce the possibility of any potential antigenic effects or other possible undesirable side effects. For example, if a desired therapeutic effect can be achieved with a smaller amount of polypeptide it may be possible to reduce or eliminate side effects associated with the administration of native IL-3 such as the stimulation of leukotriene and/or histamine release. The novel IL-3 variants of the present invention may also be useful in the activation of stem cells or progenitors which have low receptor numbers.

Compounds of this invention are preferably made by genetic engineering techniques now standard in the art U.S. Pat. No. 4,935,233 and Sambrook et al., "Molecular Cloning. A Laboratory Manual", Cold Spring Harbor Laboratory (1989)]. One method of creating the preferred hIL-3 (15–125) mutant genes is cassette mutagenesis [Wells, et al. (1985)] in which a portion of the coding sequence of hIL-3 in a plasmid is replaced with synthetic oligonucleotides that encode the desired amino acid substitutions in a portion of the gene between two restriction sites. In a similar manner amino acid substitutions could be made in the full-length hIL-3 gene, or genes encoding variants of hIL-3 in which from 1 to 14 amino acids have been deleted from the N-terminus and/or from 1 to 15 amino acids have been deleted from the C-terminus. When properly assembled these oligonucleotides would encode hIL-3 variants with the desired amino acid substitutions and/or deletions from the N-terminus and/or C-terminus. These and other mutations could be created by those skilled in the art by other mutagenesis methods including; oligonucleotide-directed mutagenesis [Zoller and Smith (1982, 1983, 1984), Smith (1985), Kunkel (1985), Taylor, et al. (1985), Deng and Nickoloff (1992)] or polymerase chain reaction (PCR) techniques [Saiki, (1985)].

Plasmid DNA can be treated with the chosen restriction endonucleases then ligated to the annealed oligonucleotides. The ligated mixtures can be used to transform competent JM101 cells to resistance to an appropriate antibiotic. Single colonies can be picked and the plasmid DNA examined by restriction analysis and/or DNA sequencing to identify plasmids with mutant hIL-3 genes.

Suitable cells or cell lines for the production of the proteins claimed in the present invention may be bacterial cells. For example, the various strains of *E. coli* are well-known as host cells in the field of biotechnology. Examples of such strains include *E. coli* strains JM101 [Yanish-Perron, et al. (1985)] and MON105 [Obukowicz, et al. (1992)]. Also included in the present invention is the expression of the IL-3 variant protein utilizing a chromosomal expression vector for *E. coli* based on the bacteriophage Mu (Weinberg et al., 1993). Various strains of *B. subtilis* may also be employed as host cells for expression of the polypeptides of the present invention. Many strains of yeast cells known to those skilled in the art are also available as host cells for expression of the polypeptides of the present invention. When expressed in the *E. coli* cytoplasm, the above-mentioned mutant hIL-3 variants of the present invention may also be constructed with Met-Ala- at the N-terminus so that upon expression the Met is cleaved off leaving Ala at the N-terminus. The IL-3 variant proteins of the present invention may include polypeptides having Met-, Ala- or Met-Ala- attached to the N-terminus. When the IL-3 variant polypeptides are expressed in the cytoplasm of *E. coli*, polypeptides with and without Met attached to the N-terminus are obtained. The N-termini of proteins made in the cytoplasm of *E. coli* are affected by posttranslational processing by methionine aminopeptidase (Ben-Bassat et al., 1987) and possibly by other peptidases. These IL-3 variant proteins may also be expressed in *E. coli* by fusing a signal peptide to the N-terminus. This signal peptide is cleaved from the polypeptide as part of the secretion process. Secretion in *E. coli* can be used to obtain the correct amino acid at the N-terminus (e.g., $Asn^{15}$ in the (15–125) hIL-3 polypeptide) due to the precise nature of the signal peptidase. This is in contrast to the heterogeneity which may be observed at the N-terminus of proteins expressed in the cytoplasm in *E. coli*.

Also suitable for use in the present invention are mammalian cells, such as Chinese hamster ovary cells (CHO). General methods for expression of foreign genes in mammalian cells are reviewed in: Kaufman, R. J. (1987) High level production of proteins in mammalian cells, in *Genetic Engineering, Principles and Methods*, Vol. 9, J. K. Setlow, editor, Plenum Press, New York. An expression vector is constructed in which a strong promoter capable of functioning in mammalian cells drives transcription of a eukaryotic secretion signal peptide coding region, which is translationally fused to the coding region for the IL-3 variant. For example, plasmids such as pcDNA I/Neo, pRc/RSV, and pRc/CMV (obtained from Invitrogen Corp., San Diego, Calif.) can be used. The eukaryotic secretion signal peptide coding region can be from the hIL-3 gene itself or it can be from another secreted mammalian protein (Bayne, M. L. et al. (1987) *Proc. Natl. Acad. Sci. USA* 84, 2638–2642). After construction of the vector containing the hIL-3 variant gene, the vector DNA is transfected into mammalian cells. Such cells can be, for example, the COS7, HeLa, BHK, CHO, or mouse L lines. The cells can be cultured, for example, in DMEM media (JRH Scientific). The hIL-3 variant secreted into the media can be recovered by standard biochemical approaches following transient expression 24–72 hours after transfection of the cells or after establishment of stable cell lines following selection for neomycin resistance. The selection of suitable mammalian host cells and methods for transformation, culture, amplification, screening and product production and purification are known in the art. See, e.g., Gething and Sambrook, *Nature*, 293:620–625 (1981), or alternatively, Kaufman et al, *Mol. Cell. Biol.*, 5(7):1750–1759 (1985) or Howley et al., U.S. Pat. No. 4,419,446. Another suitable mammalian cell line is the monkey COS-1 cell line. A similarly useful mammalian cell line is the CV-1 cell line.

Where desired, insect cells may be utilized as host cells in the method of the present invention. See, e.g. Miller et al, *Genetic Engineering*, 8:277–298 (Plenum Press 1986) and references cited therein. In addition, general methods for expression of foreign genes in insect cells using Baculovirus vectors are described in: Summers, M. D. and Smith, G. E. (1987)—A manual of methods for Baculovirus vectors and insect cell culture procedures, Texas Agricultural Experiment Station Bulletin No. 1555. An expression vector is constructed comprising a Baculovirus transfer vector, in which a strong Baculovirus promoter (such as the polyhedron promoter) drives transcription of a eukaryotic secretion signal peptide coding region, which is translationally fused to the coding region for the IL-3 variant polypeptide. For example, the plasmid pVL1392 (obtained from Invitrogen Corp., San Diego, Calif.) can be used. After construction of the vector carrying the gene encoding the IL-3 variant polypeptide, two micrograms of this DNA is cotransfected with one microgram of Baculovirus DNA (see Summers & Smith, 1987) into insect cells, strain SF9. Pure recombinant Baculovirus carrying the IL-3 variant gene is used to infect cells cultured, for example, in Excell 401 serum-free medium (JRH Biosciences, Lenexa, Kans.). The IL-3 variant protein secreted into the medium can be recovered by standard biochemical approaches. Supernatants from mammalian or insect cells expressing the IL-3 variant protein can be first concentrated using any of a number of commercial concentration units.

Coadministration or sequential treatment using IL-3 variants of the present invention with other colony stimulating factors may be useful in the treatment of diseases characterized by a decreased levels of either myeloid, erythroid, lymphoid, or megakaryocyte cells of the hematopoietic system or combinations thereof. In addition, they may be used to activate mature myeloid and/or lymphoid cells. Among conditions susceptible to treatment with the polypeptides of the present invention is leukopenia, a reduction in the number of circulating leukocytes (white cells) in the peripheral blood. Leukopenia may be induced by exposure to certain viruses or to radiation. It is often a side effect of various forms of cancer therapy, e.g., exposure to chemotherapeutic drugs, radiation and of infection or hemorrhage. Therapeutic treatment of leukopenia with these IL-3 variants of the present invention with other colony stimulating factors may avoid undesirable side effects caused by treatment with presently available drugs.

Coadministration or sequential treatment using IL-3 variants of the present invention with other colony stimulating factors may be useful in the treatment of neutropenia and, for example, in the treatment of such conditions as aplastic anemia, cyclic neutropenia, idiopathic neutropenia, Chediak-Higashi syndrome, systemic lupus erythematosus (SLE), leukemia, myelodysplastic syndrome and myelofibrosis.

The IL-3 variants of the present invention, when coadministered or used in sequential treatment with other colony stimulating factors, may be useful in the treatment or prevention of thrombocytopenia. Currently the only therapy for thrombocytopenia is platelet transfusions which are costly and carry the significant risks of infection (HIV, HBV) and alloimmunization. The IL-3 variants, when coadministered or used in sequential treatment with other colony stimulating factors, may alleviate or diminish the need for platelet transfusions. Severe thrombocytopenia may result from genetic defects such as Fanconi's Anemia, Wiscott-Aldrich, or May-Hegglin syndromes. Acquired thrombocytopenia may result from auto- or allo-antibodies as in Immune Thrombocytopenia Purpura, Systemic Lupus Erythromatosis, hemolytic anemia, or fetal maternal incompatibility. In addition, splenomegaly, disseminated intravascular coagulation, thrombotic thrombocytopenic purpura, infection or prosthetic heart valves may result in thrombocytopenia. Severe thrombocytopenia may also result from chemotherapy and/or radiation therapy or cancer. Thrombocytopenia may also result from marrow invasion by carcinoma, lymphoma, leukemia or fibrosis.

The IL-3 variants of the present invention, when coadministered or used in sequential treatment with other colony stimulating factors, may be useful in the mobilization of hematopoietic progenitors and stem cells into peripheral blood. Peripheral blood derived progenitors have been shown to be effective in reconstituting patients in the setting of autologous marrow transplantation. Hematopoietic growth factors including G-CSF and GM-CSF have been shown to enhance the number of circulating progenitors and stem cells in the peripheral blood. This has simplified the procedure for peripheral stem cell collection and dramatically decreased the cost of the procedure by decreasing the number of pheresis required. The IL-3 variants, when coadministered or used in sequential treatment with other colony stimulating factors, may be useful in mobilization of stem cells and further enhance the efficacy of peripheral stem cell transplantation.

Another projected clinical use of growth factors has been in the in vitro activation of hematopoietic progenitors and stem cells for gene therapy. In order to have the gene of interest incorporated into the genome of the hematopoietic progenitor or stem cell one needs to stimulate cell division and DNA replication. Hematopoietic stem cells cycle at a very low frequency which means that growth factors may be useful to promote gene transduction and thereby enhance the clinical prospects for gene therapy.

Many drugs may cause bone marrow suppression or hematopoietic deficiencies. Examples of such drugs are AZT, DDI, alkylating agents and anti-metabolites used in chemotherapy, antibiotics such as chloramphenicol, penicillin, gancyclovir, daunomycin and sulfa drugs, phenothiazones, tranquilizers such as meprobamate, analgesics such as aminopyrine and dipyrone, anticonvulsants such as phenytoin or carbamazepine antithyroids such as propylthiouracil and methimazole and diuretics. Coadministration or sequential treatment using IL-3 variants of the present invention with other colony stimulating factors may be useful in preventing or treating the bone marrow suppression or hematopoietic deficiencies which often occur in patients treated with these drugs.

Hematopoietic deficiencies may also occur as a result of viral, microbial or parasitic infections and as a result of treatment for renal disease or renal failure, e.g., dialysis. Coadministration or sequential treatment using IL-3 variants of the present invention with other colony stimulating factors may be useful in treating such hematopoietic deficiency.

The treatment of hematopoietic deficiency may include administration of a pharmaceutical composition containing the IL-3 variants with other colony stimulating factors to a patient. Coadministration or sequential treatment using IL-3 variants of the present invention with other colony stimulating factors may also be useful for the activation and amplification of hematopoietic precursor cells by treating these cells in vitro with the coadministration or sequential treatment using IL-3 variants of the present invention with other colony stimulating factors prior to injecting the cells into a patient.

Various immunodeficiencies e.g., in T and/or B lymphocytes, or immune disorders, e.g., rheumatoid arthritis, may also be beneficially affected by treatment with the coadministration or sequential treatment using IL-3 variants of the present invention with other colony stimulating factors molecules of the present invention. Immunodeficiencies may be the result of viral infections e.g. HTLVI, HTLVII, HTLVIII, severe exposure to radiation, cancer therapy or the result of other medical treatment. IL-3 variants of the present invention may also be employed, alone or in combination with other hematopoietins, in the treatment of other blood cell deficiencies, including thrombocytopenia (platelet deficiency), or anemia. Other uses for these novel polypeptides are in the treatment of patients recovering from bone marrow transplants in vivo and ex vivo, and in the development of monoclonal and polyclonal antibodies generated by standard methods for diagnostic or therapeutic use.

Other aspects of the present invention are methods and therapeutic compositions for treating the conditions referred to above. Such compositions comprise a therapeutically effective amount of one or more of the IL-3 variants of the present invention with other colony stimulating factors in a mixture with a pharmaceutically acceptable carrier. This composition can be administered either parenterally, intravenously or subcutaneously. When administered, the therapeutic composition for use in this invention is preferably in the form of a pyrogen-free, parenterally acceptable aqueous solution. The preparation of such a parenterally acceptable protein solution, having due regard to pH, isotonicity, stability and the like, is within the skill of the art.

The dosage regimen involved in a method for treating the above-described conditions will be determined by the attending physician considering various factors which modify the action of drugs, e.g. the condition, body weight, sex and diet of the patient, the severity of any infection, time of administration and other clinical factors. Generally, a daily regimen may be in the range of 0.2–150 $\mu$g/kg of IL-3 variant protein per kilogram of body weight. This dosage regimen is referenced to a standard level of biological activity which recognizes that native IL-3 generally possesses an $EC_{50}$ at or about 10 picoMolar to 100 picoMolar in the AML proliferation assay described herein. Therefore, dosages would be adjusted relative to the activity of a given IL-3 variant protein vs. the activity of native (reference) IL-3 and it would not be unreasonable to note that dosage regimens may include doses as low as 0.1 microgram and as high as 1 milligram per kilogram of body weight per day. In addition, there may exist specific circumstances where dosages of IL-3 variant protein would be adjusted higher or lower than the range of 10–200 micrograms per kilogram of body weight. These include co-administration with other CSF, cytokine, lymphokine, interleukin, hematopoietic growth factor or IL-3 variant or growth factors; co-administration with chemotherapeutic drugs and/or radiation; the use of glycosylated IL-3 proteins; and various patient-related issues mentioned earlier in this section. As indicated above, the therapeutic method and compositions may also include co-administration with other human factors. A non-exclusive list of other appropriate hematopoietins, CSFs, cytokines, lymphokines, hematopoietic growth factors and interleukins for simultaneous or serial co-administration with the polypeptides of the present invention includes GM-CSF, CSF-1, G-CSF, Meg-CSF (more recently referred to as c-mpl ligand), M-CSF, erythropoietin (EPO), IL-1, IL-4, IL-2, IL-5, IL-6, IL-7, IL-8, IL-9, IL-10, IL-11, IL-12, IL-13, LIF, flt3/flk2, human growth hormone, B-cell growth factor, B-cell differentiation factor and eosinophil differentiation factor, stem cell factor (SCF) also known as steel factor or c-kit ligand, or combinations thereof. The dosage recited above would be adjusted to compensate for such additional components in the therapeutic composition. Progress of the treated patient can be monitored by periodic assessment of the hematological profile, e.g., differential cell count and the like.

The present invention includes the following compositions:

1. A composition comprising:

A human interleukin-3 mutant polypeptide of the Formula:

```
Ala Pro Met Thr Gln Thr Thr Ser Leu Lys Thr Ser Trp Val Asn  [SEQ ID NO:1]
 1           5                    10                   15

Cys Xaa Xaa Xaa Xaa Xaa Xaa Xaa Xaa Xaa Xaa Xaa Xaa Xaa Xaa
             20                   25                   30

Xaa Xaa Xaa Xaa Xaa Xaa Xaa Xaa Xaa Xaa Xaa Xaa Xaa Xaa Xaa
             35                   40                   45

Xaa Xaa Xaa Xaa Xaa Xaa Xaa Xaa Xaa Xaa Xaa Xaa Xaa Xaa Xaa
             50                   55                   60

Xaa Xaa Xaa Xaa Xaa Xaa Xaa Xaa Xaa Xaa Xaa Xaa Xaa Xaa Xaa
             65                   70                   75

Xaa Xaa Xaa Xaa Xaa Xaa Xaa Xaa Xaa Xaa Xaa Xaa Xaa Xaa Xaa
             80                   85                   90

Xaa Xaa Xaa Xaa Xaa Xaa Xaa Xaa Xaa Xaa Xaa Xaa Xaa Xaa Xaa
             95                  100                  105

Xaa Phe Xaa Xaa Xaa Xaa Xaa Xaa Xaa Xaa Xaa Xaa Xaa Xaa Xaa
            110                  115                  120

Xaa Xaa Xaa Gln Gln Thr Thr Leu Ser Leu Ala Ile Phe
            125                  130
``` wherein

Xaa at position 17 is Ser, Lys, Gly, Asp, Met, Gln, or Arg;

Xaa at position 18 is Asn, His, Leu, Ile, Phe, Arg, or Gln;

Xaa at position 19 is Met, Phe, Ile, Arg, Gly, Ala, or Cys;

Xaa at position 20 is Ile, Cys, Gln, Glu, Arg, Pro, or Ala;

Xaa at position 21 is Asp, Phe, Lys, Arg, Ala, Gly, Glu, Gln, Asn, Thr, Ser or Val;

Xaa at position 22 is Glu, Trp, Pro, Ser, Ala, His, Asp, Asn, Gln, Leu, Val or Gly;

Xaa at position 23 is Ile, Val, Ala, Leu, Gly, Trp, Lys, Phe, Leu, Ser, or Arg;

Xaa at position 24 is Ile, Gly, Val, Arg, Ser, Phe, or Leu;

Xaa at position 25 is Thr, His, Gly, Gln, Arg, Pro, or Ala;

Xaa at position 26 is His, Thr, Phe, Gly, Arg, Ala, or Trp;

Xaa at position 27 is Leu, Gly, Arg, Thr, Ser, or Ala;

Xaa at position 28 is Lys, Arg, Leu, Gln, Gly, Pro, Val or Trp;

Xaa at position 29 is Gln, Asn, Leu, Pro, Arg, or Val;

Xaa at position 30 is Pro, His, Thr, Gly, Asp, Gln, Ser, Leu, or Lys;

Xaa at position 31 is Pro, Asp, Gly, Ala, Arg, Leu, or Gln;

Xaa at position 32 is Leu, Val, Arg, Gln, Asn, Gly, Ala, or Glu;

Xaa at position 33 is Pro, Leu, Gln, Ala, Thr, or Glu;

Xaa at position 34 is Leu, Val, Gly, Ser, Lys, Glu, Gln, Thr, Arg, Ala, Phe, Ile or Met;

Xaa at position 35 is Leu, Ala, Gly, Asn, Pro, Gln, or Val;

Xaa at position 36 is Asp, Leu, or Val;

Xaa at position 37 is Phe, Ser, Pro, Trp, or Ile;

Xaa at position 38 is Asn, or Ala;

Xaa at position 40 is Leu, Trp, or Arg;

Xaa at position 41 is Asn, Cys, Arg, Leu, His, Met, or Pro;

Xaa at position 42 is Gly, Asp, Ser, Cys, Asn, Lys, Thr, Leu, Val, Glu, Phe, Tyr, Ile, Met or Ala;

Xaa at position 43 is Glu, Asn, Tyr, Leu, Phe, Asp, Ala, Cys, Gln, Arg, Thr, Gly or Ser;

Xaa at position 44 is Asp, Ser, Leu, Arg, Lys, Thr, Met, Trp, Glu, Asn, Gln, Ala or Pro;

Xaa at position 45 is Gln, Pro, Phe, Val, Met, Leu, Thr, Lys, Trp, Asp, Asn, Arg, Ser, Ala, Ile, Glu or His;

Xaa at position 46 is Asp, Phe, Ser, Thr, Cys, Glu, Asn, Gln, Lys, His, Ala, Tyr, Ile, Val or Gly;

Xaa at position 47 is Ile, Gly, Val, Ser, Arg, Pro, or His;

Xaa at position 48 is Leu, Ser, Cys, Arg, Ile, His, Phe, Glu, Lys, Thr, Ala, Met, Val or Asn;

Xaa at position 49 is Met, Arg, Ala, Gly, Pro, Asn, His, or Asp;

Xaa at position 50 is Glu, Leu, Thr, Asp, Tyr, Lys, Asn, Ser, Ala, Ile, Val, His, Phe, Met or Gln;

Xaa at position 51 is Asn, Arg, Met, Pro, Ser, Thr, or His;

Xaa at position 52 is Asn, His, Arg, Leu, Gly, Ser, or Thr;

Xaa at position 53 is Leu, Thr, Ala, Gly, Glu, Pro, Lys, Ser, or Met;

Xaa at position 54 is Arg, Asp, Ile, Ser, Val, Thr, Gln, Asn, Lys, His, Ala or Leu;

Xaa at position 55 is Arg, Thr, Val, Ser, Leu, or Gly;

Xaa at position 56 is Pro, Gly, Cys, Ser, Gln, Glu, Arg, His, Thr, Ala, Tyr, Phe, Leu, Val or Lys;

Xaa at position 57 is Asn or Gly;

Xaa at position 58 is Leu, Ser, Asp, Arg, Gln, Val, or Cys;

Xaa at position 59 is Glu Tyr, His, Leu, Pro, or Arg;

Xaa at position 60 is Ala, Ser, Pro, Tyr, Asn, or Thr;

Xaa at position 61 is Phe, Asn, Glu, Pro, Lys, Arg, or Ser;

Xaa at position 62 is Asn His, Val, Arg, Pro, Thr, Asp, or Ile;

Xaa at position 63 is Arg, Tyr, Trp, Lys, Ser, His, Pro, or Val;

Xaa at position 64 is Ala, Asn, Pro, Ser, or Lys;

Xaa at position 65 is Val, Thr, Pro, His, Leu, Phe, or Ser;

Xaa at position 66 is Lys, Ile, Arg, Val, Asn, Glu, or Ser;

Xaa at position 67 is Ser, Ala, Phe, Val, Gly, Asn, Ile, Pro, or His;

Xaa at position 68 is Leu, Val, Trp, Ser, Ile, Phe, Thr, or His;

Xaa at position 69 is Gln, Ala, Pro, Thr, Glu, Arg, Trp, Gly, or Leu;

Xaa at position 70 is Asn, Leu, Val, Trp, Pro, or Ala;

Xaa at position 71 is Ala, Met, Leu, Pro, Arg, Glu, Thr, Gln, Trp, or Asn;

Xaa at position 72 is Ser, Glu, Met, Ala, His, Asn, Arg, or Asp;

Xaa at position 73 is Ala, Glu, Asp, Leu, Ser, Gly, Thr, or Arg;

Xaa at position 74 is Ile, Met, Thr, Pro, Arg, Gly, Ala;

Xaa at position 75 is Glu, Lys, Gly, Asp, Pro, Trp, Arg, Ser, Gln, or Leu;

Xaa at position 76 is Ser, Val, Ala, Asn, Trp, Glu, Pro, Gly, or Asp;

Xaa at position 77 is Ile, Ser, Arg, Thr, or Leu;

Xaa at position 78 is Leu, Ala, Ser, Glu, Phe, Gly, or Arg;

Xaa at position 79 is Lys, Thr, Asn, Met, Arg, Ile, Gly, or Asp;

Xaa at position 80 is Asn, Trp, Val, Gly, Thr, Leu, Glu, or Arg;

Xaa at position 81 is Leu, Gln, Gly, Ala, Trp, Arg, Val, or Lys;

Xaa at position 82 is Leu, Gln, Lys, Trp, Arg, Asp, Glu, Asn, His, Thr, Ser, Ala, Tyr, Phe, Ile, Met or Val;

Xaa at position 83 is Pro, Ala, Thr, Trp, Arg, or Met;

Xaa at position 84 is Cys, Glu, Gly, Arg, Met, or Val;

Xaa at position 85 is Leu, Asn, Val, or Gln;

Xaa at position 86 is Pro, Cys, Arg, Ala, or Lys;

Xaa at position 87 is Leu, Ser, Trp, or Gly;

Xaa at position 88 is Ala, Lys, Arg, Val, or Trp;

Xaa at position 89 is Thr, Asp, Cys, Leu, Val, Glu, His, Asn, or Ser;

Xaa at position 90 is Ala, Pro, Ser, Thr, Gly, Asp, Ile, or Met;

Xaa at position 91 is Ala, Pro, Ser, Thr, Phe, Leu, Asp, or His;

Xaa at position 92 is Pro, Phe, Arg, Ser, Lys, His, Ala, Gly, Ile or Leu;

Xaa at position 93 is Thr, Asp, Ser, Asn, Pro, Ala, Leu, or Arg;

Xaa at position 94 is Arg, Ile, Ser, Glu, Leu, Val, Gln, Lys, His, Ala, or Pro;

Xaa at position 95 is His, Gln, Pro, Arg, Val, Leu, Gly, Thr, Asn, Lys, Ser, Ala, Trp, Phe, Ile, or Tyr;

Xaa at position 96 is Pro, Lys, Tyr, Gly, Ile, or Thr;

Xaa at position 97 is Ile, Val, Lys, Ala, or Asn;

Xaa at position 98 is His, Ile, Asn, Leu, Asp, Ala, Thr, Glu, Gln, Ser, Phe, Met, Val, Lys, Arg, Tyr or Pro;

Xaa at position 99 is Ile, Leu, Arg, Asp, Val, Pro, Gln, Gly, Ser, Phe, or His;

Xaa at position 100 is Lys, Tyr, Leu, His, Arg, Ile, Ser, Gln, or Pro;

Xaa at position 101 is Asp, Pro, Met, Lys, His, Thr, Val, Tyr, Glu, Asn, Ser, Ala, Gly, Ile, Leu, or Gln;

Xaa at position 102 is Gly, Leu, Glu, Lys, Ser, Tyr, or Pro;

Xaa at position 103 is Asp, or Ser;

Xaa at position 104 is Trp, Val, Cys, Tyr, Thr, Met, Pro, Leu, Gln, Lys, Ala, Phe, or Gly;

Xaa at position 105 is Asn, Pro, Ala, Phe, Ser, Trp, Gln, Tyr, Leu, Lys, Ile, Asp, or His;

Xaa at position 106 is Glu, Ser, Ala, Lys, Thr, Ile, Gly, or Pro;

Xaa at position 108 is Arg, Lys, Asp, Leu, Thr, Ile, Gln, His, Ser, Ala or Pro;

Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, Ala, or Trp;

Xaa at position 111 is Leu, Ile, Arg, Asp, or Met;

Xaa at position 112 is Thr, Val, Gln, Tyr, Glu, His, Ser, or Phe;

Xaa at position 113 is Phe, Ser, Cys, His, Gly, Trp, Tyr, Asp, Lys, Leu, Ile, Val or Asn;

Xaa at position 114 is Tyr, Cys, His, Ser, Trp, Arg, or Leu;

Xaa at position 115 is Leu, Asn, Val, Pro, Arg, Ala, His, Thr, Trp, or Met;

Xaa at position 116 is Lys, Leu, Pro, Thr, Met, Asp, Val, Glu, Arg, Trp, Ser, Asn, His, Ala, Tyr, Phe, Gln, or Ile;

Xaa at position 117 is Thr, Ser, Asn, Ile, Trp, Lys, or Pro;

Xaa at position 118 is Leu, Ser, Pro, Ala, Glu, Cys, Asp, or Tyr;

Xaa at position 119 is Glu, Ser, Lys, Pro, Leu, Thr, Tyr, or Arg;

Xaa at position 120 is Asn, Ala, Pro, Leu, His, Val, or Gln;

Xaa at position 121 is Ala, Ser, Ile, Asn, Pro, Lys, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

and which can additionally have Met- preceding the amino acid in position 1; and wherein from 1 to 14 amino acids can be deleted from the N-terminus and/or from 1 to 15 amino acids can be deleted from the C-terminus; and wherein from 4 to 44 of the amino acids designated by Xaa are different from the corresponding amino acids of native (1–133) human interleukin-3;

A colony stimulating factor selected from the group consisting of GM-CSF, CSF-1, G-CSF, Meg-CSF (more recently referred to as c-mpl ligand), M-CSF, erythropoietin (EPO), IL-1, IL-4, IL-2, IL-5, IL-6, IL-7, IL-8, IL-9, IL-10, IL-11, IL-12, IL-13, LIF, flt3/flk2, human growth hormone, B-cell growth factor, B-cell differentiation factor, eosinophil differentiation factor and stem cell factor (SCF); and At least one non-toxic pharmaceutically acceptable carrier.

2. A composition, comprising: A human interleukin-3 mutant polypeptide of the Formula:

```
Ala Pro Met Thr Gln Thr Thr Ser Leu Lys Thr Ser Trp Val Asn  [SEQ ID NO:2]
 1               5                  10                  15

Cys Xaa Xaa Xaa Ile Xaa Glu Xaa Xaa Xaa Leu Lys Xaa Xaa
         20                  25                  30
```

```
                          -continued
Xaa Xaa Xaa Xaa Xaa Asp Xaa Xaa Asn Leu Asn Xaa Glu Xaa Xaa
                35                  40                  45

Xaa Ile Leu Met Xaa Xaa Asn Leu Xaa Xaa Xaa Asn Leu Glu Xaa
                50                  55                  60

Phe Xaa Xaa Xaa Xaa Xaa Xaa Xaa Xaa Asn Xaa Xaa Xaa Ile Glu
                65                  70                  75

Xaa Xaa Leu Xaa Xaa Leu Xaa Xaa Cys Xaa Pro Xaa Xaa Thr Ala
                80                  85                  90

Xaa Pro Xaa Arg Xaa Xaa Xaa Xaa Xaa Xaa Gly Asp Xaa Xaa
                95                 100                 105

Xaa Phe Xaa Xaa Lys Leu Xaa Phe Xaa Xaa Xaa Xaa Leu Glu Xaa
               110                 115                 120

Xaa Xaa Xaa Gln Gln Thr Thr Leu Ser Leu Ala Ile Phe
               125                 130
``` wherein

Xaa at position 17 is Ser, Gly, Asp, Met, or Gln;

Xaa at position 18 is Asn, His, or Ile;

Xaa at position 19 is Met or Ile;

Xaa at position 21 is Asp or Glu;

Xaa at position 23 is Ile, Ala, Leu, or Gly;

Xaa at position 24 is Ile, Val, or Leu;

Xaa at position 25 is Thr, His, Gln, or Ala;

Xaa at position 26 is His or Ala;

Xaa at position 29 is Gln, Asn, or Val;

Xaa at position 30 is Pro, Gly, or Gln;

Xaa at position 31 is Pro, Asp, Gly, or Gln;

Xaa at position 32 is Leu, Arg, Gln, Asn, Gly, Ala, or Glu;

Xaa at position 33 is Pro or Glu;

Xaa at position 34 is Leu, Val, Gly, Ser, Lys, Ala, Arg, Gin, Glu, Ile, Phe, Thr or Met;

Xaa at position 35 is Leu, Ala, Asn, Pro, Gln, or Val;

Xaa at position 37 is Phe, Ser, Pro, or Trp;

Xaa at position 38 is Asn or Ala;

Xaa at position 42 is Gly, Asp, Ser, Cys, Ala, Asn, Ile, Leu, Met, Tyr or Arg;

Xaa at position 44 is Asp or Glu;

Xaa at position 45 is Gln, Val, Met, Leu, Thr, Ala, Asn, Glu, Ser or Lys;

Xaa at position 46 is Asp, Phe, Ser, Thr, Ala, Asn Gln, Glu, His, Ile, Lys, Tyr, Val or Cys;

Xaa at position 50 is Glu, Ala, Asn, Ser or Asp;

Xaa at position 51 is Asn, Arg, Met, Pro, Ser, Thr, or His;

Xaa at position 54 is Arg or Ala;

Xaa at position 55 is Arg, Thr, Val, Leu, or Gly;

Xaa at position 56 is Pro, Gly, Ser, Gln, Ala, Arg, Asn, Glu, Leu, Thr, Val or Lys;

Xaa at position 60 is Ala or Ser;

Xaa at position 62 is Asn, Pro, Thr, or Ile;

Xaa at position 63 is Arg or Lys;

Xaa at position 64 is Ala or Asn;

Xaa at position 65 is Val or Thr;

Xaa at position 66 is Lys or Arg;

Xaa at position 67 is Ser, Phe, or His;

Xaa at position 68 is Leu, Ile, Phe, or His;

Xaa at position 69 is Gln, Ala, Pro, Thr, Glu, Arg, or Gly;

Xaa at position 71 is Ala, Pro, or Arg;

Xaa at position 72 is Ser, Glu, Arg, or Asp;

Xaa at position 73 is Ala or Leu;

Xaa at position 76 is Ser, Val, Ala, Asn, Glu, Pro, or Gly;

Xaa at position 77 is Ile or Leu;

Xaa at position 79 is Lys, Thr, Gly, Asn, Met, Arg, Ile, Gly, or Asp;

Xaa at position 80 is Asn, Gly, Glu, or Arg;

Xaa at position 82 is Leu, Gln, Trp, Arg, Asp, Ala, Asn, Glu, His, Ile, Met, Phe, Ser, Thr, Tyr or Val;

Xaa at position 83 is Pro or Thr;

Xaa at position 85 is Leu or Val;

Xaa at position 87 is Leu or Ser;

Xaa at position 88 is Ala or Trp;

Xaa at position 91 is Ala or Pro;

Xaa at position 93 is Thr, Asp, Ser, Pro, Ala, Leu, or Arg;

Xaa at position 95 is His, Pro, Arg, Val, Leu, Gly, Asn, Phe, Ser or Thr;

Xaa at position 96 is Pro or Tyr;

Xaa at position 97 is Ile or Val;

Xaa at position 98 is His, Ile, Asn, Leu, Ala, Thr, Leu, Arg, Gln, Leu, Lys, Met, Ser, Tyr, Val or Pro;

Xaa at position 99 is Ile, Leu, or Val;

Xaa at position 100 is Lys, Arg, Ile, Gln, Pro, or Ser;

Xaa at position 101 is Asp, Pro, Met, Lys, His, Thr, Pro, Asn, Ile, Leu or Tyr;

Xaa at position 104 is Trp or Leu;

Xaa at position 105 is Asn, Pro, Ala, Ser, Trp, Gln, Tyr, Leu, Lys, Ile, Asp, or His;

Xaa at position 106 is Glu or Gly;

Xaa at position 108 is Arg, Ala, or Ser;

Xaa at position 109 is Arg, Thr, Glu, Leu, or Ser;

Xaa at position 112 is Thr, Val, or Gln;

Xaa at position 114 is Tyr or Trp;

Xaa at position 115 is Leu or Ala;

Xaa at position 116 is Lys, Thr, Val, Trp, Ser, Ala, His, Met, Phe, Tyr or Ile;

Xaa at position 117 is Thr or Ser;

Xaa at position 120 is Asn, Pro, Leu, His, Val, or Gln;

Xaa at position 121 is Ala, Ser, Ile, Asn, Pro, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu.
and which can additionally have Met- preceding the amino acid in position 1; and wherein from 1 to 14 amino acids can be deleted from the N-terminus and/or from 1 to 15 amino acids can be deleted from the C-terminus; and wherein from 4 to 35 of the amino acids designated by Xaa are different from the corresponding amino acids of native (1–133)human interleukin-3;

A colony stimulating factor selected from the group consisting of GM-CSF, CSF-1, G-CSF, Meg-CSF (more recently referred to as c-mpl ligand), M-CSF, erythropoietin (EPO), IL-1, IL-4, IL-2, IL-5, IL-6, IL-7, IL-8, IL-9, IL-10, IL-11, IL-12, IL-13, LIF, flt3/flk2, human growth hormone, B-cell growth factor, B-cell differentiation factor, eosinophil differentiation factor and stem cell factor (SCF); and At least one non-toxic pharmaceutically acceptable carrier.

3. A composition of 2, wherein said human interleukin-3 mutant polypeptide is of the Formula:

```
Ala Pro Met Thr Gln Thr Thr Ser Leu Lys Thr Ser Trp Val Asn  [SEQ ID NO:3]
 1           5                   10                      15

Cys Xaa Xaa Met Ile Asp Glu Xaa Ile Xaa Xaa Leu Lys Xaa Xaa
             20                  25                      30

Pro Xaa Pro Xaa Xaa Asp Phe Xaa Asn Leu Asn Xaa Glu Asp Xaa
             35                  40                      45

Xaa Ile Leu Met Xaa Xaa Asn Leu Arg Xaa Xaa Asn Leu Glu Ala
             50                  55                      60

Phe Xaa Arg Xaa Xaa Lys Xaa Xaa Xaa Asn Ala Ser Ala Ile Glu
             65                  70                      75

Xaa Xaa Leu Xaa Xaa Leu Xaa Pro Cys Leu Pro Xaa Xaa Thr Ala
             80                  85                      90

Xaa Pro Xaa Arg Xaa Pro Ile Xaa Xaa Xaa Xaa Gly Asp Trp Xaa
             95                 100                     105

Glu Phe Xaa Xaa Lys Leu Xaa Phe Tyr Leu Xaa Xaa Leu Glu Xaa
            110                 115                     120

Xaa Xaa Xaa Gln Gln Thr Thr Leu Ser Leu Ala Ile Phe
            125                 130
``` wherein
Xaa at position 17 is Ser, Gly, Asp, or Gln;
Xaa at position 18 is Asn, His, or Ile;
Xaa at position 23 is Ile, Ala, Leu, or Gly;
Xaa at position 25 is Thr, His, or Gln;
Xaa at position 26 is His or Ala;
Xaa at position 29 is Gln or Asn;
Xaa at position 30 is Pro or Gly;
Xaa at position 32 is Leu, Arg, Asn, or Ala;
Xaa at position 34 is Leu, Val, Ser, Ala, Arg, Gln, Glu, Ile, Phe, Thr, or Met;
Xaa at position 35 is Leu, Ala, Asn, or Pro;
Xaa at position 38 is Asn or Ala;
Xaa at position 42 is Gly, Asp, Ser, Ala, Asn, Ile, Leu, Met, Tyr or Arg;
Xaa at position 45 is Gln, Val, Met, Leu, Ala, Asn, Glu, or Lys;
Xaa at position 46 is Asp, Phe, Ser, Gln, Glu, His, Val or Thr;

Xaa at position 50 is Glu Asn, Ser or Asp;
Xaa at position 51 is Asn, Arg, Pro, Thr, or His;
Xaa at position 55 is Arg, Leu, or Gly;
Xaa at position 56 is Pro, Gly, Ser, Ala, Asn, Val, Leu or Gln;
Xaa at position 62 is Asn, Pro, or Thr;
Xaa at position 64 is Ala or Asn;
Xaa at position 65 is Val or Thr;
Xaa at position 67 is Ser or Phe;
Xaa at position 68 is Leu or Phe;
Xaa at position 69 is Gln, Ala, Glu, or Arg;
Xaa at position 76 is Ser, Val, Asn, Pro, or Gly;
Xaa at position 77 is Ile or Leu;
Xaa at position 79 is Lys, Gly, Asn, Met, Arg, Ile, or Gly;
Xaa at position 80 is Asn, Gly, Glu, or Arg;
Xaa at position 82 is Leu, Gln, Trp, Arg, Asp, Asn, Glu, His, Met, Phe, Ser, Thr, Tyr or Val;
Xaa at position 87 is Leu or Ser;
Xaa at position 88 is Ala or Trp;
Xaa at position 91 is Ala or Pro;
Xaa at position 93 is Thr, Asp, or Ala;
Xaa at position 95 is His, Pro, Arg, Val, Gly, Asn, Ser or Thr;
Xaa at position 98 is His, Ile, Asn, Ala, Thr, Gln, Glu, Lys, Met, Ser, Tyr, Val or Leu;
Xaa at position 99 is Ile or Leu;
Xaa at position 100 is Lys or Arg;
Xaa at position 101 is Asp, Pro, Met, Lys, Thr, His, Pro, Asn, Ile, Leu or Tyr;
Xaa at position 105 is Asn, Pro, Ser, Ile or Asp;
Xaa at position 108 is Arg, Ala, or Ser;
Xaa at position 109 is Arg, Thr, Glu, Leu, or Ser;
Xaa at position 112 is Thr or Gln;
Xaa at position 116 is Lys, Val, Trp, Ala, His, Phe, Tyr or Ile;
Xaa at position 117 is Thr or Ser;
Xaa at position 120 is Asn, Pro, Leu, His, Val, or Gln;

Xaa at position 121 is Ala, Ser, Ile, Pro, or Asp;

Xaa at position 122 is Gln, Met, Trp, Phe, Pro, His, Ile, or Tyr;

Xaa at position 123 is Ala, Met, Glu, Ser, or Leu;

and which can additionally have Met- preceding the amino acid in position 1; and wherein from 1 to 14 amino acids can be deleted from the N-terminus and/or from 1 to 15 amino acids can be deleted from the C-terminus; and wherein from 4 to 44 of the amino acids designated by Xaa are different from the corresponding amino acids of native (1–133)human interleukin-3.

4. A composition of 3,wherein

Xaa at position 42 is Gly, Asp, Ser, Ile, Leu, Met, Tyr, or Ala;

Xaa at position 45 is Gln, Val, Met or Asn;

Xaa at position 46 is Asp, Ser, Gln, His or Val;

Xaa at position 50 is Glu or Asp;

Xaa at position 51 is Asn, Pro or Thr;

Xaa at position 62 is Asn or Pro;

Xaa at position 76 is Ser, or Pro;

Xaa at position 82 is Leu, Trp, Asp, Asn Glu, His, Phe, Ser or Tyr;

Xaa at position 95 is His, Arg, Thr, Asn or Ser;

Xaa at position 98 is His, Ile, Leu, Ala, Gln, Lys, Met, Ser, Tyr or Val;

Xaa at position 100 is Lys or Arg;

Xaa at position 101 is Asp, Pro, His, Asn, Ile or Leu;

Xaa at position 105 is Asn, or Pro;

Xaa at position 108 is Arg, Ala, or Ser;

Xaa at position 116 is Lys, Val, Trp, Ala, His, Phe, or Tyr;

Xaa at position 121 is Ala, or Ile;

Xaa at position 122 is Gln, or Ile; and

Xaa at position 123 is Ala, Met or Glu.

5. A composition, comprising:

A human interleukin-3 mutant polypeptide of the Formula:

Xaa at position 5 is Met, Phe, Ile, Arg, Gly, Ala, or Cys;

Xaa at position 6 is Ile, Cys, Gln, Glu, Arg, Pro, or Ala;

Xaa at position 7 is Asp, Phe, Lys, Arg, Ala, Gly, Glu, Gln, Asn, Thr, Ser or Val;

Xaa at position 8 is Glu, Trp, Pro, Ser, Ala, His, Asp, Asn, Gln, Leu, Val, or Gly;

Xaa at position 9 is Ile, Val, Ala, Leu, Gly, Trp, Lys, Phe, Leu, Ser, or Arg;

Xaa at position 10 is Ile, Gly, Val, Arg, Ser, Phe, or Leu;

Xaa at position 11 is Thr, His, Gly, Gln, Arg, Pro, or Ala;

Xaa at position 12 is His, Thr, Phe, Gly, Arg, Ala, or Trp;

Xaa at position 13 is Leu, Gly, Arg, Thr, Ser, or Ala;

Xaa at position 14 is Lys, Arg, Leu, Gln, Gly, Pro, Val or Trp;

Xaa at position 15 is Gln, Asn, Leu, Pro, Arg, or Val;

Xaa at position 16 is Pro, His, Thr, Gly, Asp, Gln, Ser, Leu, or Lys;

Xaa at position 17 is Pro, Asp, Gly, Ala, Arg, Leu, or Gln;

Xaa at position 18 is Leu, Val, Arg, Gln, Asn, Gly, Ala, or Glu;

Xaa at position 19 is Pro, Leu, Gln, Ala, Thr, or Glu;

Xaa at position 20 is Leu, Val, Gly, Ser, Lys, Glu, Gln, Thr, Arg, Ala, Phe, Ile or Met;

Xaa at position 21 is Leu, Ala, Gly, Asn, Pro, Gln, or Val;

Xaa at position 22 is Asp, Leu, or Val;

Xaa at position 23 is Phe, Ser, Pro, Trp, or Ile;

Xaa at position 24 is Asn, or Ala;

Xaa at position 26 is Leu, Trp, or Arg;

Xaa at position 27 is Asn, Cys, Arg, Leu, His, Met, Pro;

Xaa at position 28 is Gly, Asp, Ser, Cys, Ala, Lys, Asn, Thr, Leu, Val, Glu, Phe, Tyr, Ile or Met;

Xaa at position 29 is Glu, Asn, Tyr, Leu, Phe, Asp, Ala, Cys, Gln, Arg, Thr, Gly or Ser;

Xaa at position 30 is Asp, Ser, Leu, Arg, Lys, Thr,Met, Trp, Glu, Asn, Gln, Ala or Pro;

Xaa at position 31 is Gln, Pro, Phe, Val, Met, Leu, Thr, Lys, Asp, Asn, Arg, Ser, Ala, Ile, Glu, His or Trp;

```
Asn Cys Xaa Xaa Xaa Xaa Xaa Xaa Xaa Xaa Xaa Xaa Xaa Xaa Xaa [SEQ ID NO:4]
 1              5                   10                  15

Xaa Xaa Xaa Xaa Xaa Xaa Xaa Xaa Xaa Asn Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
                35                  40                  45

Xaa Xaa Xaa Xaa Xaa Xaa Xaa Xaa Xaa Xaa Xaa Xaa Xaa Xaa Xaa
                50                  55                  60

Xaa Xaa Xaa Xaa Xaa Xaa Xaa Xaa Xaa Xaa Xaa Xaa Xaa Xaa Xaa
                65                  70                  75

Xaa Xaa Xaa Xaa Xaa Xaa Xaa Xaa Xaa Xaa Xaa Xaa Xaa Xaa Xaa
                80                  85                  90

Xaa Xaa Phe Xaa Xaa Xaa Xaa Xaa Xaa Xaa Xaa Xaa Xaa Xaa Xaa
                95                  100                 105

Xaa Xaa Xaa Xaa Gln Gln
                110
``` wherein

Xaa at position 3 is Ser, Lys, Gly, Asp, Met, Gln, or Arg;

Xaa at position 4 is Asn, His, Leu, Ile, Phe, Arg, or Gln;

Xaa at position 32 is Asp, Phe, Ser, Thr, Cys, Glu, Asn, Gln, Lys, His, Ala, Tyr, Ile, Val or Gly;

Xaa at position 33 is Ile, Gly, Val, Ser, Arg, Pro, or His;

Xaa at position 34 is Leu, Ser, Cys, Arg, Ile, His, Phe, Glu, Lys, Thr, Ala, Met, Val or Asn;

Xaa at position 35 is Met, Arg, Ala, Gly, Pro, Asn, His, or Asp;

Xaa at position 36 is Glu, Leu, Thr, Asp, Tyr, Lys, Asn, Ser, Ala, Ile, Val, His, Phe, Met or Gln;

Xaa at position 37 is Asn, Arg, Met, Pro, Ser, Thr, or His;

Xaa at position 38 is Asn, His, Arg, Leu, Gly, Ser, or Thr;

Xaa at position 39 is Leu, Thr, Ala, Gly, Glu, Pro, Lys, Ser, Met, or;

Xaa at position 40 is Arg, Asp, Ile, Ser, Val, Thr, Gln, Asn, Lys, His, Ala or Leu;

Xaa at position 41 is Arg, Thr, Val, Ser, Leu, or Gly;

Xaa at position 42 is Pro, Gly, Cys, Ser, Gln, Glu, Arg, His, Thr, Ala, Tyr, Phe, Leu, Val or Lys;

Xaa at position 43 is Asn or Gly;

Xaa at position 44 is Leu, Ser, Asp, Arg, Gln, Val, or Cys;

Xaa at position 45 is Glu Tyr, His, Leu, Pro, or Arg;

Xaa at position 46 is Ala, Ser, Pro, Tyr, Asn, or Thr;

Xaa at position 47 is Phe, Asn, Glu, Pro, Lys, Arg, or Ser;

Xaa at position 48 is Asn, His, Val, Arg, Pro, Thr, Asp, or Ile;

Xaa at position 49 is Arg, Tyr, Trp, Lys, Ser, His, Pro, or Val;

Xaa at position 50 is Ala, Asn, Pro, Ser, or Lys;

Xaa at position 51 is Val, Thr, Pro, His, Leu, Phe, or Ser;

Xaa at position 52 is Lys, Ile, Arg, Val, Asn, Glu, or Ser;

Xaa at position 53 is Ser, Ala, Phe, Val, Gly, Asn, Ile, Pro, or His;

Xaa at position 54 is Leu, Val, Trp, Ser, Ile, Phe, Thr, or His;

Xaa at position 55 is Gln, Ala, Pro, Thr, Glu, Arg, Trp, Gly, or Leu;

Xaa at position 56 is Asn, Leu, Val, Trp, Pro, or Ala;

Xaa at position 57 is Ala, Met, Leu, Pro, Arg, Glu, Thr, Gln, Trp, or Asn;

Xaa at position 58 is Ser, Glu, Met, Ala, His, Asn, Arg, or Asp;

Xaa at position 59 is Ala, Glu, Asp, Leu, Ser, Gly, Thr, or Arg;

Xaa at position 60 is Ile, Met, Thr, Pro, Arg, Gly, Ala;

Xaa at position 61 is Glu, Lys, Gly, Asp, Pro, Trp, Arg, Ser, Gln, or Leu;

Xaa at position 62 is Ser, Val, Ala, Asn, Trp, Glu, Pro, Gly, or Asp;

Xaa at position 63 is Ile, Ser, Arg, Thr, or Leu;

Xaa at position 64 is Leu, Ala, Ser, Glu, Phe, Gly, or Arg;

Xaa at position 65 is Lys, Thr, Gly, Asn, Met, Arg, Ile, or Asp;

Xaa at position 66 is Asn, Trp, Val, Gly, Thr, Leu, Glu, or Arg;

Xaa at position 67 is Leu, Gln, Gly, Ala, Trp, Arg, Val, or Lys;

Xaa at position 68 is Leu, Gln, Lys, Trp, Arg, Asp, Glu, Asn, His, Thr, Ser, Ala, Tyr, Phe, Ile, Met or Val;

Xaa at position 69 is Pro, Ala, Thr, Trp, Arg, or Met;

Xaa at position 70 is Cys, Glu, Gly, Arg, Met, or Val;

Xaa at position 71 is Leu, Asn, Val, or Gln;

Xaa at position 72 is Pro, Cys, Arg, Ala, or Lys;

Xaa at position 73 is Leu, Ser, Trp, or Gly;

Xaa at position 74 is Ala, Lys, Arg, Val, or Trp;

Xaa at position 75 is Thr, Asp, Cys, Leu, Val, Glu, His, Asn, or Ser;

Xaa at position 76 is Ala, Pro, Ser, Thr, Gly, Asp, Ile, or Met;

Xaa at position 77 is Ala, Pro, Ser, Thr, Phe, Leu, Asp, or His;

Xaa at position 78 is Pro, Phe, Arg, Ser, Lys, His, Ala, Gly, Ile or Leu;

Xaa at position 79 is Thr, Asp, Ser, Asn, Pro, Ala, Leu, or Arg;

Xaa at position 80 is Arg, Ile, Ser, Glu, Leu, Val, Gln, Lys, His, Ala or Pro;

Xaa at position 81 is His, Gln, Pro, Arg, Val, Leu, Gly, Thr, Asn, Lys, Ser, Ala, Trp, Phe, Ile or Tyr;

Xaa at position 82 is Pro, Lys, Tyr, Gly, Ile, or Thr;

Xaa at position 83 is Ile, Val, Lys, Ala, or Asn;

Xaa at position 84 is His, Ile, Asn, Leu, Asp, Ala, Thr, Glu, Gln, Ser, Phe, Met, Val, Lys, Arg, Tyr or Pro;

Xaa at position 85 is Ile, Leu, Arg, Asp, Val, Pro, Gln, Gly, Ser, Phe, or His;

Xaa at position 86 is Lys, Tyr, Leu, His, Arg, Ile, Ser, Gln, Pro;

Xaa at position 87 is Asp, Pro, Met, Lys, His, Thr, Val, Tyr, Glu, Asn, Ser, Ala, Gly, Ile, Leu or Gln;

Xaa at position 88 is Gly, Leu, Glu, Lys, Ser, Tyr, or Pro;

Xaa at position 89 is Asp, or Ser;

Xaa at position 90 is Trp, Val, Cys, Tyr, Thr, Met, Pro, Leu, Gln, Lys, Ala, Phe, or Gly;

Xaa at position 91 is Asn, Pro, Ala, Phe, Ser, Trp, Gln, Tyr, Leu, Lys, Ile, Asp, or His;

Xaa at position 92 is Glu, Ser, Ala, Lys, Thr, Ile, Gly, or Pro;

Xaa at position 94 is Arg, Lys, Asp, Leu, Thr, Ile, Gln, His, Ser, Ala, or Pro;

Xaa at position 95 is Arg, Thr, Pro, Glu, Tyr, Leu, Ser, or Gly;

Xaa at position 96 is Lys, Asn, Thr, Leu, Gln, Arg, His, Glu, Ser, Ala or Trp;

Xaa at position 97 is Leu, Ile, Arg, Asp, or Met;

Xaa at position 98 is Thr, Val, Gln, Tyr, Glu, His, Ser, or Phe;

Xaa at position 99 is Phe, Ser, Cys, His, Gly, Trp, Tyr, Asp, Lys, Leu, Ile, Val or Asn;

Xaa at position 100 is Tyr, Cys, His, Ser, Trp, Arg, or Leu;

Xaa at position 101 is Leu, Asn, Val, Pro, Arg, Ala, His, Thr, Trp, or Met;

Xaa at position 102 is Lys, Leu, Pro, Thr, Met, Asp, Val, Glu, Arg, Trp, Ser, Asn, His, Ala, Tyr, Phe, Gln, or Ile;

Xaa at position 103 is Thr, Ser, Asn, Ile, Trp, Lys, or Pro;

Xaa at position 104 is Leu, Ser, Pro, Ala, Glu, Cys, Asp, or Tyr;

Xaa at position 105 is Glu, Ser, Lys, Pro, Leu, Thr, Tyr, or Arg;

Xaa at position 106 is Asn, Ala, Pro, Leu, His, Val, or Gln;

Xaa at position 107 is Ala, Ser, Ile, Asn, Pro, Lys, Asp, or Gly;

Xaa at position 108 is Gln, Ser, Met, Trp, Arg, Phe, Pro, His, Ile, Tyr, or Cys;

Xaa at position 109 is Ala, Met, Glu, His, Ser, Pro, Tyr, or Leu;

and which can additionally have Met- or Met-Ala- preceding the amino acid in position 1; and wherein from 4 to 44 of the amino acids designated by Xaa are different from the corresponding native amino acids of (1–133) human interleukin-3;

A colony stimulating factor selected from the group consisting of GM-CSF, CSF-1, G-CSF, Meg-CSF (more recently referred to as c-mpl ligand), M-CSF, erythropoietin (EPO), IL-1, IL-4, IL-2, IL-5, IL-6, IL-7, IL-8, IL-9, IL-10, IL-11, IL-12, IL-13, LIF, flt3/flk2, human growth hormone, B-cell growth factor, B-cell differentiation factor, eosinophil differentiation factor and stem cell factor (SCF); and At least one non-toxic pharmaceutically acceptable carrier.

6. A composition of 5, wherein said human interleukin-3 mutant polypeptide is of the Formula:

```
Asn Cys Xaa Xaa Xaa Ile Xaa Glu Xaa Xaa Xaa Xaa Leu Lys Xaa [SEQ ID NO:5]
1               5                   10                  15

Xaa Xaa Xaa Xaa Xaa Xaa Asp Xaa Xaa Asn Leu Asn Xaa Glu Xaa
                20                  25                  30

Xaa Xaa Ile Leu Met Xaa Xaa Asn Leu Xaa Xaa Xaa Asn Leu Glu
                35                  40                  45

Xaa Phe Xaa Xaa Xaa Xaa Xaa Xaa Xaa Xaa Asn Xaa Xaa Xaa Ile
                50                  55                  60

Glu Xaa Xaa Leu Xaa Xaa Leu Xaa Xaa Cys Xaa Pro Xaa Xaa Thr
                65                  70                  75

Ala Xaa Pro Xaa Arg Xaa Xaa Xaa Xaa Xaa Xaa Xaa Gly Asp Xaa
                80                  85                  90

Xaa Xaa Phe Xaa Xaa Lys Leu Xaa Phe Xaa Xaa Xaa Xaa Leu Glu
                95                  100                 105

Xaa Xaa Xaa Xaa Gln Gln
                110
``` wherein

Xaa at position 3 is Ser, Gly, Asp, Met, or Gln;

Xaa at position 4 is Asn, His, or Ile;

Xaa at position 5 is Met or Ile;

Xaa at position 7 is Asp or Glu;

Xaa at position 9 is Ile, Ala, Leu, or Gly;

Xaa at position 10 is Ile, Val, or Leu;

Xaa at position 11 is Thr, His, Gln, or Ala;

Xaa at position 12 is His or Ala;

Xaa at position 15 is Gln, Asn, or Val;

Xaa at position 16 is Pro, Gly, or Gln;

Xaa at position 17 is Pro, Asp, Gly, or Gln;

Xaa at position 18 is Leu, Arg, Gln, Asn, Gly, Ala, or Glu;

Xaa at position 19 is Pro or Glu;

Xaa at position 20 is Leu, Val, Gly, Ser, Lys, Ala, Arg, Gln, Glu, Ile, Phe, Thr or Met;

Xaa at position 21 is Leu, Ala, Asn, Pro, Gln, or Val;

Xaa at position 23 is Phe, Ser, Pro, or Trp;

Xaa at position 24 is Asn or Ala;

Xaa at position 28 is Gly, Asp, Ser, Cys, Ala, Asn, Ile, Leu, Met Tyr or Arg;

Xaa at position 30 is Asp or Glu;

Xaa at position 31 is Gln, Val, Met, Leu, Thr, Ala, Asn, Glu, Ser or Lys;

Xaa at position 32 is Asp, Phe, Ser, Thr, Ala, Asn, Gln, Glu, His, Ile, Lys, Tyr, Val or Cys;

Xaa at position 36 is Glu, Ala, Asn, Ser or Asp;

Xaa at position 37 is Asn, Arg, Met, Pro, Ser, Thr, or His;

Xaa at position 40 is Arg or Ala;

Xaa at position 41 is Arg, Thr, Val, Leu, or Gly;

Xaa at position 42 is Pro, Gly, Ser, Gln, Ala, Arg, Asn, Glu, Leu, Thr, Val or Lys;

Xaa at position 46 is Ala or Ser;

Xaa at position 48 is Asn, Pro, Thr, or Ile;

Xaa at position 49 is Arg or Lys;

Xaa at position 50 is Ala or Asn;

Xaa at position 51 is Val or Thr;

Xaa at position 52 is Lys or Arg;

Xaa at position 53 is Ser, Phe, or His;

Xaa at position 54 is Leu, Ile, Phe, or His;

Xaa at position 55 is Gln, Ala, Pro, Thr, Glu, Arg, or Gly;

Xaa at position 57 is Ala, Pro, or Arg;

Xaa at position 58 is Ser, Glu, Arg, or Asp;

Xaa at position 59 is Ala or Leu;

Xaa at position 62 is Ser, Val, Ala, Asn, Glu, Pro, or Gly;

Xaa at position 63 is Ile or Leu;

Xaa at position 65 is Lys, Thr, Gly, Asn, Met, Arg, Ile, Gly, or Asp;

Xaa at position 66 is Asn, Gly, Glu, or Arg;

Xaa at position 68 is Leu, Gln, Trp, Arg, Asp, Ala, Asn, Glu, His, Ile, Met, Phe, Ser, Thr, Tyr or Val;

Xaa at position 69 is Pro or Thr;

Xaa at position 71 is Leu or Val;

Xaa at position 73 is Leu or Ser;

Xaa at position 74 is Ala or Trp;

Xaa at position 77 is Ala or Pro;

Xaa at position 79 is Thr, Asp, Ser, Pro, Ala, Leu, or Arg;

Xaa at position 81 is His, Pro, Arg, Val, Leu, Gly, Asn, Phe, Ser or Thr;

Xaa at position 82 is Pro or Tyr;

Xaa at position 83 is Ile or Val;

Xaa at position 84 is His, Ile, Asn, Leu, Ala, Thr, Leu, Arg, Gln, Leu, Lys, Met, Ser, Tyr, Val or Pro;

Xaa at position 85 is Ile, Leu, or Val;
Xaa at position 86 is Lys, Arg, Ile, Gln, Pro, or Ser;
Xaa at position 87 is Asp, Pro, Met, Lys, His, Thr, Asn, Ile, Leu or Tyr;
Xaa at position 90 is Trp or Leu;
Xaa at position 91 is Asn, Pro, Ala, Ser, Trp, Gln, Tyr, Leu, Lys, Ile, Asp, or His;
Xaa at position 92 is Glu, or Gly;
Xaa at position 94 is Arg, Ala, or Ser;
Xaa at position 95 is Arg, Thr, Glu, Leu, or Ser;
Xaa at position 98 is Thr, Val, or Gln;
Xaa at position 100 is Tyr or Trp;
Xaa at position 101 is Leu or Ala;
Xaa at position 102 is Lys, Thr, Val, Trp, Ser, Ala, His, Met, Phe, Tyr or Ile;
Xaa at position 103 is Thr or Ser;
Xaa at position 106 is Asn, Pro, Leu, His, Val, or Gln;
Xaa at position 107 is Ala, Ser, Ile, Asn, Pro, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;
which can additionally have Met- or Met-Ala- preceding the amino acid in position 1; and wherein from 4 to 35 of the amino acids designated by Xaa are different from the corresponding amino acids of native human interleukin-3.

7. A composition of 6, wherein said human interleukin-3 mutant polypeptide is of the Formula:

Xaa at position 21 is Leu, Ala, Asn, or Pro;
Xaa at position 24 is Asn or Ala;
Xaa at position 28 is Gly, Asp, Ser, Ala, Asn, Ile, Leu, Met, Tyr or Arg;
Xaa at position 31 is Gln, Val, Met, Leu, Ala, Asn, Glu or Lys;
Xaa at position 32 is Asp, Phe, Ser, Ala, Gln, Glu, His, Val or Thr;
Xaa at position 36 is Glu, Asn, Ser or Asp;
Xaa at position 37 is Asn, Arg, Pro, Thr, or His;
Xaa at position 41 is Arg, Leu, or Gly;
Xaa at position 42 is Pro, Gly, Ser, Ala, Asn, Val, Leu or Gln;
Xaa at position 48 is Asn, Pro, or Thr;
Xaa at position 50 is Ala or Asn;
Xaa at position 51 is Val or Thr;
Xaa at position 53 is Ser or Phe;
Xaa at position 54 is Leu or Phe;
Xaa at position 55 is Gln, Ala, Glu, or Arg;
Xaa at position 62 is Ser, Val, Asn, Pro, or Gly;
Xaa at position 63 is Ile or Leu;
Xaa at position 65 is Lys, Asn, Met, Arg, Ile, or Gly;
Xaa at position 66 is Asn, Gly, Glu, or Arg;
Xaa at position 68 is Leu, Gln, Trp, Arg, Asp, Asn, Glu, His, Met, Phe, Ser, Thr, Tyr or Val;
Xaa at position 73 is Leu or Ser;
Xaa at position 74 is Ala or Trp;
Xaa at position 77 is Ala or Pro;

```
Asn Cys Xaa Xaa Met Ile Asp Glu Xaa Ile Xaa Xaa Leu Lys Xaa   [SEQ ID NO:6]
 1           5                   10                  15

Xaa Pro Xaa Pro Xaa Xaa Asp Phe Xaa Asn Leu Asn Xaa Glu Asp
            20                  25                  30

Xaa Xaa Ile Leu Met Xaa Xaa Asn Leu Arg Xaa Xaa Asn Leu Glu
                35                  40                  45

Ala Phe Xaa Arg Xaa Xaa Lys Xaa Xaa Xaa Asn Ala Ser Ala Ile
            50                  55                  60

Glu Xaa Xaa Leu Xaa Xaa Leu Xaa Pro Cys Leu Pro Xaa Xaa Thr
            65                  70                  75

Ala Xaa Pro Xaa Arg Xaa Pro Ile Xaa Xaa Xaa Xaa Gly Asp Trp
            80                  85                  90

Xaa Glu Phe Xaa Xaa Lys Leu Xaa Phe Tyr Leu Xaa Xaa Leu Glu
            95                  100                 105

Xaa Xaa Xaa Xaa Gln Gln
            110
``` wherein
Xaa at position 3 is Ser, Gly, Asp, or Gln;
Xaa at position 4 is Asn, His, or Ile;
Xaa at position 9 is Ile, Ala, Leu, or Gly;
Xaa at position 11 is Thr, His, or Gln;
Xaa at position 12 is His or Ala;
Xaa at position 15 is Gln or Asn;
Xaa at position 16 is Pro or Gly;
Xaa at position 18 is Leu, Arg, Asn, or Ala;
Xaa at position 20 is Leu, Val, Ser, Ala, Arg, Gln, Glu, Ile, Phe, Thr or Met;

Xaa at position 79 is Thr, Asp, or Ala;
Xaa at position 81 is His, Pro, Arg, Val, Gly, Asn, Ser or Thr;
Xaa at position 84 is His, Ile, Asn, Ala, Thr, Arg, Gln, Glu, Lys, Met, Ser, Tyr, Val or Leu;
Xaa at position 85 is Ile or Leu;
Xaa at position 86 is Lys or Arg;
Xaa at position 87 is Asp, Pro, Met, Lys, His, Pro, Asn, Ile, Leu or Tyr;
Xaa at position 91 is Asn, Pro, Ser, Ile or Asp;
Xaa at position 94 is Arg, Ala, or Ser;
Xaa at position 95 is Arg, Thr, Glu, Leu, or Ser;

Xaa at position 98 is Thr or Gln;
Xaa at position 102 is Lys, Val, Trp, or Ile;
Xaa at position 103 is Thr, Ala, His, Phe, Tyr or Ser;
Xaa at position 106 is Asn, Pro, Leu, His, Val, or Gln;
Xaa at position 107 is Ala, Ser, Ile, Pro, or Asp;
Xaa at position 108 is Gln, Met, Trp, Phe, Pro, His, Ile, or Tyr;
Xaa at position 109 is Ala, Met, Glu, Ser, or Leu;
and which can additionally have Met- or Met-Ala- preceding the amino acid in position 1; and wherein from 4 to 26 of the amino acids designated by Xaa are different from the corresponding amino acids of native (1–133)human interleukin-3.

8. The composition of 7, wherein
Xaa at position 17 is Ser, Lys, Asp, Met, Gln, or Arg;
Xaa at position 18 is Asn, His, Leu, Ile, Phe, Arg, or \ Gin;
Xaa at position 19 is Met, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, or Val;
Xaa at position 22 is Glu, Trp, Pro, Ser, Ala, His, or Gly;
Xaa at position 23 is Ile, Ala, Gly, Trp, Lys, Leu, Ser, or Arg;
Xaa at position 24 is Ile, Gly, Arg, or Ser;
Xaa at position 25 is Thr, His, Gly, Gln, Arg, Pro, or Ala;
Xaa at position 26 is His, Thr, Phe, Gly, Ala, or Trp;
Xaa at position 27 is Leu, Gly, Arg, Thr, Ser, or Ala;
Xaa at position 28 is Lys, Leu, Gln, Gly, Pro, Val or Trp;
Xaa at position 29 is Gln, Asn, Pro, Arg, or Val;
Xaa at position 30 is Pro, His, Thr, Gly, Asp, Gln, Ser, Leu, or Lys;
Xaa at position 31 is Pro, Asp, Gly, Arg, Leu, or Gln;
Xaa at position 32 is Leu, Arg, Gln, Asn, Gly, Ala, or Glu;
Xaa at position 33 is Pro, Leu, Gln, Thr, or Glu;
Xaa at position 34 is Leu, Gly, Ser, or Lys;
Xaa at position 35 is Leu, Ala, Gly, Asn, Pro, or Gln;
Xaa at position 36 is Asp, Leu, or Val;
Xaa at position 37 is Phe, Ser, or Pro;
Xaa at position 38 is Asn, or Ala;
Xaa at position 40 is Leu, Trp, or Arg;
Xaa at position 41 is Asn, Cys, Arg, Leu, His, Met, Pro;
Xaa at position 42 is Gly, Asp, Ser, Cys, or Ala;
Xaa at position 42 is Glu, Asn, Tyr, Leu, Phe, Asp, Ala, Cys, or Ser;
Xaa at position 44 is Asp, Ser, Leu, Arg, Lys, Thr, Met, Trp, or Pro;
Xaa at position 45 is Gln, Pro, Phe, Val, Met, Leu, Thr, Lys, or Trp;
Xaa at position 46 is Asp, Phe, Ser, Thr, Cys, or Gly;
Xaa at position 47 is Ile, Gly, Ser, Arg, Pro, or His;
Xaa at position 48 is Leu, Ser, Cys, Arg, His, Phe, or Asn;
Xaa at position 49 is Met, Arg, Ala, Gly, Pro, Asn, His, or Asp;
Xaa at position 50 is Glu, Leu, Thr, Asp, or Tyr;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or;
Xaa at position 54 is Arg, Asp, Ile, Ser, Val, Thr, Gln, or Leu;
Xaa at position 55 is Arg, Thr, Val, Ser, Leu, or Gly;
Xaa at position 56 is Pro, Gly, Cys, Ser, Gln, or Lys;
Xaa at position 57 is Asn or Gly;
Xaa at position 58 is Leu, Ser, Asp, Arg, Gln, Val, or Cys;
Xaa at position 59 is Glu Tyr, His, Leu, Pro, or Arg;
Xaa at position 60 is Ala, Ser, Tyr, Asn, or Thr;
Xaa at position 61 is Phe, Asn, Glu, Pro, Lys, Arg, or Ser;
Xaa at position 62 is Asn His, Val, Arg, Pro, Thr, or Ile;
Xaa at position 63 is Arg, Tyr, Trp, Ser, Pro, or Val;
Xaa at position 64 is Ala, Asn, Ser, or Lys;
Xaa at position 65 is Val, Thr, Pro, His, Leu, Phe, or Ser;
Xaa at position 66 is Lys, Ile, Val, Asn, Glu, or Ser;
Xaa at position 67 is Ser, Ala, Phe, Val, Gly, Asn, Ile, Pro, or His;
Xaa at position 68 is Leu, Val, Trp, Ser, Thr, or His;
Xaa at position 69 is Gln, Ala, Pro, Thr, Arg, Trp, Gly, or Leu;
Xaa at position 70 is Asn, Leu, Val, Trp, Pro, or Ala;
Xaa at position 71 is Ala, Met, Leu, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Thr, Pro, Arg, Gly, Ala;
Xaa at position 75 is Glu, Lys, Gly, Asp, Pro, Trp, Arg, Ser, or Leu;
Xaa at position 76 is Ser, Val, Ala, Asn, Trp, Glu, Pro, Gly, or Asp;
Xaa at position 77 is Ile, Ser, Arg, or Thr;
Xaa at position 78 is Leu, Ala, Ser, Glu, Gly, or Arg;
Xaa at position 79 is Lys, Thr, Gly, Asn, Met, Ile, or Asp;
Xaa at position 80 is Asn, Trp, Val, Gly, Thr, Leu, or Arg;
Xaa at position 81 is Leu, Gln, Gly, Ala, Trp, Arg, or Lys;
Xaa at position 82 is Leu, Gln, Lys, Trp, Arg, or Asp;
Xaa at position 83 is Pro, Thr, Trp, Arg, or Met;
Xaa at position 84 is Cys, Glu, Gly, Arg, Met, or Val;
Xaa at position 85 is Leu, Asn, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, or Asn;
Xaa at position 90 is Ala, Ser, Asp, Ile, or Met;
Xaa at position 91 is Ala, Ser, Thr, Phe, Leu, Asp, or His;
Xaa at position 92 is Pro, Phe, Arg, Ser, Lys, His, or Leu;
Xaa at position 93 is Thr, Asp, Ser, Asn, Pro, Ala, Leu, or Arg;
Xaa at position 94 is Arg, Ile, Ser, Glu, Leu, Val, or Pro;
Xaa at position 95 is His, Gln, Pro, Val, Leu, Thr or Tyr;
Xaa at position 96 is Pro, Lys, Tyr, Gly, Ile, or Thr;
Xaa at position 97 is Ile, Lys, Ala, or Asn;
Xaa at position 98 is His, Ile, Asn, Leu, Asp, Ala, Thr, or Pro;
Xaa at position 99 is Ile, Arg, Asp, Pro, Gln, Gly, Phe, or His;
Xaa at position 100 is Lys, Tyr, Leu, His, Ile, Ser, Gln, or Pro;

Xaa at position 101 is Asp, Pro, Met, Lys, His, Thr, Val, Tyr, or Gln;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, or His;
Xaa at position 106 is Glu, Ser, Ala, Lys, Thr, Ile, Gly, or Pro;
Xaa at position 108 is Arg, Asp, Leu, Thr, Ile, or Pro;
Xaa at position 109 is Arg, Thr, Pro, Glu, Tyr, Leu, Ser, or Gly.

9. A composition of 8, wherein said human interleukin-3 mutant polypeptide is of the Formula:

[SEQ ID NO:7]
```
                1                    5                   10
(Met)_m-Ala Pro Met Thr Gln Thr Thr Ser Leu Lys Thr
               15                   20
Ser Trp Val Asn Cys Ser Xaa Xaa Xaa Asp Glu Ile Ile
25                   30                   35
Xaa His Leu Lys Xaa Pro Pro Xaa Pro Xaa Leu Asp Xaa
               40                   45                   50
Xaa Asn Leu Asn Xaa Glu Asp Xaa Asp Ile Leu Xaa Glu
               55                   60
Xaa Asn Leu Arg Xaa Xaa Asn Leu Xaa Xaa Phe Xaa Xaa
    65                   70                   75
Ala Xaa Lys Xaa Leu Xaa Asn Ala Ser Xaa Ile Glu Xaa
               80                   85
Ile Leu Xaa Asn Leu Xaa Pro Cys Xaa Pro Xaa Xaa Thr
90                   95                  100
Ala Xaa Pro Xaa Arg Xaa Pro Ile Xaa Ile Xaa Xaa Gly
              105                  110                 115
Asp Trp Xaa Glu Phe Arg Xaa Lys Leu Xaa Phe Tyr Leu
                   120                  125
Xaa Xaa Leu Glu Xaa Ala Gln Xaa Gln Gln Thr Thr Leu
    130
Ser Leu Ala Ile Phe
``` wherein m is 0 or 1; Xaa at position 18 is Asn or Ile; Xaa at position 19 is Met, Ala or Ile; Xaa at position 20 is Ile, Pro or Ile; Xaa at position 23 is Ile, Ala or Leu; Xaa at position 25 is Thr or His; Xaa at position 29 is Gln, Arg, Val or Ile; Xaa at position 32 is Leu, Ala, Asn or Arg; Xaa at position 34 is Leu or Ser; Xaa at position 37 is Phe, Pro, or Ser; Xaa at position 38 is Asn or Ala; Xaa at position 42 is Gly, Ala, Ser, Asp or Asn; Xaa at position 45 is Gln, Val, or Met; Xaa at position 46 is Asp or Ser; Xaa at position 49 is Met, Ile, Leu or Asp; Xaa at position 50 is Glu or Asp; Xaa at position 51 is Asn Arg or Ser; Xaa at position 55 is Arg, Leu, or Thr; Xaa at position 56 is Pro or Ser; Xaa at position 59 is Glu or Leu; Xaa at position 60 is Ala or Ser; Xaa at position 62 is Asn, Val or Pro; Xaa at position 63 is Arg or His; Xaa at position 65 is Val or Ser; Xaa at position 67 is Ser, Asn, His or Gln; Xaa at position 69 is Gln or Glu; Xaa at position 73 is Ala or Gly; Xaa at position 76 is Ser, Ala or Pro; Xaa at position 79 is Lys, Arg or Ser; Xaa at position 82 is Leu, Glu, Val or Trp; Xaa at position 85 is Leu or Val; Xaa at position 87 is Leu, Ser, Tyr; Xaa at position 88 is Ala or Trp; Xaa at position 91 is Ala or Pro; Xaa at position 93 is Pro or Ser; Xaa at position 95 is His or Thr; Xaa at position 98 is His, Ile, or Thr; Xaa at position 100 is Lys or Arg; Xaa at position 101 is Asp, Ala or Met; Xaa at position 105 is Asn or Glu; Xaa at position 109 is Arg, Glu or Leu; Xaa at position 112 is Thr or Gln; Xaa at position 116 is Lys, Val, Trp or Ser; Xaa at position 117 is Thr or Ser; Xaa at position 120 is Asn, Gln, or His; Xaa at position 123 is Ala or Glu; with the proviso that from four to forty-four of the amino acids designated by Xaa are different from the corresponding amino acids of native human interleukin-3.

10. The composition of 9, wherein said human interleukin-3 mutant polypeptide is of the Formula:

[SEQ ID NO:8]
```
                    1                    5                   10
(Met_m-Ala_n)_p-Asn Cys Ser Xaa Xaa Xaa Asp Glu Xaa Ile
                   15                   20
Xaa His Leu Lys Xaa Pro Pro Xaa Pro Xaa Leu Asp Xaa
    25                   30                   35
Xaa Asn Leu Asn Xaa Glu Asp Xaa Xaa Ile Leu Xaa Glu
               40                   45
Xaa Asn Leu Arg Xaa Xaa Asn Leu Xaa Xaa Phe Xaa Xaa
50                   50                   60
Ala Xaa Lys Xaa Leu Xaa Asn Ala Ser Xaa Ile Glu Xaa
         65                   70                   75
Ile Leu Xaa Asn Xaa Xaa Pro Xys Xaa Pro Xaa Ala Thr
                    80                   85
Ala Xaa Pro Xaa Arg Xaa Pro Ile Xaa Ile Xaa Xaa Gly
         90                   95                  100
Asp Trp Xaa Glu Phe Arg Xaa Lys Leu Xaa Phe Tyr Leu
              105                  110
Xaa Xaa Leu Glu Xaa Ala Gln Xaa Gln Gln
``` wherein m is 0 or 1; n is 0 or 1; p is 0 or 1; Xaa at position 4 is Asn or Ile; xaa at position 5 is Met, Ala or Ile: Xaa at position 6 is Ile, Pro or Leu; xaa at position 9 is Ile, Ala or Leu; Xaa at position 11 is Thr or His; Xaa at position 15 is Gln, Arg, Val or Ile; Xaa at position 18 is Leu, Ala, Asn or Arg; Xaa at position 20 is Leu or Ser; Xaa at position 23 is Phe, Pro, or Ser; Xaa at position 24 is Asn or Ala; Xaa at position 28 is Gly, Ala, Ser, Asp or Asn; Xaa at position 31 is Gln, Val, or Met; Xaa at position 32 is Asp or Ser; Xaa at position 35 is Met, Ile or Asp; Xaa at position 36 is Glu or Asp; Xaa at position 37 is Asn, Arg or Ser; Xaa at position 41 is Arg, Leu, or Thr; Xaa at position 42 is Pro or Ser; Xaa at position 45 is Glu or Leu; Xaa at position 46 is Ala or Ser; Xaa at position 48 is Asn, Val or Pro; Xaa at position 49 is Arg or His; Xaa at position 51 is Val or Ser; Xaa at position 53 is Ser, Asn, His or Gln; Xaa at position 55 is Gln or Glu; Xaa at position 59 is Ala or Gly; Xaa at position 62 is Ser, Ala or Pro; Xaa at position 65 is Lys, Arg or Ser; Xaa at position 67 is Leu, Glu, or Val; Xaa at position 68 is Leu, Glu, Val or Trp; Xaa at position 71 is Leu or Val; Xaa at position 73 is Leu, Ser or Tyr; Xaa at position 74 is Ala or Trp; Xaa at position 77 is Ala or Pro; Xaa at position 79 is Pro or Ser; Xaa at position 81 is His or Thr; Xaa at position 84 is His, Ile, or Thr; Xaa at position 86 is Lys or Arg; Xaa at position 87 is Asp, Ala or Met; Xaa at position 91 is Asn or Glu; Xaa at position 95 is Arg, Glu, Leu; Xaa at position 98 Thr or Gln; Xaa at position 102 is Lys, Val, Trp or Ser; Xaa at position 103 is Thr or Ser; Xaa at position 106 is Asn, Gln, or His; Xaa at position 109 is Ala or Glu; with the proviso that from four to forty-four of the amino acids designated by Xaa are different from the corresponding amino acids of native (15–125)human interleukin-3.

11. The composition of 10, wherein said human interleukin-3 mutant polypeptide is of the Formula:

Asn Cys Ser Ile Met Ile Asp Glu   [SEQ ID NO:9]
Ile Ile His His Leu Lys Arg Pro Pro
Ala Pro Leu Leu Asp Pro Asn Asn Leu
Asn Ala Glu Asp Val Asp Ile Leu Met
Glu Asn Asn Leu Arg Arg Pro Asn Leu
Glu Ala Phe Asn Arg Ala Val Lys Ser
Leu Gln Asn Ala Ser Ala Ile Glu Ser
Ile Leu Lys Asn Leu Leu Pro Cys Leu
Pro Leu Ala Thr Ala Ala Pro Thr Arg
His Pro Ile His Ile Lys Asp Gly Asp
Trp Asn Glu Phe Arg Arg Lys Leu Thr
Phe Tyr Leu Lys Thr Leu Glu Asn Ala
Gln Ala Gln Gln;

Asn Cys Ser Ile Met Ile Asp Glu   [SEQ ID NO:10]
Ile Ile His His Leu Lys Arg Pro Pro
Asn Pro Leu Leu Asp Pro Asn Asn Leu
Asn Ser Glu Asp Met Asp Ile Leu Met
Glu Asn Asn Leu Arg Arg Pro Asn Leu
Glu Ala Phe Asn Arg Ala Val Lys Ser
Leu Gln Asn Ala Ser Ala Ile Glu Ser
Ile Leu Lys Asn Leu Leu Pro Cys Leu
Pro Leu Ala Thr Ala Ala Pro Thr Arg
His Pro Ile His Ile Lys Asp Gly Asp
Trp Asn Glu Phe Arg Arg Lys Leu Thr
Phe Tyr Leu Lys Thr Leu Glu Asn Ala
Gln Ala Gln Gln;

Asn Cys Ser Ile Met Ile Asp Glu   [SEQ ID NO:11]
Ile Ile His His Leu Lys Val Pro Pro
Ala Pro Leu Leu Asp Ser Asn Asn Leu
Asn Ser Glu Asp Met Asp Ile Leu Met
Glu Asn Asn Leu Arg Arg Pro Asn Leu
Glu Ala Phe Asn Arg Ala Val Lys Ser
Leu Gln Asn Ala Ser Ala Ile Glu Ser
Ile Leu Lys Asn Leu Leu Pro Cys Leu
Pro Leu Ala Thr Ala Ala Pro Thr Arg
His Pro Ile His Ile Lys Asp Gly Asp
Trp Asn Glu Phe Arg Arg Lys Leu Thr
Phe Tyr Leu Lys Thr Leu Glu Asn Ala
Gln Ala Gln Gln;

Asn Cys Ser Asn Met Ile Asp Glu   [SEQ ID NO:12]
Ile Ile Thr His Leu Lys Gln Pro Pro
Leu Pro Leu Leu Asp Phe Asn Asn Leu
Asn Gly Glu Asp Gln Asp Ile Leu Met
Glu Arg Asn Leu Arg Leu Pro Asn Leu
Leu Ala Phe Val Arg Ala Val Lys Asn
Leu Glu Asn Ala Ser Ala Ile Glu Ser
Ile Leu Lys Asn Leu Leu Pro Cys Leu
Pro Leu Ala Thr Ala Ala Pro Thr Arg
His Pro Ile His Ile Lys Asp Gly Asp
Trp Asn Glu Phe Arg Arg Lys Leu Thr
Phe Tyr Leu Lys Thr Leu Glu Asn Ala
Gln Ala Gln Gln;

Asn Cys Ser Asn Met Ile Asp Glu   [SEQ ID NO:13]
Ile Ile Thr His Leu Lys Gln Pro Pro
Leu Pro Leu Leu Asp Phe Asn Asn Leu
Asn Gly Glu Asp Gln Asp Ile Leu Met
Glu Arg Asn Leu Arg Leu Pro Asn Leu
Glu Ser Phe Val Arg Ala Val Lys Asn
Leu Glu Asn Ala Ser Ala Ile Glu Ser
Ile Leu Lys Asn Leu Leu Pro Cys Leu
Pro Leu Ala Thr Ala Ala Pro Thr Arg
His Pro Ile His Ile Lys Asp Gly Asp
Trp Asn Glu Phe Arg Arg Lys Leu Thr
Phe Tyr Leu Lys Thr Leu Glu Asn Ala
Gln Ala Gln Gln;

Asn Cys Ser Asn Met Ile Asp Glu   [SEQ ID NO:14]
Ile Ile Thr His Leu Lys Gln Pro Pro
Leu Pro Leu Leu Asp Phe Asn Asn Leu
Asn Gly Glu Asp Gln Asp Ile Leu Met
Glu Arg Asn Leu Arg Thr Pro Asn Leu
Leu Ala Phe Val Arg Ala Val Lys His
Leu Glu Asn Ala Ser Ala Ile Glu Ser
Ile Leu Lys Asn Leu Leu Pro Cys Leu
Pro Leu Ala Thr Ala Ala Pro Thr Arg
His Pro Ile His Ile Lys Asp Gly Asp
Trp Asn Glu Phe Arg Arg Lys Leu Thr
Phe Tyr Leu Lys Thr Leu Glu Asn Ala

```
Gln Ala Gln Gln;

Asn Cys Ser Asn Met Ile Asp Glu  [SEQ ID NO:15]

Ile Ile Thr His Leu Lys Gln Pro Pro

Leu Pro Leu Leu Asp Phe Asn Asn Leu

Asn Gly Glu Asp Gln Asp Ile Leu Met

Glu Asn Asn Leu Arg Arg Pro Asn Leu

Glu Ala Phe Asn Arg Ala Val Lys Ser

Leu Gln Asn Ala Ser Gly Ile Glu Ala

Ile Leu Arg Asn Leu Gln Pro Cys Leu

Pro Ser Ala Thr Ala Ala Pro Ser Arg

His Pro Ile Ile Ile Lys Ala Gly Asp

Trp Gln Glu Phe Arg Arg Lys Leu Thr

Phe Tyr Leu Lys Thr Leu Glu Asn Ala

Gln Ala Gln Gln;

Asn Cys Ser Asn Met Ile Asp Glu  [SEQ ID NO:16]

Ile Ile Thr His Leu Lys Gln Pro Pro

Leu Pro Leu Leu Asp Phe Asn Asn Leu

Asn Gly Glu Asp Gln Asp Ile Leu Met

Glu Asn Asn Leu Arg Arg Pro Asn Leu

Glu Ala Phe Asn Arg Ala Val Lys Ser

Leu Gln Asn Ala Ser Gly Ile Glu Ala

Ile Leu Arg Asn Leu Val Pro Cys Leu

Pro Ser Ala Thr Ala Ala Pro Ser Arg

His Pro Ile Thr Ile Lys Ala Gly Asp

Trp Gln Glu Phe Arg Arg Lys Leu Thr

Phe Tyr Leu Lys Thr Leu Glu Asn Ala

Gln Ala Gln Gln;

Asn Cys Ser Asn Met Ile Asp Glu  [SEQ ID NO:17]

Ile Ile Thr His Leu Lys Gln Pro Pro

Leu Pro Leu Leu Asp Phe Asn Asn Leu

Asn Gly Glu Asp Gln Asp Ile Leu Met

Glu Asn Asn Leu Arg Arg Pro Asn Leu

Glu Ala Phe Asn Arg Ala Val Lys Ser

Leu Gln Asn Ala Ser Ala Ile Glu Ser

Ile Leu Lys Asn Leu Leu Pro Cys Leu

Pro Leu Ala Thr Ala Ala Pro Thr Arg

His Pro Ile His Ile Lys Asp Gly Asp

Trp Asn Glu Phe Arg Glu Lys Leu Thr

Phe Tyr Leu Val Thr Leu Glu Gln Ala

Gln Glu Gln Gln;

Asn Cys Ser Asn Met Ile Asp Glu  [SEQ ID NO:18]

Ile Ile Thr His Leu Lys Gln Pro Pro

Leu Pro Leu Leu Asp Phe Asn Asn Leu

Asn Gly Glu Asp Gln Asp Ile Leu Met

Glu Asn Asn Leu Arg Arg Pro Asn Leu

Glu Ala Phe Asn Arg Ala Val Lys Ser

Leu Gln Asn Ala Ser Ala Ile Glu Ser

Ile Leu Lys Asn Leu Leu Pro Cys Leu

Pro Leu Ala Thr Ala Ala Pro Thr Arg

His Pro Ile His Ile Lys Asp Gly Asp

Trp Asn Glu Phe Arg Glu Lys Leu Thr

Phe Tyr Leu Val Ser Leu Glu His Ala

Gln Glu Gln Gln;

Asn Cys Ser Asn Met Ile Asp Glu  [SEQ ID NO:19]

Ile Ile Thr His Leu Lys Gln Pro Pro

Leu Pro Leu Leu Asp Phe Asn Asn Leu

Asn Gly Glu Asp Gln Asp Ile Leu Met

Glu Asn Asn Leu Arg Arg Pro Asn Leu

Glu Ala Phe Asn Arg Ala Val Lys Ser

Leu Gln Asn Ala Ser Gly Ile Glu Ala

Ile Leu Arg Asn Leu Gln Pro Cys Leu

Pro Ser Ala Thr Ala Ala Pro Ser Arg

His Pro Ile Ile Ile Lys Ala Gly Asp

Trp Gln Glu Phe Arg Glu Lys Leu Thr

Phe Tyr Leu Val Thr Leu Glu Gln Ala

Gln Glu Gln Gln;

Asn Cys Ser Asn Met Ile Asp Glu  [SEQ ID NO:20]

Ile Ile Thr His Leu Lys Gln Pro Pro

Leu Pro Leu Leu Asp Phe Asn Asn Leu

Asn Gly Glu Asp Gln Asp Ile Leu Met

Glu Asn Asn Leu Arg Arg Pro Asn Leu

Glu Ala Phe Asn Arg Ala Val Lys Ser

Leu Gln Asn Ala Ser Gly Ile Glu Ala

Ile Leu Arg Asn Leu Val Pro Cys Leu

Pro Ser Ala Thr Ala Ala Pro Ser Arg

His Pro Ile Thr Ile Lys Ala Gly Asp

Trp Gln Glu Phe Arg Glu Lys Leu Thr

Phe Tyr Leu Val Thr Leu Glu Gln Ala

Gln Glu Gln Gln;

Asn Cys Ser Asn Met Ile Asp Glu  [SEQ ID NO:21]
```

-continued

Ile Ile Thr His Leu Lys Gln Pro Pro
Leu Pro Leu Leu Asp Phe Asn Asn Leu
Asn Gly Glu Asp Gln Asp Ile Leu Met
Glu Asn Asn Leu Arg Arg Pro Asn Leu
Glu Ala Phe Asn Arg Ala Val Lys Ser
Leu Gln Asn Ala Ser Gly Ile Glu Ala
Ile Leu Arg Asn Leu Val Pro Cys Leu
Pro Ser Ala Thr Ala Ala Pro Ser Arg
His Pro Ile Thr Ile Lys Ala Gly Asp
Trp Gln Glu Phe Arg Glu Lys Leu Thr
Phe Tyr Leu Val Ser Leu Glu His Ala
Gln Glu Gln Gln;

Asn Cys Ser Ile Met Ile Asp Glu [SEQ ID NO:22]
Ile Ile His His Leu Lys Arg Pro Pro
Ala Pro Leu Leu Asp Pro Asn Asn Leu
Asn Ala Glu Asp Val Asp Ile Leu Met
Glu Arg Asn Leu Arg Leu Pro Asn Leu
Glu Ser Phe Val Arg Ala Val Lys Asn
Leu Glu Asn Ala Ser Ala Ile Glu Ser
Ile Leu Lys Asn Leu Leu Pro Cys Leu
Pro Leu Ala Thr Ala Ala Pro Thr Arg
His Pro Ile His Ile Lys Asp Gly Asp
Trp Asn Glu Phe Arg Arg Lys Leu Thr
Phe Tyr Leu Lys Thr Leu Glu Asn Ala
Gln Ala Gln Gln;

Asn Cys Ser Ile Met Ile Asp Glu [SEQ ID NO:23]
Ile Ile His His Leu Lys Arg Pro Pro
Asn Pro Leu Leu Asp Pro Asn Asn Leu
Asn Ser Glu Asp Met Asp Ile Leu Met
Glu Arg Asn Leu Arg Thr Pro Asn Leu
Leu Ala Phe Val Arg Ala Val Lys His
Leu Glu Asn Ala Ser Ala Ile Glu Ser
Ile Leu Lys Asn Leu Leu Pro Cys Leu
Pro Leu Ala Thr Ala Ala Pro Thr Arg
His Pro Ile His Ile Lys Asp Gly Asp
Trp Asn Glu Phe Arg Arg Lys Leu Thr
Phe Tyr Leu Lys Thr Leu Glu Asn Ala
Gln Ala Gln Gln;

Asn Cys Ser Ile Met Ile Asp Glu [SEQ ID NO:24]
Ile Ile His His Leu Lys Val Pro Pro

-continued

Ala Pro Leu Leu Asp Ser Asn Asn Leu
Asn Ser Glu Asp Met Asp Ile Leu Met
Glu Arg Asn Leu Arg Leu Pro Asn Leu
Leu Ala Phe Val Arg Ala Val Lys Asn
Leu Glu Asn Ala Ser Ala Ile Glu Ser
Ile Leu Lys Asn Leu Leu Pro Cys Leu
Pro Leu Ala Thr Ala Ala Pro Thr Arg
His Pro Ile His Ile Lys Asp Gly Asp
Trp Asn Glu Phe Arg Arg Lys Leu Thr
Phe Tyr Leu Lys Thr Leu Glu Asn Ala
Gln Ala Gln Gln;

Met Ala Asn Cys Ser Asn Met Ile Asp [SEQ ID NO:25]
Glu Ile Ile Thr His Leu Lys Gln Pro
Pro Leu Pro Leu Leu Asp Phe Asn Asn
Leu Asn Gly Glu Asp Gln Asp Ile Leu
Met Glu Asn Asn Leu Arg Arg Pro Asn
Leu Glu Ala Phe Asn Arg Ala Val Lys
Ser Leu Gln Asn Ala Ser Gly Ile Glu
Ala Ile Leu Arg Asn Leu Gln Pro Cys
Leu Pro Ser Ala Thr Ala Ala Pro Ser
Arg His Pro Ile Ile Ile Lys Ala Gly
Asp Trp Gln Glu Phe Arg Glu Lys Leu
Thr Phe Tyr Leu Val Thr Leu Glu Gln
Ala Gln Glu Gln Gln;

Met Ala Asn Cys Ser Asn Met Ile Asp [SEQ ID NO:26]
Glu Ile Ile Thr His Leu Lys Gln Pro
Pro Leu Pro Leu Leu Asp Phe Asn Asn
Leu Asn Gly Glu Asp Gln Asp Ile Leu
Met Glu Asn Asn Leu Arg Arg Pro Asn
Leu Glu Ala Phe Asn Arg Ala Val Lys
Ser Leu Gln Asn Ala Ser Gly Ile Glu
Ala Ile Leu Arg Asn Leu Val Pro Cys
Leu Pro Ser Ala Thr Ala Ala Pro Ser
Arg His Pro Ile Thr Ile Lys Ala Gly
Asp Trp Gln Glu Phe Arg Glu Lys Leu
Thr Phe Tyr Leu Val Thr Leu Glu Gln
Ala Gln Glu Gln Gln;

Met Ala Asn Cys Ser Asn Met Ile Asp [SEQ ID NO:27]
Glu Ile Ile Thr His Leu Lys Gln Pro
Pro Leu Pro Leu Leu Asp Phe Asn Asn

-continued

Leu Asn Gly Glu Asp Gln Asp Ile Leu

Met Glu Asn Asn Leu Arg Arg Pro Asn

Leu Glu Ala Phe Asn Arg Ala Val Lys

Ser Leu Gln Asn Ala Ser Gly Ile Glu

Ala Ile Leu Arg Asn Leu Val Pro Cys

Leu Pro Ser Ala Thr Ala Ala Pro Ser

Arg His Pro Ile Thr Ile Lys Ala Gly

Asp Trp Gln Glu Phe Arg Glu Lys Leu

Thr Phe Tyr Leu Val Ser Leu Glu His

Ala Gln Glu Gln Gln;

Met Ala Asn Cys Ser Ile Met Ile Asp [SEQ ID NO:28]

Glu Ile Ile His His Leu Lys Arg Pro

Pro Ala Pro Leu Leu Asp Pro Asn Asn

Leu Asn Ala Glu Asp Val Asp Ile Leu

Met Glu Arg Asn Leu Arg Leu Pro Asn

Leu Glu Ser Phe Val Arg Ala Val Lys

Asn Leu Gln Asn Ala Ser Ala Ile Glu

Ser Ile Leu Lys Asn Leu Leu Pro Cys

Leu Pro Leu Ala Thr Ala Ala Pro Thr

Arg His Pro Ile His Ile Lys Asp Gly

Asp Trp Asn Glu Phe Arg Arg Lys Leu

Thr Phe Tyr Leu Lys Thr Leu Glu Asn

Ala Gln Ala Gln Gln;

Met Ala Asn Cys Ser Ile Met Ile Asp [SEQ ID NO:29]

Glu Ile Ile His His Leu Lys Arg Pro

Pro Asn Pro Leu Leu Asp Pro Asn Asn

Leu Asn Ser Glu Asp Met Asp Ile Leu

Met Glu Arg Asn Leu Arg Thr Pro Asn

Leu Leu Ala Phe Val Arg Ala Val Lys

His Leu Glu Asn Ala Ser Ala Ile Glu

Ser Ile Leu Lys Asn Leu Leu Pro Cys

Leu Pro Leu Ala Thr Ala Ala Pro Thr

Arg His Pro Ile His Ile Lys Asp Gly

Asp Trp Asn Glu Phe Arg Arg Lys Leu

Thr Phe Tyr Leu Lys Thr Leu Glu Asn

Ala Gln Ala Gln Gln;

Met Ala Asn Cys Ser Ile Met Ile Asp [SEQ ID NO:30]

Glu Ile Ile His His Leu Lys Val Pro

Pro Ala Pro Leu Leu Asp Ser Asn Asn

Leu Asn Ser Glu Asp Met Asp Ile Leu

Met Glu Arg Asn Leu Arg Leu Pro Asn

Leu Leu Ala Phe Val Arg Ala Val Lys

Asn Leu Glu Asn Ala Ser Ala Ile Glu

Ser Ile Leu Lys Asn Leu Leu Pro Cys

Leu Pro Leu Ala Thr Ala Ala Pro Thr

Arg His Pro Ile His Ile Lys Asp Gly

Asp Trp Asn Glu Phe Arg Arg Lys Leu

Thr Phe Tyr Leu Lys Thr Leu Glu Asn

Ala Gln Ala Gln Gln;

Met Ala Asn Cys Ser Ile Met Ile Asp [SEQ ID NO:31]

Glu Ile Ile His His Leu Lys Arg Pro

Pro Ala Pro Leu Leu Asp Pro Asn Asn

Leu Asn Ala Glu Asp Val Asp Ile Leu

Met Glu Arg Asn Leu Arg Leu Pro Asn

Leu Glu Ser Phe Val Arg Ala Val Lys

Asn Leu Glu Asn Ala Ser Gly Ile Glu

Ala Ile Leu Arg Asn Leu Gln Pro Cys

Leu Pro Ser Ala Thr Ala Ala Pro Ser

Arg His Pro Ile Ile Ile Lys Ala Gly

Asp Trp Gln Glu Phe Arg Glu Lys Leu

Thr Phe Tyr Leu Val Thr Leu Glu Gln

Ala Gln Glu Gln Gln;

Met Ala Asn Cys Ser Ile Met Ile Asp [SEQ ID NO:32]

Glu Ile Ile His His Leu Lys Arg Pro

Pro Asn Pro Leu Leu Asp Pro Asn Asn

Leu Asn Ser Glu Asp Met Asp Ile Leu

Met Glu Arg Asn Leu Arg Thr Pro Asn

Leu Leu Ala Phe Val Arg Ala Val Lys

His Leu Glu Asn Ala Ser Gly Ile Glu

Ala Ile Leu Arg Asn Leu Gln Pro Cys

Leu Pro Ser Ala Thr Ala Ala Pro Ser

Arg His Pro Ile Ile Ile Lys Ala Gly

Asp Trp Gln Glu Phe Arg Glu Lys Leu

Thr Phe Tyr Leu Val Thr Leu Glu Gln

Ala Gln Glu Gln Gln;

Met Ala Asn Cys Ser Ile Met Ile Asp [SEQ ID NO:33]

Glu Ile Ile His His Leu Lys Val Pro

Pro Ala Pro Leu Leu Asp Ser Asn Asn

Leu Asn Ser Glu Asp Met Asp Ile Leu

Met Glu Arg Asn Leu Arg Leu Pro Asn

Leu Leu Ala Phe Val Arg Ala Val Lys

Asn Leu Glu Asn Ala Ser Gly Ile Glu

Ala Ile Leu Arg Asn Leu Gln Pro Cys

Leu Pro Ser Ala Thr Ala Ala Pro Ser

Arg His Pro Ile Ile Ile Lys Ala Gly

Asp Trp Gln Glu Phe Arg Glu Lys Leu

Thr Phe Tyr Leu Val Thr Leu Glu Gln

Ala Gln Glu Gln Gln;

Met Ala Asn Cys Ser Ile Met Ile Asp [SEQ ID NO:34]

Glu Ile Ile His His Leu Lys Arg Pro

Pro Ala Pro Leu Leu Asp Pro Asn Asn

Leu Asn Ala Glu Asp Val Asp Ile Leu

Met Glu Arg Asn Leu Arg Leu Pro Asn

Leu Glu Ser Phe Val Arg Ala Val Lys

Asn Leu Gln Asn Ala Ser Gly Ile Glu

Ala Ile Leu Arg Asn Leu Val Pro Cys

Leu Pro Ser Ala Thr Ala Ala Pro Ser

Arg His Pro Ile His Ile Lys Ala Gly

Asp Trp Gln Glu Phe Arg Glu Lys Leu

Thr Phe Tyr Leu Val Thr Leu Glu Gln

Ala Gln Glu Gln Gln;

Met Ala Asn Cys Ser Ile Met Ile Asp [SEQ ID NO:35]

Glu Ile Ile His His Leu Lys Val Pro

Pro Ala Pro Leu Leu Asp Ser Asn Asn

Leu Asn Ser Glu Asp Met Asp Ile Leu

Met Glu Arg Asn Leu Arg Leu Pro Asn

Leu Leu Ala Phe Val Arg Ala Val Lys

Asn Leu Glu Asn Ala Ser Gly Ile Glu

Ala Ile Leu Arg Asn Leu Val Pro Cys

Leu Pro Ser Ala Thr Ala Ala Pro Ser

Arg His Pro Ile Thr Ile Lys Ala Gly

Asp Trp Gln Glu Phe Arg Glu Lys Leu

Thr Phe Tyr Leu Val Thr Leu Glu Gln

Ala Gln Glu Gln Gln;

Met Ala Asn Cys Ser Ile Met Ile Asp [SEQ ID NO:36]

Glu Ile Ile His His Leu Lys Arg Pro

Pro Asn Pro Leu Leu Asp Pro Asn Asn

Leu Asn Ser Glu Asp Met Asp Ile Leu

Met Glu Arg Asn Leu Arg Thr Pro Asn

Leu Leu Ala Phe Val Arg Ala Val Lys

His Leu Glu Asn Ala Ser Gly Ile Glu

Ala Ile Leu Lys Asn Leu Val Pro Cys

Leu Pro Ser Ala Thr Ala Ala Pro Ser

Arg His Pro Ile Thr Ile Lys Ala Gly

Asp Trp Gln Glu Phe Arg Glu Lys Leu

Thr Phe Tyr Leu Val Ser Leu Glu His

Ala Gln Glu Gln Gln;

Met Ala Asn Cys Ser Ile Met Ile Asp [SEQ ID NO:37]

Glu Ile Ile His His Leu Lys Val Pro

Pro Ala Pro Leu Leu Asp Ser Asn Asn

Leu Asn Ser Glu Asp Met Asp Ile Leu

Met Glu Arg Asn Leu Arg Leu Pro Asn

Leu Leu Ala Phe Val Arg Ala Val Lys

Asn Leu Gln Asn Ala Ser Gly Ile Glu

Ala Ile Leu Arg Asn Leu Val Pro Cys

Leu Pro Ser Ala Thr Ala Ala Pro Ser

Arg His Pro Ile Thr Ile Lys Ala Gly

Asp Trp Gln Glu Phe Arg Glu Lys Leu

Thr Phe Tyr Leu Val Ser Leu Glu His

Ala Gln Glu Gln Gln;

Met Ala Asn Cys Ser Ile Met Ile Asp [SEQ ID NO:38]

Glu Ile Ile His His Leu Lys Arg Pro

Pro Asn Pro Leu Leu Asp Pro Asn Asn

Leu Asn Ser Glu Asp Met Asp Ile Leu

Met Glu Arg Asn Leu Arg Thr Pro Asn

Leu Leu Ala Phe Val Arg Ala Val Lys

His Leu Glu Asn Ala Ser Gly Ile Glu

Ala Ile Leu Arg Asn Leu Val Pro Cys

Leu Pro Ser Ala Thr Ala Ala Pro Ser

Arg His Pro Ile Thr Ile Lys Ala Gly

Asp Trp Gln Glu Phe Arg Glu Lys Leu

Thr Phe Tyr Leu Val Thr Leu Glu Gln

Ala Gln Glu Gln Gln;

Met Ala Asn Cys Ser Ile Met Ile Asp [SEQ ID NO:39]

Glu Ile Ile His His Leu Lys Arg Pro

Pro Ala Pro Leu Leu Asp Pro Asn Asn

Leu Asn Ala Glu Asp Val Asp Ile Leu

Met Glu Arg Asn Leu Arg Leu Pro Asn

Leu Glu Ser Phe Val Arg Ala Val Lys

Asn Leu Glu Asn Ala Ser Gly Ile Glu

Ala Ile Leu Arg Asn Leu Val Pro Cys
Leu Pro Ser Ala Thr Ala Ala Pro Ser
Arg His Pro Ile Thr Ile Lys Ala Gly
Asp Trp Gln Glu Phe Arg Glu Lys Leu
Thr Phe Tyr Leu Val Ser Leu Glu His
Ala Gln Glu Gln Gln.
Met Ala Asn Cys Ser Ile Met Ile Asp [SEQ ID NO:40]
Glu Ile Ile His His Leu Lys Arg Pro
Pro Ala Pro Leu Leu Asp Pro Asn Asn
Leu Asn Ala Glu Asp Val Asp Ile Leu
Met Asp Arg Asn Leu Arg Leu Ser Asn
Leu Glu Ser Phe Val Arg Ala Val Lys
Asn Leu Glu Asn Ala Ser Gly Ile Glu
Ala Ile Leu Arg Asn Leu Gln Pro Cys
Leu Pro Ser Ala Thr Ala Ala Pro Ser
Arg His Pro Ile Ile Ile Lys Ala Gly
Asp Trp Gln Glu Phe Arg Glu Lys Leu
Thr Phe Tyr Leu Val Thr Leu Glu Gln
Ala Gln Glu Gln Gln
Met Ala Asn Cys Ser Ile Met Ile Asp [SEQ ID NO:41]
Glu Ala Ile His His Leu Lys Arg Pro
Pro Ala Pro Ser Leu Asp Pro Asn Asn
Leu Asn Asp Glu Asp Met Ser Ile Leu
Met Glu Arg Asn Leu Arg Leu Pro Asn
Leu Glu Ser Phe Val Arg Ala Val Lys
Asn Leu Glu Asn Ala Ser Gly Ile Glu
Ala Ile Leu Arg Asn Leu Gln Pro Cys
Leu Pro Ser Ala Thr Ala Ala Pro Ser
Arg His Pro Ile Ile Ile Lys Ala Gly
Asp Trp Gln Glu Phe Arg Glu Lys Leu
Thr Phe Tyr Leu Val Thr Leu Glu Gln
Ala Gln Glu Gln Gln
Met Ala Asn Cys Ser Ile Met Ile Asp [SEQ ID NO:42]
Glu Ile Ile His His Leu Lys Arg Pro
Pro Ala Pro Leu Leu Asp Pro Asn Asn
Leu Asn Asp Glu Asp Met Ser Ile Leu
Met Glu Arg Asn Leu Arg Leu Pro Asn
Leu Glu Ser Phe Val Arg Ala Val Lys
Asn Leu Glu Asn Ala Ser Gly Ile Glu
Ala Ile Leu Arg Asn Leu Gln Pro Cys
Leu Pro Ser Ala Thr Ala Ala Pro Ser
Arg His Pro Ile Ile Ile Lys Ala Gly
Asp Trp Gln Glu Phe Arg Glu Lys Leu
Thr Phe Tyr Leu Val Thr Leu Glu Gln
Ala Gln Glu Gln Gln
Met Ala Asn Cys Ser Ile Met Ile Asp [SEQ ID NO:43]
Glu Ile Ile His His Leu Lys Arg Pro
Pro Ala Pro Leu Leu Asp Pro Asn Asn
Leu Asn Ala Glu Asp Val Asp Ile Leu
Met Asp Arg Asn Leu Arg Leu Pro Asn
Leu Glu Ser Phe Val Arg Ala Val Lys
Asn Leu Glu Asn Ala Ser Gly Ile Glu
Ala Ile Leu Arg Asn Leu Gln Pro Cys
Leu Pro Ser Ala Thr Ala Ala Pro Ser
Arg His Pro Ile Ile Ile Lys Ala Gly
Asp Trp Gln Glu Phe Arg Glu Lys Leu
Thr Phe Tyr Leu Val Thr Leu Glu Gln
Ala Gln Glu Gln Gln
Met Ala Asn Cys Ser Ile Met Ile Asp [SEQ ID NO:44]
Glu Ile Ile His His Leu Lys Arg Pro
Pro Ala Pro Leu Leu Asp Pro Asn Asn
Leu Asn Asp Glu Asp Val Ser Ile Leu
Met Glu Arg Asn Leu Arg Leu Pro Asn
Leu Glu Ser Phe Val Arg Ala Val Lys
Asn Leu Glu Asn Ala Ser Gly Ile Glu
Ala Ile Leu Arg Asn Leu Gln Pro Cys
Leu Pro Ser Ala Thr Ala Ala Pro Ser
Arg His Pro Ile Ile Ile Lys Ala Gly
Asp Trp Gln Glu Phe Arg Glu Lys Leu
Thr Phe Tyr Leu Val Thr Leu Glu Gln
Ala Gln Glu Gln Gln
Met Ala Asn Cys Ser Ile Met Ile Asp [SEQ ID NO:45]
Glu Ile Ile His His Leu Lys Arg Pro
Pro Ala Pro Leu Leu Asp Pro Asn Asn
Leu Asn Asp Glu Asp Met Ser Ile Leu
Met Glu Arg Asn Leu Arg Leu Pro Asn
Leu Glu Ser Phe Val Arg Ala Val Lys
Asn Leu Glu Asn Ala Ser Gly Ile Glu
Ala Ile Leu Arg Asn Leu Gln Pro Cys
Leu Pro Ser Ala Thr Ala Ala Pro Ser

```
Arg His Pro Ile Ile Ile Lys Ala Gly

Asp Trp Gln Glu Phe Arg Glu Lys Leu

Thr Phe Tyr Leu Val Thr Leu Glu Gln

Ala Gln Glu Gln Gln

Met Ala Tyr Pro Glu Thr Asp Tyr Lys    [SEQ ID NO:46]

Asp Asp Asp Asp Lys Asn Cys Ser Ile

Met Ile Asp Glu Ile Ile His His Leu

Lys Arg Pro Pro Ala Pro Leu Leu Asp

Pro Asn Asn Leu Asn Ala Glu Asp Val

Asp Ile Leu Met Glu Arg Asn Leu Arg

Leu Pro Asn Leu Glu Ser Phe Val Arg

Ala Val Lys Asn Leu Glu Asn Ala Ser

Gly Ile Glu Ala Ile Leu Arg Asn Leu

Gln Pro Cys Leu Pro Ser Ala Thr Ala

Ala Pro Ser Arg His Pro Ile Ile Ile

Lys Ala Gly Asp Trp Gln Glu Phe Arg

Glu Lys Leu Thr Phe Tyr Leu Val Thr

Leu Glu Gln Ala

Cambridge, England, catalogue number BBG14. This gene is carried on a pUC based plasmid designated pP0518. Many other human CSF genes can be obtained from R&D Systems, Inc. (Minn, Minn.) including IL-1 alpha, IL-1 beta, IL-2, IL-4, IL-5, IL-6, IL-7, IL-8, G-CSF, GM-CSF and LIF.

The plasmids used for production of hIL-3 in *E. coli* contain genetic elements whose use has been described (Olins et al., 1988; Olins and Rangwala, 1990). The replicon used is that of pBR327 (Covarrubias, et al., 1981) which is maintained at a copy number of about 100 in the cell (Soberon et al., 1980). A gene encoding the beta-lactamase protein is present on the plasmids. This protein confers ampicillin resistance on the cell. This resistance serves as a selectable phenotype for the presence of the plasmid in the cell.

For cytoplasmic expression vectors the transcription promoter is derived from the recA gene of *E. coli* (Sancar et al., 1980). This promoter, designated precA, includes the RNA polymerase binding site and the lexA repressor binding site (the operator). This segment of DNA provides high level transcription that is regulated even when the recA promoter is on a plasmid with the pBR327 origin of replication (Olins et al., 1988) incorporated herein by reference.

The ribosome binding site used is that from gene 10 of phage T7 (Olins et al., 1988). This is encoded in a 100 base pair (bp) fragment placed adjacent to precA. In the plasmids used herein, the recognition sequence for the enzyme NcoI (CCATGG) follows the g10-L. It is at this NcoI site that the hIL-3 genes were joined to the plasmid. It is expected that the nucleotide sequence at this junction will be recognized in mRNA as a functional start site for translation (Olins et al., 1988). The hIL-3 genes used were engineered to have a HindIII recognition site (AAGCTT) downstream from the coding sequence of the gene. At this HindIII site is a 514 base pair RsaI fragment containing the origin of replication of the single stranded phage f1 (Dente et al., 1983; Olins, et al., 1990) both incorporated herein by reference. A plasmid containing these elements is pMON2341. Another plasmid containing these elements is pMON5847 which has been deposited at the American Type Culture Collection, 12301 Parklawn Drive, Rockville, Md. 20852 under the accession number ATCC 68912.

In secretion expression plasmids the transcription promoter is derived from the ara B, A, and D genes of *E. coli* (Greenfield et al., 1978). This promoter is designated pAra-BAD and is contained on a 323 base pair SacII, BglII restriction fragment. The LamB secretion leader (Wong et al., 1988, Clement et al., 1981) is fused to the N-terminus of the hIL-3 gene at the recognition sequence for the enzyme NcoI (5'CCATGG3'). The hIL-3 genes used were engineered to have a HindIII recognition site (5'AAGCTT3') following the coding sequence of the gene.

Recombinant DNA Methods

Synthetic Gene Assembly

The hIL-3 variant genes and other CSF genes can be constructed by the assembly of synthetic oligonucleotides. Synthetic oligonucleotides were designed so that they would anneal in complementary pairs, with protruding single stranded ends, and when the pairs were properly assembled would result in a DNA sequence that encoded a portion of the desired gene. Amino acid substitutions in the hIL-3 gene were made by designing the oligonucleotides to encode the desired substitutions. The complementary oligonucleotides were annealed at concentration of 1 picomole per microliter in ligation buffer plus 50 mM NaCl. The samples were heated in a 100 ml beaker of boiling water and permitted to cool slowly to room temperature. One picomole of each of the annealed pairs of oligonucleotides were ligated with approximately 0.2 picomoles of plasmid DNA, digested with the appropriate restriction enzymes, in ligation buffer (25 mM Tris pH 8.0, 10 mM Mgcl$_2$, 10 mm dithiothreitol, 1 mM ATP, 2 mM spermidine) with T4 DNA ligase obtained from New England Biolabs (Beverly, Mass.) in a total volume of 20 μl at room temperature overnight.

Polymerase Chain Reaction

Polymerase Chain Reaction (hereafter referred to as PCR) techniques (Saiki, 1985) used the reagent kit and thermal cycler from Perkin-Elmer Cetus (Norwalk, Conn.). PCR is based on a thermostable DNA polymerase from *Thermus aquaticus*. The PCR technique is a DNA amplification method that mimics the natural DNA replication process in that the number of DNA molecules doubles after each cycle, in a way similar to in vivo replication. The DNA polymerase mediated extension is in a 5' to 3' direction. The term "primer" as used herein refers to an oligonucleotide sequence that provides an end to which the DNA polymerase can add nucleotides that were complementary to a nucleotide sequence. The latter nucleotide sequence is referred to as the "template", to which the primers were annealed. The amplified PCR product is defined as the region comprised between the 5' ends of the extension primers. Since the primers have defined sequences, the product will have discrete ends, corresponding to the primer sequences. The primer extension reaction is carried out using 20 picomoles (pmoles) of each of the oligonucleotides and 1 picogram of template plasmid DNA for 35 cycles (1 cycle is defined as 94 degrees C. for one minute, 50 degrees C. for two minutes and 72 degrees for three minutes.). The reaction mixture was extracted with an equal volume of phenol/chloroform (50% phenol and 50% chloroform, volume to volume) to remove proteins. The aqueous phase, containing the amplified DNA, and solvent phase were separated by centrifugation for 5 minutes in a microcentrifuge (Model 5414 Eppendorf Inc, Fremont Calif.). To precipitate the amplified DNA the aqueous phase was removed and transferred to a fresh tube to which was added 1/10 volume of 3 M NaOAc (pH 5.2) and 2.5 volumes of ethanol (100% stored at minus 20 degrees C.). The solution was mixed and placed on dry ice for 20 minutes. The DNA was pelleted by centrifugation for 10 minutes in a microcentrifuge and the solution was removed from the pellet. The DNA pellet was washed with 70% ethanol, ethanol removed and dried in a speedvac concentrator (Savant, Farmingdale, N.Y.). The pellet was resuspended in 25 microliters of TE (20 mM Tris-HCl pH 7.9, 1 mM EDTA). Alternatively the DNA was precipitated by adding equal volume of 4 M NH$_4$OAc and one volume of isopropanol [Treco et al., (1988)]. The solution was mixed and incubated at room temperature for 10 minutes and centrifuged. These conditions selectively precipitate DNA fragments larger than~20 bases and were used to remove oligonucleotide primers. One quarter of the reaction was digested with restriction enzymes [Higuchi, (1989)] an on completion heated to 70 degrees C. to inactivate the enzymes.

Recovery of Recombinant Plasmids from Ligation Mixes

*E. coli* JM101 cells were made competent to take up DNA. Typically, 20 to 100 ml of cells were grown in LB medium to a density of approximately 150 Klett units and then collected by centrifugation. The cells were resuspended in one half culture volume of 50 mm $CaCl_2$ and held at 4° C. for one hour. The cells were again collected by centrifugation and resuspended in one tenth culture volume of 50 mM $CaCl_2$. DNA was added to a 150 microliter volume of these cells, and the samples were held at 4° C. for 30 minutes. The samples were shifted to 42° C. for one minute, one milliliter of LB was added, and the samples were shaken at 37° C. for one hour. Cells from these samples were spread on plates containing ampicillin to select for transformants. The plates were incubated overnight at 37° C. Single colonies were picked, grown in LB supplemented with ampicillin overnight at 37° C. with shaking. From these cultures DNA was isolated for restriction analysis.

Culture Medium

LB medium (Maniatis et al., 1982) was used for growth of cells for DNA isolation. M9 minimal medium supplemented with 1.0% casamino acids, acid hydrolyzed casein, Difco (Detroit, Mich.) was used for cultures in which recombinant IL-3 variant was produced. The ingredients in the M9 medium were as follows: 3 g/liter $KH_2PO_4$, 6 g/l $Na_2HPO_4$, 0.5 g/l NaCl, 1 g/l $NH_4Cl$, 1.2 mM $MgSO_4$, 0.025 mM $CaCl_2$, 0.2% glucose (0.2% glycerol with the AraBAD promoter), 1% casamino acids, 0.1 ml/l trace minerals (per liter 108 g $FeCl_3 \cdot 6H_2O$, 4.0 g $ZnSO_4 \cdot 7H_2O$, 7.0 $CoCl_2 \cdot 2H_2O$, 7.0 g $Na_2MoO_4 \cdot 2H_2O$, 8.0 g $CuSO_4 \cdot 5H_2O$, 2.0 g $H_3BO_3$, 5.0 g $MnSO_4 \cdot H_2O$, 100 ml concentrated HCl). Bacto agar was used for solid media and ampicillin was added to both liquid and solid LB media at 200 micrograms per milliliter.

Production of IL-3 Variants in *E. coli* with Vectors Employing the recA Promoter

*E. coli* strains harboring the plasmids of interest were grown at 37° C. in M9 plus casamino acids medium with shaking in a Gyrotory water bath Model G76 from New Brunswick Scientific (Edison, N.J.). Growth was monitored with a Klett Summerson meter (green 54 filter), Klett Mfg. Co. (New York, N.Y.). At a Klett value of approximately 150, an aliquot of the culture (usually one milliliter) was removed for protein analysis. To the remaining culture, nalidixic acid (10 mg/ml) in 0.1 N NaOH was added to a final concentration of 50 µg/ml. The cultures were shaken at 37° C. for three to four hours after addition of nalidixic acid. A high degree of aeration was maintained throughout the bacterial growth in order to achieve maximal production of the desired gene product. The cells were examined under a light microscope for the presence of refractile bodies (RBs). One milliliter aliquots of the culture were removed for analysis of protein content.

Extraction, Refolding and Purification of IL-3 Variant Proteins Expressed as Refractile bodies in *E. coli*

Extraction of refractile bodies (RB's):

For each gram of RB's (and typically one gram is obtained from a 300 ml *E. coli* culture), 5 ml of a solution containing 6M guanidine hydrochloride (GnHCl), 50 mM 2-N-cyclohexylaminoethanesulfonic acid (CHES) pH 9.5 and 20 mM dithiothreitol (DTT) was added. The RB's were extracted with a Bio-Homogenizer for 15–30 seconds and gently rocked for 2 hours at 5 degrees centigrade (5° C.) to allow the protein to completely reduce and denature.

Refolding of the IL-3 muteins

The protein solution was transferred to dialysis tubing (1000 molecular weight cut-off) and dialyzed against at least 100 volumes of 4M GnHCl—50 mM CHES pH 8.0. The dialysis was continued overnight at 5° C. while gently stirring. Subsequently dialysis was continued against at least 100 volumes of 2M GnHCl—50 mM CHES pH 8.0 and dialyzed overnight at 5° C. while gently stirring.

Purification of the IL-3 muteins

The protein solution was removed from the dialysis tubing and acidified by the addition of 40% acetonitrile ($CH_3CN$)—0.2% trifluoroacetic acid (TFA) to a final concentration of 20% $CH_3CN$—0.1% TFA. This was centrifuged (16,000×g for 5 minutes) to clarify and the supernatant was loaded onto a Vydac C-18 reversed phase column (10×250 mm) available from Vydac (Hesperia, Calif.) previously equilibrated in 20% $CH_3CN$—0.1% TFA. The column was eluted with a linear gradient (0.2% $CH_3CN$/minute) between 40–50% $CH_3CN$—0.1% TFA at a flow rate of 3 ml/minute while collecting 1.5 ml fractions. The fractions were analyzed by polyacrylamide gel electrophoresis (SDS-PAGE) and the appropriate fractions pooled. The pooled material was dried by lyophilization or in a Speed Vac concentrator. The dry powder was reconstituted with 10 mM ammonium bicarbonate pH 7.5, centrifuged (16,000×g for 5 minutes) to clarify and assayed for protein concentration by the method of Bradford (1976) with bovine serum albumin as the standard. Such protein can be further analyzed by additional techniques such as, SDS-PAGE, electrospray mass spectrometry, reverse phase HPLC, capillary zone electrophoresis, amino acid composition analysis, and ELISA (enzyme-linked immunosorbent assay).

hIL-3 SANDWICH ELISA

The IL-3 variant protein concentrations can be determined using a sandwich ELISA based on an affinity purified polyclonal goat anti-rhIL-3. Microtiter plates (Dynatech Immulon II) were coated with 150 µl goat-anti-rhIL-3 at a concentration of approximately 1 µg/ml in 100 mM NaHCO3, pH 8.2. Plates were incubated overnight at room temperature in a chamber maintaining 100% humidity. Wells were emptied and the remaining reactive sites on the plate were blocked with 200 µl of solution containing 10 mM PBS, 3% BSA and 0.05% Tween 20, pH 7.4 for 1 hour at 37° C. and 100% humidity. Wells were emptied and washed 4× with 150 mm NaCl containing 0.05% Tween 20 (wash buffer). Each well then receives 150 µl of dilution buffer (10 mM PBS containing 0.1% BSA, 0.01% Tween 20, pH 7.4), containing rhIL-3 standard, control, sample or dilution buffer alone. A standard curve was prepared with concentrations ranging from 0.125 ng/ml to 5 ng/ml using a stock solution of rhIL-3 (concentration determined by amino acid composition analysis). Plates were incubated 2.5 hours at 37° C. and 100% humidity. Wells were emptied and each plate was washed 4× with wash buffer. Each well then received 150 µl of an optimal dilution (as determined in a checkerboard assay format) of goat anti-rhIL-3 conjugated to horseradish peroxidase. Plates were incubated 1.5 hours at 37° C. and 100% humidity. Wells were emptied and each plate was washed 4× with wash buffer. Each well then received 150 µl of ABTS substrate solution (Kirkegaard and Perry). Plates were incubated at room temperature until the color of the standard wells containing 5 ng/ml rhIL-3 had developed enough to yield an absorbance between 0.5–1.0 when read at a test wavelength of 410 nm and a reference wavelength of 570 nm on a Dynatech microtiter plate reader. Concentrations of immunoreactive rhIL-3 in unknown samples were calculated from the standard curve using software supplied with the plate reader.

The following examples will illustrate the invention in greater detail although it will be understood that the invention is not limited to these specific examples.

EXAMPLE 1

Isolation of 1-332 and 1-153 amino acid forms of Meg-CSF

A. Reverse transcriptase reaction Meg-CSF (more recently known as c-mpl ligand) sequence based on Genbank accession #L33410). Human fetal liver A+ RNA was obtained from Clontech (Palo Alto, Calif.). The first strand cDNA reactions were carried out using a cDNA Cycle™ Kit obtained from Invitrogen (San Diego, Calif.).

B. Polymerase chain reactions

Following the reverse transcriptase (RT) reaction, the 1-332 c-mpl ligand was amplified via PCR using the oligonucleotide primers c-mplBglII [SEQ ID NO:50] and c-mplEcoRI [SEQ ID NO:51]. Following the RT reaction, the 1-153 c-mpl ligand was amplified using the oligonucleotide primers c-mplNcoI [SEQ ID NO:52] and c-mplHindIII [SEQ ID NO:53].

EXAMPLE 2

BHK expression vector for full length c-mpl ligand

The full length c-mpl ligand PCR product is digested with BglII and EcoRI restriction enzymes for transfer to a mammalian expression vector. The expression vector, pMON3976, is digested with BamHI and EcoRI, which allows it to accept the BglII-EcoRI PCR fragments. pMON3976 is a derivative of pMON3359 which is a pUC18-based vector containing a mammalian expression cassette. The cassette, which includes a herpes simplex viral promoter IE110 (−800 to +120) and a SV40 late polyadenylation (poly-A) signal, was subcloned into the pUC18 polylinker [Hippenmeyer et al., (1993)]. The original EcoRI site 5' to the promoter was removed and a new EcoRI site added 3' to the BamHI site. These unique restriction enzyme sites are located between the promoter and poly-A signal to facilitate subcloning DNA fragments as BamHI-EcoRI or BglII-EcoRI fragments in a 5' to 3' direction for transcription and translation. The resulting plasmid encodes the polypeptide with the following amino acid sequence:

```
Met Glu Leu Thr Glu Leu Leu Leu Val Val Met Leu Leu Leu    [SEQ ID NO:55]
Thr Ala Arg Leu Thr Leu Ser Ser Pro Ala Pro Pro Ala Cys
Asp Leu Arg Val Leu Ser Lys Leu Leu Arg Asp Ser His Val
Leu His Ser Arg Leu Ser Gln Cys Pro Glu Val His Pro Leu
Pro Thr Pro Val Leu Leu Pro Ala Val Asp Phe Ser Leu Gly
Glu Trp Lys Thr Gln Met Glu Glu Thr Lys Ala Gln Asp Ile
Leu Gly Ala Val Thr Leu Leu Leu Glu Gly Val Met Ala Ala
Arg Gly Gln Leu Gly Pro Thr Cys Leu Ser Ser Leu Leu Gly
Gln Leu Ser Gly Gln Val Arg Leu Leu Leu Gly Ala Leu Gln
Ser Leu Leu Gly Thr Gln Leu Pro Pro Gln Gly Arg Thr Thr
Ala His Lys Asp Pro Asn Ala Ile Phe Leu Ser Phe Gln His
Leu Leu Arg Gly Lys Val Arg Phe Leu Met Leu Val Gly Gly
Ser Thr Leu Cys Val Arg Arg Ala Pro Pro Thr Thr Ala Val
Pro Ser Arg Thr Ser Leu Val Leu Thr Leu Asn Glu Leu Pro
Asn Arg Thr Ser Gly Leu Leu Glu Thr Asn Phe Thr Ala Ser
Ala Arg Thr Thr Gly Ser Gly Leu Leu Lys Trp Gln Gln Gly
Phe Arg Ala Lys Ile Pro Gly Leu Leu Asn Gln Thr Ser Arg
Ser Leu Asp Gln Ile Pro Gly Tyr Leu Asn Arg Ile His Glu
Leu Leu Asn Gly Thr Arg Gly Leu Phe Pro Gly Pro Ser Arg
Arg Thr Leu Gly Ala Pro Asp Ile Ser Ser Gly Thr Ser Asp
Thr Gly Ser Leu Pro Pro Asn Leu Gln Pro Gly Tyr Ser Pro
Ser Pro Thr His Pro Pro Thr Gly Gln Tyr Thr Leu Phe Pro
Leu Pro Pro Thr Leu Pro Thr Pro Val Val GLn Leu His Pro
Leu Leu Pro Asp Pro Ser Ala Pro Thr Pro Thr Pro Thr Ser
Pro Leu Leu Asn Thr Ser Tyr Thr His Ser Gln Asn Leu Ser
Gln Glu Gly
```

DNA sequence [SEQ ID NO:54] codes for the foregoing polypeptide.

EXAMPLE 3

BHK expression vector for 1-153 c-mpl ligand

The 1-153 c-mpl ligand gene product was digested with NcoI and HindIII restriction enzymes for subcloning into pMON3934. pMON3934, a mammalian expression vector, is also derived from pMON3359, but it contains a modified human IL-3 signal peptide sequence in addition to the IE110 promoter and poly-A signal. The signal peptide sequence is flanked by BamHI and NcoI restriction enzyme sites, which facilitates cloning and expression of genes as NcoI-HindIII fragments. The HindIII site is 3' to the NcoI site. The DNA sequence of the signal peptide is shown below (restriction enzyme sites are indicated above). The ATG (methionine) codon within the NcoI site is in-frame with the initiator ATG of the signal peptide (underlined);

```
BamHI
GGATCCACCATGAGCCGCCTGCCCGTCCTGCTCCTGCTCCAACTCCT
        MetSerArgLeuProValLeuLeuLeuLeuGlnLeuLeu

NcoI
GGTCCGCCCCGCCATGG [SEQ ID NO:58]
 ValArgProAlaMet  [SEQ ID NO:59]
```

The resulting plasmid was designated pMON26448. The plasmid, pMON26448, encodes the following amino acid sequence:

```
Met Glu Leu Thr Glu Leu Leu Leu Val Val Met Leu Leu Leu  [SEQ ID NO:56]

Thr Ala Arg Leu Thr Leu Ser Ser Pro Ala Pro Pro Ala Cys

Asp Leu Arg Val Leu Ser Lys Leu Leu Arg Asp Ser His Val

Leu His Ser Arg Leu Ser Gln Cys Pro Glu Val His Pro Leu

Pro Thr Pro Val Leu Leu Pro Ala Val Asp Phe Ser Leu Gly

Glu Trp Lys Thr Gln Met Glu Glu Thr Lys Ala Gln Asp Ile

Leu Gly Ala Val Thr Leu Leu Leu Glu Gly Val Met Ala Ala

Arg Gly Gln Leu Gly Pro Thr Cys Leu Ser Ser Leu Leu Gly

Gln Leu Ser Gly Gln Val Arg Leu Leu Leu Gly Ala Leu Gln

Ser Leu Leu Gly Thr Gln Leu Pro Pro Gln Gly Arg Thr Thr

Ala His Lys Asp Pro Asn Ala Ile Phe Leu Ser Phe Gln His

Leu Leu Arg Gly Lys Val Arg Phe Leu Met Leu Val Gly Gly

Ser Thr Leu Cys Val Arg
```

DNA sequence [SEQ ID NO:54] codes the foregoing amino acid sequence.

For secreted 1-153 c-mpl ligand, the N-terminal sequence should be SerProAla . . . , like that described elsewhere [de Sauvage et al., (1994)]. For the 1-332 c-mpl ligand, which contains its own secretion signal, it also should be cleaved to leave SerProAla . . . on the N-terminus. Therefore, the numbering system assumes that SerProAla . . . are the first three amino acids on either protein.

AML Proliferation Assay for Bioactive Human Interleukin-3

The factor-dependent cell line AML 193 was obtained from the American Type Culture Collection (ATCC, Rockville, Md.). This cell line, established from a patient with acute myelogenous leukemia, was a growth factor dependent cell line which displayed enhanced growth in GM/CSF supplemented medium (Lange, B., et al., (1987); Valtieri, M., et al., (1987). The ability of AML 193 cells to proliferate in the presence of human IL-3 has also been documented. (Santoli, D., et al., (1987)). A cell line variant was used, AML 193 1.3, which was adapted for long term growth in IL-3 by washing out the growth factors and starving the cytokine dependent AML 193 cells for growth factors for 24 hours. The cells were then replated at $1 \times 10^5$ cells/well in a 24 well plate in media containing 100 U/ml IL-3. It took approximately 2 months for the cells to grow rapidly in IL-3. These cells were maintained as AML 193 1.3 thereafter by supplementing tissue culture medium (see below) with human IL-3.

AML 193 1.3 cells were washed 6 times in cold Hanks balanced salt solution (HBSS, Gibco, Grand Island, N.Y.) by centrifuging cell suspensions at 250×g for 10 minutes followed by decantation of supernatant. Pelleted cells were resuspended in HBSS and the procedure was repeated until six wash cycles were completed. Cells washed six times by this procedure were resuspended in tissue culture medium at a density ranging from $2 \times 10^5$ to $5 \times 10^5$ viable cells/ml. This medium was prepared by supplementing Iscove's modified Dulbecco's Medium (IMDM, Hazelton, Lenexa, Kans.) with albumin, transferrin, lipids and 2-mercaptoethanol.

Bovine albumin (Boehringer-Mannheim, Indianapolis, Ind.) was added at 500 μg/ml; human transferrin (Boehringer-Mannheim, Indianapolis, Ind.) was added at 100 μg/ml; soybean lipid (Boehringer-Mannheim, Indianapolis, Ind.) was added at 50 μg/ml; and 2-mercaptoethanol (Sigma, St. Louis, Mo.) was added at $5 \times 10^{-5}$ M.

Serial dilutions of human interleukin-3 or human interleukin-3 variant protein (hIL-3 mutein) were made in triplicate series in tissue culture medium supplemented as stated above in 96 well Costar 3596 tissue culture plates. Each well contained 50 μl of medium containing interleukin-3 or interleukin-3 variant protein once serial dilutions were completed. Control wells contained tissue culture medium alone (negative control). AML 193 1.3 cell suspensions prepared as above were added to each well by pipetting 50 μl (2.5×10⁴ cells) into each well. Tissue culture plates were incubated at 37° C. with 5% $CO_2$ in humidified air for 3 days. On day 3, 0.5 μCi ³H-thymidine (2 Ci/mM, New England Nuclear, Boston, Mass.) was added in 50 μl of tissue culture medium. Cultures were incubated at 37° C. with 5% $CO_2$ in humidified air for 18–24 hours. Cellular DNA was harvested onto glass filter mats (Pharmacia LKB, Gaithersburg, Md.) using a TOMTEC cell harvester (TOMTEC, Orange, Conn.) which utilized a water wash cycle followed by a 70% ethanol wash cycle. Filter mats were allowed to air dry and then placed into sample bags to which scintillation fluid (Scintiverse II, Fisher Scientific, St. Louis, Mo. or BetaPlate Scintillation Fluid, Pharmacia LKB, Gaithersburg, Md.) was added. Beta emissions of samples from individual tissue culture wells were counted in a LKB Betaplate model 1205 scintillation counter (Pharmacia LKB, Gaithersburg, Md.) and data was expressed as counts per minute of ³H-thymidine incorporated into cells from each tissue culture well. Activity of each human interleukin-3 preparation or human interleukin-3 variant preparation was quantitated by measuring cell proliferation (³H-thymidine incorporation) induced by graded concentrations of interleukin-3 or interleukin-3 variant. Typically, concentration ranges from 0.05 pM–10⁵ pM were quantitated in these assays. Activity was determined by measuring the dose of interleukin-3 or interleukin-3 variant which provides 50% of maximal proliferation [$EC_{50}$=0.5×(maximum average counts per minute of ³H-thymidine incorporated per well among triplicate cultures of all concentrations of interleukin-3 tested—background proliferation measured by ³H-thymidine incorporation observed in triplicate cultures lacking interleukin-3]. This $EC_{50}$ value is also equivalent to 1 unit of bioactivity. Every assay was performed with native interleukin-3 as a reference standard so that relative activity levels could be assigned.

Methylcellulose Assay

This assay provides a reasonable approximation of the growth activity of colony stimulating factors to stimulate normal bone marrow cells to produce different types of hematopoietic colonies in vitro (Bradley et al., 1966, Pluznik et al., 1965).

Methods

Approximately 30 ml of fresh, normal, healthy bone marrow aspirate are obtained from individuals. Under sterile conditions samples are diluted 1:5 with a 1× PBS (#14040.059 Life Technologies, Gaithersburg, Md.) solution in a 50 ml conical tube (#25339-50 Corning, Corning Md.). Ficoll (Histopaque-1077 Sigma H-8889) is layered under the diluted sample and centrifuged, 300×g for 30 min. The mononuclear cell band is removed and washed two times in 1× PBS and once with 1% BSA PBS (CellPro Co., Bothel, Wash.). Mononuclear cells are counted and CD34+ cells are selected using the Ceprate LC (CD34) Kit (CellPro Co., Bothel, Wash.) column. This fractionation is performed since all stem and progenitor cells within the bone marrow display CD34 surface antigen. Alternatively whole bone marrow or peripheral blood may be used.

Cultures are set up in triplicate wells with a final volume of 0.1 ml in 48 well tissue culture plates (#3548 CoStar, Cambridge, Mass.). Culture medium is purchased from Terry Fox Labs. (HCC-4330 medium (Terry Fox Labs, Vancouver, B.C., Canada)). 600–1000 CD34+ cells are added per well. Native IL-3 and IL-3 variants are added to give final concentrations ranging from 0.001 nM–10 nM. G-CSF and GM-CSF and C-Kit ligand are added at a final concentration of 0.1 nM. Native IL-3 and IL-3 variants are supplied in house. C-Kit Ligand (#255-CS), G-CSF (#214-CS) and GM-CSF (#215-GM) are purchased from R&D Systems (Minneapolis, Minn.). Cultures are resuspended using an Eppendorf repeater and 0.1 ml is dispensed per well. Control (baseline response) cultures received no colony stimulating factors. Positive control cultures received conditioned media (PHA stimulated human cells:Terry Fox Lab. H2400). Cultures are incubated at 37° C., 5% CO2 in humidified air.

Hematopoietic colonies which are defined as greater than 50 cells are counted on the day of peak response (days 10–11) using a Nikon inverted phase microscope with a 40× objective combination. Groups of cells containing fewer than 50 cells are referred to as clusters. Alternatively colonies can be identified by spreading the colonies on a slide and stained or they can be picked, resuspended and spun onto cytospin slides for staining.

EXAMPLE 4

The synergistic effect of the IL-3 variant, pMON13288, with G-CSF was evaluated in the methylcellulose assay compared to that of native IL-3 with G-CSF. G-CSF was added to each culture at a concentration of 0.1 nM. Native IL-3 and the IL-3 variant, pMON13288, were added at final concentrations ranging from 0.001 nM to 10 nM. Colonies were counted on the day of peak response (days 10–11). pMON13288 activates more progenitor cells than native IL-3 (FIG. 2). Native IL-3 plus G-CSF and the IL-3 variant, pMON13288, plus G-CSF resulted in an increase in colony number greater than the additive effect of the individual proteins alone (FIG. 2). The synergistic effect of the IL-3 variant, pMON13288, with G-CSF was greater than that of native IL-3 with G-CSF. Hematopoietic colony forming activity of the IL-3 variant, pMON13288, was multi-lineage whereas G-CSF alone activates primarily granulocytic cells at molar equivalent doses. In FIG. 2 the concentration of IL-3 is plotted versus the colony counts per 100,000 starting CD34+ cells.

EXAMPLE 5

Figure 3:
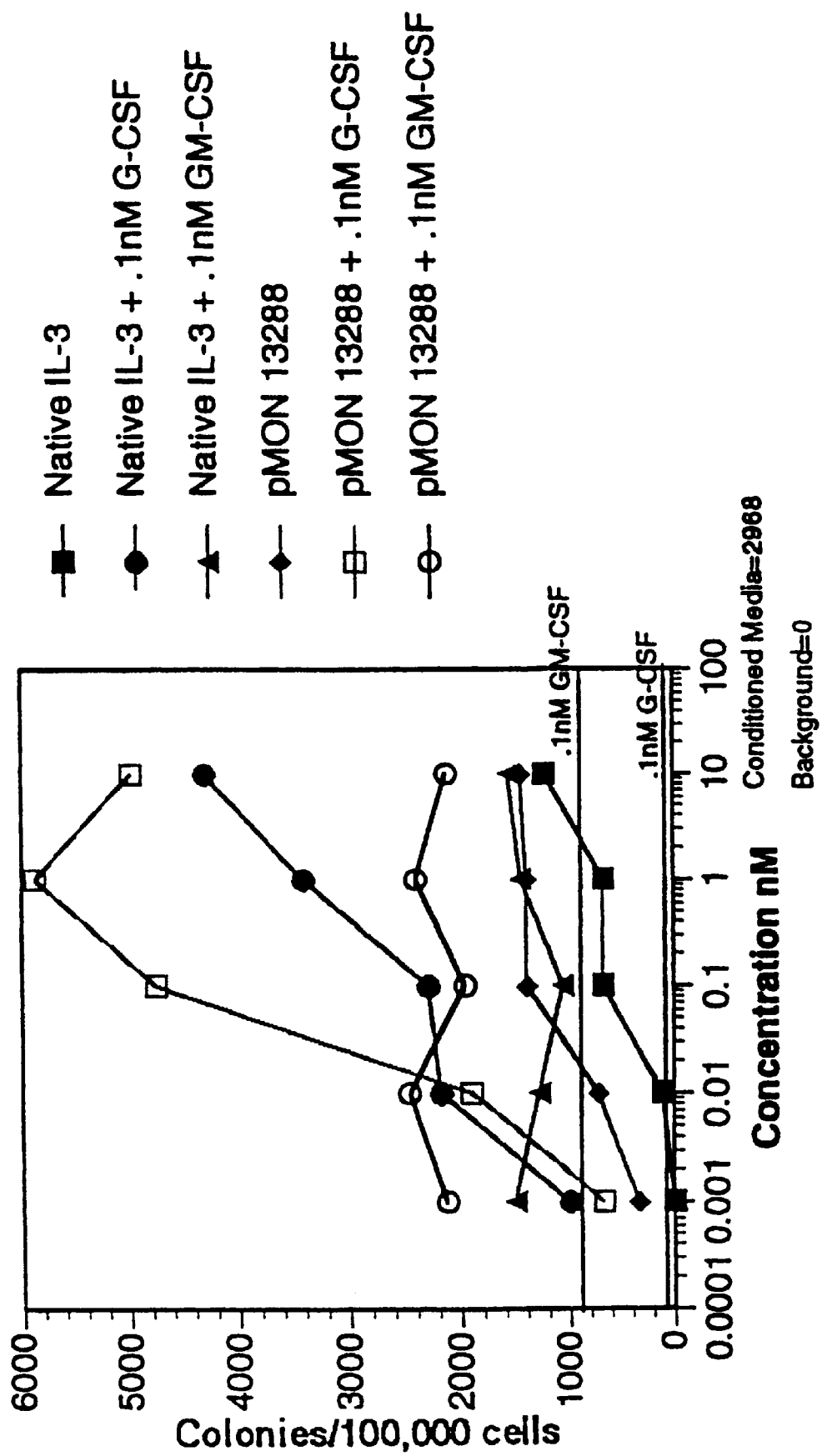
FIG. 3 shows the synergistic effects, in the methylcellulose assay, of the IL-3 variant, pMON13288, with GM-CSF compared to the synergy of native IL-3 with GM-CSF. Also shown are the effects of native IL-3 and the IL-3 variant, pMON13288, alone. The concentration of IL-3 is plotted versus the colony counts per 100,000 starting CD34+ cells.
Figure 4:
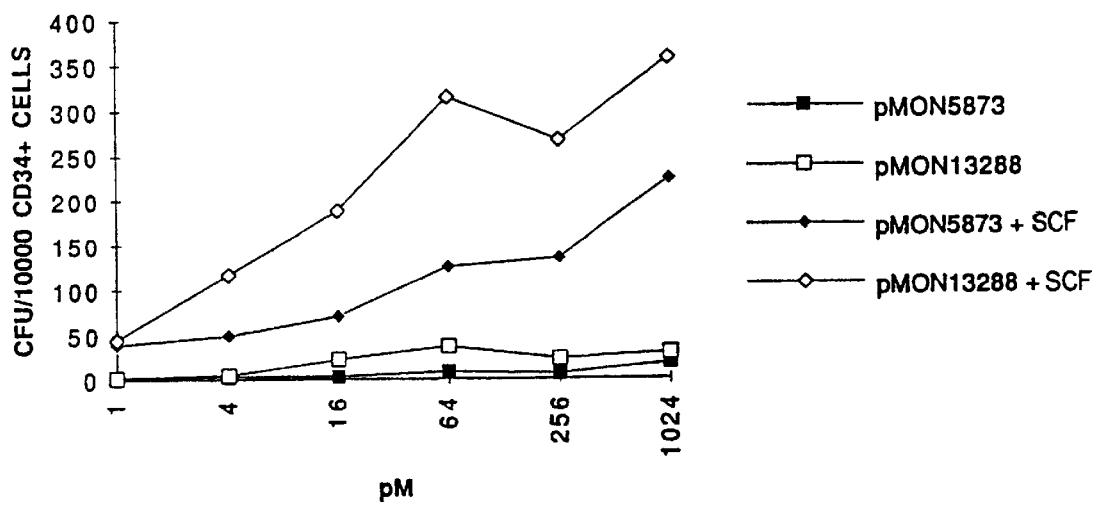
FIG. 4 shows the synergistic effects, in the cord blood assay, of the IL-3 variant, pMON13288, with stem cell factor (SCF) compared to the synergy of native IL-3 (pMON5873) with stem cell factor (SCF). Also shown are the effects of native IL-3 (pMON5873) and the IL-3 variant, pMON13288, alone. The concentration of IL-3 is plotted versus the colony counts (CFU) per 10,000 starting CD34+ cells.
Figure 5:
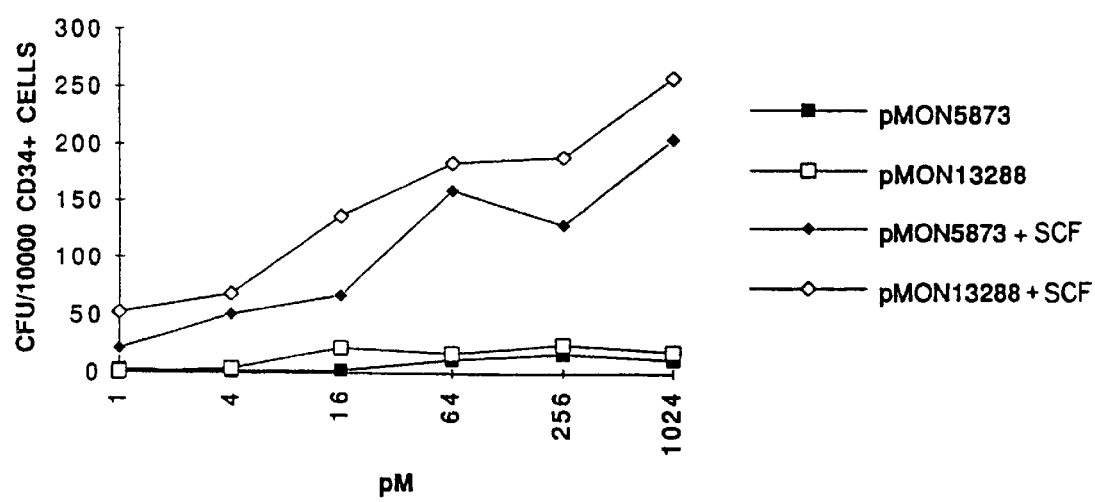
FIG. 5 shows the synergistic effects, in the cord blood assay, of the IL-3 variant, pMON13288, with stem cell factor (SCF) compared to the synergy of native IL-3

The synergistic effect of the IL-3 variant, pMON13288, with GM-CSF was evaluated in the methylcellulose assay compared to that of native IL-3 with GM-CSF. GM-CSF was added to each culture at a concentration of 0.1 nM. Native IL-3 and the IL-3 variant, pMON13288, were added at final concentrations ranging from 0.001 nM to 10 nM. Colonies were counted on the day of peak response (days 10–11). pMON13288 activates more progenitor cells than native IL-3 (FIG. 3). Native IL-3 plus GM-CSF and the IL-3 variant, pMON13288, plus GM-CSF resulted in an increase in colony number greater than the effect of the individual proteins alone (FIG. 3). The synergistic effect of the IL-3 variant, pMON13288, with GM-CSF was greater than that of native IL-3 with GM-CSF. In FIG. 3 the concentration of IL-3 is plotted versus the colony counts per 100,000 starting CD34+ cells.

EXAMPLE 6

Methylcellulose assays for native IL-3, pMON5873, were carried out in methylcellulose, with or without EPO. Although EPO increased the total number of colonies, it didn't appear to increase CFU-GM, which are of more interest. The presence of erythroid colonies also made scoring more subjective, because one must distinguish between multifocal BFU-E vs several closely associated single focus CFU-E. EPO also gave a high background of total colonies, which would tend to obscure the dose dependent response of CFU-GM to other CSFs.

Methylcellulose assays comparing native IL-3 (pMON5873) to the IL-3 variant, pMON13288 were carried out in the presence of stem cell factor (SCF) without EPO. SCF gives no background response in these assays, but appears to increase the dose dependent response of CFU-GM to both native IL-3 (PMON5873) and the IL-3 variant, pMON13288. This result is consistent with reports in the literature of in vitro synergies between IL-3 and SCF (Migliaccio et al., 1992). The IL-3 variant, pMON13288, appears to be more potent in these assays, and gives a greater maximum number of colonies (also larger) than native IL-3 (PMON5873).

Human Cord Blood Hemopoietic Growth Factor Assays

Bone marrow cells are traditionally used for in vitro assays of hematopoietic colony stimulating factor (CSF) activity. However, human bone marrow is not always available, and there is considerable variability between donors. Umbilical cord blood is comparable to bone marrow as a source of hematopoietic stem cells and progenitors (Broxmeyer et al., 1992; Mayani et al., 1993). In contrast to bone marrow, cord blood is more readily available on a regular basis. There is also a potential to reduce assay variability by pooling cells obtained fresh from several donors, or to create a bank of cryopreserved cells for this purpose. By modifying the culture conditions, and/or analyzing for lineage specific markers, it should be possible to assay specifically for granulocyte/macrophage colonies (CFU-GM), for megakaryocyte CSF activity, or for high proliferative potential colony forming cell (HPP-CFC) activity.

Methods

Mononuclear cells (MNC) are isolated from cord blood within 24 hrs of collection, using a standard density gradient (1.077 g/ml Histopaque). Cord blood MNC have been further enriched for stem cells and progenitors by several procedures, including immunomagnetic selection for CD14−, CD34+ cells; panning for SBA−, CD34+ fraction using coated flasks from Applied Immune Science (Santa Clara, Calif.); and CD34+ selection using a CellPro (Bothell, Wash.) avidin column. Either freshly isolated or cryopreserved CD34+ cell enriched fractions are used for the assay. Duplicate cultures for each serial dilution of sample (concentration range from 1 pM to 1204 pM) are prepared with 1×104 cells in 1 ml of 0.9% methycellulose containing medium without additional growth factors (Methocult H4230 from Stem Cell Technologies, Vancouver, BC.). In some experiments, Methocult H4330 containing erythropoietin (EPO) was used instead of Methocult H4230, or Stem Cell Factor (SCF), 50 ng/ml (Biosource International, Camarillo, Calif.) was added. After culturing for 7–9 days, colonies containing >30 cells are counted. In order to rule out subjective bias in scoring, assays are scored blind.

Analysis of c-mpl ligand proliferative activity
Methods
1. Bone marrow proliferation assay
a. CD34+ Cell Purification:
Between 15–20 ml bone marrow aspirates were obtained from normal allogeneic marrow donors after informed consent. Cells were diluted 1:3 in phosphate buffered saline (PBS, Gibco-BRL), 30 ml were layered over 15 ml Histopaque-1077 (Sigma) and centrifuged for 30 minutes at 300 RCF. The mononuclear interface layer was collected and washed in PBS. CD34+ cells were enriched from the mononuclear cell preparation using an affinity column per manufacturers instructions (CellPro, Inc, Bothell Wash.). After enrichment, the purity of CD34+ cells was 70% on average as determined by using flow cytometric analysis using anti CD34 monoclonal antibody conjugated to fluorescein and anti CD38 conjugated to phycoerythrin (Becton Dickinson, San Jose Calif.).

Cells were resuspended at 40,000 cells/ml in X-Vivo 10 media (Bio-Whittaker, Walkersville, Md.) and 1 ml was plated in 12-well tissue culture plates (Costar). The growth factor rhIL-3 was added at 100 ng/ml (pMON5873) was added to some wells. hIL3 variant, pMON13288 was used at 10 ng/ml or 100 ng/ml. Conditioned media from BHK cells transfected with plasmid encoding c-mpl ligand were tested by addition of 100 µl of supernatant added to 1 ml cultures (approximately a 10% dilution). Cells were incubated at 37° C. for 8–14 days at 5% $CO_2$ in a 37° C. humidified incubator.

b. Cell Harvest and Analysis:
At the end of the culture period a total cell count was obtained for each condition. For fluorescence analysis and ploidy determination cells were washed in megakaryocyte buffer (MK buffer, 13.6 mm Sodium Citrate, 1 mM Theophylline, 2.2 µM PGE1, 11 mM Glucose, 3% w/v BSA, in PBS, pH 7.4,) [See Tomer et al., Blood 70, 1987, pp. 1736–42] resuspended in 500 µl of MK buffer containing anti-CD41a FITC antibody (1:200, AMAC, Westbrook, Me.) and washed in MK buffer. For DNA analysis cells were permeablized in MK buffer containing 0.5% Tween 20 (Fisher, Fair Lawn N.J.) for 20 min. on ice followed by fixation in 0.5% Tween-20 and 1% paraformaldehyde (Fisher Chemical) for 30 minutes followed by incubation in Propidium Iodide (Calbiochem, La Jolla Calif.) (50 µg/ml) with RNA-ase (400 U/ml) in 55% v/v MK buffer (200 mOsm) for 1–2 hours on ice. Cells were analyzed on a FACScan or Vantage flow cytometer (Becton Dickinson, San Jose, Calif.). Green fluorescence (CD41a-FITC) was collected along with linear and log signals for red fluorescence (PI) to determine DNA ploidy. All cells were collected to determine the percent of cells that were CD41+. Data analysis was performed using software by LYSIS (Becton Dickinson, San Jose, Calif.). Percent of cells expressing the CD41 antigen was obtained from flow cytometry analysis (Percent). Absolute (Abs) number of CD41+ cells/ml was calculated by:

(Abs)=(Cell Count)*(Percent)/100.

2. Megakaryocyte fibrin clot assay.
CD34+ enriched population were isolated as described above. Cells were suspended at 25,000 cells/ml with/without cytokine(s) in a media consisting of a base Iscoves IMDM media supplemented with 0.3% BSA, 0.4 mg/ml apo-transferrin, 6.67 µM $FeCl_2$, 25 µg/ml $CaCl_2$, 25 µg/ml L-asparagine, 500 µg/ml E-amino-n-caproic acid and Penicillin/Streptomycin. Prior to plating into 35 mm plates, thrombin was added (0.25 Units/ml) to initiate clot formation. Cells were incubated at 37° C. for 13 days at 5% $CO_2$ in a 37° C. humidified incubator.

At the end of the culture period plates were fixed with Methanol:Acetone (1:3), air dried and stored at −20° C. until staining. A peroxidase immunocytochemistry staining procedure was used (Zymed, Histostain-SP. San Francisco, Calif.) using a cocktail of primary monoclonal antibodies consisting of anti CD41a, CD42 and CD61. Colonies were counted after staining and classified as negative, CFU-MK (small colonies, 1–2 foci and less that approx. 25 cells), BFU-MK (large, multi-foci colonies with >25 cells) or mixed colonies (mixture of both positive and negative cells).

EXAMPLE 7

Co-administration of hIL-3 variant, pMON13288 and c-mpl ligand (Meg-CSF) in liquid culture Co-administration of hIL-3 variant, pMON13288 and c-mpl ligand (Meg-CSF) has a more than additive effect on megakaryocyte expansion than either cytokine alone in the liquid culture assay CD34+ cells were isolated as described in the methods section. The assay was set up as described in the methods section except that cells were plated at 4000 cells/100 μl in a 96-well plate. pMON26448 or a mock transfectant was evaluated by adding 10 μl to each well (10% final). Supernatant from transfected BHK cells were tested +/− hIL3 variant, pMON13288 (10 ng/ml). At day 10 phenotypic analysis was performed by flow cytometry. Supernatant from pMON26448 induced selective expansion of CD41a+ cells. Total cell number increased from the 4000 cells plated to 22,000 at the end of the assay (Table 1). Addition of hIL3 variant, pMON13288 alone increased total cell numbers (19,000 cells at end of assay) with 17% of cells expressing CD41a. Combination of pMON26448 with hIL3 variant, pMON13288 resulted in 56% of cells expressing CD41a. Total cell expansion in the combination assay was more than additive with 86,000 cells/well. Both the increased total cell number and the higher percentage of cells expressing CD41a resulted in an increase in total number CD41+ cells that also was more than additive as compared to either cytokine alone (48,000 vs. 3,320 and 18,480).

TABLE 1

| Cytokine Treatment | Cells/Well | % CD41a Positive | # CD41+ Cells/Well |
|---|---|---|---|
| pMON13288 | 19,000 | 17 | 3,230 |
| pMON26448 | 22,000 | 84 | 18,480 |
| pMON26448 + pMON13288 | 86,000 | 56 | 48,160 |

EXAMPLE 8

Co-administration of hIL-3 variant pMON13288, and c-mpl ligand (Meg-CSF) in liquid culture The co-administration of hIL-3 variant, pMON13288, and c-mpl ligand (Meg-CSF) has a more than additive effect on megakaryocyte expansion than either cytokine alone in the liquid culture assay In another experiment CD34+ cells were isolated from Human bone marrow using a CD34 affinity column (Cellpro). Purified CD34+ cells were resuspended in X-Vivo tissue culture media at 40,000 cells/ml. pMON26448 or a mock transfectant (10%) was evaluated with/without hIL3 variant, pMON13288 or native IL3. At day 8 phenotypic analysis was done using flow cytometry. As was seen in the table below (Table 2a–c). IL3, both concentrations of hIL3 variant, pMON13288 and pMON26448 increased total cell number substantially. Combination of cytokines further expanded cell populations. pMON26448 increased the percent of CD41+ cells from 2% in the control group to 35%. IL3 or hIL3 variant, pMON13288 increased the percent of CD41+ cells modestly (from 2% to 5%). Combining pMON26448 with IL3 or hIL3 variant, pMON13288 resulted in a more than additive number of CD41+ cells as compared to the sum of either cytokine alone (Table 2c).

TABLE 2(a–c)

| Cytokine treatment | Media | IL-3 (100 ng/ml) | pMON13288 (10 ng/ml) | pMON13288 (100 ng/ml) |
|---|---|---|---|---|
| a. Total Cells/Well | | | | |
| Media | 30,000 | 112,000 | 275,000 | 150,000 |
| Mock | 10,000 | 153,000 | 235,000 | 260,000 |
| pMON26448 | 135,000 | 655,000 | 625,000 | 500,000 |
| b. % CD41a+ | | | | |
| Media | 2 | 7 | 5 | 5 |
| Mock | 2 | 14 | 5 | 9 |
| pMON26448 | 35 | 35 | 28 | 29 |
| c. Total CD41a+ Cells | | | | |
| Media | 600 | 7,840 | 13,750 | 7,500 |
| Mock | 200 | 21,420 | 11,750 | 23,400 |
| pMON26448 | 47,250 | 229,250 | 175,000 | 145,000 |

EXAMPLE 9

Co-administration of hIL-3 variant, pMON13288, and c-mpl ligand (Meg-CSF) in fibrin clot assay The co-administration of hIL-3 variant, pMON13288, and c-mpl ligand (Meg-CSF) has a more than additive effect on megakaryocyte than either cytokine alone.

Fibrin clot cultures were set up as described in methods section. pMON26448 is the 1-153 form of c-mpl ligand (Meg-CSF). Incubation in the presence of hIL3 variant, pMON13288 gave rise to colonies that were predominantly negative for megakaryocyte markers (86/114, (Table 3)) except for number of small CFU-MK colonies (23/114). pMON26448 alone gave rise primarily to CFU-MK colonies (172/175) with only a few number of negative colonies (3/175). Combination of hIL3 variant, pMON13288 and pMON26448 gave rise to a large number of positive colonies (295/414) that were predominantly of the BFU-MK morphology. There were a negative colonies as well (119/414). Total number of positive colonies with co-administration was more than additive than with either cytokine alone.

TABLE 3

| Cytokine treatment | Negative | CFU-MK | BFU-MK | Mixed | Total Colonies |
|---|---|---|---|---|---|
| | Colonies/Well | | | | |
| pMON13288 | 86 | 23 | 0 | 5 | 114 |
| pMON26448 | 3 | 73 | 98 | 1 | 175 |
| pMON26448 + pMON13288 | 119 | 29 | 244 | 22 | 414 |
| | Colonies/100,000 plated | | | | |
| pMON13288 | 344 | 92 | 0 | 20 | 456 |
| pMON26448 | 12 | 292 | 392 | 4 | 700 |
| pMON26448 + pMON13288 | 476 | 116 | 976 | 88 | 1656 |

IL-3 mediated sulfidoleukotriene release from human mononuclear cells

The following assay was used to measure IL-3 mediated sulfidoleukotriene release from human mononuclear cells.

Heparin-containing human blood was collected and layered onto an equal volume of Ficoll-Paque (Pharmacia #17-0840-02) ready to use medium (density 1.077 g/ml.). The Ficoll was warmed to room temperature prior to use and clear 50 ml polystyrene tubes were utilized. The Ficoll gradient was spun at 300×g for 30 minutes at room temperature using a H1000B rotor in a Sorvall RT6000B refrigerated centrifuge. The band containing the mononuclear cells was carefully removed, the volume adjusted to 50 mls with Dulbecco's phosphate-buffered saline (Gibco Laboratories cat. #310-4040PK), spun at 400×g for 10 minutes at 4° C. and the supernatant was carefully removed. The cell pellet was washed twice with HA Buffer [20 mM Hepes (Sigma #H-3375), 125 mM NaCl (Fisher #S271-500), 5 mM KCl (Sigma #P-9541), 0.5 mM glucose (Sigma #G-5000),0.025% Human Serum Albumin (Calbiochem #126654) and spun at 300×g, 10 min., 4° C. The cells were resuspended in HACM Buffer (HA buffer supplemented with 1 mM CaCl2 (Fisher #C79-500) and 1 mM MgCl2 (Fisher #M-33) at a concentration of 1×106 cells/ml and 180 µl were transferred into each well of 96 well tissue culture plates. The cells were allowed to acclimate at 37° C. for 15 minutes. The cells were primed by adding 10 µls of a 20× stock of various concentrations of cytokine to each well (typically 100000, 20000, 4000, 800, 160, 32, 6.4, 1.28, 0 fM IL3). The cells were incubated for 15 minutes at 37° C. Sulfidoleukotriene release was activated by the addition of 10 µls of 20× (1000 nM) fmet-leu-phe (Calbiochem #344252) final concentration 50 nM FMLP and incubated for 10 minutes at 37° C. The plates were spun at 350×g at 4° C. for 20 minutes. The supernatants were removed and assayed for sulfidoleukotrienes using Cayman's Leukotriene C4 EIA kit (Cat. #420211) according to manufacturers' directions. Native (15-125)hIL-3 was run as a standard control in each assay.

Further details known to those skilled in the art may be found in T. Maniatis, et al., *Molecular Cloning, A Laboratory Manual,* Cold Spring Harbor Laboratory (1982) and references cited therein, incorporated herein by reference; and in J. Sambrook, et al., *Molecular Cloning, A Laboratory Manual,* 2nd edition, Cold Spring Harbor Laboratory (1989) and references cited therein, incorporated herein by reference.

Amino acids are shown herein by standard one letter or three letter abbreviations as follows:

| Abbreviated Designation | Amino Acid | |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Additional details may be found in co-pending U.S. patent application Ser. No. PCT/US93/11197 which is hereby incorporated by reference in its entirety as if written herein.

All references, patents or applications cited herein are incorporated by reference in their entirety as if written herein.

Various other examples will be apparent to the person skilled in the art after reading the present disclosure without departing from the spirit and scope of the invention. It is intended that all such other examples be included within the scope of the appended claims.

TABLE 4

OLIGONUCLEOTIDES c-mplBglII
CATGGCAAGATCTCCGGCCAGAATGGAGCTGACTGA [SEQ ID NO:50]

c-mplEcoRI
AATAGCTGAATTCTTACCCTTCCTGAGACAGATT [SEQ ID NO:51]

c-mplNcoI
ACGTCCATGGCNTCNCCNGCNCCNCCTGCTTGTGACCTCCGAGTC
[SEQ ID NO:52]
                      (where N = G, C, T or A)

c-mplHindIII
TGACAAGCTTACCTGACGCAGAGGGTGGACCCT [SEQ ID NO:53]

TABLE 5

DNA SEQUENCES 1-153 c-mpl ligand

[SEQ ID NO:54]
ATGGCGTCTC CGGCGCCGCC TGCTTGTGAC CTCCGAGTCC

TCAGTAAACT GCTTCGTGAC TCCCATGTCC TTCACAGCAG

ACTGAGCCAG TGCCCAGAGG TTCACCCTTT GCCTACACCT

GTCCTGCTGC CTGCTGTGGA CTTTAGCTTG GGAGAATGGA

AAACCCAGAT GGAGGAGACC AAGGCACAGG ACATTCTGGG

AGCAGTGACC CTTCTGCTGG AGGGAGTGAT GGCAGCACGG

GGACAACTGG GACCCACTTG CCTCTCATCC CTCCTGGGGC

AGCTTTCTGG ACAGGTCCGT CTCCTCCTTG GGGCCCTGCA

GAGCCTCCTT GGAACCCAGC TTCCTCCACA GGGCAGGACC

ACAGCTCACA AGGATCCCAA TGCCATCTTC CTGAGCTTCC

AACACCTGCT CCGAGGAAAG GTGCGTTTCC TGATGCTTGT

AGGAGGGTCC ACCCTCTGCG TCAGG

TABLE 5-continued

DNA SEQUENCES

Full length c-mpl ligand

[SEQ ID NO:57]

```
ATGGAGCTGA CTGAATTGCT CCTCGTGGTC ATGCTTCTCC
TAACTGCAAG GCTAACGCTG TCCAGCCCGG CTCCTCCTGC
TTGTGACCTC CGAGTCCTCA GTAAACTGCT TCGTGACTCC
CATGTCCTTC ACAGCAGACT GAGCCAGTGC CCAGAGGTTC
ACCCTTTGCC TACACCTGTC CTGCTGCCTG CTGTGGACTT
TAGCTTGGGA GAATGGAAAA CCCAGATGGA GGAGACCAAG
GCACAGGACA TTCTGGGAGC AGTGACCCTT CTGCTGGAGG
GAGTGATGGC AGCACGGGGA CAACTGGGAC CCACTTGCCT
CTCATCCCTC CTGGGGCAGC TTTCTGGACA GGTCCGTCTC
CTCCTTGGGG CCCTGCAGAG CCTCCTTGGA ACCCAGCTTC
CTCCACAGGG CAGGACCACA GCTCACAAGG ATCCCAATGC
CATCTTCCTG AGCTTCCAAC ACCTGCTCCG AGGAAAGGTG
CGTTTCCTGA TGCTTGTAGG AGGGTCCACC CTCTGCGTCA
GGCGGGCCCC ACCCACCACA GCTGTCCCCA GCAGAACCTC
TCTAGTCCTC ACACTGAACG AGCTCCCAAA CAGGACTTCT
GGATTGTTGG AGACAAACTT CACTGCCTCA GCCAGAACTA
CTGGCTCTGG GCTTCTGAAG TGGCAGCAGG GATTCAGAGC
CAAGATTCCT GGTCTGCTGA ACCAAACCTC CAGGTCCCTG
GACCAAATCC CCGGATACCT GAACAGGATA CACGAACTCT
TGAATGGAAC TCGTGGACTC TTTCCTGGAC CCTCACGCAG
GACCCTAGGA GCCCCGGACA TTTCCTCAGG AACATCAGAC
ACAGGCTCCC TGCCACCCAA CCTCCAGCCT GGATATTCTC
CTTCCCCAAC CCATCCTCCT ACTGGACAGT ATACGCTCTT
CCCTCTTCCA CCCACCTTGC CCACCCCTGT GGTCCAGCTC
CACCCCCTGC TTCCTGACCC TTCTGCTCCA ACGCCCACCC
CTACCAGCCC TCTTCTAAAC ACATCCTACA CCCACTCCCA
GAATCTGTCT CAGGAAGGG
```

References

Adams, S. P., Kavka, K. S., Wykes, E. J., Holder, S. B. and Galluppi, G. R. Hindered Dialkyamino Nucleoside Phosphate reagents in the synthesis of two DNA 51-mers. *J. Am. Chem. Soc.*, 105, 661–663 (1983).

Atkinson, T. and Smith, M., in Gait, M. J., *Oligonucleotide Synthesis* (1984) (IRL Press, Oxford England).

Bachmann, B., Pedigrees of some mutant strains of *Escherichia coli* K-12, *Bacteriological Reviews*, 36:525–557 (1972).

Bayne, M. L., Expression of a synthetic gene encoding human insulin-like growth factor I in cultured mouse fibroblasts. *Proc. Natl. Acad. Sci. USA* 84, 2638–2642 (1987).

Bazan, J. F., Haemopoietic receptors and helical cytokines. *Proc. Natl. Acad. Sci. U.S.A.* 87(18):6934–8 (1990).

Ben-Bassat, A., K. Bauer, S-Y. Chang, K. Myambo, A. Boosman and S. Ching. Processing of the initiating methionine from proteins: properties of the *Escherichia coli* methionine aminopeptidase and its gene structure. *J. Bacteriol.*, 169: 751–757 (1987).

Biesma, B. et al., Effects of interleukin-3 after chemotherapy for advanced ovarian cancer. *Blood*, 80:1141–1148 (1992).

Birnboim, H. C. and J. Doly. A rapid alkaline extraction method for screening recombinant plasmid DNA. *Nucleic Acids Research*, 7(6): 1513–1523 (1979).

Bradford, M. M., A rapid and sensitive method for the quantitation of microgram quantities of protein utilizing the principle of protein-dye binding, *Analytical Biochemistry*, 72: 248–254 (1976).

Bradley, T R and Metcalf, D. The growth of mouse bone marrow cells in vitro. *Aust. Exp. Biol. Med. Sci.* 44:287–300, (1966).

Briddell, R A, Hoffman, R, Cytokine regulation of the human burst-forming unit megakaryocyte, *Blood* 76:516, (1990).

Broxmeyer, H. E. et al, Growth characteristics and expansion of human umbilical cord blood and estimation of its potential for transplantation in adults, *Proc. Natl. Acad. Sci. USA*, vol.89, 4109–4113, 1992.

Bruno, E, Miller, M E, Hoffman, R, Interacting cytokines regulate in vitro human megakaryocytopoiesis, *Blood* 76:671, (1989).

Bruno, E, Cooper, R J, Briddell, R A, Hoffman, R, Further examination of the effects of recombinant cytokines on the proliferation of human megakaryocyte, progenitor cells, *Blood* 77:2339, (1991).

Clark-Lewis, I., L. E. Hood and S. B. H. Kent. Role of disulfide bridges in determining the biological activity of interleukin 3, *Proc. Natl. Acad. Sci.*, 85: 7897–7901 (1988).

Clement, J. M. and Hofnung, M. Gene sequence of the receptor, an outer membrane protein of *E. coli* K12. *Cell*, 27: 507–514 (1981).

Covarrubias, L., L. Cervantes, A. Covarrubias, X. Soberon, I. Vichido, A. Blanco, Y. M. Kupersztoch-Portnoy and F. Bolivar. Construction and characterization of new cloning vehicles. V. Mobilization and coding properties of pBR322 and several deletion derivatives including pBR327 and pBR328. *Gene* 13: 25–35 (1981).

D'Andrea, A. D., Lodish, H. G., Wong, G. G.:Expression cloning of the murine erythropoietin receptor. *Cell* 57:277, 1989

Deng, W. P. & Nickoloff, J. A. Site-directed mutagenesis of virtually any plasmid by eliminating a unique site *Anal. Biochem.* 200:81 (1992).

Dente, L., G. Cesareni and R. Cortese, pEMBL: a new family of single stranded plasmids, *Nucleic Acids Research*, 11: 1645–1655 (1983).

Donahue, R E, Seehra, J, Metzger, M, Lefebvre, D, Rock, B, Corbone, S, Nathan, D G, Garnick, M, Seghal, P K, Laston, D, La Valle, E, McCoy, J, Schendel, P F, Norton, C, Turner, K, Yang, Y C, and Clark, S C,, Human IL-3 and GM-CSF act synergistically in stimulating hematopoiesis in primates. *Science.* 241: 1820, (1988).

de Sauvage, F. J., Haas, P. E., Spencer, S. D., Malloy, B. E., Gurney, A. L., Spencer, S. A., Darbonne, W. C., Henzel, W. J., Wong, S.C., Kuang, W., Oles, K. J., Hultgren, B., Solberg, L. A., Goeddel, D. V., and Eaton, D. L., Stimulation of megakaryocytpoiesis and thrombopoiesis by the c-Mpl ligand. *Nature* 369:533–538 (1994).

Dunn, J. J. and Studier, F. W., Complete nucleotide sequence of bacteriophage T7 DNA and the locations of T7 genetic elements. *J. Mol. Biol.* 166:477–535 (1983).

Emerson, S G, Yang, Y C, Clark, S C, and Long, M W, Human recombinant human GM-CSF and IL-s have overlapping but distinct hematopoietic activities, *J. Clin. Invest.* 82:1282, (1988).

Falk, S., G. Seipelt, A. Ganser, O. G. Ottmann, D. Hoelzer, H. J. Stutte and K. Hubner. *Hematopathology* 95: 355 (1991).

Farese, A. M., Williams, D. E., Seiler, F. R., and MacVittie, T. J., Combination protocols fo cytokine therapy with interleukin-3 and granulocyte-Macrophage colony-stimulating factor in a primate model of radiation-induced marrow aplasia. *Blood* 82(10):3012–3018 (1993).

Fling, M. E., et al. Nucleotide sequence of the transposon Tn7 gene encoding an aminoglycoside-modifying enzyme, 3"(9)-O-nucleotidyltransferase. *Nucl. Acids Res.* 13: 7095–7106 (1985).

Fukunaga, R., Ishizaka-Ikeda, E., and Nagata, S., Purification and characterization of the recptor for murine granulocyte colonystimulating factor. *J. Biol. Chem.* 265(23):14008–15 (1990).

Ganser, A., A. Lindemann, G. Seipelt, O. G. Ottmann, F. Herrmann, M. Eder, J. Frisch, G. Schulz, R. Mertelsmann and D. Hoelzer. Effects of Recombinant Human Interleukin-3 in Patients With Normal Hematopoiesis and in Patients with Bone Marrow Failure, *Blood* 76: 666 (1990).

Ganser, A, Lindemann, A, Ottmann, O G, Seipelt, G, Hess, U, Geissler, G, Kanz, L, Frisch, J, Schultz, G, Mertelsmann, R, and Hoelzer, D, Sequential in vivo treatment with two recombinant human hematopoietic growth factors (IL-3 and GM-CSF) as a new therapeutic modality to stimulate hematopoiesis: Results of a Phase I study, *Blood* 79: 2583, (1992).

Gearing, D. P., King, J. A., Gough, N. M., Nicola, N. A.: Expression cloning of a receptor for human granulocyte-macrophage colony-stimulating factor. *EMBO J* 8:3667, 1989

Gearing, D. P., Thut, C. J., VandenBos, T., Gimpel, S. D., Delaney, P. B., King, J. A., Price V., Cosman, D., Beckmann M P: Leukemia inhibitory factor receptor is structurally related to the IL-6 signal transducer, gp130. *EMBO J* 10:2839, 1991

Gearing, D. P., Comeau, M. R., Friend, D. J., Gimpel, S. D., Thut, C. J., McGourty, J., Brasher, K. K., King. J. A., Gills, S., and Mosely, B., Ziegler, S. F., and Cosman, D., The IL-6 signal transducer, GP130: an oncostatin M recptor and affinty converter for the LIF recptor. *Science* 255(5050):1434–7 (1992).

Gething and Sambrook, Cell-surface expression of influenza haemagglutinin from a cloned DNA copy of the RNA gene, *Nature*, 293: 620–625 (1981).

Gillio, A. P., C. Gasparetto, J. Laver, M. Abboud, M. A. Bonilla, M. B. Garnick and R. J. O'Reilly. *J. Clin. Invest.* 85: 1560 (1990).

Goodwin, R. G., Friend, D. J., Ziegler, S. F., Jerry, R., Falk, B. A., Gimpel, S. D., Cosman, D., Dower, S. K., March, C. J., Namen, A. E., Cloning of the human and murine interleukin-7 receptors: demonstration of a sloble form and homology to a new receptor superfamily. *Cell* 60(6):941–51 (1990).

Gouy, M. and G. Gautier, Codon usage in bacteria: Correlation with gene expressivity, *Nucleic Acids Research*, 10: 7055–7074 (1982).

Greenfield, L., T. Boone, and G. Wilcox. DNA sequence of the araBAD promoter in *Escherichia coli* B/r. *Proc. Natl. Acad. Sci. USA*, 75: 4724–4728 (1978).

Harada, N., Castle, B. E., Gorman, D. M., Itoh, N., Schreurs, J., Barrett R. L., Howard, M., Miyajima, A.: Expression cloning of a cDNA encoding the murine interleukin 4 receptor based on ligand binding. *Proc Natl Acad Sci USA* 87:857, 1990

Higuchi, R, (1989) in *PCR Technology*, H. A. Erlich ed., Stockton Press, N.Y. chapter 2–6.

Hippenmeyer, P., and Highkin M. High level, stable production of recombinant proteins in mammalian cell culture using the herpesvirus VP16 transactivator. *Bio/Technology* 11: 1037–1041 (1993).

Hunkapiller, M. W., R. W. Hewick, R. J. Dreyer and L. E. Hood. High sensitivity sequencing with a gas-phase sequenator. *Methods in Enzymology* 153: 399–413 (1983).

Kaufman, et al., Coamplification and Coexpression of Human Tissue-Type Plasminogen Activator and Murine Dihydrofolate Reductase Sequences in Chinese Hamster Ovary Cells, *Mol. Cell. Biol.*, 5(7): 1750–1759 (1985).

Kaufman, R. J. High level production of proteins in mammalian cells, in *Genetic Engineering, Principles and Methods*, Vol. 9, J. K. Setlow, editor, Plenum Press, New York (1987).

Kelso, A., Gough, N. M.: Coexpession of granulocyte-macrophage colony-stimulating factor gamma-interferon and interleukins-3 and 4 is random in murine alloreactive T lymphocyte clones. *Proc Natl Acad Sci USA* 85:9189, 1988.

Kitamura, T, Tange, T, Terasawa, T, Chiba, S, Kuwaki, T, Miyagawa, K, Piao, Y, Miyazono, K, Urabe, A, and Takaku, F, Establishment and Characterization of a Unique Human Cell Line That Proliferates Dependently on GM-CSF or Erythropoietin, *Journal of Cellular Physiology*, 140: 323–334 (1989).

Kitamura, T., Sato, N., Arai, K., Miyajima, A.: Expression cloning of the human IL-3 receptor cDNA reveals a shared beta subunit for the human IL-3 and GM-CSF receptors. *Cell* 66:1165, 1991.

Kondo, M., Takeshita, T., Ishii, N., Nakamura, M., Watanabe, S., Arai, K-I, Sugamura, K.: Sharing of the Interleukin-2 (IL-2) Receptor gamma Chain Between Receptors for IL-2 and Il-4. *Science* 262:1874, Dec. 17, 1993.

Krumwieh, D, Weinmann, E, Seiler, F R, Different effects of interleukin-3 (IL-3) on the hematopoiesis of subhuman primates due to various combinations with GM-CSF and G-CSF, *Int. J. Cell Cloning* 8: 229, (1990).

Kunkel, T. A. Rapid and efficient site-specific mutagenesis without phenotypic selection. *Proc. Natl. Acad. Sci. USA*, 82: 488–492 (1985).

Laemmli, U. K., Cleavage of structural proteins during assembly of the head of bacteriophage T4, *Nature*, 227:680–685 (1970).

Lange, B., M. Valtieri, D. Santoli, D. Caracciolo, F. Mavilio, I. Gemperlein, C. Griffin, B. Emanuel, J. Finan, P. Nowell, and G. Rovera. Growth factor requirements of childhood acute leukemia: establishment of GM-CSF-dependent cell lines. *Blood* 70:192 (1987).

Maekawa, T., Metcalf, D., Gearing, D. P.: Enhanced suppression of human myeloid leukemic cell lines by combination of IL-6, LIF, GM-CSF and G-CSF, *Int J Cancer* 45:353, 1989.

Mahler, H. R. and E. H. Cordes, in *Biological Chemistry*, p. 128, New York, Harper and Row (1966).

Maniatis, T., E. F. Fritsch and J. Sambrook, *Molecular Cloning, A Laboratory Manual.* Cold Spring Harbor Laboratory (1982).

Marinus, M. G. Location of DNA methylation genes on the *Escherichia coli* K-12 genetic map. *Molec. Gen. Genet.* 127: 47–55 (1973).

McBride, L. J. and Caruthers, M. H. An investigation of several deoxynucleoside phosphoramidites. *Tetrahedron Lett.*, 24, 245–248 (1983).

Messing, J., A multipurpose cloning system based on the single-stranded DNA bacteriophage M13. *Recombinant DNA Technical Bulletin*, NIH Publication No. 79–99, Vol. 2, No. 2, pp. 43–48 (1979).

Mayani, H. et al, Cytokine-induced selective expansion and maturation of erythroid versus myeloid progenitors from purified cord blood precursor cells, *Blood*, vol. 81, 3252–3258,1993.

Mazur, E et al, *Blood* 57:277–286, (1981).

Metcalf, D., Begley, C. G., Williamson, D., Nice, E. C., DeLamarter, J., Mermod J-J, Thatcher, D., Schmidt, A.: Hemopoietic responses in mice injected with purified recombinant murine GM-CSF. *Exp Hematol* 15:1, 1987.

Metcalf, D.: The molecular control of cell division, differentiation commitment and maturation in haemopoietic cells. *Nature* 339:27, 1989.

Metcalf, D., Nicola, N. A.: Direct proliferative actions of stem cell factor on murine bone marrow cells in vitro. Effects of combinatin with colony-stimulating factors. *Proc Natl Acad Sci USA* 88:6239, 1991.

Metcalf, D, Nicola, N A, The clonal proliferation of normal mouse hematopoietic cells: Enhancement and suppression by colony stimulating factor combinations, *Blood* 79: 2861, (1992).

Metcalf, D, Hematopoietic Regulators: Redundancy or Subtlety. *Blood*, 182: 3515–3523 (1993).

Migliaccio, G. et al, Long-term generation of colony-forming cells in liquid culture of CD34+ cord blood cells in the presence of recombinant human Stem Cell Factor, *Blood*, vol. 79, 2620–2627, 1992.

Neu, H. C. and L. A. Heppel. The release of enzymes from *Escherichia coli* by osmotic shock and during the formation of spheroplasts. *J. Biol. Chem.*, 240: 3685–3692 (1965).

Noguchi, M., Nakamura, Y., Russell, S. M., Ziegler, S. F., Tsang, M., Xiqing, C., Leonard, W. J.: Interleukin-2 Receptor g Chain: A Functional Component of the Interleukin-7 Receptor. *Science* 262:1877, Dec. 17, 1993.

Nordon, P, and Potter, M, A Macrophage-Derived Factor Required by plasmacytomas for Survival and Proliferation in Vitro, *Science* 233:566, (1986).

Obukowicz, M. G., Staten, N. R. and Krivi, G. G., Enhanced Heterologous Gene Expression in Novel rpoH Mutants of *Escherichia coli*. *Applied and Environmental Microbiology* 58, No. 5, p. 1511–1523 (1992).

Olins, P. O., C. S. Devine, S. H. Rangwala and K. S. Kavka, The T7 phage gene 10 leader RNA, a ribosome-binding site that dramatically enhances the expression of foreign genes in *Escherichia coli*, *Gene*, 73:227–235 (1988).

Olins, P. O. and S. H. Rangwala, Vector for enhanced translation of foreign genes in *Escherichia coli*, *Methods in Enzymology*, 185: 115–119 (1990).

Ploemacher, R E, van Soest, P L, Voorwinden, H, and Boudewijn, A, Interleukin-12 Synergizes with Interleukin-3 and Steel Factor to Enhance Recovery of Murine Hemopoietic Stem Cells in Liquid Culture, *Leukimia*, 7: no 6, 1381–1388, (1993).

Pluznik, D H and Sachs, L. Cloning of normal "mast" cells in tissue culture. *J Cell Comp Physiol* 66:319–324 (1965).

Postmus, et al., Effects of recombinant human interleukin-3 in patients with relapsed small-cell lung cancer treated with chemotherapy: a dose-finding study. *J. Clin. Oncol.*, 10:1131–1140 (1992).

Prober, J. M., G. L. Trainor, R. J. Dam, F. W. Hobbs, C. W. Robertson, R. J. Zagursky, A. J. Cocuzza, M. A. Jensen and K. Baumeister. A system for rapid DNA sequencing with fluorescent chain-terminating dideoxynucleotides. *Science* 238: 336–341 (1987).

Renart J., J. Reiser and G. R. Stark, Transfer of proteins from gels to diazobenzyloxymethyl-paper and detection with anti-sera: a method for studying antibody specificity and antigen structure, *Proc. Natl. Acad. Sci. USA*, 76:3116–3120 (1979).

Robinson, B E, McGrath, H E, Quesenberry, P J, Recombinant murine GM-CSF has megakaryocyte stimulating action and augments megakaryocyte colony stimulating by IL-3. *J. Clin. Invest.* 79: 1548, (1987).

Russell, S. M., Keegan, A. D., Harada, N., Nakamura, Y., Noguchi, M., Leland, P., Friedmann, M. C., Miyajima, A., Puri, R. K., Paul, W. E., Leonard, W. J.: Interleukin-2 Receptor g Chain: A Functional Component of the Interleukin-4 Receptor. *Science* 262:1880, Dec. 17, 1993.

Saiki, R. K., Schorf, S., Faloona, F., Mullis, K. B., Horn, G. T., Erlich, H. A. and Arnheim, N., Enzymatic Amplification of β-Globin Genomic Sequences and Restriction Site Analysis for Diagnosis of Sickle Cell Anemia, *Science*, 230: 1350–1354 (1985).

Sambrook, J., et al., *Molecular Cloning, A Laboratory Manual*, 2nd edition, Cold Spring Harbor Laboratory (1989).

Sancar, A., C. Stachelek, W. Konigsberg and W. D. Rupp, Sequences of the recA gene and protein, *Proc. Natl. Acad. Sci.*, 77: 2611–2615 (1980).

Sanger, F., S. Nicklen and A. R. Coulson. DNA sequencing with chain-terminating inhibitors. *Proc. Natl. Acad. Sci. USA* 74: 5463–5467 (1977).

Santoli, D., Y. Yang, S. C. Clark, B. L. Kreider, D. Caracciolo, and G. Rovera. Synergistic and antagonistic effects of recombinant human interleukin (IL-3), IL-1, granulocyte and macrophage colony-stimulating factors (G-CSF and M-CSF) on the growth of GM-CSF-dependent leukemic cell lines. *J. Immunol.* 139:348 (1987).

Sherr, C. J.: Colony-stimulating factor-1 receptor. *Blood* 75:1, 1990.

Smith, M. In vitro mutagenesis. *Ann. Rev. Genet.*, 19:423–462 (1985).

Soberon, X., L. Covarrubias and F. Bolivar, Construction and characterization of new cloning vehicles. IV. Deletion derivatives of pBR322 and pBR325, *Gene*, 9: 211–223 (1980).

Sonoda, Y, Yang, Y C, Wong, G G, Clark, S C, Ogawa, M, Analysis in serum-free culture of the targets of recombinant human hemopoietic growth factors: IL-3 and GM-CSF are specific for early development stages, *Proc Natl Acad Sci USA*. 85: 4360, (1988).

Stader, J. A. and T. J. Silhavy. Engineering *Escherichia coli* to secrete heterologous gene products, *Methods in Enzymology*, 185: 166–87 (1990).

Stahl, C P, Winton, E F, Monroe, M C, Haff, E, Holman, R C, Meyers, L A, Liehl,E, and Evatt, B, Differential effects of sequential, simultaneous and single agent IL-3 and and GM-CSF on megakaryocyte maturation and platelet response in primates, *Blood,* 80: 2479, (1992).

Summers, M. D. and G. E. Smith. A manual of methods for Baculovirus vectors and insect cell culture procedures. *Texas Agricultural Experiment Station Bulletin No.* 1555 (1987).

Taga, T., Hibi, M., Yamasaki, K., Yasukswa, K., Matsuda, T., Hirano, T., and Kishimoto, T. Interleukin-6 triggers the association of its receptor with a possibele signal transducer, gp130. *Cell* 58(3):573–81 (1989).

Takaki, S., Tominage, A., Hitoshi, Y., Mita S., Sonada, E., Yamaguchi, N., Takatsu, K.: Molecular cloning and expression of the murine interleukin-5 receptor. *EMBO J* 9:4367, 1990.

Taylor, J. W., Ott, J. and Eckstein, F. The rapid generation of oligonucleotide-directed mutants at high frequency using phosphorothioate modified DNA. *Nucl. Acids Res.,* 13:8764–8785 (1985).

Tomer, A., Harker, L. A., and Burstein, S. A. Purification of human megakaryocytes by Fluoresence-activated cell sorting. *Blood* 70(6):1735–1742 (1987). Treco, D. A., (1989) in *Current protocols in Molecular Biology,* Seidman et al., eds. J Wiley N.Y., unit 2.1.

Valtieri, M., D. Santoli, D. Caracciolo, B. L. Kreider, S. W. Altmann, D. J. Tweardy, I. Gemperlein, F. Mavilio, B. J. Lange and G. Rovera. Establishment and characterization of an undifferentiated human T leukemia cell line which requires granulocyte-macrophage colony stimulating factor for growth. *J. Immunol.* 138:4042 (1987).

Voet, D., W. B. Gatzer, R. A. Cox, P. Doty. Absorption spectra of the common bases. *Biopolymers* 1: 193 (1963).

Weinberg, R. A., De Ciechi, P. A., Obukowicz, M.: A chromosomal expression vector for *Escherichia coli* based on the bacteriophage Mu. *Gene* 126 (1993) 25–33.

Wells, J. A., Vasser, M., and Powers, D. B. Cassette mutagenesis: an effective method for generation of multiple mutants at defined sites. *Gene,* 34:315–323 (1985).

Wong, Y. Y., R. Seetharam, C. Kotts, R. A. Heeren, B. K. Klein, S. B. Braford, K. J. Mathis, B. F. Bishop, N. R. Siegel, C. E. Smith and W. C. Tacon. Expression of secreted IGF-1 in *Escherichia coli. Gene,* 68: 193–203 (1988).

Yanisch-Perron, C., J. Viera and J. Messing. Improved M13 phage cloning vectors and host strains: nucleotide sequences of the M13mp18 and pUC19 vectors. *Gene* 33: 103–119 (1985).

Yamasaki, K., Taga, T., Hirata, Y., Yawata, H., Kawanishi, Y., Seed, B., Taniguchi, T., Hirano, T., Kishimoto, T.: Cloning and expression of the human interleukin-6 (BSF-2?IFN beta 2) receptor. *Science* 241:825, 1988.

Yarden Y., Kuang, W-J., Yang-Feng, T., Coussens, L., Munemitsu, S., Dull, T. J., Chen, E., Schlesinger, J., Francke, U., Ullrich, A., Human proto-oncogene c-kit: A new cell surface receptor tyrosine kinase for an unidentified ligand. *EMBO J* 6:3341, 1987.

Zoller, M. J. and Smith, M. Oligonucleotide-directed mutagenesis using M13-derived vectors: an efficient and general procedure for the production of point mutations in any fragment of DNA. *Nucleic Acid Research,* 10: 6487–6500 (1982).

Zoller, M. J. and Smith, M. Oligonucleotide-directed mutagenesis of DNA fragments cloned into M13 vectors. *Methods in Enzymology,* 100:468–500 (1983).

Zoller, M. J. and Smith, M. Oligonucleotide-directed Mutagenesis: A simple method using two oligonucleotide primers and a single-stranded DNA template. *DNA* 3: 479 (1984).

```

What is claimed is:

1. A method of treating a patient having a hematopoietic disorder comprising; administering to said patient a therapeutically effective amount of a composition comprising;
   a modified human interleukin-3 (hIL-3) amino acid sequence, wherein said modified sequence differs from the sequence of native (1–133) hIL-3 by the replacement of from 4 to about 44 of the residues corresponding to positions 17–118 of native (1–133) hIL-3 by other amino acids, with the proviso that the residues corresponding to positions 101 and 116 are not Ala or Val, respectively, and with the proviso that no more than one of the amino acids at positions 63, 82, 87, 98, and 112 are different from the corresponding amino acids in native human interleukin-3; wherein said modified sequence optionally further differs from the sequence of native (1–133) hIL-3 by the deletion of from 1 to 14 residues from the N-terminus of native (1–133) hIL-3, the deletion of from 1 to 15 residues from the C-terminus of native (1–133) hIL-3, or both; and wherein said modified interleukin-3 (hIL-3) amino acid sequence has increased activity, relative to native human interleukin-3, in at least one assay selected from the group consisting of: AML cell proliferation, TF-1 cell proliferation and Methylcellulose assay;
   a factor selected from the group consisting of: a colony stimulating factor, a cytokine a lymphokine, an interleukin and a hematopoietic growth factor.

2. A method of treating a patient having a hematopoietic disorder comprising; administering to said patient a therapeutically effective amount of a composition comprising:
   a biologically active human interleukin-3 variant polypeptide, said polypeptide comprising a sequence selected from the group consisting of:
   (a) the sequence of SEQ ID NO:1; and
   (b) a polypeptide comprising an N-terminal methionine residue, alanine residue or methionine-alanine di-peptide immediately preceding said sequence according to (a);
wherein;
   Xaa at position 17 is Ser, Lys, Gly, Asp, Met, Gln, or Arg;
   Xaa at position 18 is Asn, His, Leu, Ile, Phe, Arg, or Gln;
   Xaa at position 19 is Met, Phe, Ile, Arg, Gly, Ala, or Cys;
   Xaa at position 20 is Ile, Cys, Gln, Glu, Arg, Pro, or Ala;
   Xaa at position 21 is Asp, Phe, Lys, Arg, Ala, Gly, Glu, Gln, Asn, Thr, Ser or Val;
   Xaa at position 22 is Glu, Trp, Pro, Ser, Ala, His, Asp, Asn, Gln, Leu, Val or Gly;
   Xaa at position 23 is Ile, Val, Ala, Leu, Gly, Trp, Lys, Phe, Ser, or Arg;
   Xaa at position 24 is Ile, Gly, Val, Arg, Ser, Phe, or Leu;
   Xaa at position 25 is Thr, His, Gly, Gln, Arg, Pro, or Ala;
   Xaa at position 26 is His, Thr, Phe, Gly, Arg, Ala, or Trp;
   Xaa at position 27 is Leu, Gly, Arg, Thr, Ser, or Ala;
   Xaa at position 28 is Lys, Arg, Leu, Gln, Gly, Pro, Val or Trp;
   Xaa at position 29 is Gln, Asn, Leu, Pro, Arg, or Val;
   Xaa at position 30 is Pro, His, Thr, Gly, Asp, Gln, Ser, Leu, or Lys;
   Xaa at position 31 is Pro, Asp, Gly, Ala, Arg, Leu, or Gln;
   Xaa at position 32 is Leu, Val, Arg, Gln, Asn, Gly, Ala, or Glu;
   Xaa at position 33 is Pro, Leu, Gln, Ala, Thr, or Glu;
   Xaa at position 34 is Leu, Val, Gly, Ser, Lys, Glu, Gln, Thr, Arg, Ala, Phe, Ile or Met;
   Xaa at position 35 is Leu, Ala, Gly, Asn, Pro, Gln, or Val;
   Xaa at position 36 is Asp, Leu, or Val;
   Xaa at position 37 is Phe, Ser, Pro, Trp, or Ile;
   Xaa at position 38 is Asn, or Ala;
   Xaa at position 40 is Leu, Trp, or Arg;
   Xaa at position 41 is Asn, Cys, Arg, Leu, His, Met, or Pro;
   Xaa at position 42 is Gly, Asp, Ser, Cys, Asn, Lys, Thr, Leu, Val, Glu, Phe, Tyr, Ile, Met or Ala;
   Xaa at position 43 is Glu, Asn, Tyr, Leu, Phe, Asp, Ala, Cys, Gln, Arg, Thr, Gly or Ser;
   Xaa at position 44 is Asp, Ser, Leu, Arg, Lys, Thr, Met, Trp, Glu, Asn, Gln, Ala or Pro;
   Xaa at position 45 is Gln, Pro, Phe, Val, Met, Leu, Thr, Lys, Trp, Asp, Asn, Arg, Ser, Ala, Ile, Glu or His;
   Xaa at position 46 is Asp, Phe, Ser, Thr, Cys, Glu, Asn, Gln, Lys, His, Ala, Tyr, Ile, Val or Gly;
   Xaa at position 47 is Ile, Gly, Val, Ser, Arg, Pro, or His;
   Xaa at position 48 is Leu, Ser, Cys, Arg, Ile, His, Phe, Glu, Lys, Thr, Ala, Met, Val or Asn;
   Xaa at position 49 is Met, Arg, Ala, Gly, Pro, Asn, His, or Asp;
   Xaa at position 50 is Glu, Leu, Thr, Asp, Tyr, Lys, Asn, Ser, Ala, Ile, Val, His, Phe, Met or Gln;
   Xaa at position 51 is Asn, Arg, Met, Pro, Ser, Thr, or His;
   Xaa at position 52 is Asn, His, Arg, Leu, Gly, Ser, or Thr;
   Xaa at position 53 is Leu, Thr, Ala, Gly, Glu, Pro, Lys, Ser, or Met;
   Xaa at position 54 is Arg, Asp, Ile, Ser, Val, Thr, Gln, Asn, Lys, His, Ala or Leu;
   Xaa at position 55 is Arg, Thr, Val, Ser, Leu, or Gly;
   Xaa at position 56 is Pro, Gly, Cys, Ser, Gln, Glu, Arg, His, Thr, Ala, Tyr, Phe, Leu, Val or Lys;

Xaa at position 57 is Asn or Gly;

Xaa at position 58 is Leu, Ser, Asp, Arg, Gln, Val, or Cys;

Xaa at position 59 is Glu, Tyr, His, Leu, Pro, or Arg;

Xaa at position 60 is Ala, Ser, Pro, Tyr, Asn, or Thr;

Xaa at position 61 is Phe, Asn, Glu, Pro, Lys, Arg, or Ser;

Xaa at position 62 is Asn, His, Val, Arg, Pro, Thr, Asp, or Ile;

Xaa at position 63 is Arg, Tyr, Trp, Lys, Ser, His, Pro, or Val;

Xaa at position 64 is Ala, Asn, Pro, Ser, or Lys;

Xaa at position 65 is Val, Thr, Pro, His, Leu, Phe, or Ser;

Xaa at position 66 is Lys, Ile, Arg, Val, Asn, Glu, or Ser;

Xaa at position 67 is Ser, Ala, Phe, Val, Gly, Asn, Ile, Pro, or His;

Xaa at position 68 is Leu, Val, Trp, Ser, Ile, Phe, Thr, or His;

Xaa at position 69 is Gln, Ala, Pro, Thr, Glu, Arg, Trp, Gly, or Leu;

Xaa at position 70 is Asn, Leu, Val, Trp, Pro, or Ala;

Xaa at position 71 is Ala, Met, Leu, Pro, Arg, Glu, Thr, Gln, Trp, or Asn;

Xaa at position 72 is Ser, Glu, Met, Ala, His, Asn, Arg, or Asp;

Xaa at position 73 is Ala, Glu, Asp, Leu, Ser, Gly, Thr, or Arg;

Xaa at position 74 is Ile, Met, Thr, Pro, Arg, Gly, Ala;

Xaa at position 75 is Glu, Lys, Gly, Asp, Pro, Trp, Arg, Ser, Gln, or Leu;

Xaa at position 76 is Ser, Val, Ala, Asn, Trp, Glu, Pro, Gly, or Asp;

Xaa at position 77 is Ile, Ser, Arg, Thr, or Leu;

Xaa at position 78 is Leu, Ala, Ser, Glu, Phe, Gly, or Arg;

Xaa at position 79 is Lys, Thr, Asn, Met, Arg, Ile, Gly, or Asp;

Xaa at position 80 is Asn, Trp, Val, Gly, Thr, Leu, Glu, or Arg;

Xaa at position 81 is Leu, Gln, Gly, Ala, Trp, Arg, Val, or Lys;

Xaa at position 82 is Leu, Gln, Lys, Trp, Arg, Asp, Glu, Asn, His, Thr, Ser, Ala, Tyr, Phe, Ile, Met or Val;

Xaa at position 83 is Pro, Ala, Thr, Trp, Arg, or Met;

Xaa at position 84 is Cys, Glu, Gly, Arg, Met, or Val;

Xaa at position 85 is Leu, Asn, Val, or Gln;

Xaa at position 86 is Pro, Cys, Arg, Ala, or Lys;

Xaa at position 87 is Leu, Ser, Trp, or Gly;

Xaa at position 88 is Ala, Lys, Arg, Val, or Trp;

Xaa at position 89 is Thr, Asp, Cys, Leu, Val, Glu, His, Asn, or Ser;

Xaa at position 90 is Ala, Pro, Ser, Thr, Gly, Asp, Ile, or Met;

Xaa at position 91 is Ala, Pro, Ser, Thr, Phe, Leu, Asp, or His;

Xaa at position 92 is Pro, Phe, Arg, Ser, Lys, His, Ala, Gly, Ile or Leu;

Xaa at position 93 is Thr, Asp, Ser, Asn, Pro, Ala, Leu, or Arg;

Xaa at position 94 is Arg, Ile, Ser, Glu, Leu, Val, Gln, Lys, His, Ala, or Pro;

Xaa at position 95 is His, Gln, Pro, Arg, Val, Leu, Gly, Thr, Asn, Lys, Ser, Ala, Trp, Phe, Ile, or Tyr;

Xaa at position 96 is Pro, Lys, Tyr, Gly, Ile, or Thr;

Xaa at position 97 is Ile, Val, Lys, Ala, or Asn;

Xaa at position 98 is His, Ile, Asn, Leu, Asp, Ala, Thr, Glu, Gln, Ser, Phe, Met, Val, Lys, Arg, Tyr or Pro;

Xaa at position 99 is Ile, Leu, Arg, Asp, Val, Pro, Gln, Gly, Ser, Phe, or His;

Xaa at position 100 is Lys, Tyr, Leu, His, Arg, Ile, Ser, Gln, or Pro;

Xaa at position 101 is Asp;

Xaa at position 102 is Gly, Leu, Glu, Lys, Ser, Tyr, or Pro;

Xaa at position 103 is Asp, or Ser;

Xaa at position 104 is Trp, Val, Cys, Tyr, Thr, Met, Pro, Leu, Gln, Lys, Ala, Phe, or Gly;

Xaa at position 105 is Asn, Pro, Ala, Phe, Ser, Trp, Gln, Tyr, Leu, Lys, Ile, Asp, or His;

Xaa at position 106 is Glu, Ser, Ala, Lys, Thr, Ile, Gly, or Pro;

Xaa at position 108 is Arg, Lys, Asp, Leu, Thr, Ile, Gln, His, Ser, Ala or Pro;

Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, Ala, or Trp;

Xaa at position 111 is Leu, Ile, Arg, Asp, or Met;

Xaa at position 112 is Thr, Val, Gln, Tyr, Glu, His, Ser, or Phe;

Xaa at position 113 is Phe, Ser, Cys, His, Gly, Trp, Tyr, Asp, Lys, Leu, Ile, Val or Asn;

Xaa at position 114 is Tyr, Cys, His, Ser, Trp, Arg, or Leu;

Xaa at position 115 is Leu, Asn, Val, Pro, Arg, Ala, His, Thr, Trp, or Met;

Xaa at position 116 is Lys;

Xaa at position 117 is Thr, Ser, Asn, Ile, Trp, Lys, or Pro;

Xaa at position 118 is Leu, Ser, Pro, Ala, Glu, Cys, Asp, or Tyr;

Xaa at position 119 is Glu, Ser, Lys, Pro, Leu, Thr, Tyr, or Arg;

Xaa at position 120 is Asn, Ala, Pro, Leu, His, Val, or Gln;

Xaa at position 121 is Ala, Ser, Ile, Asn, Pro, Lys, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

wherein from 6 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus of said sequence of SEQ ID NO:1; and a factor selected from the group consisting of: a colony stimulating factor, a cytokine, a lymphokine, an interleukin, and a hematopoietic growth factor.

3. The method of claim 2, wherein (a) is the sequence of SEQ ID NO:3;

wherein

Xaa at position 17 is Ser, Gly, Asp, or Gln;

Xaa at position 18 is Asn, His, or Ile;

Xaa at position 23 is Ile, Ala, Leu, or Gly;

Xaa at position 25 is Thr, His, or Gln;

Xaa at position 26 is His or Ala;
Xaa at position 29 is Gln or Asn;
Xaa at position 30 is Pro or Gly;
Xaa at position 32 is Leu, Arg, Asn, or Ala;
Xaa at position 34 is Leu, Val, Ser, Ala, Arg, Gln, Glu, Ile, Phe, Thr, or Met;
Xaa at position 35 is Leu, Ala, Asn, or Pro;
Xaa at position 38 is Asn or Ala;
Xaa at position 42 is Gly, Asp, Ser, Ala, Asn, Ile, Leu, Met, Tyr or Arg;
Xaa at position 45 is Gln, Val, Met, Leu, Ala, Asn, Glu, or Lys;
Xaa at position 46 is Asp, Phe, Ser, Gln, Glu, His, Val or Thr;
Xaa at position 50 is Glu, Asn, Ser or Asp;
Xaa at position 51 is Asn, Arg, Pro, Thr, or His;
Xaa at position 55 is Arg, Leu, or Gly;
Xaa at position 56 is Pro, Gly, Ser, Ala, Asn, Val, Leu or Gln;
Xaa at position 62 is Asn, Pro, or Thr;
Xaa at position 64 is Ala or Asn;
Xaa at position 65 is Val or Thr;
Xaa at position 67 is Ser or Phe;
Xaa at position 68 is Leu or Phe;
Xaa at position 69 is Gln, Ala, Glu, or Arg;
Xaa at position 76 is Ser, Val, Asn, Pro, or Gly;
Xaa at position 77 is Ile or Leu;
Xaa at position 79 is Lys, Asn, Met, Arg, Ile, or Gly;
Xaa at position 80 is Asn, Gly, Glu, or Arg;
Xaa at position 82 is Leu, Gln, Trp, Arg, Asp, Asn, Glu, His, Met, Phe, Ser, Thr, Tyr or Val;
Xaa at position 87 is Leu or Ser;
Xaa at position 88 is Ala or Trp;
Xaa at position 91 is Ala or Pro;
Xaa at position 93 is Thr, Asp, or Ala;
Xaa at position 95 is His, Pro, Arg, Val, Gly, Asn, Ser or Thr;
Xaa at position 98 is His, Ile, Asn, Ala, Thr, Gln, Glu, Lys, Met, Ser, Tyr, Val or Leu;
Xaa at position 99 is Ile or Leu;
Xaa at position 100 is Lys or Arg;
Xaa at position 101 is Asp;
Xaa at position 105 is Asn, Pro, Ser, Ile or Asp;
Xaa at position 108 is Arg, Ala, or Ser;
Xaa at position 109 is Arg, Thr, Glu, Leu, or Ser;
Xaa at position 112 is Thr or Gln;
Xaa at position 116 is Lys;
Xaa at position 120 is Asn, Pro, Leu, His, Val, or Gln;
Xaa at position 121 is Ala, Ser, Ile, Pro, or Asp;
Xaa at position 122 is Gln, Met, Trp, Phe, Pro, His, Ile, or Tyr;
Xaa at position 123 is Ala, Met, Glu, Ser, or Leu;
wherein from 6 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus of said sequence of SEQ ID No: 3.

4. The method of claim 2, wherein in said human interleukin-3 mutant polypeptide, the amino acids which differ from the corresponding residue in native human interleukin-3 are selected from the group consisting of:

position 42 wherein Xaa is Gly, Asp, Ser, Ile, Leu, Met, Tyr, or Ala;

position 45 wherein Xaa is Gin, Val, Met or Asn;

position 46 wherein Xaa is Asp, Ser, Gin, His or Val;

position 50 wherein Xaa is Glu or Asp;

position 51 wherein Xaa is Asn, Pro or Thr;

position 62 wherein Xaa is Asn or Pro;

position 76 wherein Xaa is Ser, or Pro;

position 82 wherein Xaa is Leu, Trp, Asp, Asn, Glu, His, Phe, Ser or Tyr;

position 95 wherein Xaa is His, Arg, Thr, Asn or Ser;

position 98 wherein Xaa is His, Ile, Leu, Ala, Gin, Lys, Met, Ser, Tyr or Val;

position 100 wherein Xaa is Lys or Arg;

position 105 wherein Xaa is Asn, or Pro;

position 108 wherein Xaa is Arg, Ala, or Ser;

position 121 wherein Xaa is Ala, or Ile;

position 122 wherein Xaa is Gin, or Ile; and position 123 wherein Xaa is Ala, Met or Glu;

wherein from 6 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus.

5. A method of treating a patient having a hematopoietic disorder comprising; administering to said patient a therapeutically effective amount of a composition comprising;

a biologically active human interleukin-3 variant polypeptide, said polypeptide comprising a sequence selected from the group consisting of:

(a) the sequence of SEQ ID NO:4; and (b) a polypeptide comprising an N-terminal residue, alanine residue or methionine-alanine di-peptide immediately preceding said sequence according to (a);

wherein;

Xaa at position 3 is Ser, Lys, Gly, Asp, Met, Gln, or Arg;

Xaa at position 4 is Asn, His, Leu, Ile, Phe, Arg, or Gln;

Xaa at position 5 is Met, Phe, Ile, Arg, Gly, Ala, or Cys;

Xaa at position 6 is Ile, Cys, Gln, Glu, Arg, Pro, or Ala;

Xaa at position 7 is Asp, Phe, Lys, Arg, Ala, Gly, Glu, Gln, Asn, Thr, Ser or Val;

Xaa at position 8 is Glu, Trp, Pro, Ser, Ala, His, Asp, Asn, Gln, Leu, Val, or Gly;

Xaa at position 9 is Ile, Val, Ala, Leu, Gly, Trp, Lys, Phe, Ser, or Arg;

Xaa at position 10 is Ile, Gly, Val, Arg, Ser, Phe, or Leu;

Xaa at position 11 is Thr, His, Gly, Gln, Arg, Pro, or Ala;

Xaa at position 12 is His, Thr, Phe, Gly, Arg, Ala, or Trp;

Xaa at position 13 is Leu, Gly, Arg, Thr, Ser, or Ala;

Xaa at position 14 is Lys, Arg, Leu, Gln, Gly, Pro, Val or Trp;

Xaa at position 15 is Gln, Asn, Leu, Pro, Arg, or Val;

Xaa at position 16 is Pro, His, Thr, Gly, Asp, Gln, Ser, Leu, or Lys;

Xaa at position 17 is Pro, Asp, Gly, Ala, Arg, Leu, or Gln;

Xaa at position 18 is Leu, Val, Arg, Gln, Asn, Gly, Ala, or Glu;

Xaa at position 19 is Pro, Leu, Gln, Ala, Thr, or Glu;
Xaa at position 20 is Leu, Val, Gly, Ser, Lys, Glu, Gln, Thr, Arg, Ala, Phe, Ile or Met;
Xaa at position 21 is Leu, Ala, Gly, Asn, Pro, Gln, or Val;
Xaa at position 22 is Asp, Leu, or Val;
Xaa at position 23 is Phe, Ser, Pro, Trp, or Ile;
Xaa at position 24 is Asn, or Ala;
Xaa at position 26 is Leu, Trp, or Arg;
Xaa at position 27 is Asn, Cys, Arg, Leu, His, Met, Pro;
Xaa at position 28 is Gly, Asp, Ser, Cys, Ala, Lys, Asn, Thr, Leu, Val, Glu, Phe, Tyr, Ile or Met;
Xaa at position 29 is Glu, Asn, Tyr, Leu, Phe, Asp, Ala, Cys, Gln, Arg, Thr, Gly or Ser;
Xaa at position 30 is Asp, Ser, Leu, Arg, Lys, Thr, Met, Trp, Glu, Asn, Gln, Ala or Pro;
Xaa at position 31 is Gln, Pro, Phe, Val, Met, Leu, Thr, Lys, Asp, Asn, Arg, Ser, Ala, Ile, Glu, His or Trp;
Xaa at position 32 is Asp, Phe, Ser, Thr, Cys, Glu, Asn, Gln, Lys, His, Ala, Tyr, Ile, Val or Gly;
Xaa at position 33 is Ile, Gly, Val, Ser, Arg, Pro, or His;
Xaa at position 34 is Leu, Ser, Cys, Arg, Ile, His, Phe, Glu, Lys, Thr, Ala, Met, Val or Asn;
Xaa at position 35 is Met, Arg, Ala, Gly, Pro, Asn, His, or Asp;
Xaa at position 36 is Glu, Leu, Thr, Asp, Tyr, Lys, Asn, Ser, Ala, Ile, Val, His, Phe, Met or Gln;
Xaa at position 37 is Asn, Arg, Met, Pro, Ser, Thr, or His;
Xaa at position 38 is Asn, His, Arg, Leu, Gly, Ser, or Thr;
Xaa at position 39 is Leu, Thr, Ala, Gly, Glu, Pro, Lys, Ser, or Met;
Xaa at position 40 is Arg, Asp, Ile, Ser, Val, Thr, Gln, Asn, Lys, His, Ala or Leu;
Xaa at position 41 is Arg, Thr, Val, Ser, Leu, or Gly;
Xaa at position 42 is Pro, Gly, Cys, Ser, Gln, Glu, Arg, His, Thr, Ala, Tyr, Phe, Leu, Val or Lys;
Xaa at position 43 is Asn or Gly;
Xaa at position 44 is Leu, Ser, Asp, Arg, Gln, Val, or Cys;
Xaa at position 45 is Glu, Tyr, His, Leu, Pro, or Arg;
Xaa at position 46 is Ala, Ser, Pro, Tyr, Asn, or Thr;
Xaa at position 47 is Phe, Asn, Glu, Pro, Lys, Arg, or Ser;
Xaa at position 48 is Asn, His, Val, Arg, Pro, Thr, Asp, or Ile;
Xaa at position 49 is Arg, Tyr, Trp, Lys, Ser, His, Pro, or Val;
Xaa at position 50 is Ala, Asn, Pro, Ser, or Lys;
Xaa at position 51 is Val, Thr, Pro, His, Leu, Phe, or Ser;
Xaa at position 52 is Lys, Ile, Arg, Val, Asn, Glu, or Ser;
Xaa at position 53 is Ser, Ala, Phe, Val, Gly, Asn, Ile, Pro, or His;
Xaa at position 54 is Leu, Val, Trp, Ser, Ile, Phe, Thr, or His;
Xaa at position 55 is Gln, Ala, Pro, Thr, Glu, Arg, Trp, Gly, or Leu;
Xaa at position 56 is Asn, Leu, Val, Trp, Pro, or Ala;
Xaa at position 57 is Ala, Met, Leu, Pro, Arg, Glu, Thr, Gln, Trp, or Asn;
Xaa at position 58 is Ser, Glu, Met, Ala, His, Asn, Arg, or Asp;
Xaa at position 59 is Ala, Glu, Asp, Leu, Ser, Gly, Thr, or Arg;
Xaa at position 60 is Ile, Met, Thr, Pro, Arg, Gly, Ala;
Xaa at position 61 is Glu, Lys, Gly, Asp, Pro, Trp, Arg, Ser, Gln, or Leu;
Xaa at position 62 is Ser, Val, Ala, Asn, Trp, Glu, Pro, Gly, or Asp;
Xaa at position 63 is Ile, Ser, Arg, Thr, or Leu;
Xaa at position 64 is Leu,, Ala, Ser, Glu, Phe, Gly, or Arg;
Xaa at position 65 is Lys, Thr, Gly, Asn, Met, Arg, Ile, or Asp;
Xaa at position 66 is Asn, Trp, Val, Gly, Thr, Leu, Glu, or Arg;
Xaa at position 67 is Leu, Gln, Gly, Ala, Trp, Arg, Val, or Lys;
Xaa at position 68 is Leu, Gln, Lys, Trp, Arg, Asp, Glu, Asn, His, Thr, Ser, Ala, Tyr, Phe, Ile, Met or Val;
Xaa at position 69 is Pro, Ala, Thr, Trp, Arg, or Met;
Xaa at position 70 is Cys, Glu, Gly, Arg, Met, or Val;
Xaa at position 71 is Leu, Asn, Val, or Gln;
Xaa at position 72 is Pro, Cys, Arg, Ala, or Lys;
Xaa at position 73 is Leu, Ser, Trp, or Gly;
Xaa at position 74 is Ala, Lys, Arg, Val, or Trp;
Xaa at position 75 is Thr, Asp, Cys, Leu, Val, Glu, His, Asn, or Ser;
Xaa at position 76 is Ala, Pro, Ser, Thr, Gly, Asp, Ile, or Met;
Xaa at position 77 is Ala, Pro, Ser, Thr, Phe, Leu, Asp, or His;
Xaa at position 78 is Pro, Phe, Arg, Ser, Lys, His, Ala, Gly, Ile or Leu;
Xaa at position 79 is Thr, Asp, Ser, Asn, Pro, Ala, Leu, or Arg;
Xaa at position 80 is Arg, Ile, Ser, Glu, Leu, Val, Gln, Lys, His, Ala or Pro;
Xaa at position 81 is His, Gln, Pro, Arg, Val, Leu, Gly, Thr, Asn, Lys, Ser, Ala, Trp, Phe, Ile or Tyr;
Xaa at position 82 is Pro, Lys, Tyr, Gly, Ile, or Thr;
Xaa at position 83 is Ile, Val, Lys, Ala, or Asn;
Xaa at position 84 is His, Ile, Asn, Leu, Asp, Ala, Thr, Glu, Gln, Ser, Phe, Met, Val, Lys, Arg, Tyr or Pro;
Xaa at position 85 is Ile, Leu, Arg, Asp, Val, Pro, Gln, Gly, Ser, Phe, or His;
Xaa at position 86 is Lys, Tyr, Leu, His, Arg, Ile, Ser, Gln, Pro;
Xaa at position 87 is Asp;
Xaa at position 88 is Gly, Leu, Glu, Lys, Ser, Tyr, or Pro;
Xaa at position 89 is Asp, or Ser;
Xaa at position 90 is Trp, Val, Cys, Tyr, Thr, Met, Pro, Leu, Gln, Lys, Ala, Phe, or Gly;
Xaa at position 91 is Asn, Pro, Ala, Phe, Ser, Trp, Gln, Tyr, Leu, Lys, Ile, Asp, or His;
Xaa at position 92 is Glu, Ser, Ala, Lys, Thr, Ile, Gly, or Pro;
Xaa at position 94 is Arg, Lys, Asp, Leu, Thr, Ile, Gln, His, Ser, Ala, or Pro;
Xaa at position 95 is Arg, Thr, Pro, Glu, Tyr, Leu, Ser, or Gly;
Xaa at position 96 is Lys, Asn, Thr, Leu, Gln, Arg, His, Glu, Ser, Ala or Trp;
Xaa at position 97 is Leu, Ile, Arg, Asp, or Met;
Xaa at position 98 is Thr, Val, Gln, Tyr, Glu, His, Ser, or Phe;

Xaa at position 99 is Phe, Ser, Cys, His, Gly, Trp, Tyr, Asp, Lys, Leu, Ile, Val or Asn;

Xaa at position 100 is Tyr, Cys, His, Ser, Trp, Arg, or Leu;

Xaa at position 101 is Leu, Asn, Val, Pro, Arg, Ala, His, Thr, Trp, or Met;

Xaa at position 102 is Lys;

Xaa at position 103 is Thr, Ser, Asn, Ile, Trp, Lys, or Pro;

Xaa at position 104 is Leu, Ser, Pro, Ala, Glu, Cys, Asp, or Tyr;

Xaa at position 105 is Glu, Ser, Lys, Pro, Leu, Thr, Tyr, or Arg;

Xaa at position 106 is Asn, Ala, Pro, Leu, His, Val, or Gln;

Xaa at position 107 is Ala, Ser, Ile, Asn, Pro, Lys, Asp, or Gly;

Xaa at position 108 is Gln, Ser, Met, Trp, Arg, Phe, Pro, His, Ile, Tyr, or Cys;

Xaa at position 109 is Ala, Met, Glu, His, Ser, Pro, Tyr, or Leu;

wherein from 6 to about 44 of the amino acids designated by Xaa are different from the corresponding native amino acids of (1–133) human interleukin-3; and a factor selected from the group consisting of: a colony stimulating factor, a cytokine, a lymphokine, an interleukin, and a hematopoietic growth factor.

6. The method of claim 5, wherein (a) is the sequence of SEQ ID NO:6;
wherein

Xaa at position 3 is Ser, Gly, Asp, or Gln;

Xaa at position 4 is Asn, His, or Ile;

Xaa at position 9 is Ile, Ala, Leu, or Gly;

Xaa at position 11 is Thr, His, or Gln;

Xaa at position 12 is His or Ala;

Xaa at position 15 is Gln or Asn;

Xaa at position 16 is Pro or Gly;

Xaa at position 18 is Leu, Arg, Asn, or Ala;

Xaa at position 20 is Leu, Val, Ser, Ala, Arg, Gln, Glu, Ile, Phe, Thr or Met;

Xaa at position 21 is Leu, Ala, Asn, or Pro;

Xaa at position 24 is Asn or Ala;

Xaa at position 28 is Gly, Asp, Ser, Ala, Asn, Ile, Leu, Met, Tyr or Arg;

Xaa at position 31 is Gln, Val, Met, Leu, Ala, Asn, Glu or Lys;

Xaa at position 32 is Asp, Phe, Ser, Ala, Gln, Glu, His, Val or Thr;

Xaa at position 36 is Glu, Asn, Ser or Asp;

Xaa at position 37 is Asn, Arg, Pro, Thr, or His;

Xaa at position 41 is Arg, Leu, or Gly;

Xaa at position 42 is Pro, Gly, Ser, Ala, Asn, Val, Leu or Gln;

Xaa at position 48 is Asn, Pro, or Thr;

Xaa at position 50 is Ala or Asn;

Xaa at position 51 is Val or Thr;

Xaa at position 53 is Ser or Phe;

Xaa at position 54 is Leu or Phe;

Xaa at position 55 is Gln, Ala, Glu, or Arg;

Xaa at position 62 is Ser, Val, Asn, Pro, or Gly;

Xaa at position 63 is Ile or Leu;

Xaa at position 65 is Lys, Asn, Met, Arg, Ile, or Gly;

Xaa at position 66 is Asn, Gly, Glu, or Arg;

Xaa at position 68 is Leu, Gln, Trp, Arg, Asp, Asn, Glu, His, Met, Phe, Ser, Thr, Tyr or Val;

Xaa at position 73 is Leu or Ser;

Xaa at position 74 is Ala or Trp;

Xaa at position 77 is Ala or Pro;

Xaa at position 79 is Thr, Asp, or Ala;

Xaa at position 81 is His, Pro, Arg, Val, Gly, Asn, Ser or Thr;

Xaa at position 84 is His, Ile, Asn, Ala, Thr, Arg, Gln, Glu, Lys, Met, Ser, Tyr, Val or Leu;

Xaa at position 85 is Ile or Leu;

Xaa at position 86 is Lys or Arg;

Xaa at position 87 is Asp;

Xaa at position 91 is Asn, Pro, Ser, Ile or Asp;

Xaa at position 94 is Arg, Ala, or Ser;

Xaa at position 95 is Arg, Thr, Glu, Leu, or Ser;

Xaa at position 98 is Thr or Gln;

Xaa at position 102 is Lys;

Xaa at position 103 is Thr, Ala, His, Phe, Tyr or Ser;

Xaa at position 106 is Asn, Pro, Leu, His, Val, or Gln;

Xaa at position 107 is Ala, Ser, Ile, Pro, or Asp;

Xaa at position 108 is Gln, Met, Trp, Phe, Pro, His, Ile, or Tyr;

Xaa at position 109 is Ala, Met, Glu, Ser, or Leu;
wherein from 6 to about 44 of the amino acids designated by Xaa are different from the corresponding amino acids of native (1–133) human interleukin-3.

7. A method of treating a patient having a hematopoietic disorder comprising; administering to said patient a therapeutically effective amount of a composition comprising;

a biologically active human interleukin-3 variant polypeptide, said polypeptide comprising a sequence selected from the group consisting of:
(a) the sequence of SEQ ID NO:8; and
(b) a polypeptide comprising an N-terminal residue, alanine residue or methionine-alanine di-peptide immediately preceding said sequence according to (a);

wherein;

Xaa at position 4 is Asn or Ile;

Xaa at position 5 is Met, Ala or Ile;

Xaa at position 6 is Ile, Pro or Leu;

Xaa at position 9 is Ile, Ala or Leu;

Xaa at position 11 is Thr or His;

Xaa at position 15 is Gln, Arg, Val or Leu;

Xaa at position 18 is Leu, Ala, Asn or Arg;

Xaa at position 20 is Leu or Ser;

Xaa at position 23 is Phe, Pro, or Ser;

Xaa at position 24 is Asn or Ala;

Xaa at position 28 is Gly, Ala, Ser, Asp or Asn;

Xaa at position 31 is Gln, Val, or Met;

Xaa at position 32 is Asp or Ser;

Xaa at position 35 is Met, Ile, Leu or Asp;

Xaa at position 36 is Glu or Asp;

Xaa at position 37 is Asn, Arg or Ser;

Xaa at position 41 is Arg, Leu, or Thr;

Xaa at position 42 is Pro or Ser;

Xaa at position 45 is Glu or Leu;

Xaa at position 46 is Ala or Ser;

Xaa at position 48 is Asn, Val or Pro;
Xaa at position 49 is Arg or His;
Xaa at position 51 is Val or Ser;
Xaa at position 53 is Ser, Asn, His or Gly;
Xaa at position 55 is Gln or Glu;
Xaa at position 59 is Ala or Gly;
Xaa at position 62 is Ser, Ala or Pro;
Xaa at position 65 is Lys, Arg or Ser;
Xaa at position 67 is Leu, Glu, or Val;
Xaa at position 68 is Leu, Glu, Val or Trp;
Xaa at position 71 is Leu or Val;
Xaa at position 73 is Leu, Ser or Trp;
Xaa at position 74 is Ala or Trp;
Xaa at position 77 is Ala or Pro;
Xaa at position 79 is Pro or Ser;
Xaa at position 81 is His or Thr;
Xaa at position 84 is His, Ile, or Thr;
Xaa at position 86 is Lys or Arg;
Xaa at position 87 is Asp;
Xaa at position 91 is Asn or Gln;
Xaa at position 95 is Arg, Glu, Leu;
Xaa at position 98 is Thr or Gln;
Xaa at position 102 is Lys;
Xaa at position 103 is Thr or Ser;
Xaa at position 106 is Asn, Gln, or His;
Xaa at position 109 is Ala or Glu;
   wherein from 6 to about 44 of the amino acids designated by Xaa are different from the corresponding amino acids of native (1–133) human interleukin-31.

8. The method of claim 1, 2, 3, 4, 5, 6, or 7 wherein said factor is selected from the group consisting of; GM-CSF, CSF-1, G-CSF, G-CSF (Ser$^{17}$), M-CSF, erythropoietin (EPO), IL-1, IL-4, IL-2, IL-5, IL-6, IL-7, IL-8, IL-9, IL-10, IL-11, IL-12, IL-13, LIF, flt3 ligand, human growth hormone, B-cell growth factor, B-cell differentiation factor, eosinophil differentiation factor and stem cell factor (SCF).

9. The method according to claim 1, 2, 3, 4, 5, 6, or 7 wherein said hematopoietic disorder is a result of a viral infection, bacterial infection or fungal infection.

10. The method according to claim 1, 2, 3, 4, 5, 6, or 7 wherein said hematopoietic disorder is a result of cancer radiation therapy or chemotherapy or a bone marrow suppressive drug.

11. The method according to claim 8 wherein said hematopoietic disorder is a result of a viral infection, bacterial infection or fungal infection.

12. The method according to claim 8 wherein said hematopoietic disorder is the result of cancer radiation therapy or chemotherapy or a bone marrow suppressive drug.

13. A method of treating a patient comprising the steps of;
   (i) administering to said patient, an amount effective to promote the proliferation and/or differentiation of hematopoietic cells in said patient of a composition comprising;
      a modified human interleukin-3 (hIL-3) amino acid sequence, wherein said modified sequence differs from the sequence of native (1–133) hIL-3 by the replacement of from 4 to about 44 of the residues corresponding to positions 17–118 of native (1–133) hIL-3 by other amino acids, with the proviso that the residues corresponding to positions 101 and 116 are not Ala or Val, respectively, and with the proviso that no more than one of the amino acids at positions 63, 82, 87, 98, and 112 are different from the corresponding amino acids in native human interleukin-3; wherein said modified sequence optionally further differs from the sequence of native (1–133) hIL-3 by the deletion of from 1 to 14 residues from the N-terminus of native (1–133) hIL-3, the deletion of from 1 to 15 residues from the C-terminus of native (1–133) hIL-3, or both; and wherein said modified interleukin-3 (hIL-3) amino acid sequence has increased activity, relative to native human interleukin-3, in at least one assay selected from the group consisting of: AML cell proliferation, TF-1 cell proliferation and Methylcellulose assay;
   a factor selected from the group consisting of: a colony stimulating factor, a cytokine a lymphokine, an interleukin and a hematopoietic growth factor,
   (ii) removing hematopoietic cells from said patient;
   (iii) administering cancer radiation therapy or chemotherapy to said patient; and
   (iv) returning said hematopoietic cells to said patient.

14. A method of treating a patient comprising the steps of:
   (i) administering to said patient, an amount effective to promote the proliferation and/or differentiation of hematopoietic cells in said patient of a composition comprising;
   a biologically active human interleukin-3 variant polypeptide, said polypeptide comprising a sequence selected from the group consisting of:
      (a) the sequence of SEQ ID NO:1; and
      (b) a polypeptide comprising an N-terminal methionine residue, alanine residue or methionine-alanine di-peptide immediately preceding said sequence according to (a);
wherein;
Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;

Xaa at position 36 is Asp, Leu, or Val;

Xaa at position 37 is Phe, Ser, Pro, Trp, or Ile;

Xaa at position 38 is Asn, or Ala;

Xaa at position 40 is Leu, Trp, or Arg;

Xaa at position 41 is Asn, Cys, Arg, Leu, His, Met, or Pro;

Xaa at position 42 is Gly, Asp, Ser, Cys, Asn, Lys, Thr, Leu, Val, Glu, Phe, Tyr, Ile, Met or Ala;

Xaa at position 43 is Glu, Asn, Tyr, Leu, Phe, Asp, Ala, Cys, Gln, Arg, Thr, Gly or Ser;

Xaa at position 44 is Asp, Ser, Leu, Arg, Lys, Thr, Met, Trp, Glu, Asn, Gln, Ala or Pro;

Xaa at position 45 is Gln, Pro, Phe, Val, Met, Leu, Thr, Lys, Trp, Asp, Asn, Arg, Ser, Ala, Ile, Glu or His;

Xaa at position 46 is Asp, Phe, Ser, Thr, Cys, Glu, Asn, Gln, Lys, His, Ala, Tyr, Ile, Val or Gly;

Xaa at position 47 is Ile, Gly, Val, Ser, Arg, Pro, or His;

Xaa at position 48 is Leu, Ser, Cys, Arg, Ile, His, Phe, Glu, Lys, Thr, Ala, Met, Val or Asn;

Xaa at position 49 is Met, Arg, Ala, Gly, Pro, Asn, His, or Asp;

Xaa at position 50 is Glu, Leu, Thr, Asp, Tyr, Lys, Asn, Ser, Ala, Ile, Val, His, Phe, Met or Gln;

Xaa at position 51 is Asn, Arg, Met, Pro, Ser, Thr, or His;

Xaa at position 52 is Asn, His, Arg, Leu, Gly, Ser, or Thr;

Xaa at position 53 is Leu, Thr, Ala, Gly, Glu, Pro, Lys, Ser, or Met;

Xaa at position 54 is Arg, Asp, Ile, Ser, Val, Thr, Gln, Asn, Lys, His, Ala or Leu;

Xaa at position 55 is Arg, Thr, Val, Ser, Leu, or Gly;

Xaa at position 56 is Pro, Gly, Cys, Ser, Gln, Glu, Arg, His, Thr, Ala, Tyr, Phe, Leu, Val or Lys;

Xaa at position 57 is Asn or Gly;

Xaa at position 58 is Leu, Ser, Asp, Arg, Gln, Val, or Cys;

Xaa at position 59 is Glu, Tyr, His, Leu, Pro, or Arg;

Xaa at position 60 is Ala, Ser, Pro, Tyr, Asn, or Thr;

Xaa at position 61 is Phe, Asn, Glu, Pro, Lys, Arg, or Ser;

Xaa at position 62 is Asn, His, Val, Arg, Pro, Thr, Asp, or Ile;

Xaa at position 63 is Arg, Tyr, Trp, Lys, Ser, His, Pro, or Val;

Xaa at position 64 is Ala, Asn, Pro, Ser, or Lys;

Xaa at position 65 is Val, Thr, Pro, His, Leu, Phe, or Ser;

Xaa at position 66 is Lys, Ile, Arg, Val, Asn, Glu, or Ser;

Xaa at position 67 is Ser, Ala, Phe, Val, Gly, Asn, Ile, Pro, or His;

Xaa at position 68 is Leu, Val, Trp, Ser, Ile, Phe, Thr, or His;

Xaa at position 69 is Gln, Ala, Pro, Thr, Glu, Arg, Trp, Gly, or Leu;

Xaa at position 70 is Asn, Leu, Val, Trp, Pro, or Ala;

Xaa at position 71 is Ala, Met, Leu, Pro, Arg, Glu, Thr, Gln, Trp, or Asn;

Xaa at position 72 is Ser, Glu, Met, Ala, His, Asn, Arg, or Asp;

Xaa at position 73 is Ala, Glu, Asp, Leu, Ser, Gly, Thr, or Arg;

Xaa at position 74 is Ile, Met, Thr, Pro, Arg, Gly, Ala;

Xaa at position 75 is Glu, Lys, Gly, Asp, Pro, Trp, Arg, Ser, Gln, or Leu;

Xaa at position 76 is Ser, Val, Ala, Asn, Trp, Glu, Pro, Gly, or Asp;

Xaa at position 77 is Ile, Ser, Arg, Thr, or Leu;

Xaa at position 78 is Leu, Ala, Ser, Glu, Phe, Gly, or Arg;

Xaa at position 79 is Lys, Thr, Asn, Met, Arg, Ile, Gly, or Asp;

Xaa at position 80 is Asn, Trp, Val, Gly, Thr, Leu, Glu, or Arg;

Xaa at position 81 is Leu, Gln, Gly, Ala, Trp, Arg, Val, or Lys;

Xaa at position 82 is Leu, Gln, Lys, Trp, Arg, Asp, Glu, Asn, His, Thr, Ser, Ala, Tyr, Phe, Ile, Met or Val;

Xaa at position 83 is Pro, Ala, Thr, Trp, Arg, or Met;

Xaa at position 84 is Cys, Glu, Gly, Arg, Met, or Val;

Xaa at position 85 is Leu, Asn, Val, or Gln;

Xaa at position 86 is Pro, Cys, Arg, Ala, or Lys;

Xaa at position 87 is Leu, Ser, Trp, or Gly;

Xaa at position 88 is Ala, Lys, Arg, Val, or Trp;

Xaa at position 89 is Thr, Asp, Cys, Leu, Val, Glu, His, Asn, or Ser;

Xaa at position 90 is Ala, Pro, Ser, Thr, Gly, Asp, Ile, or Met;

Xaa at position 91 is Ala, Pro, Ser, Thr, Phe, Leu, Asp, or His;

Xaa at position 92 is Pro, Phe, Arg, Ser, Lys, His, Ala, Gly, Ile or Leu;

Xaa at position 93 is Thr, Asp, Ser, Asn, Pro, Ala, Leu, or Arg;

Xaa at position 94 is Arg, Ile, Ser, Glu, Leu, Val, Gln, Lys, His, Ala, or Pro;

Xaa at position 95 is His, Gln, Pro, Arg, Val, Leu, Gly, Thr, Asn, Lys, Ser, Ala, Trp, Phe, Ile, or Tyr;

Xaa at position 96 is Pro, Lys, Tyr, Gly, Ile, or Thr;

Xaa at position 97 is Ile, Val, Lys, Ala, or Asn;

Xaa at position 98 is His, Ile, Asn, Leu, Asp, Ala, Thr, Glu, Gln, Ser, Phe, Met, Val, Lys, Arg, Tyr or Pro;

Xaa at position 99 is Ile, Leu, Arg, Asp, Val, Pro, Gln, Gly, Ser, Phe, or His;

Xaa at position 100 is Lys, Tyr, Leu, His, Arg, Ile, Ser, Gln, or Pro;

Xaa at position 101 is Asp;

Xaa at position 102 is Gly, Leu, Glu, Lys, Ser, Tyr, or Pro;

Xaa at position 103 is Asp, or Ser;

Xaa at position 104 is Trp, Val, Cys, Tyr, Thr, Met, Pro, Leu, Gln, Lys, Ala, Phe, or Gly;

Xaa at position 105 is Asn, Pro, Ala, Phe, Ser, Trp, Gln, Tyr, Leu, Lys, Ile, Asp, or His;

Xaa at position 106 is Glu, Ser, Ala, Lys, Thr, Ile, Gly, or Pro;

Xaa at position 108 is Arg, Lys, Asp, Leu, Thr, Ile, Gln, His, Ser, Ala or Pro;

Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, Ala, or Trp;

Xaa at position 111 is Leu, Ile, Arg, Asp, or Met;

Xaa at position 112 is Thr, Val, Gln, Tyr, Glu, His, Ser, or Phe;

Xaa at position 113 is Phe, Ser, Cys, His, Gly, Trp, Tyr, Asp, Lys, Leu, Ile, Val or Asn;

Xaa at position 114 is Tyr, Cys, His, Ser, Trp, Arg, or Leu;

Xaa at position 115 is Leu, Asn, Val, Pro, Arg, Ala, His, Thr, Trp, or Met;

Xaa at position 116 is Lys;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
wherein from 6 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus of said sequence of SEQ ID NO:1; and
a factor selected from the group consisting of: a colony stimulating factor, a cytokine, a lymphokine, an interleukin, and a hematopoietic growth factor;
(ii) removing hematopoietic cells from said patient;
(iii) administering cancer radiation therapy or chemotherapy to said patient; and
(iv) returning said hematopoietic cells to said patient.

15. The method of claim 14, wherein (a) is the sequence of SEQ ID NO:3;
wherein
Xaa at position 17 is Ser, Gly, Asp, or Gln;
Xaa at position 18 is Asn, His, or Ile;
Xaa at position 23 is Ile, Ala, Leu, or Gly;
Xaa at position 25 is Thr, His, or Gln;
Xaa at position 26 is His or Ala;
Xaa at position 29 is Gln or Asn;
Xaa at position 30 is Pro or Gly;
Xaa at position 32 is Leu, Arg, Asn, or Ala;
Xaa at position 34 is Leu, Val, Ser, Ala, Arg, Gln, Glu, Ile, Phe, Thr, or Met;
Xaa at position 35 is Leu, Ala, Asn, or Pro;
Xaa at position 38 is Asn or Ala;
Xaa at position 42 is Gly, Asp, Ser, Ala, Asn, Ile, Leu, Met, Tyr or Arg;
Xaa at position 45 is Gln, Val, Met, Leu, Ala, Asn, Glu, or Lys;
Xaa at position 46 is Asp, Phe, Ser, Gln, Glu, His, Val or Thr;
Xaa at position 50 is Glu, Asn, Ser or Asp;
Xaa at position 51 is Asn, Arg, Pro, Thr, or His;
Xaa at position 55 is Arg, Leu, or Gly;
Xaa at position 56 is Pro, Gly, Ser, Ala, Asn, Val, Leu or Gln;
Xaa at position 62 is Asn, Pro, or Thr;
Xaa at position 64 is Ala or Asn;
Xaa at position 65 is Val or Thr;
Xaa at position 67 is Ser or Phe;
Xaa at position 68 is Leu or Phe;
Xaa at position 69 is Gln, Ala, Glu, or Arg;
Xaa at position 76 is Ser, Val, Asn, Pro, or Gly;
Xaa at position 77 is Ile or Leu;
Xaa at position 79 is Lys, Asn, Met, Arg, Ile, or Gly;
Xaa at position 80 is Asn, Gly, Glu, or Arg;
Xaa at position 82 is Leu, Gln, Trp, Arg, Asp, Asn, Glu, His, Met, Phe, Ser, Thr, Tyr or Val;
Xaa at position 87 is Leu or Ser;
Xaa at position 88 is Ala or Trp;
Xaa at position 91 is Ala or Pro;
Xaa at position 93 is Thr, Asp, or Ala;
Xaa at position 95 is His, Pro, Arg, Val, Gly, Asn, Ser or Thr;
Xaa at position 98 is His, Ile, Asn, Ala, Thr, Gln, Glu, Lys, Met, Ser, Tyr, Val or Leu;
Xaa at position 99 is Ile or Leu;
Xaa at position 100 is Lys or Arg;
Xaa at position 101 is Asp;
Xaa at position 105 is Asn, Pro, Ser, Ile or Asp;
Xaa at position 108 is Arg, Ala, or Ser;
Xaa at position 109 is Arg, Thr, Glu, Leu, or Ser;
Xaa at position 112 is Thr or Gln;
Xaa at position 116 is Lys;
Xaa at position 120 is Asn, Pro, Leu, His, Val, or Gln;
Xaa at position 121 is Ala, Ser, Ile, Pro, or Asp;
Xaa at position 122 is Gln, Met, Trp, Phe, Pro, His, Ile, or Tyr;
Xaa at position 123 is Ala, Met, Glu, Ser, or Leu;
wherein from 6 to about 44 of the amino acids designated by Xaa are different from the corresponding amino acids of native (1–133)human interleukin-3; and wherein from 1 to 14 amino acids are optionally deleted from the N-terminus and/or from 1 to 15 amino acids are optionally deleted from the C-terminus of said sequence of SEQ ID No: 3.

16. The method of claim 14, wherein in said human interleukin-3 mutant polypeptide, the amino acids which differ from the corresponding residue in native human interleukin-3 are selected from the group consisting of:
position 42 wherein Xaa is Gly, Asp, Ser, Ile, Leu, Met, Tyr, or Ala;
position 45 wherein Xaa is Gln, Val, Met or Asn;
position 46 wherein Xaa is Asp, Ser, Gln, His or Val;
position 50 wherein Xaa is Glu or Asp;
position 51 wherein Xaa is Asn, Pro or Thr;
position 62 wherein Xaa is Asn or Pro;
position 76 wherein Xaa is Ser, or Pro;
position 82 wherein Xaa is Leu, Trp, Asp, Asn, Glu, His, Phe, Ser or Tyr;
position 95 wherein Xaa is His, Arg, Thr, Asn or Ser;
position 98 wherein Xaa is His, Ile, Leu, Ala, Gln, Lys, Met, Ser, Tyr or Val;
position 100 wherein Xaa is Lys or Arg;
position 105 wherein Xaa is Asn, or Pro;
position 108 wherein Xaa is Arg, Ala, or Ser;
position 121 wherein Xaa is Ala, or Ile;
position 122 wherein Xaa is Gln, or Ile; and
position 123 wherein Xaa is Ala, Met or Glu;
wherein from 6 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus.

17. A method of treating a patient comprising the steps of:
(i) administering to said patient, an amount effective to promote the proliferation and/or differentiation of hematopoietic cells in said patient of a composition comprising;
a biologically active human interleukin-3 variant polypeptide said polypeptide comprising a sequence, selected from the group consisting of:
(a) the sequence of SEQ ID NO:4; and
(b) a polypeptide comprising an N-terminal methionine residue, alanine residue or methionine-alanine di-peptide immediately preceding said sequence according to (a);
wherein;
Xaa at position 3 is Ser, Lys, Gly, Asp, Met, Gln, or Arg;
Xaa at position 4 is Asn, His, Leu, Ile, Phe, Arg, or Gln;
Xaa at position 5 is Met, Phe, Ile, Arg, Gly, Ala, or Cys;
Xaa at position 6 is Ile, Cys, Gln, Glu, Arg, Pro, or Ala;
Xaa at position 7 is Asp, Phe, Lys, Arg, Ala, Gly, Glu, Gln, Asn, Thr, Ser or Val;
Xaa at position 8 is Glu, Trp, Pro, Ser, Ala, His, Asp, Asn, Gln, Leu, Val, or Gly;
Xaa at position 9 is Ile, Val, Ala, Leu, Gly, Trp, Lys, Phe, Ser, or Arg;
Xaa at position 10 is Ile, Gly, Val, Arg, Ser, Phe, or Leu;
Xaa at position 11 is Thr, His, Gly, Gln, Arg, Pro, or Ala;
Xaa at position 12 is His, Thr, Phe, Gly, Arg, Ala, or Trp;
Xaa at position 13 is Leu, Gly, Arg, Thr, Ser, or Ala;
Xaa at position 14 is Lys, Arg, Leu, Gln, Gly, Pro, Val or Trp;
Xaa at position 15 is Gln, Asn, Leu, Pro, Arg, or Val;
Xaa at position 16 is Pro, His, Thr, Gly, Asp, Gln, Ser, Leu, or Lys;
Xaa at position 17 is Pro, Asp, Gly, Ala, Arg, Leu, or Gln;
Xaa at position 18 is Leu, Val, Arg, Gln, Asn, Gly, Ala, or Glu;
Xaa at position 19 is Pro, Leu, Gln, Ala, Thr, or Glu;
Xaa at position 20 is Leu, Val, Gly, Ser, Lys, Glu, Gln, Thr, Arg, Ala, Phe, Ile or Met;
Xaa at position 21 is Leu, Ala, Gly, Asn, Pro, Gln, or Val;
Xaa at position 22 is Asp, Leu, or Val;
Xaa at position 23 is Phe, Ser, Pro, Trp, or Ile;
Xaa at position 24 is Asn, or Ala;
Xaa at position 26 is Leu, Trp, or Arg;
Xaa at position 27 is Asn, Cys, Arg, Leu, His, Met, Pro;
Xaa at position 28 is Gly, Asp, Ser, Cys, Ala, Lys, Asn, Thr, Leu, Val, Glu, Phe, Tyr, Ile or Met;
Xaa at position 29 is Glu, Asn, Tyr, Leu, Phe, Asp, Ala, Cys, Gln, Arg, Thr, Gly or Ser;
Xaa at position 30 is Asp, Ser, Leu, Arg, Lys, Thr, Met, Trp, Glu, Asn, Gln, Ala or Pro;
Xaa at position 31 is Gln, Pro, Phe, Val, Met, Leu, Thr, Lys, Asp, Asn, Arg, Ser, Ala, Ile, Glu, His or Trp;
Xaa at position 32 is Asp, Phe, Ser, Thr, Cys, Glu, Asn, Gln, Lys, His, Ala, Tyr, Ile, Val or Gly;
Xaa at position 33 is Ile, Gly, Val, Ser, Arg, Pro, or His;
Xaa at position 34 is Leu, Ser, Cys, Arg, Ile, His, Phe, Glu, Lys, Thr, Ala, Met, Val or Asn;
Xaa at position 35 is Met, Arg, Ala, Gly, Pro, Asn, His, or Asp;
Xaa at position 36 is Glu, Leu, Thr, Asp, Tyr, Lys, Asn, Ser, Ala, Ile, Val, His, Phe, Met or Gln;
Xaa at position 37 is Asn, Arg, Met, Pro, Ser, Thr, or His;
Xaa at position 38 is Asn, His, Arg, Leu, Gly, Ser, or Thr;
Xaa at position 39 is Leu, Thr, Ala, Gly, Glu, Pro, Lys, Ser, or Met;
Xaa at position 40 is Arg, Asp, Ile, Ser, Val, Thr, Gln, Asn, Lys, His, Ala or Leu;
Xaa at position 41 is Arg, Thr, Val, Ser, Leu, or Gly;
Xaa at position 42 is Pro, Gly, Cys, Ser, Gln, Glu, Arg, His, Thr, Ala, Tyr, Phe, Leu, Val or Lys;
Xaa at position 43 is Asn or Gly;
Xaa at position 44 is Leu, Ser, Asp, Arg, Gln, Val, or Cys;
Xaa at position 45 is Glu, Tyr, His, Leu, Pro, or Arg;
Xaa at position 46 is Ala, Ser, Pro, Tyr, Asn, or Thr;
Xaa at position 47 is Phe, Asn, Glu, Pro, Lys, Arg, or Ser;
Xaa at position 48 is Asn, His, Val, Arg, Pro, Thr, Asp, or Ile;
Xaa at position 49 is Arg, Tyr, Trp, Lys, Ser, His, Pro, or Val;
Xaa at position 50 is Ala, Asn, Pro, Ser, or Lys;
Xaa at position 51 is Val, Thr, Pro, His, Leu, Phe, or Ser;
Xaa at position 52 is Lys, Ile, Arg, Val, Asn, Glu, or Ser;
Xaa at position 53 is Ser, Ala, Phe, Val, Gly, Asn, Ile, Pro, or His;
Xaa at position 54 is Leu, Val, Trp, Ser, Ile, Phe, Thr, or His;
Xaa at position 55 is Gln, Ala, Pro, Thr, Glu, Arg, Trp, Gly, or Leu;
Xaa at position 56 is Asn, Leu, Val, Trp, Pro, or Ala;
Xaa at position 57 is Ala, Met, Leu, Pro, Arg, Glu, Thr, Gln, Trp, or Asn;
Xaa at position 58 is Ser, Glu, Met, Ala, His, Asn, Arg, or Asp;
Xaa at position 59 is Ala, Glu, Asp, Leu, Ser, Gly, Thr, or Arg;
Xaa at position 60 is Ile, Met, Thr, Pro, Arg, Gly, Ala;
Xaa at position 61 is Glu, Lys, Gly, Asp, Pro, Trp, Arg, Ser, Gln, or Leu;
Xaa at position 62 is Ser, Val, Ala, Asn, Trp, Glu, Pro, Gly, or Asp;
Xaa at position 63 is Ile, Ser, Arg, Thr, or Leu;
Xaa at position 64 is Leu, Ala, Ser, Glu, Phe, Gly, or Arg;
Xaa at position 65 is Lys, Thr, Gly, Asn, Met, Arg, Ile, or Asp;
Xaa at position 66 is Asn, Trp, Val, Gly, Thr, Leu, Glu, or Arg;
Xaa at position 67 is Leu, Gln, Gly, Ala, Trp, Arg, Val, or Lys;
Xaa at position 68 is Leu, Gln, Lys, Trp, Arg, Asp, Glu, Asn, His, Thr, Ser, Ala, Tyr, Phe, Ile, Met or Val;
Xaa at position 69 is Pro, Ala, Thr, Trp, Arg, or Met;
Xaa at position 70 is Cys, Glu, Gly, Arg, Met, or Val;
Xaa at position 71 is Leu, Asn, Val, or Gln;
Xaa at position 72 is Pro, Cys, Arg, Ala, or Lys;
Xaa at position 73 is Leu, Ser, Trp, or Gly;
Xaa at position 74 is Ala, Lys, Arg, Val, or Trp;
Xaa at position 75 is Thr, Asp, Cys, Leu, Val, Glu, His, Asn, or Ser;
Xaa at position 76 is Ala, Pro, Ser, Thr, Gly, Asp, Ile, or Met;
Xaa at position 77 is Ala, Pro, Ser, Thr, Phe, Leu, Asp, or His;

Xaa at position 78 is Pro, Phe, Arg, Ser, Lys, His, Ala, Gly, Ile or Leu;

Xaa at position 79 is Thr, Asp, Ser, Asn, Pro, Ala, Leu, or Arg;

Xaa at position 80 is Arg, Ile, Ser, Glu, Leu, Val, Gln, Lys, His, Ala or Pro;

Xaa at position 81 is His, Gln, Pro, Arg, Val, Leu, Gly, Thr, Asn, Lys, Ser, Ala, Trp, Phe, Ile or Tyr;

Xaa at position 82 is Pro, Lys, Tyr, Gly, Ile, or Thr;

Xaa at position 83 is Ile, Val, Lys, Ala, or Asn;

Xaa at position 84 is His, Ile, Asn, Leu, Asp, Ala, Thr, Glu, Gln, Ser, Phe, Met, Val, Lys, Arg, Tyr or Pro;

Xaa at position 85 is Ile, Leu, Arg, Asp, Val, Pro, Gln, Gly, Ser, Phe, or His;

Xaa at position 86 is Lys, Tyr, Leu, His, Arg, Ile, Ser, Gln, Pro;

Xaa at position 87 is Asp;

Xaa at position 88 is Gly, Leu, Glu, Lys, Ser, Tyr, or Pro;

Xaa at position 89 is Asp, or Ser;

Xaa at position 90 is Trp, Val, Cys, Tyr, Thr, Met, Pro, Leu, Gln, Lys, Ala, Phe, or Gly;

Xaa at position 91 is Asn, Pro, Ala, Phe, Ser, Trp, Gln, Tyr, Leu, Lys, Ile, Asp, or His;

Xaa at position 92 is Glu, Ser, Ala, Lys, Thr, Ile, Gly, or Pro;

Xaa at position 94 is Arg, Lys, Asp, Leu, Thr, Ile, Gln, His, Ser, Ala, or Pro;

Xaa at position 95 is Arg, Thr, Pro, Glu, Tyr, Leu, Ser, or Gly;

Xaa at position 96 is Lys, Asn, Thr, Leu, Gln, Arg, His, Glu, Ser, Ala or Trp;

Xaa at position 97 is Leu, Ile, Arg, Asp, or Met;

Xaa at position 98 is Thr, Val, Gln, Tyr, Glu, His, Ser, or Phe;

Xaa at position 99 is Phe, Ser, Cys, His, Gly, Trp, Tyr, Asp, Lys, Leu, Ile, Val or Asn;

Xaa at position 100 is Tyr, Cys, His, Ser, Trp, Arg, or Leu;

Xaa at position 101 is Leu, Asn, Val, Pro, Arg, Ala, His, Thr, Trp, or Met;

Xaa at position 102 is Lys;

Xaa at position 103 is Thr, Ser, Asn, Ile, Trp, Lys, or Pro;

Xaa at position 104 is Leu, Ser, Pro, Ala, Glu, Cys, Asp, or Tyr;

Xaa at position 105 is Glu, Ser, Lys, Pro, Leu, Thr, Tyr, or Arg;

Xaa at position 106 is Asn, Ala, Pro, Leu, His, Val, or Gln;

Xaa at position 107 is Ala, Ser, Ile, Asn, Pro, Lys, Asp, or Gly;

Xaa at position 108 is Gln, Ser, Met, Trp, Arg, Phe, Pro, His, Ile, Tyr, or Cys;

Xaa at position 109 is Ala, Met, Glu, His, Ser, Pro, Tyr, or Leu;

wherein from 6 to about 44 of the amino acids designated by Xaa are different from the corresponding native amino acids of (1–133) human interleukin-3; and a factor selected from the group consisting of: a colony stimulating factor, a cytokine, a lymphokine, an interleukin, and a hematopoietic growth factor;

(ii) removing hematopoietic cells from said patient;

(iii) administering cancer radiation therapy of chemotherapy to said patient; and (iv) returning said hematopoietic cells to said patient.

18. The method of claim 17, wherein (a) is the sequence of SEQ ID NO:6;

wherein

Xaa at position 3 is Ser, Gly, Asp, or Gln;

Xaa at position 4 is Asn, His, or Ile;

Xaa at position 9 is Ile, Ala, Leu, or Gly;

Xaa at position 11 is Thr, His, or Gln;

Xaa at position 12 is His or Ala;

Xaa at position 15 is Gln or Asn;

Xaa at position 16 is Pro or Gly;

Xaa at position 18 is Leu, Arg, Asn, or Ala;

Xaa at position 20 is Leu, Val, Ser, Ala, Arg, Gln, Glu, Ile, Phe, Thr or Met;

Xaa at position 21 is Leu, Ala, Asn, or Pro;

Xaa at position 24 is Asn or Ala;

Xaa at position 28 is Gly, Asp, Ser, Ala, Asn, Ile, Leu, Met, Tyr or Arg;

Xaa at position 31 is Gln, Val, Met, Leu, Ala, Asn, Glu or Lys;

Xaa at position 32 is Asp, Phe, Ser, Ala, Gln, Glu, His, Val or Thr;

Xaa at position 36 is Glu, Asn, Ser or Asp;

Xaa at position 37 is Asn, Arg, Pro, Thr, or His;

Xaa at position 41 is Arg, Leu, or Gly;

Xaa at position 42 is Pro, Gly, Ser, Ala, Asn, Val, Leu or Gln;

Xaa at position 48 is Asn, Pro, or Thr;

Xaa at position 50 is Ala or Asn;

Xaa at position 51 is Val or Thr;

Xaa at position 53 is Ser or Phe;

Xaa at position 54 is Leu or Phe;

Xaa at position 55 is Gln, Ala, Glu, or Arg;

Xaa at position 62 is Ser, Val, Asn, Pro, or Gly;

Xaa at position 63 is Ile or Leu;

Xaa at position 65 is Lys, Asn, Met, Arg, Ile, or Gly;

Xaa at position 66 is Asn, Gly, Glu, or Arg;

Xaa at position 68 is Leu, Gln, Trp, Arg, Asp, Asn, Glu, His, Met, Phe, Ser, Thr, Tyr or Val;

Xaa at position 73 is Leu or Ser;

Xaa at position 74 is Ala or Trp;

Xaa at position 77 is Ala or Pro;

Xaa at position 79 is Thr, Asp, or Ala;

Xaa at position 81 is His, Pro, Arg, Val, Gly, Asn, Ser or Thr;

Xaa at position 84 is His, Ile, Asn, Ala, Thr, Arg, Gln, Glu, Lys, Met, Ser, Tyr, Val or Leu;

Xaa at position 85 is Ile or Leu;

Xaa at position 86 is Lys or Arg;

Xaa at position 87 is Asp;

Xaa at position 91 is Asn, Pro, Ser, Ile or Asp;

Xaa at position 94 is Arg, Ala, or Ser;

Xaa at position 95 is Arg, Thr, Glu, Leu, or Ser;

Xaa at position 98 is Thr or Gln;

Xaa at position 102 is Lys;

Xaa at position 103 is Thr, Ala, His, Phe, Tyr or Ser;

Xaa at position 106 is Asn, Pro, Leu, His, Val, or Gln;

Xaa at position 107 is Ala, Ser, Ile, Pro, or Asp;

Xaa at position 108 is Gln, Met, Trp, Phe, Pro, His, Ile, or Tyr;

Xaa at position 109 is Ala, Met, Glu, Ser, or Leu;

wherein from 6 to about 44 of the amino acids designated by Xaa are different from the corresponding amino acids of native (1–133) human interleukin-3.

19. A method of treating a patient comprising the steps of:
(i) administering to said patient, an amount effective to promote the proliferation and/or differentiation of hematopoietic cells in said patient of a composition comprising;
a biologically active human interleukin-3 variant polypeptide, said polypeptide comprising a sequence selected from the group consisting of:
(a) the sequence of SEQ ID NO:8; and
(b) a polypeptide comprising an N-terminal residue, alanine residue or methionine-alanine di-peptide immediately preceding said sequence according to (a);

wherein;

Xaa at position 4 is Asn or Ile;

Xaa at position 5 is Met, Ala or Ile;

Xaa at position 6 is Ile, Pro or Leu;

Xaa at position 9 is Ile, Ala or Leu;

Xaa at position 11 is Thr or His;

Xaa at position 15 is Gln, Arg, Val or Leu;

Xaa at position 18 is Leu, Ala, Asn or Arg;

Xaa at position 20 is Leu or Ser;

Xaa at position 23 is Phe, Pro, or Ser;

Xaa at position 24 is Asn or Ala;

Xaa at position 28 is Gly, Ala, Ser, Asp or Asn;

Xaa at position 31 is Gln, Val, or Met;

Xaa at position 32 is Asp or Ser;

Xaa at position 35 is Met, Ile, Leu or Asp;

Xaa at position 36 is Glu or Asp;

Xaa at position 37 is Asn, Arg or Ser;

Xaa at position 41 is Arg, Leu, or Thr;

Xaa at position 42 is Pro or Ser;

Xaa at position 45 is Glu or Leu;

Xaa at position 46 is Ala or Ser;

Xaa at position 48 is Asn, Val or Pro;

Xaa at position 49 is Arg or His;

Xaa at position 51 is Val or Ser;

Xaa at position 53 is Ser, Asn, His or Gly;

Xaa at position 55 is Gln or Glu;

Xaa at position 59 is Ala or Gly;

Xaa at position 62 is Ser, Ala or Pro;

Xaa at position 65 is Lys, Arg or Ser;

Xaa at position 67 is Leu, Glu, or Val;

Xaa at position 68 is Leu, Glu, Val or Trp;

Xaa at position 71 is Leu or Val;

Xaa at position 73 is Leu, Ser or Trp;

Xaa at position 74 is Ala or Trp;

Xaa at position 77 is Ala or Pro;

Xaa at position 79 is Pro or Ser;

Xaa at position 81 is His or Thr;

Xaa at position 84 is His, Ile, or Thr;

Xaa at position 86 is Lys or Arg;

Xaa at position 87 is Asp;

Xaa at position 91 is Asn or Gln;

Xaa at position 95 is Arg, Glu, Leu;

Xaa at position 98 is Thr or Gln;

Xaa at position 102 is Lys;

Xaa at position 103 is Thr or Ser;

Xaa at position 106 is Asn, Gln, or His;

Xaa at position 109 is Ala or Glu;

wherein from 6 to about 44 of the amino acids designated by Xaa are different from the corresponding amino acids of native (1–133) human interleukin-3; and a factor selected from the group consisting of: a colony stimulating factor, a cytokine, a lymphokine, an interleukin, and a hematopoietic growth factor;

(ii) removing hematopoietic cells from said patient;

(iii) administering cancer radiation therapy or chemotherapy to said patient; and (iv) returning said hematopoietic cells to said patient.

20. The method of claim 13, 14, 15, 16, 17, 18, or 19, wherein said factor is selected from the group consisting of; GM-CSF, CSF-1, G-CSF, G-CSF (Ser$^{17}$), M-CSF, erythropoietin (EPO), IL-1, IL-4, IL-2, IL-5, IL-6, IL-7, IL-8, IL-9, IL-10, IL-11, IL-12, IL-13, LIF, flt3 ligand, human growth hormone, B-cell growth factor, B-cell differentiation factor, eosinophil differentiation factor and stem cell factor (SCF).

21. A method of treating a patient having a side effect of cancer chemotherapy or radiation therapy comprising; administering to said patient a therapeutically effective amount of a composition comprising;

a modified human interleukin-3 (hIL-3) amino acid sequence, wherein said modified sequence differs from the sequence of native (1–133) hIL-3 by the replacement of from 4 to about 44 of the residues corresponding to positions 17–118 of native (1–133) hIL-3 by other amino acids, with the proviso that the residues corresponding to positions 101 and 116 are not Ala or Val, respectively, and with the proviso that no more than one of the amino acids at positions 63, 82, 87, 98, and 112 are different from the corresponding amino acids in native human interleukin-3; wherein said modified sequence optionally further differs from the sequence of native (1–133) hIL-3 by the deletion of from 1 to 14 residues from the N-terminus of native (1–133) hIL-3, the deletion of from 1 to 15 residues from the C-terminus of native (1–133) hIL-3, or both; and wherein said modified interleukin-3 (hIL-3) amino acid sequence has increased activity, relative to native human interleukin-3, in at least one assay selected from the group consisting of: AML cell proliferation, TF-1 cell proliferation and Methylcellulose assay;

a factor selected from the group consisting of: a colony stimulating factor, a cytokine a lymphokine, an interleukin and a hematopoietic growth factor.

22. A method of treating a patient having a side effect of cancer chemotherapy or radiation therapy comprising; administering to said patient a therapeutically effective amount of a composition comprising;

a biologically active human interleukin-3 variant polypeptide, said polypeptide comprising a sequence selected from the group consisting of:
(a) the sequence of SEQ ID NO:1; and
(b) a polypeptide comprising an N-terminal residue, alanine residue or methionine-alanine di-peptide immediately preceding said sequence according to (a);

wherein;

Xaa at position 17 is Ser, Lys, Gly, Asp, Met, Gln, or Arg;

Xaa at position 18 is Asn, His, Leu, Ile, Phe, Arg, or Gln;

Xaa at position 19 is Met, Phe, Ile, Arg, Gly, Ala, or Cys;

Xaa at position 20 is Ile, Cys, Gln, Glu, Arg, Pro, or Ala;

Xaa at position 21 is Asp, Phe, Lys, Arg, Ala, Gly, Glu, Gln, Asn, Thr, Ser or Val;

Xaa at position 22 is Glu, Trp, Pro, Ser, Ala, His, Asp, Asn, Gln, Leu, Val or Gly;

Xaa at position 23 is Ile, Val, Ala, Leu, Gly, Trp, Lys, Phe, Ser, or Arg;

Xaa at position 24 is Ile, Gly, Val, Arg, Ser, Phe, or Leu;

Xaa at position 25 is Thr, His, Gly, Gln, Arg, Pro, or Ala;

Xaa at position 26 is His, Thr, Phe, Gly, Arg, Ala, or Trp;

Xaa at position 27 is Leu, Gly, Arg, Thr, Ser, or Ala;

Xaa at position 28 is Lys, Arg, Leu, Gln, Gly, Pro, Val or Trp;

Xaa at position 29 is Gln, Asn, Leu, Pro, Arg, or Val;

Xaa at position 30 is Pro, His, Thr, Gly, Asp, Gln, Ser, Leu, or Lys;

Xaa at position 31 is Pro, Asp, Gly, Ala, Arg, Leu, or Gln;

Xaa at position 32 is Leu, Val, Arg, Gln, Asn, Gly, Ala, or Glu;

Xaa at position 33 is Pro, Leu, Gln, Ala, Thr, or Glu;

Xaa at position 34 is Leu, Val, Gly, Ser, Lys, Glu, Gln, Thr, Arg, Ala, Phe, Ile or Met;

Xaa at position 35 is Leu, Ala, Gly, Asn, Pro, Gln, or Val;

Xaa at position 36 is Asp, Leu, or Val;

Xaa at position 37 is Phe, Ser, Pro, Trp, or Ile;

Xaa at position 38 is Asn, or Ala;

Xaa at position 40 is Leu, Trp, or Arg;

Xaa at position 41 is Asn, Cys, Arg, Leu, His, Met, or Pro;

Xaa at position 42 is Gly, Asp, Ser, Cys, Asn, Lys, Thr, Leu, Val, Glu, Phe, Tyr, Ile, Met or Ala;

Xaa at position 43 is Glu, Asn, Tyr, Leu, Phe, Asp, Ala, Cys, Gln, Arg, Thr, Gly or Ser;

Xaa at position 44 is Asp, Ser, Leu, Arg, Lys, Thr, Met, Trp, Glu, Asn, Gln, Ala or Pro;

Xaa at position 45 is Gln, Pro, Phe, Val, Met, Leu, Thr, Lys, Trp, Asp, Asn, Arg, Ser, Ala, Ile, Glu or His;

Xaa at position 46 is Asp, Phe, Ser, Thr, Cys, Glu, Asn, Gln, Lys, His, Ala, Tyr, Ile, Val or Gly;

Xaa at position 47 is Ile, Gly, Val, Ser, Arg, Pro, or His;

Xaa at position 48 is Leu, Ser, Cys, Arg, Ile, His, Phe, Glu, Lys, Thr, Ala, Met, Val or Asn;

Xaa at position 49 is Met, Arg, Ala, Gly, Pro, Asn, His, or Asp;

Xaa at position 50 is Glu, Leu, Thr, Asp, Tyr, Lys, Asn, Ser, Ala, Ile, Val, His, Phe, Met or Gln;

Xaa at position 51 is Asn, Arg, Met, Pro, Ser, Thr, or His;

Xaa at position 52 is Asn, His, Arg, Leu, Gly, Ser, or Thr;

Xaa at position 53 is Leu, Thr, Ala, Gly, Glu, Pro, Lys, Ser, or Met;

Xaa at position 54 is Arg, Asp, Ile, Ser, Val, Thr, Gln, Asn, Lys, His, Ala or Leu;

Xaa at position 55 is Arg, Thr, Val, Ser, Leu, or Gly;

Xaa at position 56 is Pro, Gly, Cys, Ser, Gln, Glu, Arg, His, Thr, Ala, Tyr, Phe, Leu, Val or Lys;

Xaa at position 57 is Asn or Gly;

Xaa at position 58 is Leu, Ser, Asp, Arg, Gln, Val, or Cys;

Xaa at position 59 is Glu, Tyr, His, Leu, Pro, or Arg;

Xaa at position 60 is Ala, Ser, Pro, Tyr, Asn, or Thr;

Xaa at position 61 is Phe, Asn, Glu, Pro, Lys, Arg, or Ser;

Xaa at position 62 is Asn, His, Val, Arg, Pro, Thr, Asp, or Ile;

Xaa at position 63 is Arg, Tyr, Trp, Lys, Ser, His, Pro, or Val;

Xaa at position 64 is Ala, Asn, Pro, Ser, or Lys;

Xaa at position 65 is Val, Thr, Pro, His, Leu, Phe, or Ser;

Xaa at position 66 is Lys, Ile, Arg, Val, Asn, Glu, or Ser;

Xaa at position 67 is Ser, Ala, Phe, Val, Gly, Asn, Ile, Pro, or His;

Xaa at position 68 is Leu, Val, Trp, Ser, Ile, Phe, Thr, or His;

Xaa at position 69 is Gln, Ala, Pro, Thr, Glu, Arg, Trp, Gly, or Leu;

Xaa at position 70 is Asn, Leu, Val, Trp, Pro, or Ala;

Xaa at position 71 is Ala, Met, Leu, Pro, Arg, Glu, Thr, Gln, Trp, or Asn;

Xaa at position 72 is Ser, Glu, Met, Ala, His, Asn, Arg, or Asp;

Xaa at position 73 is Ala, Glu, Asp, Leu, Ser, Gly, Thr, or Arg;

Xaa at position 74 is Ile, Met, Thr, Pro, Arg, Gly, Ala;

Xaa at position 75 is Glu, Lys, Gly, Asp, Pro, Trp, Arg, Ser, Gln, or Leu;

Xaa at position 76 is Ser, Val, Ala, Asn, Trp, Glu, Pro, Gly, or Asp;

Xaa at position 77 is Ile, Ser, Arg, Thr, or Leu;

Xaa at position 78 is Leu, Ala, Ser, Glu, Phe, Gly, or Arg;

Xaa at position 79 is Lys, Thr, Asn, Met, Arg, Ile, Gly, or Asp;

Xaa at position 80 is Asn, Trp, Val, Gly, Thr, Leu, Glu, or Arg;

Xaa at position 81 is Leu, Gln, Gly, Ala, Trp, Arg, Val, or Lys;

Xaa at position 82 is Leu, Gln, Lys, Trp, Arg, Asp, Glu, Asn, His, Thr, Ser, Ala, Tyr, Phe, Ile, Met or Val;

Xaa at position 83 is Pro, Ala, Thr, Trp, Arg, or Met;

Xaa at position 84 is Cys, Glu, Gly, Arg, Met, or Val;

Xaa at position 85 is Leu, Asn, Val, or Gln;

Xaa at position 86 is Pro, Cys, Arg, Ala, or Lys;

Xaa at position 87 is Leu, Ser, Trp, or Gly;

Xaa at position 88 is Ala, Lys, Arg, Val, or Trp;

Xaa at position 89 is Thr, Asp, Cys, Leu, Val, Glu, His, Asn, or Ser;

Xaa at position 90 is Ala, Pro, Ser, Thr, Gly, Asp, Ile, or Met;

Xaa at position 91 is Ala, Pro, Ser, Thr, Phe, Leu, Asp, or His;

Xaa at position 92 is Pro, Phe, Arg, Ser, Lys, His, Ala, Gly, Ile or Leu;

Xaa at position 93 is Thr, Asp, Ser, Asn, Pro, Ala, Leu, or Arg;

Xaa at position 94 is Arg, Ile, Ser, Glu, Leu, Val, Gln, Lys, His, Ala, or Pro;

Xaa at position 95 is His, Gln, Pro, Arg, Val, Leu, Gly, Thr, Asn, Lys, Ser, Ala, Trp, Phe, Ile, or Tyr;

Xaa at position 96 is Pro, Lys, Tyr, Gly, Ile, or Thr;

Xaa at position 97 is Ile, Val, Lys, Ala, or Asn;

Xaa at position 98 is His, Ile, Asn, Leu, Asp, Ala, Thr, Glu, Gln, Ser, Phe, Met, Val, Lys, Arg, Tyr or Pro;

Xaa at position 99 is Ile, Leu, Arg, Asp, Val, Pro, Gln, Gly, Ser, Phe, or His;

Xaa at position 100 is Lys, Tyr, Leu, His, Arg, Ile, Ser, Gln, or Pro;

Xaa at position 101 is Asp;

Xaa at position 102 is Gly, Leu, Glu, Lys, Ser, Tyr, or Pro;

Xaa at position 103 is Asp, or Ser;

Xaa at position 104 is Trp, Val, Cys, Tyr, Thr, Met, Pro, Leu, Gln, Lys, Ala, Phe, or Gly;

Xaa at position 105 is Asn, Pro, Ala, Phe, Ser, Trp, Gln, Tyr, Leu, Lys, Ile, Asp, or His;

Xaa at position 106 is Glu, Ser, Ala, Lys, Thr, Ile, Gly, or Pro;

Xaa at position 108 is Arg, Lys, Asp, Leu, Thr, Ile, Gln, His, Ser, Ala or Pro;

Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, Ala, or Trp;

Xaa at position 111 is Leu, Ile, Arg, Asp, or Met;

Xaa at position 112 is Thr, Val, Gln, Tyr, Glu, His, Ser, or Phe;

Xaa at position 113 is Phe, Ser, Cys, His, Gly, Trp, Tyr, Asp, Lys, Leu, Ile, Val or Asn;

Xaa at position 114 is Tyr, Cys, His, Ser, Trp, Arg, or Leu;

Xaa at position 115 is Leu, Asn, Val, Pro, Arg, Ala, His, Thr, Trp, or Met;

Xaa at position 116 is Lys;

Xaa at position 117 is Thr, Ser, Asn, Ile, Trp, Lys, or Pro;

Xaa at position 118 is Leu, Ser, Pro, Ala, Glu, Cys, Asp, or Tyr;

Xaa at position 119 is Glu, Ser, Lys, Pro, Leu, Thr, Tyr, or Arg;

Xaa at position 120 is Asn, Ala, Pro, Leu, His, Val, or Gln;

Xaa at position 121 is Ala, Ser, Ile, Asn, Pro, Lys, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

wherein from 6 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus of said sequence of SEQ ID NO:1; and a factor selected from the group consisting of: a colony stimulating factor, a cytokine, a lymphokine, an interleukin, and a hematopoietic growth factor.

23. The method of claim 22, wherein (a) is the sequence of SEQ ID NO:3;

wherein

Xaa at position 17 is Ser, Gly, Asp, or Gln;

Xaa at position 18 is Asn, His, or Ile;

Xaa at position 23 is Ile, Ala, Leu, or Gly;

Xaa at position 25 is Thr, His, or Gln;

Xaa at position 26 is His or Ala;

Xaa at position 29 is Gln or Asn;

Xaa at position 30 is Pro or Gly;

Xaa at position 32 is Leu, Arg, Asn, or Ala;

Xaa at position 34 is Leu, Val, Ser, Ala, Arg, Gln, Glu, Ile, Phe, Thr, or Met;

Xaa at position 35 is Leu, Ala, Asn, or Pro;

Xaa at position 38 is Asn or Ala;

Xaa at position 42 is Gly, Asp, Ser, Ala, Asn, Ile, Leu, Met, Tyr or Arg;

Xaa at position 45 is Gln, Val, Met, Leu, Ala, Asn, Glu, or Lys;

Xaa at position 46 is Asp, Phe, Ser, Gln, Glu, His, Val or Thr;

Xaa at position 50 is Glu, Asn, Ser or Asp;

Xaa at position 51 is Asn, Arg, Pro, Thr, or His;

Xaa at position 55 is Arg, Leu, or Gly;

Xaa at position 56 is Pro, Gly, Ser, Ala, Asn, Val, Leu or Gln;

Xaa at position 62 is Asn, Pro, or Thr;

Xaa at position 64 is Ala or Asn;

Xaa at position 65 is Val or Thr;

Xaa at position 67 is Ser or Phe;

Xaa at position 68 is Leu or Phe;

Xaa at position 69 is Gln, Ala, Glu, or Arg;

Xaa at position 76 is Ser, Val, Asn, Pro, or Gly;

Xaa at position 77 is Ile or Leu;

Xaa at position 79 is Lys, Asn, Met, Arg, Ile, or Gly;

Xaa at position 80 is Asn, Gly, Glu, or Arg;

Xaa at position 82 is Leu, Gln, Trp, Arg, Asp, Asn, Glu, His, Met, Phe, Ser, Thr, Tyr or Val;

Xaa at position 87 is Leu or Ser;

Xaa at position 88 is Ala or Trp;

Xaa at position 91 is Ala or Pro;

Xaa at position 93 is Thr, Asp, or Ala;

Xaa at position 95 is His, Pro, Arg, Val, Gly, Asn, Ser or Thr;

Xaa at position 98 is His, Ile, Asn, Ala, Thr, Gln, Glu, Lys, Met, Ser, Tyr, Val or Leu;

Xaa at position 99 is Ile or Leu;

Xaa at position 100 is Lys or Arg;

Xaa at position 101 is Asp;

Xaa at position 105 is Asn, Pro, Ser, Ile or Asp;

Xaa at position 108 is Arg, Ala, or Ser;

Xaa at position 109 is Arg, Thr, Glu, Leu, or Ser;

Xaa at position 112 is Thr or Gln;

Xaa at position 116 is Lys;

Xaa at position 120 is Asn, Pro, Leu, His, Val, or Gln;

Xaa at position 121 is Ala, Ser, Ile, Pro, or Asp;

Xaa at position 122 is Gln, Met, Trp, Phe, Pro, His, Ile, or Tyr;

Xaa at position 123 is Ala, Met, Glu, Ser, or Leu;

wherein from 6 to about 44 of the amino acids designated by Xaa are different from the corresponding amino acids of native (1–133)human interleukin-3; and wherein from 1 to 14 amino acids are optionally deleted from the N-terminus and/or from 1 to 15 amino acids are optionally deleted from the C-terminus of said sequence of SEQ ID No: 3.

24. The method of claim 22, wherein in said human interleukin-3 mutant polypeptide, the amino acids which differ from the corresponding residue in native human interleukin-3 are selected from the group consisting of:
position 42 wherein Xaa is Gly, Asp, Ser, Ile, Leu, Met, Tyr, or Ala;
position 45 wherein Xaa is Gln, Val, Met or Asn;
position 46 wherein Xaa is Asp, Ser, Gln, His or Val;
position 50 wherein Xaa is Glu or Asp;
position 51 wherein Xaa is Asn, Pro or Thr;
position 62 wherein Xaa is Asn or Pro;
position 76 wherein Xaa is Ser, or Pro;
position 82 wherein Xaa is Leu, Trp, Asp, Asn, Glu, His, Phe, Ser or Tyr;
position 95 wherein Xaa is His, Arg, Thr, Asn or Ser;
position 98 wherein Xaa is His, Ile, Leu, Ala, Gln, Lys, Met, Ser, Tyr or Val;
position 100 wherein Xaa is Lys or Arg;
position 105 wherein Xaa is Asn, or Pro;
position 108 wherein Xaa is Arg, Ala, or Ser;
position 121 wherein Xaa is Ala, or Ile;
position 122 wherein Xaa is Gln, or Ile; and
position 123 wherein Xaa is Ala, Met or Glu;
wherein from 6 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus.

25. A method of treating a patient having a side effect of cancer chemotherapy or radiation therapy comprising administering to said patient a therapeutically effective amount of a composition comprising;
a biologically active human interleukin-3 variant polypeptide, said polypeptide comprising a sequence selected from the group consisting of:
(a) the sequence of SEQ ID NO:4; and
(b) a polypeptide comprising an N-terminal residue, alanine residue or methionine-alanine di-peptide immediately preceding said sequence according to (a);
wherein;
Xaa at position 3 is Ser, Lys, Gly, Asp, Met, Gln, or Arg;
Xaa at position 4 is Asn, His, Leu, Ile, Phe, Arg, or Gln;
Xaa at position 5 is Met, Phe, Ile, Arg, Gly, Ala, or Cys;
Xaa at position 6 is Ile, Cys, Gln, Glu, Arg, Pro, or Ala;
Xaa at position 7 is Asp, Phe, Lys, Arg, Ala, Gly, Glu, Gln, Asn, Thr, Ser or Val;
Xaa at position 8 is Glu, Trp, Pro, Ser, Ala, His, Asp, Asn, Gln, Leu, Val, or Gly;
Xaa at position 9 is Ile, Val, Ala, Leu, Gly, Trp, Lys, Phe, Ser, or Arg;
Xaa at position 10 is Ile, Gly, Val, Arg, Ser, Phe, or Leu;
Xaa at position 11 is Thr, His, Gly, Gln, Arg, Pro, or Ala;
Xaa at position 12 is His, Thr, Phe, Gly, Arg, Ala, or Trp;
Xaa at position 13 is Leu, Gly, Arg, Thr, Ser, or Ala;
Xaa at position 14 is Lys, Arg, Leu, Gln, Gly, Pro, Val or Trp;
Xaa at position 15 is Gln, Asn, Leu, Pro, Arg, or Val;
Xaa at position 16 is Pro, His, Thr, Gly, Asp, Gln, Ser, Leu, or Lys;
Xaa at position 17 is Pro, Asp, Gly, Ala, Arg, Leu, or Gln;
Xaa at position 18 is Leu, Val, Arg, Gln, Asn, Gly, Ala, or Glu;

Xaa at position 19 is Pro, Leu, Gln, Ala, Thr, or Glu;
Xaa at position 20 is Leu, Val, Gly, Ser, Lys, Glu, Gln, Thr, Arg, Ala, Phe, Ile or Met;
Xaa at position 21 is Leu, Ala, Gly, Asn, Pro, Gln, or Val;
Xaa at position 22 is Asp, Leu, or Val;
Xaa at position 23 is Phe, Ser, Pro, Trp, or Ile;
Xaa at position 24 is Asn, or Ala;
Xaa at position 26 is Leu, Trp, or Arg;
Xaa at position 27 is Asn, Cys, Arg, Leu, His, Met, Pro;
Xaa at position 28 is Gly, Asp, Ser, Cys, Ala, Lys, Asn, Thr, Leu, Val, Glu, Phe, Tyr, Ile or Met;
Xaa at position 29 is Glu, Asn, Tyr, Leu, Phe, Asp, Ala, Cys, Gln, Arg, Thr, Gly or Ser;
Xaa at position 30 is Asp, Ser, Leu, Arg, Lys, Thr, Met, Trp, Glu, Asn, Gln, Ala or Pro;
Xaa at position 31 is Gln, Pro, Phe, Val, Met, Leu, Thr, Lys, Asp, Asn, Arg, Ser, Ala, Ile, Glu, His or Trp;
Xaa at position 32 is Asp, Phe, Ser, Thr, Cys, Glu, Asn, Gln, Lys, His, Ala, Tyr, Ile, Val or Gly;
Xaa at position 33 is Ile, Gly, Val, Ser, Arg, Pro, or His;
Xaa at position 34 is Leu, Ser, Cys, Arg, Ile, His, Phe, Glu, Lys, Thr, Ala, Met, Val or Asn;
Xaa at position 35 is Met, Arg, Ala, Gly, Pro, Asn, His, or Asp;
Xaa at position 36 is Glu, Leu, Thr, Asp, Tyr, Lys, Asn, Ser, Ala, Ile, Val, His, Phe, Met or Gln;
Xaa at position 37 is Asn, Arg, Met, Pro, Ser, Thr, or His;
Xaa at position 38 is Asn, His, Arg, Leu, Gly, Ser, or Thr;
Xaa at position 39 is Leu, Thr, Ala, Gly, Glu, Pro, Lys, Ser, or Met;
Xaa at position 40 is Arg, Asp, Ile, Ser, Val, Thr, Gln, Asn, Lys, His, Ala or Leu;
Xaa at position 41 is Arg, Thr, Val, Ser, Leu, or Gly;
Xaa at position 42 is Pro, Gly, Cys, Ser, Gln, Glu, Arg, His, Thr, Ala, Tyr, Phe, Leu, Val or Lys;
Xaa at position 43 is Asn or Gly;
Xaa at position 44 is Leu, Ser, Asp, Arg, Gln, Val, or Cys;
Xaa at position 45 is Glu, Tyr, His, Leu, Pro, or Arg;
Xaa at position 46 is Ala, Ser, Pro, Tyr, Asn, or Thr;
Xaa at position 47 is Phe, Asn, Glu, Pro, Lys, Arg, or Ser;
Xaa at position 48 is Asn, His, Val, Arg, Pro, Thr, Asp, or Ile;
Xaa at position 49 is Arg, Tyr, Trp, Lys, Ser, His, Pro, or Val;
Xaa at position 50 is Ala, Asn, Pro, Ser, or Lys;
Xaa at position 51 is Val, Thr, Pro, His, Leu, Phe, or Ser;
Xaa at position 52 is Lys, Ile, Arg, Val, Asn, Glu, or Ser;
Xaa at position 53 is Ser, Ala, Phe, Val, Gly, Asn, Ile, Pro, or His;
Xaa at position 54 is Leu, Val, Trp, Ser, Ile, Phe, Thr, or His;
Xaa at position 55 is Gln, Ala, Pro, Thr, Glu, Arg, Trp, Gly, or Leu;
Xaa at position 56 is Asn, Leu, Val, Trp, Pro, or Ala;
Xaa at position 57 is Ala, Met, Leu, Pro, Arg, Glu, Thr, Gln, Trp, or Asn;
Xaa at position 58 is Ser, Glu, Met, Ala, His, Asn, Arg, or Asp;
Xaa at position 59 is Ala, Glu, Asp, Leu, Ser, Gly, Thr, or Arg;

Xaa at position 60 is Ile, Met, Thr, Pro, Arg, Gly, Ala;

Xaa at position 61 is Glu, Lys, Gly, Asp, Pro, Trp, Arg, Ser, Gln, or Leu;

Xaa at position 62 is Ser, Val, Ala, Asn, Trp, Glu, Pro, Gly, or Asp;

Xaa at position 63 is Ile, Ser, Arg, Thr, or Leu;

Xaa at position 64 is Leu, Ala, Ser, Glu, Phe, Gly, or Arg;

Xaa at position 65 is Lys, Thr, Gly, Asn, Met, Arg, Ile, or Asp;

Xaa at position 66 is Asn, Trp, Val, Gly, Thr, Leu, Glu, or Arg;

Xaa at position 67 is Leu, Gln, Gly, Ala, Trp, Arg, Val, or Lys;

Xaa at position 68 is Leu, Gln, Lys, Trp, Arg, Asp, Glu, Asn, His, Thr, Ser, Ala, Tyr, Phe, Ile, Met or Val;

Xaa at position 69 is Pro, Ala, Thr, Trp, Arg, or Met;

Xaa at position 70 is Cys, Glu, Gly, Arg, Met, or Val;

Xaa at position 71 is Leu, Asn, Val, or Gln;

Xaa at position 72 is Pro, Cys, Arg, Ala, or Lys;

Xaa at position 73 is Leu, Ser, Trp, or Gly;

Xaa at position 74 is Ala, Lys, Arg, Val, or Trp;

Xaa at position 75 is Thr, Asp, Cys, Leu, Val, Glu, His, Asn, or Ser;

Xaa at position 76 is Ala, Pro, Ser, Thr, Gly, Asp, Ile, or Met;

Xaa at position 77 is Ala, Pro, Ser, Thr, Phe, Leu, Asp, or His;

Xaa at position 78 is Pro, Phe, Arg, Ser, Lys, His, Ala, Gly, Ile or Leu;

Xaa at position 79 is Thr, Asp, Ser, Asn, Pro, Ala, Leu, or Arg;

Xaa at position 80 is Arg, Ile, Ser, Glu, Leu, Val, Gln, Lys, His, Ala or Pro;

Xaa at position 81 is His, Gln, Pro, Arg, Val, Leu, Gly, Thr, Asn, Lys, Ser, Ala, Trp, Phe, Ile or Tyr;

Xaa at position 82 is Pro, Lys, Tyr, Gly, Ile, or Thr;

Xaa at position 83 is Ile, Val, Lys, Ala, or Asn;

Xaa at position 84 is His, Ile, Asn, Leu, Asp, Ala, Thr, Glu, Gln, Ser, Phe, Met, Val, Lys, Arg, Tyr or Pro;

Xaa at position 85 is Ile, Leu, Arg, Asp, Val, Pro, Gln, Gly, Ser, Phe, or His;

Xaa at position 86 is Lys, Tyr, Leu, His, Arg, Ile, Ser, Gln, Pro;

Xaa at position 87 is Asp;

Xaa at position 88 is Gly, Leu, Glu, Lys, Ser, Tyr, or Pro;

Xaa at position 89 is Asp, or Ser;

Xaa at position 90 is Trp, Val, Cys, Tyr, Thr, Met, Pro, Leu, Gln, Lys, Ala, Phe, or Gly;

Xaa at position 91 is Asn, Pro, Ala, Phe, Ser, Trp, Gln, Tyr, Leu, Lys, Ile, Asp, or His;

Xaa at position 92 is Glu, Ser, Ala, Lys, Thr, Ile, Gly, or Pro;

Xaa at position 94 is Arg, Lys, Asp, Leu, Thr, Ile, Gln, His, Ser, Ala, or Pro;

Xaa at position 95 is Arg, Thr, Pro, Glu, Tyr, Leu, Ser, or Gly;

Xaa at position 96 is Lys, Asn, Thr, Leu, Gln, Arg, His, Glu, Ser, Ala or Trp;

Xaa at position 97 is Leu, Ile, Arg, Asp, or Met;

Xaa at position 98 is Thr, Val, Gln, Tyr, Glu, His, Ser, or Phe;

Xaa at position 99 is Phe, Ser, Cys, His, Gly, Trp, Tyr, Asp, Lys, Leu, Ile, Val or Asn;

Xaa at position 100 is Tyr, Cys, His, Ser, Trp, Arg, or Leu;

Xaa at position 101 is Leu, Asn, Val, Pro, Arg, Ala, His, Thr, Trp, or Met;

Xaa at position 102 is Lys;

Xaa at position 103 is Thr, Ser, Asn, Ile, Trp, Lys, or Pro;

Xaa at position 104 is Leu, Ser, Pro, Ala, Glu, Cys, Asp, or Tyr;

Xaa at position 105 is Glu, Ser, Lys, Pro, Leu, Thr, Tyr, or Arg;

Xaa at position 106 is Asn, Ala, Pro, Leu, His, Val, or Gln;

Xaa at position 107 is Ala, Ser, Ile, Asn, Pro, Lys, Asp, or Gly;

Xaa at position 108 is Gln, Ser, Met, Trp, Arg, Phe, Pro, His, Ile, Tyr, or Cys;

Xaa at position 109 is Ala, Met, Glu, His, Ser, Pro, Tyr, or Leu;

wherein from 6 to about 44 of the amino acids designated by Xaa are different from the corresponding native amino acids of (1–133) human interleukin-3; and a factor selected from the group consisting of: a colony stimulating factor, a cytokine, a lymphokine, an interleukin, and a hematopoietic growth factory.

26. The method of claim 25, wherein (a) is the sequence of SEQ ID NO:6;

wherein

Xaa at position 3 is Ser, Gly, Asp, or Gln;

Xaa at position 4 is Asn, His, or Ile;

Xaa at position 9 is Ile, Ala, Leu, or Gly;

Xaa at position 11 is Thr, His, or Gln;

Xaa at position 12 is His or Ala;

Xaa at position 15 is Gln or Asn;

Xaa at position 16 is Pro or Gly;

Xaa at position 18 is Leu, Arg, Asn, or Ala;

Xaa at position 20 is Leu, Val, Ser, Ala, Arg, Gln, Glu, Ile, Phe, Thr or Met;

Xaa at position 21 is Leu, Ala, Asn, or Pro;

Xaa at position 24 is Asn or Ala;

Xaa at position 28 is Gly, Asp, Ser, Ala, Asn, Ile, Leu, Met, Tyr or Arg;

Xaa at position 31 is Gln, Val, Met, Leu, Ala, Asn, Glu or Lys;

Xaa at position 32 is Asp, Phe, Ser, Ala, Gln, Glu, His, Val or Thr;

Xaa at position 36 is Glu, Asn, Ser or Asp;

Xaa at position 37 is Asn, Arg, Pro, Thr, or His;

Xaa at position 41 is Arg, Leu, or Gly;

Xaa at position 42 is Pro, Gly, Ser, Ala, Asn, Val, Leu or Gln;

Xaa at position 48 is Asn, Pro, or Thr;

Xaa at position 50 is Ala or Asn;

Xaa at position 51 is Val or Thr;

Xaa at position 53 is Ser or Phe;

Xaa at position 54 is Leu or Phe;

Xaa at position 55 is Gln, Ala, Glu, or Arg;

Xaa at position 62 is Ser, Val, Asn, Pro, or Gly;

Xaa at position 63 is Ile or Leu;

Xaa at position 65 is Lys, Asn, Met, Arg, Ile, or Gly;

Xaa at position 66 is Asn, Gly, Glu, or Arg;

Xaa at position 68 is Leu, Gln, Trp, Arg, Asp, Asn, Glu, His, Met, Phe, Ser, Thr, Tyr or Val;
Xaa at position 73 is Leu or Ser;
Xaa at position 74 is Ala or Trp;
Xaa at position 77 is Ala or Pro;
Xaa at position 79 is Thr, Asp, or Ala;
Xaa at position 81 is His, Pro, Arg, Val, Gly, Asn, Ser or Thr;
Xaa at position 84 is His, Ile, Asn, Ala, Thr, Arg, Gln, Glu, Lys, Met, Ser, Tyr, Val or Leu;
Xaa at position 85 is Ile or Leu;
Xaa at position 86 is Lys or Arg;
Xaa at position 87 is Asp;
Xaa at position 91 is Asn, Pro, Ser, Ile or Asp;
Xaa at position 94 is Arg, Ala, or Ser;
Xaa at position 95 is Arg, Thr, Glu, Leu, or Ser;
Xaa at position 98 is Thr or Gln;
Xaa at position 102 is Lys;
Xaa at position 103 is Thr, Ala, His, Phe, Tyr or Ser;
Xaa at position 106 is Asn, Pro, Leu, His, Val, or Gln;
Xaa at position 107 is Ala, Ser, Ile, Pro, or Asp;
Xaa at position 108 is Gln, Met, Trp, Phe, Pro, His, Ile, or Tyr;
Xaa at position 109 is Ala, Met, Glu, Ser, or Leu;
wherein from 6 to about 44 of the amino acids designated by Xaa are different from the corresponding amino acids of native (1–133) human interleukin-3.

27. A method of treating a patient having a side effect of cancer chemotherapy or radiation therapy comprising; administering to said patient a therapeutically effective amount of a composition comprising;
a biologically active human interleukin-3 variant polypeptide, said polypeptide comprising a sequence selected from the group consisting of:
(a) the sequence of SEQ ID NO:8; and
(b) a polypeptide comprising an N-terminal residue, alanine residue or methionine-alanine di-peptide immediately preceding said sequence according to (a);
wherein;
Xaa at position 4 is Asn or Ile;
Xaa at position 5 is Met, Ala or Ile;
Xaa at position 6 is Ile, Pro or Leu;
Xaa at position 9 is Ile, Ala or Leu;
Xaa at position 11 is Thr or His;
Xaa at position 15 is Gln, Arg, Val or Leu;
Xaa at position 18 is Leu, Ala, Asn or Arg;
Xaa at position 20 is Leu or Ser;
Xaa at position 23 is Phe, Pro, or Ser;
Xaa at position 24 is Asn or Ala;
Xaa at position 28 is Gly, Ala, Ser, Asp or Asn;
Xaa at position 31 is Gln, Val, or Met;
Xaa at position 32 is Asp or Ser;
Xaa at position 35 is Met, Ile, Leu or Asp;
Xaa at position 36 is Glu or Asp;
Xaa at position 37 is Asn, Arg or Ser;
Xaa at position 41 is Arg, Leu, or Thr;
Xaa at position 42 is Pro or Ser;
Xaa at position 45 is Glu or Leu;
Xaa at position 46 is Ala or Ser;
Xaa at position 48 is Asn, Val or Pro;
Xaa at position 49 is Arg or His;
Xaa at position 51 is Val or Ser;
Xaa at position 53 is Ser, Asn, His or Gly;
Xaa at position 55 is Gln or Glu;
Xaa at position 59 is Ala or Gly;
Xaa at position 62 is Ser, Ala or Pro;
Xaa at position 65 is Lys, Arg or Ser;
Xaa at position 67 is Leu, Glu, or Val;
Xaa at position 68 is Leu, Glu, Val or Trp;
Xaa at position 71 is Leu or Val;
Xaa at position 73 is Leu, Ser or Trp;
Xaa at position 74 is Ala or Trp;
Xaa at position 77 is Ala or Pro;
Xaa at position 79 is Pro or Ser;
Xaa at position 81 is His or Thr;
Xaa at position 84 is His, Ile, or Thr;
Xaa at position 86 is Lys or Arg;
Xaa at position 87 is Asp;
Xaa at position 91 is Asn or Gln;
Xaa at position 95 is Arg, Glu, Leu;
Xaa at position 98 is Thr or Gln;
Xaa at position 102 is Lys;
Xaa at position 103 is Thr or Ser;
Xaa at position 106 is Asn, Gln, or His;
Xaa at position 109 is Ala or Glu;
wherein from 6 to about 44 of the amino acids designated by Xaa are different from the corresponding amino acids of native (1–133) human interleukin-3; and
a factor selected from the group consisting of: a colony stimulating factor, a cytokine, a lymphokine, an interleukin, and a hematopoietic growth factor.

28. The method of claim 21, 22, 23, 24, 26, or 27 wherein said factor is selected from the group consisting of; GM-CSF, CSF-1, G-CSF, G-CSF (Ser$^{17}$), M-CSF, erythropoietin (EPO), IL-1, IL-4, IL-2, IL-5, IL-6, IL-7, IL-8, IL-9, IL-10, IL-11, IL-12, IL-13, LIF, flt3 ligand, human growth hormone, B-cell growth factor, B-cell differentiation factor, eosinophil differentiation factor and stem cell factor (SCF).

29. A method of treating a patient having a hematopoietic disorder consisting of; administering to said patient a therapeutically effective amount of a composition consisting essentially of;
a modified human interleukin-3 (hIL-3) amino acid sequence, wherein said modified sequence differs from the sequence of native (1–133) hIL-3 by the replacement of from 4 to about 44 of the residues corresponding to positions 17–118 of native (1–133) hIL-3 by other amino acids, with the proviso that the residues corresponding to positions 101 and 116 are not Ala or Val, respectively, and with the proviso that no more than one of the amino acids at positions 63, 82, 87, 98, and 112 are different from the corresponding amino acids in native human interleukin-3; wherein said modified sequence optionally further differs from the sequence of native (1–133) hIL-3 by the deletion of from 1 to 14 residues from the N-terminus of native (1–133) hIL-3, the deletion of from 1 to 15 residues from the C-terminus of native (1–133) hIL-3, or both; and wherein said modified interleukin-3 (hIL-3) amino acid sequence has increased activity, relative to native human interleukin-3, in at least one assay selected from the group consisting of: AML cell proliferation, TF-1 cell proliferation and Methylcellulose assay;

a factor selected from the group consisting of: a colony stimulating factor, a cytokine a lymphokine, an interleukin and a hematopoietic growth factor.

30. A method of treating a patient having a hematopoietic disorder consisting of; administering to said patient a composition consisting essentially of;

a biologically active human interleukin-3 variant polypeptide, said polypeptide consisting of a sequence selected from the group consisting of:
(a) the sequence of SEQ ID NO:1; and
(b) a polypeptide consisting of an N-terminal residue, alanine residue or methionine-alanine di-peptide immediately preceding said sequence according to (a);

wherein;

Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu, Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Lys, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;
Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;
Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;

Xaa at position 90 is Ala, Pro, Ser, Thr, Gly, Asp, Ile, or Met;

Xaa at position 91 is Ala, Pro, Ser, Thr, Phe, Leu, Asp, or His;

Xaa at position 92 is Pro, Phe, Arg, Ser, Lys, His, Ala, Gly, Ile or Leu;

Xaa at position 93 is Thr, Asp, Ser, Asn, Pro, Ala, Leu, or Arg;

Xaa at position 94 is Arg, Ile, Ser, Glu, Leu, Val, Gln, Lys, His, Ala, or Pro;

Xaa at position 95 is His, Gln, Pro, Arg, Val, Leu, Gly, Thr, Asn, Lys, Ser, Ala, Trp, Phe, Ile, or Tyr;

Xaa at position 96 is Pro, Lys, Tyr, Gly, Ile, or Thr;

Xaa at position 97 is Ile, Val, Lys, Ala, or Asn;

Xaa at position 98 is His, Ile, Asn, Leu, Asp, Ala, Thr, Glu, Gln, Ser, Phe, Met, Val, Lys, Arg, Tyr or Pro;

Xaa at position 99 is Ile, Leu, Arg, Asp, Val, Pro, Gln, Gly, Ser, Phe, or His;

Xaa at position 100 is Lys, Tyr, Leu, His, Arg, Ile, Ser, Gln, or Pro;

Xaa at position 101 is Asp;

Xaa at position 102 is Gly, Leu, Glu, Lys, Ser, Tyr, or Pro;

Xaa at position 103 is Asp, or Ser;

Xaa at position 104 is Trp, Val, Cys, Tyr, Thr, Met, Pro, Leu, Gln, Lys, Ala, Phe, or Gly;

Xaa at position 105 is Asn, Pro, Ala, Phe, Ser, Trp, Gln, Tyr, Leu, Lys, Ile, Asp, or His;

Xaa at position 106 is Glu, Ser, Ala, Lys, Thr, Ile, Gly, or Pro;

Xaa at position 108 is Arg, Lys, Asp, Leu, Thr, Ile, Gln, His, Ser, Ala or Pro;

Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, Ala, or Trp;

Xaa at position 111 is Leu, Ile, Arg, Asp, or Met;

Xaa at position 112 is Thr, Val, Gln, Tyr, Glu, His, Ser, or Phe;

Xaa at position 113 is Phe, Ser, Cys, His, Gly, Trp, Tyr, Asp, Lys, Leu, Ile, Val or Asn;

Xaa at position 114 is Tyr, Cys, His, Ser, Trp, Arg, or Leu;

Xaa at position 115 is Leu, Asn, Val, Pro, Arg, Ala, His, Thr, Trp, or Met;

Xaa at position 116 is Lys;

Xaa at position 117 is Thr, Ser, Asn, Ile, Trp, Lys, or Pro;

Xaa at position 118 is Leu, Ser, Pro, Ala, Glu, Cys, Asp, or Tyr;

Xaa at position 119 is Glu, Ser, Lys, Pro, Leu, Thr, Tyr, or Arg;

Xaa at position 120 is Asn, Ala, Pro, Leu, His, Val, or Gln;

Xaa at position 121 is Ala, Ser, Ile, Asn, Pro, Lys, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

wherein from 6 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus of said sequence of SEQ ID NO:1;

a factor selected from the group consisting of: a colony stimulating factor, a cytokine, a lymphokine, an interleukin, and a hematopoietic growth factor; and at least one pharmaceutically acceptable carrier.

31. The method of claim 30, wherein (a) is the sequence of SEQ ID NO:3;

wherein

Xaa at position 17 is Ser, Gly, Asp, or Gln;

Xaa at position 18 is Asn, His, or Ile;

Xaa at position 23 is Ile, Ala, Leu, or Gly;

Xaa at position 25 is Thr, His, or Gln;

Xaa at position 26 is His or Ala;

Xaa at position 29 is Gln or Asn;

Xaa at position 30 is Pro or Gly;

Xaa at position 32 is Leu, Arg, Asn, or Ala;

Xaa at position 34 is Leu, Val, Ser, Ala, Arg, Gln, Glu, Ile, Phe, Thr, or Met;

Xaa at position 35 is Leu, Ala, Asn, or Pro;

Xaa at position 38 is Asn or Ala;

Xaa at position 42 is Gly, Asp, Ser, Ala, Asn, Ile, Leu, Met, Tyr or Arg;

Xaa at position 45 is Gln, Val, Met, Leu, Ala, Asn, Glu, or Lys;

Xaa at position 46 is Asp, Phe, Ser, Gln, Glu, His, Val or Thr;

Xaa at position 50 is Glu, Asn, Ser or Asp;

Xaa at position 51 is Asn, Arg, Pro, Thr, or His;

Xaa at position 55 is Arg, Leu, or Gly;

Xaa at position 56 is Pro, Gly, Ser, Ala, Asn, Val, Leu or Gln;

Xaa at position 62 is Asn, Pro, or Thr;

Xaa at position 64 is Ala or Asn;

Xaa at position 65 is Val or Thr;

Xaa at position 67 is Ser or Phe;

Xaa at position 68 is Leu or Phe;

Xaa at position 69 is Gln, Ala, Glu, or Arg;

Xaa at position 76 is Ser, Val, Asn, Pro, or Gly;

Xaa at position 77 is Ile or Leu;

Xaa at position 79 is Lys, Asn, Met, Arg, Ile, or Gly;

Xaa at position 80 is Asn, Gly, Glu, or Arg;

Xaa at position 82 is Leu, Gln, Trp, Arg, Asp, Asn, Glu, His, Met, Phe, Ser, Thr, Tyr or Val;

Xaa at position 87 is Leu or Ser;

Xaa at position 88 is Ala or Trp;

Xaa at position 91 is Ala or Pro;

Xaa at position 93 is Thr, Asp, or Ala;

Xaa at position 95 is His, Pro, Arg, Val, Gly, Asn, Ser or Thr;

Xaa at position 98 is His, Ile, Asn, Ala, Thr, Gln, Glu, Lys, Met, Ser, Tyr, Val or Leu;

Xaa at position 99 is Ile or Leu;

Xaa at position 100 is Lys or Arg;

Xaa at position 101 is Asp;

Xaa at position 105 is Asn, Pro, Ser, Ile or Asp;

Xaa at position 108 is Arg, Ala, or Ser;

Xaa at position 109 is Arg, Thr, Glu, Leu, or Ser;

Xaa at position 112 is Thr or Gln;

Xaa at position 116 is Lys;

Xaa at position 120 is Asn, Pro, Leu, His, Val, or Gln;

Xaa at position 121 is Ala, Ser, Ile, Pro, or Asp;

Xaa at position 122 is Gln, Met, Trp, Phe, Pro, His, Ile, or Tyr;

Xaa at position 123 is Ala, Met, Glu, Ser, or Leu;

wherein from 6 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus of said sequence of SEQ ID No: 3.

32. The method of claim 30, wherein in said human interleukin-3 mutant polypeptide, the amino acids which differ from the corresponding residue in native human interleukin-3 are selected from the group consisting of:

position 42 wherein Xaa is Gly, Asp, Ser, Ile, Leu, Met, Tyr, or Ala;

position 45 wherein Xaa is Gln, Val, Met or Asn;

position 46 wherein Xaa is Asp, Ser, Gln, His or Val;

position 50 wherein Xaa is Glu or Asp;

position 51 wherein Xaa is Asn, Pro or Thr;

position 62 wherein Xaa is Asn or Pro;

position 76 wherein Xaa is Ser, or Pro;

position 82 wherein Xaa is Leu, Trp, Asp, Asn, Glu, His, Phe, Ser or Tyr;

position 95 wherein Xaa is His, Arg, Thr, Asn or Ser;

position 98 wherein Xaa is His, Ile, Leu, Ala, Gln, Lys, Met, Ser, Tyr or Val;

position 100 wherein Xaa is Lys or Arg;

position 105 wherein Xaa is Asn, or Pro;

position 108 wherein Xaa is Arg, Ala, or Ser;

position 121 wherein Xaa is Ala, or Ile;

position 122 wherein Xaa is Gln, or Ile; and position 123 wherein Xaa is Ala, Met or Glu;

wherein from 6 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus.

33. A method of treating a patient having a hematopoietic disorder consisting of; administering to said patient a composition consisting essentially of;

a biologically active human interleukin-3 variant polypeptide, said polypeptide consisting of a sequence selected from the group consisting of:

(a) the sequence of SEQ ID NO:4; and (b) a polypeptide consisting of an N-terminal residue, alanine residue or methionine-alanine di-peptide immediately preceding said sequence according to (a);

wherein;

Xaa at position 3 is Ser, Lys, Gly, Asp, Met, Gln, or Arg;

Xaa at position 4 is Asn, His, Leu, Ile, Phe, Arg, or Gln;

Xaa at position 5 is Met, Phe, Ile, Arg, Gly, Ala, or Cys;

Xaa at position 6 is Ile, Cys, Gln, Glu, Arg, Pro, or Ala;

Xaa at position 7 is Asp, Phe, -Lys, Arg, Ala, Gly, Glu, Gln, Asn, Thr, Ser or Val;

Xaa at position 8 is Glu, Trp, Pro, Ser, Ala, His, Asp, Asn, Gln, Leu, Val, or Gly;

Xaa at position 9 is Ile, Val, Ala, Leu, Gly, Trp, Lys, Phe, Ser, or Arg;

Xaa at position 10 is Ile, Gly, Val, Arg, Ser, Phe, or Leu;

Xaa at position 11 is Thr, His, Gly, Gln, Arg, Pro, or Ala;

Xaa at position 12 is His, Thr, Phe, Gly, Arg, Ala, or Trp;

Xaa at position 13 is Leu, Gly, Arg, Thr, Ser, or Ala;

Xaa at position 14 is Lys, Arg, Leu, Gln, Gly, Pro, Val or Trp;

Xaa at position 15 is Gln, Asn, Leu, Pro, Arg, or Val;

Xaa at position 16 is Pro, His, Thr, Gly, Asp, Gln, Ser, Leu, or Lys;

Xaa at position 17 is Pro, Asp, Gly, Ala, Arg, Leu, or Gln;

Xaa at position 18 is Leu, Val, Arg, Gln, Asn, Gly, Ala, or Glu;

Xaa at position 19 is Pro, Leu, Gln, Ala, Thr, or Glu;

Xaa at position 20 is Leu, Val, Gly, Ser, Lys, Glu, Gln, Thr, Arg, Ala, Phe, Ile or Met;

Xaa at position 21 is Leu, Ala, Gly, Asn, Pro, Gln, or Val;

Xaa at position 22 is Asp, Leu, or Val;

Xaa at position 23 is Phe, Ser, Pro, Trp, or Ile;

Xaa at position 24 is Asn, or Ala;

Xaa at position 26 is Leu, Trp, or Arg;

Xaa at position 27 is Asn, Cys, Arg, Leu, His, Met, Pro;

Xaa at position 28 is Gly, Asp, Ser, Cys, Ala, Lys, Asn, Thr, Leu, Val, Glu, Phe, Tyr, Ile or Met;

Xaa at position 29 is Glu, Asn, Tyr, Leu, Phe, Asp, Ala, Cys, Gln, Arg, Thr, Gly or Ser;

Xaa at position 30 is Asp, Ser, Leu, Arg, Lys, Thr, Met, Trp, Glu, Asn, Gln, Ala or Pro;

Xaa at position 31 is Gln, Pro, Phe, Val, Met, Leu, Thr, Lys, Asp, Asn, Arg, Ser, Ala, Ile, Glu, His or Trp;

Xaa at position 32 is Asp, Phe, Ser, Thr, Cys, Glu, Asn, Gln, Lys, His, Ala, Tyr, Ile, Val or Gly;

Xaa at position 33 is Ile, Gly, Val, Ser, Arg, Pro, or His;

Xaa at position 34 is Leu, Ser, Cys, Arg, Ile, His, Phe, Glu, Lys, Thr, Ala, Met, Val or Asn;

Xaa at position 35 is Met, Arg, Ala, Gly, Pro, Asn, His, or Asp;

Xaa at position 36 is Glu, Leu, Thr, Asp, Tyr, Lys, Asn, Ser, Ala, Ile, Val, His, Phe, Met or Gln;

Xaa at position 37 is Asn, Arg, Met, Pro, Ser, Thr, or His;

Xaa at position 38 is Asn, His, Arg, Leu, Gly, Ser, or Thr;

Xaa at position 39 is Leu, Thr, Ala, Gly, Glu, Pro, Lys, Ser, or Met;

Xaa at position 40 is Arg, Asp, Ile, Ser, Val, Thr, Gln, Asn, Lys, His, Ala or Leu;

Xaa at position 41 is Arg, Thr, Val, Ser, Leu, or Gly;

Xaa at position 42 is Pro, Gly, Cys, Ser, Gln, Glu, Arg, His, Thr, Ala, Tyr, Phe, Leu, Val or Lys;

Xaa at position 43 is Asn or Gly;

Xaa at position 44 is Leu, Ser, Asp, Arg, Gln, Val, or Cys;

Xaa at position 45 is Glu, Tyr, His, Leu, Pro, or Arg;

Xaa at position 46 is Ala, Ser, Pro, Tyr, Asn, or Thr;

Xaa at position 47 is Phe, Asn, Glu, Pro, Lys, Arg, or Ser;

Xaa at position 48 is Asn, His, Val, Arg, Pro, Thr, Asp, or Ile;

Xaa at position 49 is Arg, Tyr, Trp, Lys, Ser, His, Pro, or Val;

Xaa at position 50 is Ala, Asn, Pro, Ser, or Lys;

Xaa at position 51 is Val, Thr, Pro, His, Leu, Phe, or Ser;

Xaa at position 52 is Lys, Ile, Arg, Val, Asn, Glu, or Ser;

Xaa at position 53 is Ser, Ala, Phe, Val, Gly, Asn, Ile, Pro, or His;

Xaa at position 54 is Leu, Val, Trp, Ser, Ile, Phe, Thr, or His;

Xaa at position 55 is Gln, Ala, Pro, Thr, Glu, Arg, Trp, Gly, or Leu;

Xaa at position 56 is Asn, Leu, Val, Trp, Pro, or Ala;

Xaa at position 57 is Ala, Met, Leu, Pro, Arg, Glu, Thr, Gln, Trp, or Asn;

Xaa at position 58 is Ser, Glu, Met, Ala, His, Asn, Arg, or Asp;

Xaa at position 59 is Ala, Glu, Asp, Leu, Ser, Gly, Thr, or Arg;

Xaa at position 60 is Ile, Met, Thr, Pro, Arg, Gly, Ala;

Xaa at position 61 is Glu, Lys, Gly, Asp, Pro, Trp, Arg, Ser, Gln, or Leu;

Xaa at position 62 is Ser, Val, Ala, Asn, Trp, Glu, Pro, Gly, or Asp;

Xaa at position 63 is Ile, Ser, Arg, Thr, or Leu;

Xaa at position 64 is Leu, Ala, Ser, Glu, Phe, Gly, or Arg;

Xaa at position 65 is Lys, Thr, Gly, Asn, Met, Arg, Ile, or Asp;

Xaa at position 66 is Asn, Trp, Val, Gly, Thr, Leu, Glu, or Arg;

Xaa at position 67 is Leu, Gln, Gly, Ala, Trp, Arg, Val, or Lys;

Xaa at position 68 is Leu, Gln, Lys, Trp, Arg, Asp, Glu, Asn, His, Thr, Ser, Ala, Tyr, Phe, Ile, Met or Val;

Xaa at position 69 is Pro, Ala, Thr, Trp, Arg, or Met;

Xaa at position 70 is Cys, Glu, Gly, Arg, Met, or Val;

Xaa at position 71 is Leu, Asn, Val, or Gln;

Xaa at position 72 is Pro, Cys, Arg, Ala, or Lys;

Xaa at position 73 is Leu, Ser, Trp, or Gly;

Xaa at position 74 is Ala, Lys, Arg, Val, or Trp;

Xaa at position 75 is Thr, Asp, Cys, Leu, Val, Glu, His, Asn, or Ser;

Xaa at position 76 is Ala, Pro, Ser, Thr, Gly, Asp, Ile, or Met;

Xaa at position 77 is Ala, Pro, Ser, Thr, Phe, Leu, Asp, or His;

Xaa at position 78 is Pro, Phe, Arg, Ser, Lys, His, Ala, Gly, Ile or Leu;

Xaa at position 79 is Thr, Asp, Ser, Asn, Pro, Ala, Leu, or Arg;

Xaa at position 80 is Arg, Ile, Ser, Glu, Leu, Val, Gln, Lys, His, Ala or Pro;

Xaa at position 81 is His, Gln, Pro, Arg, Val, Leu, Gly, Thr, Asn, Lys, Ser, Ala, Trp, Phe, Ile or Tyr;

Xaa at position 82 is Pro, Lys, Tyr, Gly, Ile, or Thr;

Xaa at position 83 is Ile, Val, Lys, Ala, or Asn;

Xaa at position 84 is His, Ile, Asn, Leu, Asp, Ala, Thr, Glu, Gln, Ser, Phe, Met, Val, Lys, Arg, Tyr or Pro;

Xaa at position 85 is Ile, Leu, Arg, Asp, Val, Pro, Gln, Gly, Ser, Phe, or His;

Xaa at position 86 is Lys, Tyr, Leu, His, Arg, Ile, Ser, Gln, Pro;

Xaa at position 87 is Asp;

Xaa at position 88 is Gly, Leu, Glu, Lys, Ser, Tyr, or Pro;

Xaa at position 89 is Asp, or Ser;

Xaa at position 90 is Trp, Val, Cys, Tyr, Thr, Met, Pro, Leu, Gln, Lys, Ala, Phe, or Gly;

Xaa at position 91 is Asn, Pro, Ala, Phe, Ser, Trp, Gln, Tyr, Leu, Lys, Ile, Asp, or His;

Xaa at position 92 is Glu, Ser, Ala, Lys, Thr, Ile, Gly, or Pro;

Xaa at position 94 is Arg, Lys, Asp, Leu, Thr, Ile, Gln, His, Ser, Ala, or Pro;

Xaa at position 95 is Arg, Thr, Pro, Glu, Tyr, Leu, Ser, or Gly;

Xaa at position 96 is Lys, Asn, Thr, Leu, Gln, Arg, His, Glu, Ser, Ala or Trp;

Xaa at position 97 is Leu, Ile, Arg, Asp, or Met;

Xaa at position 98 is Thr, Val, Gln, Tyr, Glu, His, Ser, or Phe;

Xaa at position 99 is Phe, Ser, Cys, His, Gly, Trp, Tyr, Asp, Lys, Leu, Ile, Val or Asn;

Xaa at position 100 is Tyr, Cys, His, Ser, Trp, Arg, or Leu;

Xaa at position 101 is Leu, Asn, Val, Pro, Arg, Ala, His, Thr, Trp, or Met;

Xaa at position 102 is Lys;

Xaa at position 103 is Thr, Ser, Asn, Ile, Trp, Lys, or Pro;

Xaa at position 104 is Leu, Ser, Pro, Ala, Glu, Cys, Asp, or Tyr;

Xaa at position 105 is Glu, Ser, Lys, Pro, Leu, Thr, Tyr, or Arg;

Xaa at position 106 is Asn, Ala, Pro, Leu, His, Val, or Gln;

Xaa at position 107 is Ala, Ser, Ile, Asn, Pro, Lys, Asp, or Gly;

Xaa at position 108 is Gln, Ser, Met, Trp, Arg, Phe, Pro, His, Ile, Tyr, or Cys;

Xaa at position 109 is Ala, Met, Glu, His, Ser, Pro, Tyr, or Leu;

wherein from 6 to about 44 of the amino acids designated by Xaa are different from the corresponding native amino acids of (1–133) human interleukin-3;

a factor selected from the group consisting of: a colony stimulating factor, a cytokine, a lymphokine, an interleukin, and a hematopoietic growth factor; and at least one pharmaceutically acceptable carrier.

34. The method of claim 23, wherein (a) is the sequence of SEQ ID NO:6;

wherein

Xaa at position 3 is Ser, Gly, Asp, or Gln;

Xaa at position 4 is Asn, His, or Ile;

Xaa at position 9 is Ile, Ala, Leu, or Gly;

Xaa at position 11 is Thr, His, or Gln;

Xaa at position 12 is His or Ala;

Xaa at position 15 is Gln or Asn;

Xaa at position 16 is Pro or Gly;

Xaa at position 18 is Leu, Arg, Asn, or Ala;

Xaa at position 20 is Leu, Val, Ser, Ala, Arg, Gln, Glu, Ile, Phe, Thr or Met;

Xaa at position 21 is Leu, Ala, Asn, or Pro;

Xaa at position 24 is Asn or Ala;

Xaa at position 28 is Gly, Asp, Ser, Ala, Asn, Ile, Leu, Met, Tyr or Arg;

Xaa at position 31 is Gln, Val, Met, Leu, Ala, Asn, Glu or Lys;

Xaa at position 32 is Asp, Phe, Ser, Ala, Gln, Glu, His, Val or Thr;

Xaa at position 36 is Glu, Asn, Ser or Asp;

Xaa at position 37 is Asn, Arg, Pro, Thr, or His;
Xaa at position 41 is Arg, Leu, or Gly;
Xaa at position 42 is Pro, Gly, Ser, Ala, Asn, Val, Leu or Gln;
Xaa at position 48 is Asn, Pro, or Thr;
Xaa at position 50 is Ala or Asn;
Xaa at position 51 is Val or Thr;
Xaa at position 53 is Ser or Phe;
Xaa at position 54 is Leu or Phe;
Xaa at position 55 is Gln, Ala, Glu, or Arg;
Xaa at position 62 is Ser, Val, Asn, Pro, or Gly;
Xaa at position 63 is Ile or Leu;
Xaa at position 65 is Lys, Asn, Met, Arg, Ile, or Gly;
Xaa at position 66 is Asn, Gly, Glu, or Arg;
Xaa at position 68 is Leu, Gln, Trp, Arg, Asp, Asn, Glu, His, Met, Phe, Ser, Thr, Tyr or Val;
Xaa at position 73 is Leu or Ser;
Xaa at position 74 is Ala or Trp;
Xaa at position 77 is Ala or Pro;
Xaa at position 79 is Thr, Asp, or Ala;
Xaa at position 81 is His, Pro, Arg, Val, Gly, Asn, Ser or Thr;
Xaa at position 84 is His, Ile, Asn, Ala, Thr, Arg, Gln, Glu, Lys, Met, Ser, Tyr, Val or Leu;
Xaa at position 85 is Ile or Leu;
Xaa at position 86 is Lys or Arg;
Xaa at position 87 is Asp;
Xaa at position 91 is Asn, Pro, Ser, Ile or Asp;
Xaa at position 94 is Arg, Ala, or Ser;
Xaa at position 95 is Arg, Thr, Glu, Leu, or Ser;
Xaa at position 98 is Thr or Gln;
Xaa at position 102 is Lys;
Xaa at position 103 is Thr, Ala, His, Phe, Tyr or Ser;
Xaa at position 106 is Asn, Pro, Leu, His, Val, or Gln;
Xaa at position 107 is Ala, Ser, Ile, Pro, or Asp;
Xaa at position 108 is Gln, Met, Trp, Phe, Pro, His, Ile, or Tyr;
Xaa at position 109 is Ala, Met, Glu, Ser, or Leu;
wherein from 6 to about 44 of the amino acids designated by Xaa are different from the corresponding amino acids of native (1–133) human interleukin-3.

35. A method of treating a patient having a hematopoietic disorder consisting of; administering to said patient a composition consisting essentially of;
a biologically active human interleukin-3 variant polypeptide, said polypeptide consisting of a sequence selected from the group consisting of:
(a) the sequence of SEQ ID NO:8; and
(b) a polypeptide consisting of an N-terminal residue, alanine residue or methionine-alanine di-peptide immediately preceding said sequence according to (a);
wherein;
Xaa at position 4 is Asn or Ile;
Xaa at position 5 is Met, Ala or Ile;
Xaa at position 6 is Ile, Pro or Leu;
Xaa at position 9 is Ile, Ala or Leu;
Xaa at position 11 is Thr or His;
Xaa at position 15 is Gln, Arg, Val or Leu;
Xaa at position 18 is Leu, Ala, Asn or Arg;
Xaa at position 20 is Leu or Ser;
Xaa at position 23 is Phe, Pro, or Ser;
Xaa at position 24 is Asn or Ala;
Xaa at position 28 is Gly, Ala, Ser, Asp or Asn;
Xaa at position 31 is Gln, Val, or Met;
Xaa at position 32 is Asp or Ser;
Xaa at position 35 is Met, Ile, Leu or Asp;
Xaa at position 36 is Glu or Asp;
Xaa at position 37 is Asn, Arg or Ser;
Xaa at position 41 is Arg, Leu, or Thr;
Xaa at position 42 is Pro or Ser;
Xaa at position 45 is Glu or Leu;
Xaa at position 46 is Ala or Ser;
Xaa at position 48 is Asn, Val or Pro;
Xaa at position 49 is Arg or His;
Xaa at position 51 is Val or Ser;
Xaa at position 53 is Ser, Asn, His or Gly;
Xaa at position 55 is Gln or Glu;
Xaa at position 59 is Ala or Gly;
Xaa at position 62 is Ser, Ala or Pro;
Xaa at position 65 is Lys, Arg or Ser;
Xaa at position 67 is Leu, Glu, or Val;
Xaa at position 68 is Leu, Glu, Val or Trp;
Xaa at position 71 is Leu or Val;
Xaa at position 73 is Leu, Ser or Trp;
Xaa at position 74 is Ala or Trp;
Xaa at position 77 is Ala or Pro;
Xaa at position 79 is Pro or Ser;
Xaa at position 81 is His or Thr;
Xaa at position 84 is His, Ile, or Thr;
Xaa at position 86 is Lys or Arg;
Xaa at position 87 is Asp;
Xaa at position 91 is Asn or Gln;
Xaa at position 95 is Arg, Glu, Leu;
Xaa at position 98 is Thr or Gln;
Xaa at position 102 is Lys;
Xaa at position 103 is Thr or Ser;
Xaa at position 106 is Asn, Gln, or His;
Xaa at position 109 is Ala or Glu;
wherein from 6 to about 44 of the amino acids designated by Xaa are different from the corresponding amino acids of native (1–133) human interleukin-3;
a factor selected from the group consisting of: a colony stimulating factor, a cytokine, a lymphokine, an interleukin, and a hematopoietic growth factor; and
at least one pharmaceutically acceptable carrier.

36. The method of claim 29, 30, 31, 32, 33, 34, or 35 wherein said factor is selected from the group consisting of; GM-CSF, CSF-1, G-CSF, G-CSF (Ser$^{17}$), M-CSF, erythropoietin (EPO), IL-1, IL-4, IL-2, IL-5, IL-6, IL-7, IL-8, IL-9, IL-10, IL-11, IL-12, IL-13, LIF, flt3 ligand, human growth hormone, B-cell growth factor, B-cell differentiation factor, eosinophil differentiation factor and stem cell factor (SCF).

37. The method according to claim 29, 30, 31, 32, 33, 34, or 35 wherein said hematopoietic disorder is a result of a viral infection, bacterial infection or fungal infection.

38. The method according to claim 29, 30, 31, 32, 33, 34, or 35 wherein said hematopoietic disorder is a result of cancer radiation therapy or chemotherapy or a bone marrow suppressive drug.

39. The method according to claim 36 wherein said hematopoietic disorder is a result of a viral infection, bacterial infection or fungal infection.

40. The method according to claim 36 wherein said hematopoietic disorder is a result of cancer radiation therapy or chemotherapy or a bone marrow suppressive drug.

41. A method of treating a patient consisting of;
  (i) administering to said patient, an amount effective to promote the proliferation and/or differentiation of hematopoietic cells in said patient of a composition consisting essentially of;
  a modified human interleukin-3 (hIL-3) amino acid sequence, wherein said modified sequence differs from the sequence of native (1–133) hIL-3 by the replacement of from 4 to about 44 of the residues corresponding to positions 17–118 of native (1–133) hIL-3 by other amino acids, with the proviso that the residues corresponding to positions 101 and 116 are not Ala or Val, respectively, and with the proviso that no more than one of the amino acids at positions 63, 82, 87, 98, and 112 are different from the corresponding amino acids in native human interleukin-3; wherein said modified sequence optionally further differs from the sequence of native (1–133) hIL-3 by the deletion of from 1 to 14 residues from the N-terminus of native (1–133) hIL-3, the deletion of from 1 to 15 residues from the C-terminus of native (1–133) hIL-3, or both; and wherein said modified interleukin-3 (hIL-3) amino acid sequence has increased activity, relative to native human interleukin-3, in at least one assay selected from the group consisting of: AML cell proliferation, TF-1 cell proliferation and Methylcellulose assay;
  a factor selected from the group consisting of: a colony stimulating factor, a cytokine a lymphokine, an interleukin and a hematopoietic growth factor; and at least one pharmaceutically acceptable carrier;
  (ii) removing hematopoietic cells from said patient;
  (iii) administering cancer radiation therapy or chemotherapy to said patient; and
  (iv) returning said hematopoietic cells to said patient.

42. A method of treating a patient consisting of the steps of:
  (i) administering to said patient, an amount effective to promote the proliferation and/or differentiation of hematopoietic cells in said patient of a composition consisting essentially of;
  a biologically active human interleukin-3 variant polypeptide, said polypeptide consisting of a sequence selected from the group consisting of:
    (a) the sequence of SEQ ID NO:1; and
    (b) a polypeptide consisting of an N-terminal methionine residue, alanine residue or methionine-alanine di-peptide immediately preceding said sequence according to (a);
  wherein;
    Xaa at position 17 is Ser, Lys, Gly, Asp, Met, Gln, or Arg;
    Xaa at position 18 is Asn, His, Leu, Ile, Phe, Arg, or Gln;
    Xaa at position 19 is Met, Phe, Ile, Arg, Gly, Ala, or Cys;
    Xaa at position 20 is Ile, Cys, Gln, Glu, Arg, Pro, or Ala;
    Xaa at position 21 is Asp, Phe, Lys, Arg, Ala, Gly, Glu, Gln, Asn, Thr, Ser or Val;
    Xaa at position 22 is Glu, Trp, Pro, Ser, Ala, His, Asp, Asn, Gln, Leu, Val or Gly;
    Xaa at position 23 is Ile, Val, Ala, Leu, Gly, Trp, Lys, Phe, Ser, or Arg;
    Xaa at position 24 is Ile, Gly, Val, Arg, Ser, Phe, or Leu;
    Xaa at position 25 is Thr, His, Gly, Gln, Arg, Pro, or Ala;
    Xaa at position 26 is His, Thr, Phe, Gly, Arg, Ala, or Trp;
    Xaa at position 27 is Leu, Gly, Arg, Thr, Ser, or Ala;
    Xaa at position 28 is Lys, Arg, Leu, Gln, Gly, Pro, Val or Trp;
    Xaa at position 29 is Gln, Asn, Leu, Pro, Arg, or Val;
    Xaa at position 30 is Pro, His, Thr, Gly, Asp, Gln, Ser, Leu, or Lys;
    Xaa at position 31 is Pro, Asp, Gly, Ala, Arg, Leu, or Gln;
    Xaa at position 32 is Leu, Val, Arg, Gln, Asn, Gly, Ala, or Glu;
    Xaa at position 33 is Pro, Leu, Gln, Ala, Thr, or Glu;
    Xaa at position 34 is Leu, Val, Gly, Ser, Lys, Glu, Gln, Thr, Arg, Ala, Phe, Ile or Met;
    Xaa at position 35 is Leu, Ala, Gly, Asn, Pro, Gln, or Val;
    Xaa at position 36 is Asp, Leu, or Val;
    Xaa at position 37 is Phe, Ser, Pro, Trp, or Ile;
    Xaa at position 38 is Asn, or Ala;
    Xaa at position 40 is Leu, Trp, or Arg;
    Xaa at position 41 is Asn, Cys, Arg, Leu, His, Met, or Pro;
    Xaa at position 42 is Gly, Asp, Ser, Cys, Asn, Lys, Thr, Leu, Val, Glu, Phe, Tyr, Ile, Met or Ala;
    Xaa at position 43 is Glu, Asn, Tyr, Leu, Phe, Asp, Ala, Cys, Gln, Arg, Thr, Gly or Ser;
    Xaa at position 44 is Asp, Ser, Leu, Arg, Lys, Thr, Met, Trp, Glu, Asn, Gln, Ala or Pro;
    Xaa at position 45 is Gln, Pro, Phe, Val, Met, Leu, Thr, Lys, Trp, Asp, Asn, Arg, Ser, Ala, Ile, Glu or His;
    Xaa at position 46 is Asp, Phe, Ser, Thr, Cys, Glu, Asn, Gln, Lys, His, Ala, Tyr, Ile, Val or Gly;
    Xaa at position 47 is Ile, Gly, Val, Ser, Arg, Pro, or His;
    Xaa at position 48 is Leu, Ser, Cys, Arg, Ile, His, Phe, Glu, Lys, Thr, Ala, Met, Val or Asn;
    Xaa at position 49 is Met, Arg, Ala, Gly, Pro, Asn, His, or Asp;
    Xaa at position 50 is Glu, Leu, Thr, Asp, Tyr, Lys, Asn, Ser, Ala, Ile, Val, His, Phe, Met or Gln;
    Xaa at position 51 is Asn, Arg, Met, Pro, Ser, Thr, or His;
    Xaa at position 52 is Asn, His, Arg, Leu, Gly, Ser, or Thr;
    Xaa at position 53 is Leu, Thr, Ala, Gly, Glu, Pro, Lys, Ser, or Met;
    Xaa at position 54 is Arg, Asp, Ile, Ser, Val, Thr, Gln, Asn, Lys, His, Ala or Leu;
    Xaa at position 55 is Arg, Thr, Val, Ser, Leu, or Gly;
    Xaa at position 56 is Pro, Gly, Cys, Ser, Gln, Glu, Arg, His, Thr, Ala, Tyr, Phe, Leu, Val or Lys;
    Xaa at position 57 is Asn or Gly;
    Xaa at position 58 is Leu, Ser, Asp, Arg, Gln, Val, or Cys;
    Xaa at position 59 is Glu, Tyr, His, Leu, Pro, or Arg;
    Xaa at position 60 is Ala, Ser, Pro, Tyr, Asn, or Thr;
    Xaa at position 61 is Phe, Asn, Glu, Pro, Lys, Arg, or Ser;
    Xaa at position 62 is Asn, His, Val, Arg, Pro, Thr, Asp, or Ile;
    Xaa at position 63 is Arg, Tyr, Trp, Lys, Ser, His, Pro, or Val;
    Xaa at position 64 is Ala, Asn, Pro, Ser, or Lys;
    Xaa at position 65 is Val, Thr, Pro, His, Leu, Phe, or Ser;
    Xaa at position 66 is Lys, Ile, Arg, Val, Asn, Glu, or Ser;

Xaa at position 67 is Ser, Ala, Phe, Val, Gly, Asn, Ile, Pro, or His;

Xaa at position 68 is Leu, Val, Trp, Ser, Ile, Phe, Thr, or His;

Xaa at position 69 is Gln, Ala, Pro, Thr, Glu, Arg, Trp, Gly, or Leu;

Xaa at position 70 is Asn, Leu, Val, Trp, Pro, or Ala;

Xaa at position 71 is Ala, Met, Leu, Pro, Arg, Glu, Thr, Gln, Trp, or Asn;

Xaa at position 72 is Ser, Glu, Met, Ala, His, Asn, Arg, or Asp;

Xaa at position 73 is Ala, Glu, Asp, Leu, Ser, Gly, Thr, or Arg;

Xaa at position 74 is Ile, Met, Thr, Pro, Arg, Gly, Ala;

Xaa at position 75 is Glu, Lys, Gly, Asp, Pro, Trp, Arg, Ser, Gln, or Leu;

Xaa at position 76 is Ser, Val, Ala, Asn, Trp, Glu, Pro, Gly, or Asp;

Xaa at position 77 is Ile, Ser, Arg, Thr, or Leu;

Xaa at position 78 is Leu, Ala, Ser, Glu, Phe, Gly, or Arg;

Xaa at position 79 is Lys, Thr, Asn, Met, Arg, Ile, Gly, or Asp;

Xaa at position 80 is Asn, Trp, Val, Gly, Thr, Leu, Glu, or Arg;

Xaa at position 81 is Leu, Gln, Gly, Ala, Trp, Arg, Val, or Lys;

Xaa at position 82 is Leu, Gln, Lys, Trp, Arg, Asp, Glu, Asn, His, Thr, Ser, Ala, Tyr, Phe, Ile, Met or Val;

Xaa at position 83 is Pro, Ala, Thr, Trp, Arg, or Met;

Xaa at position 84 is Cys, Glu, Gly, Arg, Met, or Val;

Xaa at position 85 is Leu, Asn, Val, or Gln;

Xaa at position 86 is Pro, Cys, Arg, Ala, or Lys;

Xaa at position 87 is Leu, Ser, Trp, or Gly;

Xaa at position 88 is Ala, Lys, Arg, Val, or Trp;

Xaa at position 89 is Thr, Asp, Cys, Leu, Val, Glu, His, Asn, or Ser;

Xaa at position 90 is Ala, Pro, Ser, Thr, Gly, Asp, Ile, or Met;

Xaa at position 91 is Ala, Pro, Ser, Thr, Phe, Leu, Asp, or His;

Xaa at position 92 is Pro, Phe, Arg, Ser, Lys, His, Ala, Gly, Ile or Leu;

Xaa at position 93 is Thr, Asp, Ser, Asn, Pro, Ala, Leu, or Arg;

Xaa at position 94 is Arg, Ile, Ser, Glu, Leu, Val, Gln, Lys, His, Ala, or Pro;

Xaa at position 95 is His, Gln, Pro, Arg, Val, Leu, Gly, Thr, Asn, Lys, Ser, Ala, Trp, Phe, Ile, or Tyr;

Xaa at position 96 is Pro, Lys, Tyr, Gly, Ile, or Thr;

Xaa at position 97 is Ile, Val, Lys, Ala, or Asn;

Xaa at position 98 is His, Ile, Asn, Leu, Asp, Ala, Thr, Glu, Gln, Ser, Phe, Met, Val, Lys, Arg, Tyr or Pro;

Xaa at position 99 is Ile, Leu, Arg, Asp, Val, Pro, Gln, Gly, Ser, Phe, or His;

Xaa at position 100 is Lys, Tyr, Leu, His, Arg, Ile, Ser, Gln, or Pro;

Xaa at position 101 is Asp;

Xaa at position 102 is Gly, Leu, Glu, Lys, Ser, Tyr, or Pro;

Xaa at position 103 is Asp, or Ser;

Xaa at position 104 is Trp, Val, Cys, Tyr, Thr, Met, Pro, Leu, Gln, Lys, Ala, Phe, or Gly;

Xaa at position 105 is Asn, Pro, Ala, Phe, Ser, Trp, Gln, Tyr, Leu, Lys, Ile, Asp, or His;

Xaa at position 106 is Glu, Ser, Ala, Lys, Thr, Ile, Gly, or Pro;

Xaa at position 108 is Arg, Lys, Asp, Leu, Thr, Ile, Gln, His, Ser, Ala or Pro;

Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, Ala, or Trp;

Xaa at position 111 is Leu, Ile, Arg, Asp, or Met;

Xaa at position 112 is Thr, Val, Gln, Tyr, Glu, His, Ser, or Phe;

Xaa at position 113 is Phe, Ser, Cys, His, Gly, Trp, Tyr, Asp, Lys, Leu, Ile, Val or Asn;

Xaa at position 114 is Tyr, Cys, His, Ser, Trp, Arg, or Leu;

Xaa at position 115 is Leu, Asn, Val, Pro, Arg, Ala, His, Thr, Trp, or Met;

Xaa at position 116 is Lys;

Xaa at position 117 is Thr, Ser, Asn, Ile, Trp, Lys, or Pro;

Xaa at position 118 is Leu, Ser, Pro, Ala, Glu, Cys, Asp, or Tyr;

Xaa at position 119 is Glu, Ser, Lys, Pro, Leu, Thr, Tyr, or Arg;

Xaa at position 120 is Asn, Ala, Pro, Leu, His, Val, or Gln;

Xaa at position 121 is Ala, Ser, Ile, Asn, Pro, Lys, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

wherein from 6 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus of said sequence of SEQ ID NO:1;

a factor selected from the group consisting of: a colony stimulating factor, a cytokine, a lymphokine, an interleukin, and a hematopoietic growth factor; and at least one pharmaceutically acceptable carrier;

(ii) removing hematopoietic cells from said patient;

(iii) administering cancer radiation therapy or chemotherapy to said patient; and (iv) returning said hematopoietic cells to said patient.

43. The method of claim 42, wherein (a) is the sequence of SEQ ID NO:3;

wherein

Xaa at position 17 is Ser, Gly, Asp, or Gln;

Xaa at position 18 is Asn, His, or Ile;

Xaa at position 23 is Ile, Ala, Leu, or Gly;

Xaa at position 25 is Thr, His, or Gln;

Xaa at position 26 is His or Ala;

Xaa at position 29 is Gln or Asn;

Xaa at position 30 is Pro or Gly;

Xaa at position 32 is Leu, Arg, Asn, or Ala;

Xaa at position 34 is Leu, Val, Ser, Ala, Arg, Gln, Glu, Ile, Phe, Thr, or Met;

Xaa at position 35 is Leu, Ala, Asn, or Pro;

Xaa at position 38 is Asn or Ala;

Xaa at position 42 is Gly, Asp, Ser, Ala, Asn, Ile, Leu, Met, Tyr or Arg;

Xaa at position 45 is Gln, Val, Met, Leu, Ala, Asn, Glu, or Lys;

Xaa at position 46 is Asp, Phe, Ser, Gln, Glu, His, Val or Thr;

Xaa at position 50 is Glu, Asn, Ser or Asp;

Xaa at position 51 is Asn, Arg, Pro, Thr, or His;

Xaa at position 55 is Arg, Leu, or Gly;

Xaa at position 56 is Pro, Gly, Ser, Ala, Asn, Val, Leu or Gln;

Xaa at position 62 is Asn, Pro, or Thr;

Xaa at position 64 is Ala or Asn;

Xaa at position 65 is Val or Thr;

Xaa at position 67 is Ser or Phe;

Xaa at position 68 is Leu or Phe;

Xaa at position 69 is Gln, Ala, Glu, or Arg;

Xaa at position 76 is Ser, Val, Asn, Pro, or Gly;

Xaa at position 77 is Ile or Leu;

Xaa at position 79 is Lys, Asn, Met, Arg, Ile, or Gly;

Xaa at position 80 is Asn, Gly, Glu, or Arg;

Xaa at position 82 is Leu, Gln, Trp, Arg, Asp, Asn, Glu, His, Met, Phe, Ser, Thr, Tyr or Val;

Xaa at position 87 is Leu or Ser;

Xaa at position 88 is Ala or Trp;

Xaa at position 91 is Ala or Pro;

Xaa at position 93 is Thr, Asp, or Ala;

Xaa at position 95 is His, Pro, Arg, Val, Gly, Asn, Ser or Thr;

Xaa at position 98 is His, Ile, Asn, Ala, Thr, Gln, Glu, Lys, Met, Ser, Tyr, Val or Leu;

Xaa at position 99 is Ile or Leu;

Xaa at position 100 is Lys or Arg;

Xaa at position 101 is Asp;

Xaa at position 105 is Asn, Pro, Ser, Ile or Asp;

Xaa at position 108 is Arg, Ala, or Ser;

Xaa at position 109 is Arg, Thr, Glu, Leu, or Ser;

Xaa at position 112 is Thr or Gln;

Xaa at position 116 is Lys;

Xaa at position 120 is Asn, Pro, Leu, His, Val, or Gln;

Xaa at position 121 is Ala, Ser, Ile, Pro, or Asp;

Xaa at position 122 is Gln, Met, Trp, Phe, Pro, His, Ile, or Tyr;

Xaa at position 123 is Ala, Met, Glu, Ser, or Leu;

wherein from 6 to about 44 of the amino acids designated by Xaa are different from the corresponding amino acids of native (1–133)human interleukin-3; and wherein from 1 to 14 amino acids are optionally deleted from the N-terminus and/or from 1 to 15 amino acids are optionally deleted from the C-terminus of said sequence of SEQ ID No: 3.

44. The method of claim 42, wherein in said human interleukin-3 mutant polypeptide, the amino acids which differ from the corresponding residue in native human interleukin-3 are selected from the group consisting of:

position 42 wherein Xaa is Gly, Asp, Ser, Ile, Leu, Met, Tyr, or Ala;

position 45 wherein Xaa is Gln, Val, Met or Asn;

position 46 wherein Xaa is Asp, Ser, Gln, His or Val;

position 50 wherein Xaa is Glu or Asp;

position 51 wherein Xaa is Asn, Pro or Thr;

position 62 wherein Xaa is Asn or Pro;

position 76 wherein Xaa is Ser, or Pro;

position 82 wherein Xaa is Leu, Trp, Asp, Asn, Glu, His, Phe, Ser or Tyr;

position 95 wherein Xaa is His, Arg, Thr, Asn or Ser;

position 98 wherein Xaa is His, Ile, Leu, Ala, Gln, Lys, Met, Ser, Tyr or Val;

position 100 wherein Xaa is Lys or Arg;

position 105 wherein Xaa is Asn, or Pro;

position 108 wherein Xaa is Arg, Ala, or Ser;

position 121 wherein Xaa is Ala, or Ile;

position 122 wherein Xaa is Gln, or Ile; and position 123 wherein Xaa is Ala, Met or Glu;

wherein from 6 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus.

45. A method of treating a patient consisting of the steps of:

(i) administering to said patient, an amount effective to promote the proliferation and/or differentiation of hematopoietic cells in said patient of a composition consisting essentially of;

a biologically active human interleukin-3 variant polypeptide, said polypeptide consisting of a sequence selected from the group consisting of:

(a) the sequence of SEQ ID NO:4; and (b) a polypeptide consisting of an N-terminal methionine residue, alanine residue or methionine-alanine di-peptide immediately preceding said sequence according to (a);

wherein

Xaa at position 3 is Ser, Lys, Gly, Asp, Met, Gln, or Arg;

Xaa at position 4 is Asn, His, Leu, Ile, Phe, Arg, or Gln;

Xaa at position 5 is Met, Phe, Ile, Arg, Gly, Ala, or Cys;

Xaa at position 6 is Ile, Cys, Gln, Glu, Arg, Pro, or Ala;

Xaa at position 7 is Asp, Phe, Lys, Arg, Ala, Gly, Glu, Gln, Asn, Thr, Ser or Val;

Xaa at position 8 is Glu, Trp, Pro, Ser, Ala, His, Asp, Asn, Gln, Leu, Val, or Gly;

Xaa at position 9 is Ile, Val, Ala, Leu, Gly, Trp, Lys, Phe, Ser, or Arg;

Xaa at position 10 is Ile, Gly, Val, Arg, Ser, Phe, or Leu;

Xaa at position 11 is Thr, His, Gly, Gln, Arg, Pro, or Ala;

Xaa at position 12 is His, Thr, Phe, Gly, Arg, Ala, or Trp;

Xaa at position 13 is Leu, Gly, Arg, Thr, Ser, or Ala;

Xaa at position 14 is Lys, Arg, Leu, Gln, Gly, Pro, Val or Trp;

Xaa at position 15 is Gln, Asn, Leu, Pro, Arg, or Val;

Xaa at position 16 is Pro, His, Thr, Gly, Asp, Gln, Ser, Leu, or Lys;

Xaa at position 17 is Pro, Asp, Gly, Ala, Arg, Leu, or Gln;

Xaa at position 18 is Leu, Val, Arg, Gln, Asn, Gly, Ala, or Glu;

Xaa at position 19 is Pro, Leu, Gln, Ala, Thr, or Glu;

Xaa at position 20 is Leu, Val, Gly, Ser, Lys, Glu, Gln, Thr, Arg, Ala, Phe, Ile or Met;

Xaa at position 21 is Leu, Ala, Gly, Asn, Pro, Gln, or Val;

Xaa at position 22 is Asp, Leu, or Val;

Xaa at position 23 is Phe, Ser, Pro, Trp, or Ile;

Xaa at position 24 is Asn, or Ala;

Xaa at position 26 is Leu, Trp, or Arg;

Xaa at position 27 is Asn, Cys, Arg, Leu, His, Met, Pro;

Xaa at position 28 is Gly, Asp, Ser, Cys, Ala, Lys, Asn, Thr, Leu, Val, Glu, Phe, Tyr, Ile or Met;

Xaa at position 29 is Glu, Asn, Tyr, Leu, Phe, Asp, Ala, Cys, Gln, Arg, Thr, Gly or Ser;

Xaa at position 30 is Asp, Ser, Leu, Arg, Lys, Thr, Met, Trp, Glu, Asn, Gln, Ala or Pro;

Xaa at position 31 is Gln, Pro, Phe, Val, Met, Leu, Thr, Lys, Asp, Asn, Arg, Ser, Ala, Ile, Glu, His or Trp;

Xaa at position 32 is Asp, Phe, Ser, Thr, Cys, Glu, Asn, Gln, Lys, His, Ala, Tyr, Ile, Val or Gly;

Xaa at position 33 is Ile, Gly, Val, Ser, Arg, Pro, or His;

Xaa at position 34 is Leu, Ser, Cys, Arg, Ile, His, Phe, Glu, Lys, Thr, Ala, Met, Val or Asn;

Xaa at position 35 is Met, Arg, Ala, Gly, Pro, Asn, His, or Asp;

Xaa at position 36 is Glu, Leu, Thr, Asp, Tyr, Lys, Asn, Ser, Ala, Ile, Val, His, Phe, Met or Gln;

Xaa at position 37 is Asn, Arg, Met, Pro, Ser, Thr, or His;

Xaa at position 38 is Asn, His, Arg, Leu, Gly, Ser, or Thr;

Xaa at position 39 is Leu, Thr, Ala, Gly, Glu, Pro, Lys, Ser, or Met;

Xaa at position 40 is Arg, Asp, Ile, Ser, Val, Thr, Gln, Asn, Lys, His, Ala or Leu;

Xaa at position 41 is Arg, Thr, Val, Ser, Leu, or Gly;

Xaa at position 42 is Pro, Gly, Cys, Ser, Gln, Glu, Arg, His, Thr, Ala, Tyr, Phe, Leu, Val or Lys;

Xaa at position 43 is Asn or Gly;

Xaa at position 44 is Leu, Ser, Asp, Arg, Gln, Val, or Cys;

Xaa at position 45 is Glu, Tyr, His, Leu, Pro, or Arg;

Xaa at position 46 is Ala, Ser, Pro, Tyr, Asn, or Thr;

Xaa at position 47 is Phe, Asn, Glu, Pro, Lys, Arg, or Ser;

Xaa at position 48 is Asn, His, Val, Arg, Pro, Thr, Asp, or Ile;

Xaa at position 49 is Arg, Tyr, Trp, Lys, Ser, His, Pro, or Val;

Xaa at position 50 is Ala, Asn, Pro, Ser, or Lys;

Xaa at position 51 is Val, Thr, Pro, His, Leu, Phe, or Ser;

Xaa at position 52 is Lys, Ile, Arg, Val, Asn, Glu, or Ser;

Xaa at position 53 is Ser, Ala, Phe, Val, Gly, Asn, Ile, Pro, or His;

Xaa at position 54 is Leu, Val, Trp, Ser, Ile, Phe, Thr, or His;

Xaa at position 55 is Gln, Ala, Pro, Thr, Glu, Arg, Trp, Gly, or Leu;

Xaa at position 56 is Asn, Leu, Val, Trp, Pro, or Ala;

Xaa at position 57 is Ala, Met, Leu, Pro, Arg, Glu, Thr, Gln, Trp, or Asn;

Xaa at position 58 is Ser, Glu, Met, Ala, His, Asn, Arg, or Asp;

Xaa at position 59 is Ala, Glu, Asp, Leu, Ser, Gly, Thr, or Arg;

Xaa at position 60 is Ile, Met, Thr, Pro, Arg, Gly, Ala;

Xaa at position 61 is Glu, Lys, Gly, Asp, Pro, Trp, Arg, Ser, Gln, or Leu;

Xaa at position 62 is Ser, Val, Ala, Asn, Trp, Glu, Pro, Gly, or Asp;

Xaa at position 63 is Ile, Ser, Arg, Thr, or Leu;

Xaa at position 64 is Leu, Ala, Ser, Glu, Phe, Gly, or Arg;

Xaa at position 65 is Lys, Thr, Gly, Asn, Met, Arg, Ile, or Asp;

Xaa at position 66 is Asn, Trp, Val, Gly, Thr, Leu, Glu, or Arg;

Xaa at position 67 is Leu, Gln, Gly, Ala, Trp, Arg, Val, or Lys;

Xaa at position 68 is Leu, Gln, Lys, Trp, Arg, Asp, Glu, Asn, His, Thr, Ser, Ala, Tyr, Phe, Ile, Met or Val;

Xaa at position 69 is Pro, Ala, Thr, Trp, Arg, or Met;

Xaa at position 70 is Cys, Glu, Gly, Arg, Met, or Val;

Xaa at position 71 is Leu, Asn, Val, or Gln;

Xaa at position 72 is Pro, Cys, Arg, Ala, or Lys;

Xaa at position 73 is Leu, Ser, Trp, or Gly;

Xaa at position 74 is Ala, Lys, Arg, Val, or Trp;

Xaa at position 75 is Thr, Asp, Cys, Leu, Val, Glu, His, Asn, or Ser;

Xaa at position 76 is Ala, Pro, Ser, Thr, Gly, Asp, Ile, or Met;

Xaa at position 77 is Ala, Pro, Ser, Thr, Phe, Leu, Asp, or His;

Xaa at position 78 is Pro, Phe, Arg, Ser, Lys, His, Ala, Gly, Ile or Leu;

Xaa at position 79 is Thr, Asp, Ser, Asn, Pro, Ala, Leu, or Arg;

Xaa at position 80 is Arg, Ile, Ser, Glu, Leu, Val, Gln, Lys, His, Ala or Pro;

Xaa at position 81 is His, Gln, Pro, Arg, Val, Leu, Gly, Thr, Asn, Lys, Ser, Ala, Trp, Phe, Ile or Tyr;

Xaa at position 82 is Pro, Lys, Tyr, Gly, Ile, or Thr;

Xaa at position 83 is Ile, Val, Lys, Ala, or Asn;

Xaa at position 84 is His, Ile, Asn, Leu, Asp, Ala, Thr, Glu, Gln, Ser, Phe, Met, Val, Lys, Arg, Tyr or Pro;

Xaa at position 85 is Ile, Leu, Arg, Asp, Val, Pro, Gln, Gly, Ser, Phe, or His;

Xaa at position 86 is Lys, Tyr, Leu, His, Arg, Ile, Ser, Gln, Pro;

Xaa at position 87 is Asp;

Xaa at position 88 is Gly, Leu, Glu, Lys, Ser, Tyr, or Pro;

Xaa at position 89 is Asp, or Ser;

Xaa at position 90 is Trp, Val, Cys, Tyr, Thr, Met, Pro, Leu, Gln, Lys, Ala, Phe, or Gly;

Xaa at position 91 is Asn, Pro, Ala, Phe, Ser, Trp, Gln, Tyr, Leu, Lys, Ile, Asp, or His;

Xaa at position 92 is Glu, Ser, Ala, Lys, Thr, Ile, Gly, or Pro;

Xaa at position 94 is Arg, Lys, Asp, Leu, Thr, Ile, Gln, His, Ser, Ala, or Pro;

Xaa at position 95 is Arg, Thr, Pro, Glu, Tyr, Leu, Ser, or Gly;

Xaa at position 96 is Lys, Asn, Thr, Leu, Gln, Arg, His, Glu, Ser, Ala or Trp;

Xaa at position 97 is Leu, Ile, Arg, Asp, or Met;

Xaa at position 98 is Thr, Val, Gln, Tyr, Glu, His, Ser, or Phe;

Xaa at position 99 is Phe, Ser, Cys, His, Gly, Trp, Tyr, Asp, Lys, Leu, Ile, Val or Asn;

Xaa at position 100 is Tyr, Cys, His, Ser, Trp, Arg, or Leu;

Xaa at position 101 is Leu, Asn, Val, Pro, Arg, Ala, His, Thr, Trp, or Met;

Xaa at position 102 is Lys;
Xaa at position 103 is Thr, Ser, Asn, Ile, Trp, Lys, or Pro;
Xaa at position 104 is Leu, Ser, Pro, Ala, Glu, Cys, Asp, or Tyr;
Xaa at position 105 is Glu, Ser, Lys, Pro, Leu, Thr, Tyr, or Arg;
Xaa at position 106 is Asn, Ala, Pro, Leu, His, Val, or Gln;
Xaa at position 107 is Ala, Ser, Ile, Asn, Pro, Lys, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;
wherein from 6 to about 44 of the amino acids designated by Xaa are different from the corresponding native amino acids of (1–133) human interleukin-3;
a factor selected from the group consisting of: a colony stimulating factor, a cytokine, a lymphokine, an interleukin, and a hematopoietic growth factor; and
at least one pharmaceutically acceptable carrier;
(ii) removing hematopoietic cells from said patient;
(iii) administering cancer radiation therapy of chemotherapy to said patient; and
(iv) returning said hematopoietic cells to said patient.

46. The method of claim 45, wherein (a) is the sequence of SEQ ID NO:6;
wherein
Xaa at position 3 is Ser, Gly, Asp, or Gln;
Xaa at position 4 is Asn, His, or Ile;
Xaa at position 9 is Ile, Ala, Leu, or Gly;
Xaa at position 11 is Thr, His, or Gln;
Xaa at position 12 is His or Ala;
Xaa at position 15 is Gln or Asn;
Xaa at position 16 is Pro or Gly;
Xaa at position 18 is Leu, Arg, Asn, or Ala;
Xaa at position 20 is Leu, Val, Ser, Ala, Arg, Gln, Glu, Ile, Phe, Thr or Met;
Xaa at position 21 is Leu, Ala, Asn, or Pro;
Xaa at position 24 is Asn or Ala;
Xaa at position 28 is Gly, Asp, Ser, Ala, Asn, Ile, Leu, Met, Tyr or Arg;
Xaa at position 31 is Gln, Val, Met, Leu, Ala, Asn, Glu or Lys;
Xaa at position 32 is Asp, Phe, Ser, Ala, Gln, Glu, His, Val or Thr;
Xaa at position 36 is Glu, Asn, Ser or Asp;
Xaa at position 37 is Asn, Arg, Pro, Thr, or His;
Xaa at position 41 is Arg, Leu, or Gly;
Xaa at position 42 is Pro, Gly, Ser, Ala, Asn, Val, Leu or Gln;
Xaa at position 48 is Asn, Pro, or Thr;
Xaa at position 50 is Ala or Asn;
Xaa at position 51 is Val or Thr;
Xaa at position 53 is Ser or Phe;
Xaa at position 54 is Leu or Phe;
Xaa at position 55 is Gln, Ala, Glu, or Arg;
Xaa at position 62 is Ser, Val, Asn, Pro, or Gly;
Xaa at position 63 is Ile or Leu;
Xaa at position 65 is Lys, Asn, Met, Arg, Ile, or Gly;
Xaa at position 66 is Asn, Gly, Glu, or Arg;
Xaa at position 68 is Leu, Gln, Trp, Arg, Asp, Asn, Glu, His, Met, Phe, Ser, Thr, Tyr or Val;
Xaa at position 73 is Leu or Ser;
Xaa at position 74 is Ala or Trp;
Xaa at position 77 is Ala or Pro;
Xaa at position 79 is Thr, Asp, or Ala;
Xaa at position 81 is His, Pro, Arg, Val, Gly, Asn, Ser or Thr;
Xaa at position 84 is His, Ile, Asn, Ala, Thr, Arg, Gln, Glu, Lys, Met, Ser, Tyr, Val or Leu;
Xaa at position 85 is Ile or Leu;
Xaa at position 86 is Lys or Arg;
Xaa at position 87 is Asp;
Xaa at position 91 is Asn, Pro, Ser, Ile or Asp;
Xaa at position 94 is Arg, Ala, or Ser;
Xaa at position 95 is Arg, Thr, Glu, Leu, or Ser;
Xaa at position 98 is Thr or Gln;
Xaa at position 102 is Lys;
Xaa at position 103 is Thr, Ala, His, Phe, Tyr or Ser;
Xaa at position 106 is Asn, Pro, Leu, His, Val, or Gln;
Xaa at position 107 is Ala, Ser, Ile, Pro, or Asp;
Xaa at position 108 is Gln, Met, Trp, Phe, Pro, His, Ile, or Tyr;
Xaa at position 109 is Ala, Met, Glu, Ser, or Leu;
wherein from 6 to about 44 of the amino acids designated by Xaa are different from the corresponding amino acids of native (1–133) human interleukin-3.

47. A method of treating a patient consisting of the steps of:
(i) administering to said patient, an amount effective to promote the proliferation and/or differentiation of hematopoietic cells in said patient of a composition consisting essentially of;
a biologically active human interleukin-3 variant polypeptide, said polypeptide consisting of a sequence selected from the group consisting of:
(a) the sequence of SEQ ID NO:8; and
(b) a polypeptide consisting of an N-terminal methionine residue, alanine residue or methionine-alanine di-peptide immediately preceding said sequence according to (a);
wherein;
Xaa at position 4 is Asn or Ile;
Xaa at position 5 is Met, Ala or Ile;
Xaa at position 6 is Ile, Pro or Leu;
Xaa at position 9 is Ile, Ala or Leu;
Xaa at position 11 is Thr or His;
Xaa at position 15 is Gln, Arg, Val or Leu;
Xaa at position 18 is Leu, Ala, Asn or Arg;
Xaa at position 20 is Leu or Ser;
Xaa at position 23 is Phe, Pro, or Ser;
Xaa at position 24 is Asn or Ala;
Xaa at position 28 is Gly, Ala, Ser, Asp or Asn;
Xaa at position 31 is Gln, Val, or Met;
Xaa at position 32 is Asp or Ser;
Xaa at position 35 is Met, Ile, Leu or Asp;
Xaa at position 36 is Glu or Asp;
Xaa at position 37 is Asn, Arg or Ser;
Xaa at position 41 is Arg, Leu, or Thr;

Xaa at position 42 is Pro or Ser;
Xaa at position 45 is Glu or Leu;
Xaa at position 46 is Ala or Ser;
Xaa at position 48 is Asn, Val or Pro;
Xaa at position 49 is Arg or His;
Xaa at position 51 is Val or Ser;
Xaa at position 53 is Ser, Asn, His or Gly;
Xaa at position 55 is Gln or Glu;
Xaa at position 59 is Ala or Gly;
Xaa at position 62 is Ser, Ala or Pro;
Xaa at position 65 is Lys, Arg or Ser;
Xaa at position 67 is Leu, Glu, or Val;
Xaa at position 68 is Leu, Glu, Val or Trp;
Xaa at position 71 is Leu or Val;
Xaa at position 73 is Leu, Ser or Trp;
Xaa at position 74 is Ala or Trp;
Xaa at position 77 is Ala or Pro;
Xaa at position 79 is Pro or Ser;
Xaa at position 81 is His or Thr;
Xaa at position 84 is His, Ile, or Thr;
Xaa at position 86 is Lys or Arg;
Xaa at position 87 is Asp;
Xaa at position 91 is Asn or Gln;
Xaa at position 95 is Arg, Glu, Leu;
Xaa at position 98 is Thr or Gln;
Xaa at position 102 is Lys;
Xaa at position 103 is Thr or Ser;
Xaa at position 106 is Asn, Gln, or His;
Xaa at position 109 is Ala or Glu;
wherein from 6 to about 44 of the amino acids designated by Xaa are different from the corresponding amino acids of native (1–133) human interleukin-3;
a factor selected from the group consisting of: a colony stimulating factor, a cytokine, a lymphokine, an interleukin, and a hematopoietic growth factor; and
at least one pharmaceutically acceptable carrier;
(ii) removing hematopoietic cells from said patient;
(iii) administering cancer radiation therapy or chemotherapy to said patient; and
(iv) returning said hematopoietic cells to said patient.

48. The method of claim 41, 42, 43, 44, 45, 46 or 47 wherein said factor is selected from the group consisting of; GM-CSF, CSF-1, G-CSF, G-CSF (Ser$^{17}$), M-CSF, erythropoietin (EPO), IL-1, IL-4, IL-2, IL-5, IL-6, IL-7, IL-8, IL-9, IL-10, IL-11, IL-12, IL-13, LIF, flt3 ligand, human growth hormone, B-cell growth factor, B-cell differentiation factor, eosinophil differentiation factor and stem cell factor (SCF).

49. A method of treating a patient having a side effect of cancer chemotherapy or radiation therapy consisting of; administering to said patient a therapeutically effective amount of a composition consisting essentially of;
 a modified human interleukin-3 (hIL-3) amino acid sequence, wherein said modified sequence differs from the sequence of native (1–133) hIL-3 by the replacement of from 4 to about 44 of the residues corresponding to positions 17–118 of native (1–133) hIL-3 by other amino acids, with the proviso that the residues corresponding to positions 101 and 116 are not Ala or Val, respectively, and with the proviso that no more than one of the amino acids at positions 63, 82, 87, 98, and 112 are different from the corresponding amino acids in native human interleukin-3; wherein said modified sequence optionally further differs from the sequence of native (1–133) hIL-3 by the deletion of from 1 to 14 residues from the N-terminus of native (1–133) hIL-3, the deletion of from 1 to 15 residues from the C-terminus of native (1–133) hIL-3, or both; and wherein said modified interleukin-3 (hIL-3) amino acid sequence has increased activity, relative to native human interleukin-3, in at least one assay selected from the group consisting of: AML cell proliferation, TF-1 cell proliferation and Methylcellulose assay;
 a factor selected from the group consisting of: a colony stimulating factor, a cytokine a lymphokine, an interleukin and a hematopoietic growth factor.

50. A method of treating a patient having a side effect of cancer chemotherapy or radiation therapy consisting of; administering to said patient a composition consisting essentially of;
 a biologically active human interleukin-3 variant polypeptide, said polypeptide consisting of a sequence selected from the group consisting of:
  (a) the sequence of SEQ ID NO:1; and
  (b) a polypeptide consisting of an N-terminal residue, alanine residue or methionine-alanine di-peptide immediately preceding said sequence according to (a);
wherein;
 Xaa at position 17 is Ser, Lys, Gly, Asp, Met, Gln, or Arg;
 Xaa at position 18 is Asn, His, Leu, Ile, Phe, Arg, or Gln;
 Xaa at position 19 is Met, Phe, Ile, Arg, Gly, Ala, or Cys;
 Xaa at position 20 is Ile, Cys, Gln, Glu, Arg, Pro, or Ala;
 Xaa at position 21 is Asp, Phe, Lys, Arg, Ala, Gly, Glu, Gln, Asn, Thr, Ser or Val;
 Xaa at position 22 is Glu, Trp, Pro, Ser, Ala, His, Asp, Asn, Gln, Leu, Val or Gly;
 Xaa at position 23 is Ile, Val, Ala, Leu, Gly, Trp, Lys, Phe, Ser, or Arg;
 Xaa at position 24 is Ile, Gly, Val, Arg, Ser, Phe, or Leu;
 Xaa at position 25 is Thr, His, Gly, Gln, Arg, Pro, or Ala;
 Xaa at position 26 is His, Thr, Phe, Gly, Arg, Ala, or Trp;
 Xaa at position 27 is Leu, Gly, Arg, Thr, Ser, or Ala;
 Xaa at position 28 is Lys, Arg, Leu, Gln, Gly, Pro, Val or Trp;
 Xaa at position 29 is Gln, Asn, Leu, Pro, Arg, or Val;
 Xaa at position 30 is Pro, His, Thr, Gly, Asp, Gln, Ser, Leu, or Lys;
 Xaa at position 31 is Pro, Asp, Gly, Ala, Arg, Leu, or Gln;
 Xaa at position 32 is Leu, Val, Arg, Gln, Asn, Gly, Ala, or Glu;
 Xaa at position 33 is Pro, Leu, Gln, Ala, Thr, or Glu;
 Xaa at position 34 is Leu, Val, Gly, Ser, Lys, Glu, Gln, Thr, Arg, Ala, Phe, Ile or Met;
 Xaa at position 35 is Leu, Ala, Gly, Asn, Pro, Gln, or Val;
 Xaa at position 36 is Asp, Leu, or Val;
 Xaa at position 37 is Phe, Ser, Pro, Trp, or Ile;
 Xaa at position 38 is Asn, or Ala;
 Xaa at position 40 is Leu, Trp, or Arg;
 Xaa at position 41 is Asn, Cys, Arg, Leu, His, Met, or Pro;
 Xaa at position 42 is Gly, Asp, Ser, Cys, Asn, Lys, Thr, Leu, Val, Glu, Phe, Tyr, Ile, Met or Ala;
 Xaa at position 43 is Glu, Asn, Tyr, Leu, Phe, Asp, Ala, Cys, Gln, Arg, Thr, Gly or Ser;

Xaa at position 44 is Asp, Ser, Leu, Arg, Lys, Thr, Met, Trp, Glu, Asn, Gln, Ala or Pro;

Xaa at position 45 is Gln, Pro, Phe, Val, Met, Leu, Thr, Lys, Trp, Asp, Asn, Arg, Ser, Ala, Ile, Glu or His;

Xaa at position 46 is Asp, Phe, Ser, Thr, Cys, Glu, Asn, Gln, Lys, His, Ala, Tyr, Ile, Val or Gly;

Xaa at position 47 is Ile, Gly, Val, Ser, Arg, Pro, or His;

Xaa at position 48 is Leu, Ser, Cys, Arg, Ile, His, Phe, Glu, Lys, Thr, Ala, Met, Val or Asn;

Xaa at position 49 is Met, Arg, Ala, Gly, Pro, Asn, His, or Asp;

Xaa at position 50 is Glu, Leu, Thr, Asp, Tyr, Lys, Asn, Ser, Ala, Ile, Val, His, Phe, Met or Gln;

Xaa at position 51 is Asn, Arg, Met, Pro, Ser, Thr, or His;

Xaa at position 52 is Asn, His, Arg, Leu, Gly, Ser, or Thr;

Xaa at position 53 is Leu, Thr, Ala, Gly, Glu, Pro, Lys, Ser, or Met;

Xaa at position 54 is Arg, Asp, Ile, Ser, Val, Thr, Gln, Asn, Lys, His, Ala or Leu;

Xaa at position 55 is Arg, Thr, Val, Ser, Leu, or Gly;

Xaa at position 56 is Pro, Gly, Cys, Ser, Gln, Glu, Arg, His, Thr, Ala, Tyr, Phe, Leu, Val or Lys;

Xaa at position 57 is Asn or Gly;

Xaa at position 58 is Leu, Ser, Asp, Arg, Gln, Val, or Cys;

Xaa at position 59 is Glu, Tyr, His, Leu, Pro, or Arg;

Xaa at position 60 is Ala, Ser, Pro, Tyr, Asn, or Thr;

Xaa at position 61 is Phe, Asn, Glu, Pro, Lys, Arg, or Ser;

Xaa at position 62 is Asn, His, Val, Arg, Pro, Thr, Asp, or Ile;

Xaa at position 63 is Arg, Tyr, Trp, Lys, Ser, His, Pro, or Val;

Xaa at position 64 is Ala, Asn, Pro, Ser, or Lys;

Xaa at position 65 is Val, Thr, Pro, His, Leu, Phe, or Ser;

Xaa at position 66 is Lys, Ile, Arg, Val, Asn, Glu, or Ser;

Xaa at position 67 is Ser, Ala, Phe, Val, Gly, Asn, Ile, Pro, or His;

Xaa at position 68 is Leu, Val, Trp, Ser, Ile, Phe, Thr, or His;

Xaa at position 69 is Gln, Ala, Pro, Thr, Glu, Arg, Trp, Gly, or Leu;

Xaa at position 70 is Asn, Leu, Val, Trp, Pro, or Ala;

Xaa at position 71 is Ala, Met, Leu, Pro, Arg, Glu, Thr, Gln, Trp, or Asn;

Xaa at position 72 is Ser, Glu, Met, Ala, His, Asn, Arg, or Asp;

Xaa at position 73 is Ala, Glu, Asp, Leu, Ser, Gly, Thr, or Arg;

Xaa at position 74 is Ile, Met, Thr, Pro, Arg, Gly, Ala;

Xaa at position 75 is Glu, Lys, Gly, Asp, Pro, Trp, Arg, Ser, Gln, or Leu;

Xaa at position 76 is Ser, Val, Ala, Asn, Trp, Glu, Pro, Gly, or Asp;

Xaa at position 77 is Ile, Ser, Arg, Thr, or Leu;

Xaa at position 78 is Leu, Ala, Ser, Glu, Phe, Gly, or Arg;

Xaa at position 79 is Lys, Thr, Asn, Met, Arg, Ile, Gly, or Asp;

Xaa at position 80 is Asn, Trp, Val, Gly, Thr, Leu, Glu, or Arg;

Xaa at position 81 is Leu, Gln, Gly, Ala, Trp, Arg, Val, or Lys;

Xaa at position 82 is Leu, Gln, Lys, Trp, Arg, Asp, Glu, Asn, His, Thr, Ser, Ala, Tyr, Phe, Ile, Met or Val;

Xaa at position 83 is Pro, Ala, Thr, Trp, Arg, or Met;

Xaa at position 84 is Cys, Glu, Gly, Arg, Met, or Val;

Xaa at position 85 is Leu, Asn, Val, or Gln;

Xaa at position 86 is Pro, Cys, Arg, Ala, or Lys;

Xaa at position 87 is Leu, Ser, Trp, or Gly;

Xaa at position 88 is Ala, Lys, Arg, Val, or Trp;

Xaa at position 89 is Thr, Asp, Cys, Leu, Val, Glu, His, Asn, or Ser;

Xaa at position 90 is Ala, Pro, Ser, Thr, Gly, Asp, Ile, or Met;

Xaa at position 91 is Ala, Pro, Ser, Thr, Phe, Leu, Asp, or His;

Xaa at position 92 is Pro, Phe, Arg, Ser, Lys, His, Ala, Gly, Ile or Leu;

Xaa at position 93 is Thr, Asp, Ser, Asn, Pro, Ala, Leu, or Arg;

Xaa at position 94 is Arg, Ile, Ser, Glu, Leu, Val, Gln, Lys, His, Ala, or Pro;

Xaa at position 95 is His, Gln, Pro, Arg, Val, Leu, Gly, Thr, Asn, Lys, Ser, Ala, Trp, Phe, Ile, or Tyr;

Xaa at position 96 is Pro, Lys, Tyr, Gly, Ile, or Thr;

Xaa at position 97 is Ile, Val, Lys, Ala, or Asn;

Xaa at position 98 is His, Ile, Asn, Leu, Asp, Ala, Thr, Glu, Gln, Ser, Phe, Met, Val, Lys, Arg, Tyr or Pro;

Xaa at position 99 is Ile, Leu, Arg, Asp, Val, Pro, Gln, Gly, Ser, Phe, or His;

Xaa at position 100 is Lys, Tyr, Leu, His, Arg, Ile, Ser, Gln, or Pro;

Xaa at position 101 is Asp;

Xaa at position 102 is Gly, Leu, Glu, Lys, Ser, Tyr, or Pro;

Xaa at position 103 is Asp, or Ser;

Xaa at position 104 is Trp, Val, Cys, Tyr, Thr, Met, Pro, Leu, Gln, Lys, Ala, Phe, or Gly;

Xaa at position 105 is Asn, Pro, Ala, Phe, Ser, Trp, Gln, Tyr, Leu, Lys, Ile, Asp, or His;

Xaa at position 106 is Glu, Ser, Ala, Lys, Thr, Ile, Gly, or Pro;

Xaa at position 108 is Arg, Lys, Asp, Leu, Thr, Ile, Gln, His, Ser, Ala or Pro;

Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, Ala, or Trp;

Xaa at position 111 is Leu, Ile, Arg, Asp, or Met;

Xaa at position 112 is Thr, Val, Gln, Tyr, Glu, His, Ser, or Phe;

Xaa at position 113 is Phe, Ser, Cys, His, Gly, Trp, Tyr, Asp, Lys, Leu, Ile, Val or Asn;

Xaa at position 114 is Tyr, Cys, His, Ser, Trp, Arg, or Leu;

Xaa at position 115 is Leu, Asn, Val, Pro, Arg, Ala, His, Thr, Trp, or Met;

Xaa at position 116 is Lys;

Xaa at position 117 is Thr, Ser, Asn, Ile, Trp, Lys, or Pro;

Xaa at position 118 is Leu, Ser, Pro, Ala, Glu, Cys, Asp, or Tyr;

Xaa at position 119 is Glu, Ser, Lys, Pro, Leu, Thr, Tyr, or Arg;

Xaa at position 120 is Asn, Ala, Pro, Leu, His, Val, or Gln;

Xaa at position 121 is Ala, Ser, Ile, Asn, Pro, Lys, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

wherein from 6 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus of said sequence of SEQ ID NO:1; and a factor selected from the group consisting of: a colony stimulating factor, a cytokine, a lymphokine, an interleukin, and a hematopoietic growth factor and at least one pharmaceutically acceptable carrier.

51. The method of claim 50, wherein (a) is the sequence of SEQ ID NO:3;
wherein Xaa at position 17 is Ser, Gly, Asp, or Gln;

Xaa at position 18 is Asn, His, or Ile;

Xaa at position 23 is Ile, Ala, Leu, or Gly;

Xaa at position 25 is Thr, His, or Gln;

Xaa at position 26 is His or Ala;

Xaa at position 29 is Gln or Asn;

Xaa at position 30 is Pro or Gly;

Xaa at position 32 is Leu, Arg, Asn, or Ala;

Xaa at position 34 is Leu, Val, Ser, Ala, Arg, Gln, Glu, Ile, Phe, Thr, or Met;

Xaa at position 35 is Leu, Ala, Asn, or Pro;

Xaa at position 38 is Asn or Ala;

Xaa at position 42 is Gly, Asp, Ser, Ala, Asn, Ile, Leu, Met, Tyr or Arg;

Xaa at position 45 is Gln, Val, Met, Leu, Ala, Asn, Glu, or Lys;

Xaa at position 46 is Asp, Phe, Ser, Gln, Glu, His, Val or Thr;

Xaa at position 50 is Glu, Asn, Ser or Asp;

Xaa at position 51 is Asn, Arg, Pro, Thr, or His;

Xaa at position 55 is Arg, Leu, or Gly;

Xaa at position 56 is Pro, Gly, Ser, Ala, Asn, Val, Leu or Gln;

Xaa at position 62 is Asn, Pro, or Thr;

Xaa at position 64 is Ala or Asn;

Xaa at position 65 is Val or Thr;

Xaa at position 67 is Ser or Phe;

Xaa at position 68 is Leu or Phe;

Xaa at position 69 is Gln, Ala, Glu, or Arg;

Xaa at position 76 is Ser, Val, Asn, Pro, or Gly;

Xaa at position 77 is Ile or Leu;

Xaa at position 79 is Lys, Asn, Met, Arg, Ile, or Gly;

Xaa at position 80 is Asn, Gly, Glu, or Arg;

Xaa at position 82 is Leu, Gln, Trp, Arg, Asp, Asn, Glu, His, Met, Phe, Ser, Thr, Tyr or Val;

Xaa at position 87 is Leu or Ser;

Xaa at position 88 is Ala or Trp;

Xaa at position 91 is Ala or Pro;

Xaa at position 93 is Thr, Asp, or Ala;

Xaa at position 95 is His, Pro, Arg, Val, Gly, Asn, Ser or Thr;

Xaa at position 98 is His, Ile, Asn, Ala, Thr, Gln, Glu, Lys, Met, Ser, Tyr, Val or Leu;

Xaa at position 99 is Ile or Leu;

Xaa at position 100 is Lys or Arg;

Xaa at position 101 is Asp;

Xaa at position 105 is Asn, Pro, Ser, Ile or Asp;

Xaa at position 108 is Arg, Ala, or Ser;

Xaa at position 109 is Arg, Thr, Glu, Leu, or Ser;

Xaa at position 112 is Thr or Gln;

Xaa at position 116 is Lys;

Xaa at position 120 is Asn, Pro, Leu, His, Val, or Gln;

Xaa at position 121 is Ala, Ser, Ile, Pro, or Asp;

Xaa at position 122 is Gln, Met, Trp, Phe, Pro, His, Ile, or Tyr;

Xaa at position 123 is Ala, Met, Glu, Ser, or Leu;

wherein from 6 to about 44 of the amino acids designated by Xaa are different from the corresponding amino acids of native (1–133)human interleukin-3; and wherein from 1 to 14 amino acids are optionally deleted from the N-terminus and/or from 1 to 15 amino acids are optionally deleted from the C-terminus of said sequence of SEQ ID No: 3.

52. The method of claim 50, wherein in said human interleukin-3 mutant polypeptide, the amino acids which differ from the corresponding residue in native human interleukin-3 are selected from the group consisting of:

position 42 wherein Xaa is Gly, Asp, Ser, Ile, Leu, Met, Tyr, or Ala;

position 45 wherein Xaa is Gin, Val, Met or Asn;

position 46 wherein Xaa is Asp, Ser, Gln, His or Val;

position 50 wherein Xaa is Glu or Asp;

position 51 wherein Xaa is Asn, Pro or Thr;

position 62 wherein Xaa is Asn or Pro;

position 76 wherein Xaa is Ser, or Pro;

position 82 wherein Xaa is Leu, Trp, Asp, Asn, Glu, His, Phe, Ser or Tyr;

position 95 wherein Xaa is His, Arg, Thr, Asn or Ser;

position 98 wherein Xaa is His, Ile, Leu, Ala, Gln, Lys, Met, Ser, Tyr or Val;

position 100 wherein Xaa is Lys or Arg;

position 105 wherein Xaa is Asn, or Pro;

position 108 wherein Xaa is Arg, Ala, or Ser;

position 121 wherein Xaa is Ala, or Ile;

position 122 wherein Xaa is Gln, or Ile; and position 123 wherein Xaa is Ala, Met or Glu;

wherein from 6 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus.

53. A method of treating a patient having a side effect of cancer chemotherapy or radiation therapy consisting of administering to said patient a composition consisting essentially of;

a biologically active human interleukin-3 variant polypeptide, said polypeptide consisting of a sequence selected from the group consisting of:

(a) the sequence of SEQ ID NO:4; and (b) a polypeptide consisting of an N-terminal residue, alanine residue or methionine-alanine di-peptide immediately preceding said sequence according to (a);

wherein;

Xaa at position 3 is Ser, Lys, Gly, Asp, Met, Gln, or Arg;

Xaa at position 4 is Asn, His, Leu, Ile, Phe, Arg, or Gln;

Xaa at position 5 is Met, Phe, Ile, Arg, Gly, Ala, or Cys;

Xaa at position 6 is Ile, Cys, Gln, Glu, Arg, Pro, or Ala;

Xaa at position 7 is Asp, Phe, Lys, Arg, Ala, Gly, Glu, Gln, Asn, Thr, Ser or Val;

Xaa at position 8 is Glu, Trp, Pro, Ser, Ala, His, Asp, Asn, Gln, Leu, Val, or Gly;

Xaa at position 9 is Ile, Val, Ala, Leu, Gly, Trp, Lys, Phe, Ser, or Arg;

Xaa at position 10 is Ile, Gly, Val, Arg, Ser, Phe, or Leu;

Xaa at position 11 is Thr, His, Gly, Gln, Arg, Pro, or Ala;

Xaa at position 12 is His, Thr, Phe, Gly, Arg, Ala, or Trp;

Xaa at position 13 is Leu, Gly, Arg, Thr, Ser, or Ala;

Xaa at position 14 is Lys, Arg, Leu, Gln, Gly, Pro, Val or Trp;

Xaa at position 15 is Gln, Asn, Leu, Pro, Arg, or Val;

Xaa at position 16 is Pro, His, Thr, Gly, Asp, Gln, Ser, Leu, or Lys;

Xaa at position 17 is Pro, Asp, Gly, Ala, Arg, Leu, or Gln;

Xaa at position 18 is Leu, Val, Arg, Gln, Asn, Gly, Ala, or Glu;

Xaa at position 19 is Pro, Leu, Gln, Ala, Thr, or Glu;

Xaa at position 20 is Leu, Val, Gly, Ser, Lys, Glu, Gln, Thr, Arg, Ala, Phe, Ile or Met;

Xaa at position 21 is Leu, Ala, Gly, Asn, Pro, Gln, or Val;

Xaa at position 22 is Asp, Leu, or Val;

Xaa at position 23 is Phe, Ser, Pro, Trp, or Ile;

Xaa at position 24 is Asn, or Ala;

Xaa at position 26 is Leu, Trp, or Arg;

Xaa at position 27 is Asn, Cys, Arg, Leu, His, Met, Pro;

Xaa at position 28 is Gly, Asp, Ser, Cys, Ala, Lys, Asn, Thr, Leu, Val, Glu, Phe, Tyr, Ile or Met;

Xaa at position 29 is Glu, Asn, Tyr, Leu, Phe, Asp, Ala, Cys, Gln, Arg, Thr, Gly or Ser;

Xaa at position 30 is Asp, Ser, Leu, Arg, Lys, Thr, Met, Trp, Glu, Asn, Gln, Ala or Pro;

Xaa at position 31 is Gln, Pro, Phe, Val, Met, Leu, Thr, Lys, Asp, Asn, Arg, Ser, Ala, Ile, Glu, His or Trp;

Xaa at position 32 is Asp, Phe, Ser, Thr, Cys, Glu, Asn, Gln, Lys, His, Ala, Tyr, Ile, Val or Gly;

Xaa at position 33 is Ile, Gly, Val, Ser, Arg, Pro, or His;

Xaa at position 34 is Leu, Ser, Cys, Arg, Ile, His, Phe, Glu, Lys, Thr, Ala, Met, Val or Asn;

Xaa at position 35 is Met, Arg, Ala, Gly, Pro, Asn, His, or Asp;

Xaa at position 36 is Glu, Leu, Thr, Asp, Tyr, Lys, Asn, Ser, Ala, Ile, Val, His, Phe, Met or Gln;

Xaa at position 37 is Asn, Arg, Met, Pro, Ser, Thr, or His;

Xaa at position 38 is Asn, His, Arg, Leu, Gly, Ser, or Thr;

Xaa at position 39 is Leu, Thr, Ala, Gly, Glu, Pro, Lys, Ser, or Met;

Xaa at position 40 is Arg, Asp, Ile, Ser, Val, Thr, Gln, Asn, Lys, His, Ala or Leu;

Xaa at position 41 is Arg, Thr, Val, Ser, Leu, or Gly;

Xaa at position 42 is Pro, Gly, Cys, Ser, Gln, Glu, Arg, His, Thr, Ala, Tyr, Phe, Leu, Val or Lys;

Xaa at position 43 is Asn or Gly;

Xaa at position 44 is Leu, Ser, Asp, Arg, Gln, Val, or Cys;

Xaa at position 45 is Glu, Tyr, His, Leu, Pro, or Arg;

Xaa at position 46 is Ala, Ser, Pro, Tyr, Asn, or Thr;

Xaa at position 47 is Phe, Asn, Glu, Pro, Lys, Arg, or Ser;

Xaa at position 48 is Asn, His, Val, Arg, Pro, Thr, Asp, or Ile;

Xaa at position 49 is Arg, Tyr, Trp, Lys, Ser, His, Pro, or Val;

Xaa at position 50 is Ala, Asn, Pro, Ser, or Lys;

Xaa at position 51 is Val, Thr, Pro, His, Leu, Phe, or Ser;

Xaa at position 52 is Lys, Ile, Arg, Val, Asn, Glu, or Ser;

Xaa at position 53 is Ser, Ala, Phe, Val, Gly, Asn, Ile, Pro, or His;

Xaa at position 54 is Leu, Val, Trp, Ser, Ile, Phe, Thr, or His;

Xaa at position 55 is Gln, Ala, Pro, Thr, Glu, Arg, Trp, Gly, or Leu;

Xaa at position 56 is Asn, Leu, Val, Trp, Pro, or Ala;

Xaa at position 57 is Ala, Met, Leu, Pro, Arg, Glu, Thr, Gln, Trp, or Asn;

Xaa at position 58 is Ser, Glu, Met, Ala, His, Asn, Arg, or Asp;

Xaa at position 59 is Ala, Glu, Asp, Leu, Ser, Gly, Thr, or Arg;

Xaa at position 60 is Ile, Met, Thr, Pro, Arg, Gly, Ala;

Xaa at position 61 is Glu, Lys, Gly, Asp, Pro, Trp, Arg, Ser, Gln, or Leu;

Xaa at position 62 is Ser, Val, Ala, Asn, Trp, Glu, Pro, Gly, or Asp;

Xaa at position 63 is Ile, Ser, Arg, Thr, or Leu;

Xaa at position 64 is Leu, Ala, Ser, Glu, Phe, Gly, or Arg;

Xaa at position 65 is Lys, Thr, Gly, Asn, Met, Arg, Ile, or Asp;

Xaa at position 66 is Asn, Trp, Val, Gly, Thr, Leu, Glu, or Arg;

Xaa at position 67 is Leu, Gln, Gly, Ala, Trp, Arg, Val, or Lys;

Xaa at position 68 is Leu, Gln, Lys, Trp, Arg, Asp, Glu, Asn, His, Thr, Ser, Ala, Tyr, Phe, Ile, Met or Val;

Xaa at position 69 is Pro, Ala, Thr, Trp, Arg, or Met;

Xaa at position 70 is Cys, Glu, Gly, Arg, Met, or Val;

Xaa at position 71 is Leu, Asn, Val, or Gln;

Xaa at position 72 is Pro, Cys, Arg, Ala, or Lys;

Xaa at position 73 is Leu, Ser, Trp, or Gly;

Xaa at position 74 is Ala, Lys, Arg, Val, or Trp;

Xaa at position 75 is Thr, Asp, Cys, Leu, Val, Glu, His, Asn, or Ser;

Xaa at position 76 is Ala, Pro, Ser, Thr, Gly, Asp, Ile, or Met;

Xaa at position 77 is Ala, Pro, Ser, Thr, Phe, Leu, Asp, or His;

Xaa at position 78 is Pro, Phe, Arg, Ser, Lys, His, Ala, Gly, Ile or Leu;

Xaa at position 79 is Thr, Asp, Ser, Asn, Pro, Ala, Leu, or Arg;

Xaa at position 80 is Arg, Ile, Ser, Glu, Leu, Val, Gln, Lys, His, Ala or Pro;

Xaa at position 81 is His, Gln, Pro, Arg, Val, Leu, Gly, Thr, Asn, Lys, Ser, Ala, Trp, Phe, Ile or Tyr;

Xaa at position 82 is Pro, Lys, Tyr, Gly, Ile, or Thr;

Xaa at position 83 is Ile, Val, Lys, Ala, or Asn;
Xaa at position 84 is His, Ile, Asn, Leu, Asp, Ala, Thr, Glu, Gln, Ser, Phe, Met, Val, Lys, Arg, Tyr or Pro;
Xaa at position 85 is Ile, Leu, Arg, Asp, Val, Pro, Gln, Gly, Ser, Phe, or His;
Xaa at position 86 is Lys, Tyr, Leu, His, Arg, Ile, Ser, Gln, Pro;
Xaa at position 87 is Asp;
Xaa at position 88 is Gly, Leu, Glu, Lys, Ser, Tyr, or Pro;
Xaa at position 89 is Asp, or Ser;
Xaa at position 90 is Trp, Val, Cys, Tyr, Thr, Met, Pro, Leu, Gln, Lys, Ala, Phe, or Gly;
Xaa at position 91 is Asn, Pro, Ala, Phe, Ser, Trp, Gln, Tyr, Leu, Lys, Ile, Asp, or His;
Xaa at position 92 is Glu, Ser, Ala, Lys, Thr, Ile, Gly, or Pro;
Xaa at position 94 is Arg, Lys, Asp, Leu, Thr, Ile, Gln, His, Ser, Ala, or Pro;
Xaa at position 95 is Arg, Thr, Pro, Glu, Tyr, Leu, Ser, or Gly;
Xaa at position 96 is Lys, Asn, Thr, Leu, Gln, Arg, His, Glu, Ser, Ala or Trp;
Xaa at position 97 is Leu, Ile, Arg, Asp, or Met;
Xaa at position 98 is Thr, Val, Gln, Tyr, Glu, His, Ser, or Phe;
Xaa at position 99 is Phe, Ser, Cys, His, Gly, Trp, Tyr, Asp, Lys, Leu, Ile, Val or Asn;
Xaa at position 100 is Tyr, Cys, His, Ser, Trp, Arg, or Leu;
Xaa at position 101 is Leu, Asn, Val, Pro, Arg, Ala, His, Thr, Trp, or Met;
Xaa at position 102 is Lys;
Xaa at position 103 is Thr, Ser, Asn, Ile, Trp, Lys, or Pro;
Xaa at position 104 is Leu, Ser, Pro, Ala, Glu, Cys, Asp, or Tyr;
Xaa at position 105 is Glu, Ser, Lys, Pro, Leu, Thr, Tyr, or Arg;
Xaa at position 106 is Asn, Ala, Pro, Leu, His, Val, or Gln;
Xaa at position 107 is Ala, Ser, Ile, Asn, Pro, Lys, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;
wherein from 6 to about 44 of the amino acids designated by Xaa are different from the corresponding native amino acids of (1–133) human interleukin-3;

a factor selected from the group consisting of: a colony stimulating factor, a cytokine, a lymphokine, an interleukin, and a hematopoietic growth factor and at least one pharmaceutically acceptable carrier.

54. The method of claim 53 wherein (a) is the sequence of SEQ ID NO:6;

wherein

Xaa at position 3 is Ser, Gly, Asp, or Gln;

Xaa at position 4 is Asn, His, or Ile;

Xaa at position 9 is Ile, Ala, Leu, or Gly;

Xaa at position 11 is Thr, His, or Gln;

Xaa at position 12 is His or Ala;

Xaa at position 15 is Gln or Asn;

Xaa at position 16 is Pro or Gly;

Xaa at position 18 is Leu, Arg, Asn, or Ala;

Xaa at position 20 is Leu, Val, Ser, Ala, Arg, Gln, Glu, Ile, Phe, Thr or Met;

Xaa at position 21 is Leu, Ala, Asn, or Pro;

Xaa at position 24 is Asn or Ala;

Xaa at position 28 is Gly, Asp, Ser, Ala, Asn, Ile, Leu, Met, Tyr or Arg;

Xaa at position 31 is Gln, Val, Met, Leu, Ala, Asn, Glu or Lys;

Xaa at position 32 is Asp, Phe, Ser, Ala, Gln, Glu, His, Val or Thr;

Xaa at position 36 is Giu, Asn, Ser or Asp;

Xaa at position 37 is Asn, Arg, Pro, Thr, or His;

Xaa at position 41 is Arg, Leu, or Gly;

Xaa at position 42 is Pro, Gly, Ser, Ala, Asn, Val, Leu or Gln;

Xaa at position 48 is Asn, Pro, or Thr;

Xaa at position 50 is Ala or Asn;

Xaa at position 51 is Val or Thr;

Xaa at position 53 is Ser or Phe;

Xaa at position 54 is Leu or Phe;

Xaa at position 55 is Gln, Ala, Glu, or Arg;

Xaa at position 62 is Ser, Val, Asn, Pro, or Gly;

Xaa at position 63 is Ile or Leu;

Xaa at position 65 is Lys, Asn, Met, Arg, Ile, or Gly;

Xaa at position 66 is Asn, Gly, Glu, or Arg;

Xaa at position 68 is Leu, Gln, Trp, Arg, Asp, Asn, Glu, His, Met, Phe, Ser, Thr, Tyr or Val;

Xaa at position 73 is Leu or Ser;

Xaa at position 74 is Ala or Trp;

Xaa at position 77 is Ala or Pro;

Xaa at position 79 is Thr, Asp, or Ala;

Xaa at position 81 is His, Pro, Arg, Val, Gly, Asn, Ser or Thr;

Xaa at position 84 is His, Ile, Asn, Ala, Thr, Arg, Gln, Glu, Lys, Met, Ser, Tyr, Val or Leu;

Xaa at position 85 is Ile or Leu;

Xaa at position 86 is Lys or Arg;

Xaa at position 87 is Asp;

Xaa at position 91 is Asn, Pro, Ser, Ile or Asp;

Xaa at position 94 is Arg, Ala, or Ser;

Xaa at position 95 is Arg, Thr, Glu, Leu, or Ser;

Xaa at position 98 is Thr or Gln;

Xaa at position 102 is Lys;

Xaa at position 103 is Thr, Ala, His, Phe, Tyr or Ser;

Xaa at position 106 is Asn, Pro, Leu, His, Val, or Gln;

Xaa at position 107 is Ala, Ser, Ile, Pro, or Asp;

Xaa at position 108 is Gln, Met, Trp, Phe, Pro, His, Ile, or Tyr;

Xaa at position 109 is Ala, Met, Glu, Ser, or Leu;

wherein from 6 to about 44 of the amino acids designated by Xaa are different from the corresponding amino acids of native (1–133) human interleukin-3.

55. A method of treating a patient having a side effect of cancer chemotherapy or radiation therapy consisting of; administering to said patient a composition consisting essentially of;

a biologically active human interleukin-3 variant polypeptide, said polypeptide consisting of a sequence selected from the group consisting of:

(a) the sequence of SEQ ID NO:8; and
(b) a polypeptide consisting of an N-terminal residue, alanine residue or methionine-alanine di-peptide immediately preceding said sequence according to (a);

wherein;

Xaa at position 4 is Asn or Ile;
Xaa at position 5 is Met, Ala or Ile;
Xaa at position 6 is Ile, Pro or Leu;
Xaa at position 9 is Ile, Ala or Leu;
Xaa at position 11 is Thr or His;
Xaa at position 15 is Gln, Arg, Val or Leu;
Xaa at position 18 is Leu, Ala, Asn or Arg;
Xaa at position 20 is Leu or Ser;
Xaa at position 23 is Phe, Pro, or Ser;
Xaa at position 24 is Asn or Ala;
Xaa at position 28 is Gly, Ala, Ser, Asp or Asn;
Xaa at position 31 is Gln, Val, or Met;
Xaa at position 32 is Asp or Ser;
Xaa at position 35 is Met, Ile, Leu or Asp;
Xaa at position 36 is Glu or Asp;
Xaa at position 37 is Asn, Arg or Ser;
Xaa at position 41 is Arg, Leu, or Thr;
Xaa at position 42 is Pro or Ser;
Xaa at position 45 is Glu or Leu;
Xaa at position 46 is Ala or Ser;
Xaa at position 48 is Asn, Val or Pro;
Xaa at position 49 is Arg or His;
Xaa at position 51 is Val or Ser;
Xaa at position 53 is Ser, Asn, His or Gly;
Xaa at position 55 is Gln or Glu;
Xaa at position 59 is Ala or Gly;
Xaa at position 62 is Ser, Ala or Pro;
Xaa at position 65 is Lys, Arg or Ser;
Xaa at position 67 is Leu, Glu, or Val;
Xaa at position 68 is Leu, Glu, Val or Trp;
Xaa at position 71 is Leu or Val;
Xaa at position 73 is Leu, Ser or Trp;
Xaa at position 74 is Ala or Trp;
Xaa at position 77 is Ala or Pro;
Xaa at position 79 is Pro or Ser;
Xaa at position 81 is His or Thr;
Xaa at position 84 is His, Ile, or Thr;
Xaa at position 86 is Lys or Arg;
Xaa at position 87 is Asp, Ala or Met;
Xaa at position 91 is Asn or Gln;
Xaa at position 95 is Arg, Glu, Leu;
Xaa at position 98 is Thr or Gln;
Xaa at position 102 is Lys, Val, Trp or Ser;
Xaa at position 103 is Thr or Ser;
Xaa at position 106 is Asn, Gln, or His;
Xaa at position 109 is Ala or Glu;

wherein from 6 to about 44 of the amino acids designated by Xaa are different from the corresponding amino acids of native (1–133) human interleukin-3.

56. The method of claim 49, 50, 51, 52, 53, 54, or 55 wherein said factor is selected from the group consisting of; GM-CSF, CSF-1, G-CSF, G-CSF (Ser$^{17}$), M-CSF, erythropoietin (EPO), IL-1, IL-4, IL-2, IL-5, IL-6, IL-7, IL-8, IL-9, IL-10, IL-11, IL-12, IL-13, LIF, flt3 ligand, human growth hormone, B-cell growth factor, B-cell differentiation factor, eosinophil differentiation factor and stem cell factor (SCF).

* * * * *

                        SEQUENCE LISTING (1) GENERAL INFORMATION:

(iii) NUMBER OF SEQUENCES: 58

(2) INFORMATION FOR SEQ ID NO:1:

(i) SEQUENCE CHARACTERISTICS:
        (A) LENGTH: 133 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- may or may not precede the
            amino acid in position 1"

(ix) FEATURE:
        (A) NAME/KEY: Modified-site
        (B) LOCATION: 17
        (D) OTHER INFORMATION: /note= "Xaa at position 17 is Ser,
            Lys, Gly, Asp, Met, Gln, or Arg"

(ix) FEATURE:
        (A) NAME/KEY: Modified-site
        (B) LOCATION: 18
        (D) OTHER INFORMATION: /note= "Xaa at position 18 is Asn,
            His, Leu, Ile, Phe, Arg, or Gln"
```

-continued

```
(ix) FEATURE:
     (A) NAME/KEY: Modified-site
     (B) LOCATION: 19
     (D) OTHER INFORMATION: /note= "Xaa at positiion 19 is Met,
         Phe, Ile, Arg, Gly, Ala, or Cys"

(ix) FEATURE:
     (A) NAME/KEY: Modified-site
     (B) LOCATION: 20
     (D) OTHER INFORMATION: /note= "Xaa at position 20 is Ile,
         Cys, Gln, Glu, Arg, Pro, or Ala"

(ix) FEATURE:
     (A) NAME/KEY: Modified-site
     (B) LOCATION: 21
     (D) OTHER INFORMATION: /note= "Xaa at position 21 is Asp,
         Phe, Lys, Arg, Ala, Gly, Glu, Gln, Asn, Thr, Ser,
         or Val"

(ix) FEATURE:
     (A) NAME/KEY: Modified-site
     (B) LOCATION: 22
     (D) OTHER INFORMATION: /note= "Xaa at position 22 is Glu,
         Trp, Pro, Ser, Ala, His, Asp, Asn, Gln, Leu, Val,
         or Gly"

(ix) FEATURE:
     (A) NAME/KEY: Modified-site
     (B) LOCATION: 23
     (D) OTHER INFORMATION: /note= "Xaa at position 23 is Ile,
         Val, Ala, Leu, Gly, Trp, Lys, Phe, Ser, or
         Arg"

(ix) FEATURE:
     (A) NAME/KEY: Modified-site
     (B) LOCATION: 24
     (D) OTHER INFORMATION: /note= "Xaa at position 24 is Ile,
         Gly, Val, Arg, Ser, Phe, or Leu"

(ix) FEATURE:
     (A) NAME/KEY: Modified-site
     (B) LOCATION: 25
     (D) OTHER INFORMATION: /note= "Xaa at position 25 is Thr,
         His, Gly, Gln, Arg, Pro, or Ala"

(ix) FEATURE:
     (A) NAME/KEY: Modified-site
     (B) LOCATION: 26
     (D) OTHER INFORMATION: /note= "Xaa at position 26 is His,
         Thr, Phe, Gly, Arg, Ala, or Trp"

(ix) FEATURE:
     (A) NAME/KEY: Modified-site
     (B) LOCATION: 27
     (D) OTHER INFORMATION: /note= "Xaa at position 27 is Leu,
         Gly, Arg, Thr, Ser, or Ala"

(ix) FEATURE:
     (A) NAME/KEY: Modified-site
     (B) LOCATION: 28
     (D) OTHER INFORMATION: /note= "Xaa at position 28 is Lys,
         Arg, Leu, Gln, Gly, Pro, Val, or Trp"

(ix) FEATURE:
     (A) NAME/KEY: Modified-site
     (B) LOCATION: 29
     (D) OTHER INFORMATION: /note= "Xaa at position 29 is Gln,
         Asn, Leu, Pro, Arg, or Val"

(ix) FEATURE:
     (A) NAME/KEY: Modified-site
     (B) LOCATION: 30
     (D) OTHER INFORMATION: /note= "Xaa at position 30 is Pro,
         His, Thr, Gly, Asp, Gln, Ser, Leu, or Lys"

(ix) FEATURE:
     (A) NAME/KEY: Modified-site
     (B) LOCATION: 31
```

(D) OTHER INFORMATION: /note= "Xaa at position 31 is Pro,
            Asp, Gly, Ala, Arg, Leu, or Gln"

(ix) FEATURE:
        (A) NAME/KEY: Modified-site
        (B) LOCATION: 32
        (D) OTHER INFORMATION: /note= "Xaa at position 32 is Leu,
            Val, Arg, Gln, Asn, Gly, Ala, or Glu"

(ix) FEATURE:
        (A) NAME/KEY: Modified-site
        (B) LOCATION: 33
        (D) OTHER INFORMATION: /note= "Xaa at position 33 is Pro,
            Leu, Gln, Ala, Thr, or Glu"

(ix) FEATURE:
        (A) NAME/KEY: Modified-site
        (B) LOCATION: 34
        (D) OTHER INFORMATION: /note= "Xaa at position 34 is Leu,
            Val, Gly, Ser, Lys, Glu, Gln, Thr, Arg, Ala, Phe,
            Ile, or Met"

(ix) FEATURE:
        (A) NAME/KEY: Modified-site
        (B) LOCATION: 35
        (D) OTHER INFORMATION: /note= "Xaa at position 35 is Leu,
            Ala, Gly, Asn, Pro, Gln, or Val"

(ix) FEATURE:
        (A) NAME/KEY: Modified-site
        (B) LOCATION: 36
        (D) OTHER INFORMATION: /note= "Xaa at position 36 is Asp,
            Leu, or Val"

(ix) FEATURE:
        (A) NAME/KEY: Modified-site
        (B) LOCATION: 37
        (D) OTHER INFORMATION: /note= "Xaa at position 37 is Phe,
            Ser, Pro, Trp, or Ile"

(ix) FEATURE:
        (A) NAME/KEY: Modified-site
        (B) LOCATION: 38
        (D) OTHER INFORMATION: /note= "Xaa at position 38 is Asn,
            or Ala"

(ix) FEATURE:
        (A) NAME/KEY: Modified-site
        (B) LOCATION: 40
        (D) OTHER INFORMATION: /note= "Xaa at position 40 is Leu,
            Trp, or Arg"

(ix) FEATURE:
        (A) NAME/KEY: Modified-site
        (B) LOCATION: 41
        (D) OTHER INFORMATION: /note= "Xaa at position 41 is Asn,
            Cys, Arg, Leu, His, Met, or Pro"

(ix) FEATURE:
        (A) NAME/KEY: Modified-site
        (B) LOCATION: 42
        (D) OTHER INFORMATION: /note= "Xaa at position 42 is Gly,
            Asp, Ser, Cys, Asn, Lys, Thr, Leu, Val, Glu, Phe, Tyr,
            Ile, Met, or Ala"

(ix) FEATURE:
        (A) NAME/KEY: Modified-site
        (B) LOCATION: 43
        (D) OTHER INFORMATION: /note= "Xaa at position 43 is Glu,
            Asn, Tyr, Leu, Phe, Asp, Ala, Cys, Gln, Arg, Thr, Gly,
            or Ser"

(ix) FEATURE:
        (A) NAME/KEY: Modified-site
        (B) LOCATION: 44
        (D) OTHER INFORMATION: /note= "Xaa at position 44 is Asp,
            Ser, Leu, Arg, Lys, Thr, Met, Trp, Glu, Asn, Gln, Ala,
            or Pro"

-continued (ix) FEATURE:
    (A) NAME/KEY: Modified-site
    (B) LOCATION: 45
    (D) OTHER INFORMATION: /note= "Xaa at position 45 is Gln,
        Pro, Phe, Val, Met, Leu, Thr, Lys, Trp, Asp, Asn, Arg,
        Ser, Ala, Ile, Glu, or His"

(ix) FEATURE:
    (A) NAME/KEY: Modified-site
    (B) LOCATION: 46
    (D) OTHER INFORMATION: /note= "Xaa at position 46 is Asp,
        Phe, Ser, Thr, Cys, Glu, Asn, Gln, Lys, His, Ala, Tyr,
        Ile, Val, or Gly"

(ix) FEATURE:
    (A) NAME/KEY: Modified-site
    (B) LOCATION: 47
    (D) OTHER INFORMATION: /note= "Xaa at position 47 is Ile,
        Gly, Val, Ser, Arg, Pro, or His"

(ix) FEATURE:
    (A) NAME/KEY: Modified-site
    (B) LOCATION: 48
    (D) OTHER INFORMATION: /note= "Xaa at position 48 is Leu,
        Ser, Cys, Arg, Ile, His, Phe, Glu, Lys, Thr, Ala, Met,
        Val, or Asn"

(ix) FEATURE:
    (A) NAME/KEY: Modified-site
    (B) LOCATION: 49
    (D) OTHER INFORMATION: /note= "Xaa at position 49 is Met,
        Arg, Ala, Gly, Pro, Asn, His, or Asp"

(ix) FEATURE:
    (A) NAME/KEY: Modified-site
    (B) LOCATION: 50
    (D) OTHER INFORMATION: /note= "Xaa at position 50 is Glu,
        Leu, Thr, Asp, Tyr, Lys, Asn, Ser, Ala, Ile, Val, His,
        Phe, Met, or Gln"

(ix) FEATURE:
    (A) NAME/KEY: Modified-site
    (B) LOCATION: 51
    (D) OTHER INFORMATION: /note= "Xaa at position 51 is Asn,
        Arg, Met, Pro, Ser, Thr, or His"

(ix) FEATURE:
    (A) NAME/KEY: Modified-site
    (B) LOCATION: 52
    (D) OTHER INFORMATION: /note= "Xaa at position 52 is Asn,
        His, Arg, Leu, Gly, Ser, or Thr"

(ix) FEATURE:
    (A) NAME/KEY: Modified-site
    (B) LOCATION: 53
    (D) OTHER INFORMATION: /note= "Xaa at position 53 is
        Leu, Thr, Ala, Gly, Glu, Pro, Lys, Ser, or Met"

(ix) FEATURE:
    (A) NAME/KEY: Modified-site
    (B) LOCATION: 54
    (D) OTHER INFORMATION: /note= "Xaa at position 54 is Arg,
        Asp, Ile, Ser, Val, Thr, Gln, Asn, Lys, His, Ala,
        or Leu"

(ix) FEATURE:
    (A) NAME/KEY: Modified-site
    (B) LOCATION: 55
    (D) OTHER INFORMATION: /note= "Xaa at position 55 is Arg,
        Thr, Val, Ser, Leu, or Gly"

(ix) FEATURE:
    (A) NAME/KEY: Modified-site
    (B) LOCATION: 56
    (D) OTHER INFORMATION: /note= "Xaa at position 56 is Pro,
        Gly, Cys, Ser, Gln, Glu, Arg, His, Thr, Ala, Tyr,
        Phe, Leu, Val, or Lys"

(ix) FEATURE:

```
        (A) NAME/KEY: Modified-site
        (B) LOCATION: 57
        (D) OTHER INFORMATION: /note= "Xaa at position 57 is Asn
            or Gly"

(ix) FEATURE:
        (A) NAME/KEY: Modified-site
        (B) LOCATION: 58
        (D) OTHER INFORMATION: /note= "Xaa at position 58 is Leu,
            Ser, Asp, Arg, Gln, Val, or Cys"

(ix) FEATURE:
        (A) NAME/KEY: Modified-site
        (B) LOCATION: 59
        (D) OTHER INFORMATION: /note= "Xaa at position 59 is Glu,
            Tyr, His, Leu, Pro, or Arg"

(ix) FEATURE:
        (A) NAME/KEY: Modified-site
        (B) LOCATION: 60
        (D) OTHER INFORMATION: /note= "Xaa at position 60 is Ala,
            Ser, Pro, Tyr, Asn, or Thr"

(ix) FEATURE:
        (A) NAME/KEY: Modified-site
        (B) LOCATION: 61
        (D) OTHER INFORMATION: /note= "Xaa at position 61 is Phe,
            Asn, Glu, Pro, Lys, Arg, or Ser"

(ix) FEATURE:
        (A) NAME/KEY: Modified-site
        (B) LOCATION: 62
        (D) OTHER INFORMATION: /note= "Xaa at position 62 is Asn,
            His, Val, Arg, Pro, Thr, Asp, or Ile"

(ix) FEATURE:
        (A) NAME/KEY: Modified-site
        (B) LOCATION: 63
        (D) OTHER INFORMATION: /note= "Xaa at position 63 is Arg,
            Tyr, Trp, Lys, Ser, His, Pro, or Val"

(ix) FEATURE:
        (A) NAME/KEY: Modified-site
        (B) LOCATION: 64
        (D) OTHER INFORMATION: /note= "Xaa at position 64 is Ala,
            Asn, Pro, Ser, or Lys"

(ix) FEATURE:
        (A) NAME/KEY: Modified-site
        (B) LOCATION: 65
        (D) OTHER INFORMATION: /note= "Xaa at position 65 is Val,
            Thr, Pro, His, Leu, Phe, or Ser"

(ix) FEATURE:
        (A) NAME/KEY: Modified-site
        (B) LOCATION: 66
        (D) OTHER INFORMATION: /note= "Xaa at position 66 is Lys,
            Ile, Arg, Val, Asn, Glu, or Ser"

(ix) FEATURE:
        (A) NAME/KEY: Modified-site
        (B) LOCATION: 67
        (D) OTHER INFORMATION: /note= "Xaa at position 67 is Ser,
            Ala, Phe, Val, Gly, Asn, Ile, Pro, or His"

(ix) FEATURE:
        (A) NAME/KEY: Modified-site
        (B) LOCATION: 68
        (D) OTHER INFORMATION: /note= "Xaa at position 68 is Leu,
            Val, Trp, Ser, Ile, Phe, Thr, or His"

(ix) FEATURE:
        (A) NAME/KEY: Modified-site
        (B) LOCATION: 69
        (D) OTHER INFORMATION: /note= "Xaa at position 69 is Gln,
            Ala, Pro, Thr, Glu, Arg, Trp, Gly, or Leu"

(ix) FEATURE:
        (A) NAME/KEY: Modified-site
```

(B) LOCATION: 70
        (D) OTHER INFORMATION: /note= "Xaa at position 70 is Asn,
            Leu, Val, Trp, Pro, or Ala"

(ix) FEATURE:
        (A) NAME/KEY: Modified-site
        (B) LOCATION: 71
        (D) OTHER INFORMATION: /note= "Xaa at position 71 is
            Ala, Met, Leu, Pro, Arg, Glu, Thr, Gln, Trp,
            or Asn"

(ix) FEATURE:
        (A) NAME/KEY: Modified-site
        (B) LOCATION: 72
        (D) OTHER INFORMATION: /note= "Xaa at position 72 is Ser,
            Glu, Met, Ala, His, Asn, Arg, or Asp"

(ix) FEATURE:
        (A) NAME/KEY: Modified-site
        (B) LOCATION: 73
        (D) OTHER INFORMATION: /note= "Xaa at position 73 is Ala,
            Glu, Asp, Leu, Ser, Gly, Thr, or Arg"

(ix) FEATURE:
        (A) NAME/KEY: Modified-site
        (B) LOCATION: 74
        (D) OTHER INFORMATION: /note= "Xaa at position 74 is Ile,
            Met, Thr, Pro, Arg, Gly, or Ala"

(ix) FEATURE:
        (A) NAME/KEY: Modified-site
        (B) LOCATION: 75
        (D) OTHER INFORMATION: /note= "Xaa at position 75 is
            Glu, Lys, Gly, Asp, Pro, Trp, Arg, Ser, Gln,
            or Leu"

(ix) FEATURE:
        (A) NAME/KEY: Modified-site
        (B) LOCATION: 76
        (D) OTHER INFORMATION: /note= "Xaa at position 76 is Ser,
            Val, Ala, Asn, Trp, Glu, Pro, Gly, or Asp"

(ix) FEATURE:
        (A) NAME/KEY: Modified-site
        (B) LOCATION: 77
        (D) OTHER INFORMATION: /note= "Xaa at position 77 is Ile,
            Ser, Arg, Thr, or Leu"

(ix) FEATURE:
        (A) NAME/KEY: Modified-site
        (B) LOCATION: 78
        (D) OTHER INFORMATION: /note= "Xaa at position 78 is Leu,
            Ala, Ser, Glu, Phe, Gly, or Arg"

(ix) FEATURE:
        (A) NAME/KEY: Modified-site
        (B) LOCATION: 79
        (D) OTHER INFORMATION: /note= "Xaa at position 79 is Lys, Thr,
            Asn, Met, Arg, Ile, Gly, or Asp"

(ix) FEATURE:
        (A) NAME/KEY: Modified-site
        (B) LOCATION: 80
        (D) OTHER INFORMATION: /note= "Xaa at position 80 is Asn,
            Trp, Val, Gly, Thr, Leu, Glu, or Arg"

(ix) FEATURE:
        (A) NAME/KEY: Modified-site
        (B) LOCATION: 81
        (D) OTHER INFORMATION: /note= "Xaa at position 81 is Leu,
            Gln, Gly, Ala, Trp, Arg, Val, or Lys"

(ix) FEATURE:
        (A) NAME/KEY: Modified-site
        (B) LOCATION: 82
        (D) OTHER INFORMATION: /note= "Xaa at position 82 is Leu,
            Gln, Lys, Trp, Arg, Asp, Glu, Asn, His, Thr, Ser, Ala,
            Tyr, Phe, Ile, Met, or Val"

```
(ix) FEATURE:
    (A) NAME/KEY: Modified-site
    (B) LOCATION: 83
    (D) OTHER INFORMATION: /note= "Xaa at position 83 is Pro,
        Ala, Thr, Trp, Arg, or Met"

(ix) FEATURE:
    (A) NAME/KEY: Modified-site
    (B) LOCATION: 84
    (D) OTHER INFORMATION: /note= "Xaa at position 84 is Cys,
        Glu, Gly, Arg, Met, or Val"

(ix) FEATURE:
    (A) NAME/KEY: Modified-site
    (B) LOCATION: 85
    (D) OTHER INFORMATION: /note= "Xaa at position 85 is Leu,
        Asn, Val, or Gln"

(ix) FEATURE:
    (A) NAME/KEY: Modified-site
    (B) LOCATION: 86
    (D) OTHER INFORMATION: /note= "Xaa at position 86 is Pro,
        Cys, Arg, Ala, or Lys"

(ix) FEATURE:
    (A) NAME/KEY: Modified-site
    (B) LOCATION: 87
    (D) OTHER INFORMATION: /note= "Xaa at position 87 is Leu,
        Ser, Trp, or Gly"

(ix) FEATURE:
    (A) NAME/KEY: Modified-site
    (B) LOCATION: 88
    (D) OTHER INFORMATION: /note= "Xaa at position 88 is Ala,
        Lys, Arg, Val, or Trp"

(ix) FEATURE:
    (A) NAME/KEY: Modified-site
    (B) LOCATION: 89
    (D) OTHER INFORMATION: /note= "Xaa at position 89 is Thr,
        Asp, Cys, Leu, Val, Glu, His, Asn, or Ser"

(ix) FEATURE:
    (A) NAME/KEY: Modified-site
    (B) LOCATION: 90
    (D) OTHER INFORMATION: /note= "Xaa at position 90 is Ala,
        Pro, Ser, Thr, Gly, Asp, Ile, or Met"

(ix) FEATURE:
    (A) NAME/KEY: Modified-site
    (B) LOCATION: 91
    (D) OTHER INFORMATION: /note= "Xaa at position 91 is Ala,
        Pro, Ser, Thr, Phe, Leu, Asp, or His"

(ix) FEATURE:
    (A) NAME/KEY: Modified-site
    (B) LOCATION: 92
    (D) OTHER INFORMATION: /note= "Xaa at position 92 is Pro,
        Phe, Arg, Ser, Lys, His, Ala, Gly, Ile, or Leu"

(ix) FEATURE:
    (A) NAME/KEY: Modified-site
    (B) LOCATION: 93
    (D) OTHER INFORMATION: /note= "Xaa at position 93 is Thr,
        Asp, Ser, Asn, Pro, Ala, Leu, or Arg"

(ix) FEATURE:
    (A) NAME/KEY: Modified-site
    (B) LOCATION: 94
    (D) OTHER INFORMATION: /note= "Xaa at position 94 is Arg,
        Ile, Ser, Glu, Leu, Val, Gln, Lys, His, Ala, or Pro"

(ix) FEATURE:
    (A) NAME/KEY: Modified-site
    (B) LOCATION: 95
    (D) OTHER INFORMATION: /note= "Xaa at position 95 is His,
        Gln, Pro, Arg, Val, Leu, Gly, Thr, Asn, Lys, Ser, Ala,
        Trp, Phe, Ile, or Tyr"
```

```
    (ix) FEATURE:
         (A) NAME/KEY: Modified-site
         (B) LOCATION: 96
         (D) OTHER INFORMATION: /note= "Xaa at position 96 is Pro,
             Lys, Tyr, Gly, Ile, or Thr"

(ix) FEATURE:
         (A) NAME/KEY: Modified-site
         (B) LOCATION: 97
         (D) OTHER INFORMATION: /note= "Xaa at position 97 is Ile,
             Val, Lys, Ala, or Asn"

(ix) FEATURE:
         (A) NAME/KEY: Modified-site
         (B) LOCATION: 98
         (D) OTHER INFORMATION: /note= "Xaa at position 98 is His,
             Ile, Asn, Leu, Asp, Ala, Thr, Glu, Gln, Ser, Phe, Met,
             Val, Lys, Arg, Tyr, or Pro"

(ix) FEATURE:
         (A) NAME/KEY: Modified-site
         (B) LOCATION: 99
         (D) OTHER INFORMATION: /note= "Xaa at position 99 is Ile,
             Leu, Arg, Asp, Val, Pro, Gln, Gly, Ser, Phe,
             or His"

(ix) FEATURE:
         (A) NAME/KEY: Modified-site
         (B) LOCATION: 100
         (D) OTHER INFORMATION: /note= "Xaa at position 100 is
             Lys, Tyr, Leu, His, Arg, Ile, Ser, Gln, or Pro"

(ix) FEATURE:
         (A) NAME/KEY: Modified-site
         (B) LOCATION: 101
         (D) OTHER INFORMATION: /note= "Xaa at position 101 is
             Asp, Pro, Met, Lys, His, Thr, Val, Tyr, Glu, Asn, Ser,
             Ala, Gly, Ile, Leu, or Gln"

(ix) FEATURE:
         (A) NAME/KEY: Modified-site
         (B) LOCATION: 102
         (D) OTHER INFORMATION: /note= "Xaa at position 102 is Gly,
             Leu, Glu, Lys, Ser, Tyr, or Pro"

(ix) FEATURE:
         (A) NAME/KEY: Modified-site
         (B) LOCATION: 103
         (D) OTHER INFORMATION: /note= "Xaa at position 103 is Asp,
             or Ser"

(ix) FEATURE:
         (A) NAME/KEY: Modified-site
         (B) LOCATION: 104
         (D) OTHER INFORMATION: /note= "Xaa at position 104 is
             Trp, Val, Cys, Tyr, Thr, Met, Pro, Leu, Gln, Lys, Ala,
             Phe, or Gly"

(ix) FEATURE:
         (A) NAME/KEY: Modified-site
         (B) LOCATION: 105
         (D) OTHER INFORMATION: /note= "Xaa at position 105 is
             Asn, Pro, Ala, Phe, Ser, Trp, Gln, Tyr, Leu, Lys, Ile,
             Asp, or His"

(ix) FEATURE:
         (A) NAME/KEY: Modified-site
         (B) LOCATION: 106
         (D) OTHER INFORMATION: /note= "Xaa at position 106 is Glu,
             Ser, Ala, Lys, Thr, Ile, Gly, or Pro"

(ix) FEATURE:
         (A) NAME/KEY: Modified-site
         (B) LOCATION: 108
         (D) OTHER INFORMATION: /note= "Xaa at position 108 is Arg,
             Lys, Asp, Leu, Thr, Ile, Gln, His, Ser, Ala, or Pro"

(ix) FEATURE:
         (A) NAME/KEY: Modified-site
```

```
          (B) LOCATION: 109
          (D) OTHER INFORMATION: /note= "Xaa at position 109 is Arg,
              Thr, Pro, Glu, Tyr, Leu, Ser, or Gly"

(ix) FEATURE:
          (A) NAME/KEY: Modified-site
          (B) LOCATION: 110
          (D) OTHER INFORMATION: /note= "Xaa at position 110 is Lys,
              Ala, Asn, Thr, Leu, Arg, Gln, His, Glu, Ser, Ala,
              or Trp"

(ix) FEATURE:
          (A) NAME/KEY: Modified-site
          (B) LOCATION: 111
          (D) OTHER INFORMATION: /note= "Xaa at position 111 is Leu,
              Ile, Arg, Asp, or Met"

(ix) FEATURE:
          (A) NAME/KEY: Modified-site
          (B) LOCATION: 112
          (D) OTHER INFORMATION: /note= "Xaa at position 112 is Thr,
              Val, Gln, Tyr, Glu, His, Ser, or Phe"

(ix) FEATURE:
          (A) NAME/KEY: Modified-site
          (B) LOCATION: 113
          (D) OTHER INFORMATION: /note= "Xaa at position 113 is Phe,
              Ser, Cys, His, Gly, Trp, Tyr, Asp, Lys, Leu, Ile, Val,
              or Asn"

(ix) FEATURE:
          (A) NAME/KEY: Modified-site
          (B) LOCATION: 114
          (D) OTHER INFORMATION: /note= "Xaa at position 114 is Tyr,
              Cys, His, Ser, Trp, Arg, or Leu"

(ix) FEATURE:
          (A) NAME/KEY: Modified-site
          (B) LOCATION: 115
          (D) OTHER INFORMATION: /note= "Xaa at position 115 is
              Leu, Asn, Val, Pro, Arg, Ala, His, Thr, Trp, or
              Met"

(ix) FEATURE:
          (A) NAME/KEY: Modified-site
          (B) LOCATION: 116
          (D) OTHER INFORMATION: /note= "Xaa at position 116 is Lys,
              Leu, Pro, Thr, Met, Asp, Val, Glu, Arg, Trp, Ser,
              Asn, His, Ala, Tyr, Phe, Gln, or Ile"

(ix) FEATURE:
          (A) NAME/KEY: Modified-site
          (B) LOCATION: 117
          (D) OTHER INFORMATION: /note= "Xaa at position 117 is Thr,
              Ser, Asn, Ile, Trp, Lys, or Pro"

(ix) FEATURE:
          (A) NAME/KEY: Modified-site
          (B) LOCATION: 118
          (D) OTHER INFORMATION: /note= "Xaa at position 118 is Leu,
              Ser, Pro, Ala, Glu, Cys, Asp, or Tyr"

(ix) FEATURE:
          (A) NAME/KEY: Modified-site
          (B) LOCATION: 119
          (D) OTHER INFORMATION: /note= "Xaa at position 119 is Glu,
              Ser, Lys, Pro, Leu, Thr, Tyr, or Arg"

(ix) FEATURE:
          (A) NAME/KEY: Modified-site
          (B) LOCATION: 120
          (D) OTHER INFORMATION: /note= "Xaa at position 120 is Asn,
              Ala, Pro, Leu, His, Val, or Gln"

(ix) FEATURE:
          (A) NAME/KEY: Modified-site
          (B) LOCATION: 121
          (D) OTHER INFORMATION: /note= "Xaa at position 121 is Ala,
              Ser, Ile, Asn, Pro, Lys, Asp, or Gly"
```

(ix) FEATURE:
              (A) NAME/KEY: Modified-site
              (B) LOCATION: 122
              (D) OTHER INFORMATION: /note= "Xaa at position 122 is
                    Gln, Ser, Met, Trp, Arg, Phe, Pro, His, Ile, Tyr,
                    or Cys"

(ix) FEATURE:
              (A) NAME/KEY: Modified-site
              (B) LOCATION: 123
              (D) OTHER INFORMATION: /note= "Xaa at position 123 is Ala,
                    Met, Glu, His, Ser, Pro, Tyr, or Leu"

(xi) SEQUENCE DESCRIPTION: SEQ ID NO:1:

Ala Pro Met Thr Gln Thr Thr Ser Leu Lys Thr Ser Trp Val Asn Cys
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Asn Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa
65              70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Phe Xaa Xaa Xaa Xaa Xaa
            100                 105                 110

Xaa Xaa Xaa Xaa Xaa Xaa Xaa Xaa Xaa Xaa Xaa Gln Gln Thr Thr Leu
        115                 120                 125

Ser Leu Ala Ile Phe
    130

(2) INFORMATION FOR SEQ ID NO:2:

(i) SEQUENCE CHARACTERISTICS:
          (A) LENGTH: 133 amino acids
          (B) TYPE: amino acid
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /note= "Met- may or may not precede
                the amino acid in position 1"

(ix) FEATURE:
          (A) NAME/KEY: Modified-site
          (B) LOCATION: 17
          (D) OTHER INFORMATION: /note= "Xaa at position 17 is Ser,
                Gly, Asp, Met, or Gln"

(ix) FEATURE:
          (A) NAME/KEY: Modified-site
          (B) LOCATION: 18
          (D) OTHER INFORMATION: /note= "Xaa at position 18 is Asn,
                His, or Ile"

(ix) FEATURE:
          (A) NAME/KEY: Modified-site
          (B) LOCATION: 19
          (D) OTHER INFORMATION: /note= "Xaa at position 19 is Met
                or Ile"

(ix) FEATURE:
          (A) NAME/KEY: Modified-site

```
         (B) LOCATION: 21
         (D) OTHER INFORMATION: /note="Xaa at position 21 is Asp
             or Glu"

(ix) FEATURE:
     (A) NAME/KEY: Modified-site
     (B) LOCATION: 23
     (D) OTHER INFORMATION: /note= "Xaa at position 23 is Ile,
         Ala, Leu, or Gly"

(ix) FEATURE:
     (A) NAME/KEY: Modified-site
     (B) LOCATION: 24
     (D) OTHER INFORMATION: /note= "Xaa at position 24 is Ile,
         Val, or Leu"

(ix) FEATURE:
     (A) NAME/KEY: Modified-site
     (B) LOCATION: 25
     (D) OTHER INFORMATION: /note= "Xaa at position 25 is Thr,
         His, Gln, or Ala"

(ix) FEATURE:
     (A) NAME/KEY: Modified-site
     (B) LOCATION: 26
     (D) OTHER INFORMATION: /note= "Xaa at position 26 is His
         or Ala"

(ix) FEATURE:
     (A) NAME/KEY: Modified-site
     (B) LOCATION: 29
     (D) OTHER INFORMATION: /note= "Xaa at position 29 is Gln,
         Asn, or Val"

(ix) FEATURE:
     (A) NAME/KEY: Modified-site
     (B) LOCATION: 30
     (D) OTHER INFORMATION: /note= "Xaa at position 30 is Pro,
         Gly, or Gln"

(ix) FEATURE:
     (A) NAME/KEY: Modified-site
     (B) LOCATION: 31
     (D) OTHER INFORMATION: /note= "Xaa at position 31 is Pro,
         Asp, Gly, or Gln"

(ix) FEATURE:
     (A) NAME/KEY: Modified-site
     (B) LOCATION: 32
     (D) OTHER INFORMATION: /note= "Xaa at position 32 is Leu,
         Arg, Gln, Asn, Gly, Ala, or Glu"

(ix) FEATURE:
     (A) NAME/KEY: Modified-site
     (B) LOCATION: 33
     (D) OTHER INFORMATION: /note= "Xaa at position 33 is Pro
         or Glu"

(ix) FEATURE:
     (A) NAME/KEY: Modified-site
     (B) LOCATION: 34
     (D) OTHER INFORMATION: /note= "Xaa at position 34 is Leu,
         Val, Gly, Ser, Lys, Ala, Arg, Gln, Glu, Ile, Phe,
         Thr, or Met"

(ix) FEATURE:
     (A) NAME/KEY: Modified-site
     (B) LOCATION: 35
     (D) OTHER INFORMATION: /note= "Xaa at position 35 is Leu,
         Ala, Asn, Pro, Gln, or Val"

(ix) FEATURE:
     (A) NAME/KEY: Modified-site
     (B) LOCATION: 37
     (D) OTHER INFORMATION: /note= "Xaa at position 37 is Phe,
         Ser, Pro, or Trp"

(ix) FEATURE:
     (A) NAME/KEY: Modified-site
```

(B) LOCATION: 38
        (D) OTHER INFORMATION: /note="Xaa at position 38 is Asn
            or Ala"

(ix) FEATURE:
        (A) NAME/KEY: Modified-site
        (B) LOCATION: 42
        (D) OTHER INFORMATION: /note= "Xaa at position 42 is Gly,
            Asp, Ser, Cys, Ala, Asn, Ile, Leu, Met, Tyr,
            or Arg"

(ix) FEATURE:
        (A) NAME/KEY: Modified-site
        (B) LOCATION: 44
        (D) OTHER INFORMATION: /note="Xaa at position 44 is Asp
            or Glu"

(ix) FEATURE:
        (A) NAME/KEY: Modified-site
        (B) LOCATION: 45
        (D) OTHER INFORMATION: /note= "Xaa at position 45 is Gln,
            Val, Met, Leu, Thr, Ala, Asn, Glu, Ser, or Lys"

(ix) FEATURE:
        (A) NAME/KEY: Modified-site
        (B) LOCATION: 46
        (D) OTHER INFORMATION: /note= "Xaa at position 46 is Asp,
            Phe, Ser, Thr, Ala, Asn, Gln, Glu, His, Ile,
            Lys, Tyr, Val, or Cys"

(ix) FEATURE:
        (A) NAME/KEY: Modified-site
        (B) LOCATION: 50
        (D) OTHER INFORMATION: /note= "Xaa at position 50 is Glu,
            Ala, Asn, Ser, or Asp"

(ix) FEATURE:
        (A) NAME/KEY: Modified-site
        (B) LOCATION: 51
        (D) OTHER INFORMATION: /note= "Xaa at position 51 is Asn,
            Arg, Met, Pro, Ser, Thr, or His"

(ix) FEATURE:
        (A) NAME/KEY: Modified-site
        (B) LOCATION: 54
        (D) OTHER INFORMATION: /note="Xaa at position 54 is Arg
            or Ala"

(ix) FEATURE:
        (A) NAME/KEY: Modified-site
        (B) LOCATION: 55
        (D) OTHER INFORMATION: /note= "Xaa at position 55 is Arg,
            Thr, Val, Leu, or Gly"

(ix) FEATURE:
        (A) NAME/KEY: Modified-site
        (B) LOCATION: 56
        (D) OTHER INFORMATION: /note= "Xaa at position 56 is Pro,
            Gly, Ser, Gln, Ala, Arg, Asn, Glu, Leu, Thr, Val,
            or Lys"

(ix) FEATURE:
        (A) NAME/KEY: Modified-site
        (B) LOCATION: 60
        (D) OTHER INFORMATION: /note= "Xaa at position 60 is Ala
            or Ser"

(ix) FEATURE:
        (A) NAME/KEY: Modified-site
        (B) LOCATION: 62
        (D) OTHER INFORMATION: /note= "Xaa at position 62 is Asn,
            Pro, Thr, or Ile"

(ix) FEATURE:
        (A) NAME/KEY: Modified-site
        (B) LOCATION: 63
        (D) OTHER INFORMATION: /note= "Xaa at position 63 is Arg
            or Lys"

-continued

```
(ix) FEATURE:
    (A) NAME/KEY: Modified-site
    (B) LOCATION: 64
    (D) OTHER INFORMATION: /note= "Xaa at position 64 is Ala
        or Asn"

(ix) FEATURE:
    (A) NAME/KEY: Modified-site
    (B) LOCATION: 65
    (D) OTHER INFORMATION: /note= "Xaa at position 65 is Val
        or Thr"

(ix) FEATURE:
    (A) NAME/KEY: Modified-site
    (B) LOCATION: 66
    (D) OTHER INFORMATION: /note= "Xaa at position 66 is Lys
        or Arg"

(ix) FEATURE:
    (A) NAME/KEY: Modified-site
    (B) LOCATION: 67
    (D) OTHER INFORMATION: /note= "Xaa at position 67 is Ser
        Phe or His"

(ix) FEATURE:
    (A) NAME/KEY: Modified-site
    (B) LOCATION: 68
    (D) OTHER INFORMATION: /note= "Xaa at position 68 is Leu,
        Ile, Phe, or His"

(ix) FEATURE:
    (A) NAME/KEY: Modified-site
    (B) LOCATION: 69
    (D) OTHER INFORMATION: /note= "Xaa at position 69 is Gln,
        Ala, Pro, Thr, Glu, Arg, or Gly"

(ix) FEATURE:
    (A) NAME/KEY: Modified-site
    (B) LOCATION: 71
    (D) OTHER INFORMATION: /note= "Xaa at position 71 is Ala,
        Pro, or Arg"

(ix) FEATURE:
    (A) NAME/KEY: Modified-site
    (B) LOCATION: 72
    (D) OTHER INFORMATION: /note= "Xaa at position 72 is Ser,
        Glu, Arg, or Asp"

(ix) FEATURE:
    (A) NAME/KEY: Modified-site
    (B) LOCATION: 73
    (D) OTHER INFORMATION: /note= "Xaa at position 73 is Ala
        or Leu"

(ix) FEATURE:
    (A) NAME/KEY: Modified-site
    (B) LOCATION: 76
    (D) OTHER INFORMATION: /note= "Xaa at position 76 is Ser,
        Val, Ala, Asn, Glu, Pro, or Gly"

(ix) FEATURE:
    (A) NAME/KEY: Modified-site
    (B) LOCATION: 77
    (D) OTHER INFORMATION: /note= "Xaa at position 77 is Ile
        or Leu"

(ix) FEATURE:
    (A) NAME/KEY: Modified-site
    (B) LOCATION: 79
    (D) OTHER INFORMATION: /note= "Xaa at position 79 is
        Lys, Thr, Gly, Asn, Met, Arg, Ile, Gly, or Asp"

(ix) FEATURE:
    (A) NAME/KEY: Modified-site
    (B) LOCATION: 80
    (D) OTHER INFORMATION: /note= "Xaa at position 80 is Asn,
        Gly, Glu, or Arg"

(ix) FEATURE:
```

(A) NAME/KEY: Modified-site
           (B) LOCATION: 82
           (D) OTHER INFORMATION: /note= "Xaa at position 82 is Leu,
               Gln, Trp, Arg, Asp, Ala, Asn, Glu, His, Ile,
               Met, Phe, Ser, Thr, Tyr, or Val"

(ix) FEATURE:
           (A) NAME/KEY: Modified-site
           (B) LOCATION: 83
           (D) OTHER INFORMATION: /note= "Xaa at position 83 is Pro
               or Thr"

(ix) FEATURE:
           (A) NAME/KEY: Modified-site
           (B) LOCATION: 85
           (D) OTHER INFORMATION: /note= "Xaa at position 85 is Leu
               or Val"

(ix) FEATURE:
           (A) NAME/KEY: Modified-site
           (B) LOCATION: 87
           (D) OTHER INFORMATION: /note= "Xaa at position 87 is Leu
               or Ser"

(ix) FEATURE:
           (A) NAME/KEY: Modified-site
           (B) LOCATION: 88
           (D) OTHER INFORMATION: /note= "Xaa at position 88 is Ala
               or Trp"

(ix) FEATURE:
           (A) NAME/KEY: Modified-site
           (B) LOCATION: 91
           (D) OTHER INFORMATION: /note= "Xaa at position 91 is Ala
               or Pro"

(ix) FEATURE:
           (A) NAME/KEY: Modified-site
           (B) LOCATION: 93
           (D) OTHER INFORMATION: /note= "Xaa at position 93 is Thr,
               Asp, Ser, Pro, Ala, Leu, or Arg"

(ix) FEATURE:
           (A) NAME/KEY: Modified-site
           (B) LOCATION: 95
           (D) OTHER INFORMATION: /note= "Xaa at position 95 is His,
               Pro, Arg, Val, Leu, Gly, Asn, Phe, Ser, or Thr"

(ix) FEATURE:
           (A) NAME/KEY: Modified-site
           (B) LOCATION: 96
           (D) OTHER INFORMATION: /note= "Xaa at position 96 is Pro
               or Tyr"

(ix) FEATURE:
           (A) NAME/KEY: Modified-site
           (B) LOCATION: 97
           (D) OTHER INFORMATION: /note= "Xaa at position 97 is Ile
               or Val"

(ix) FEATURE:
           (A) NAME/KEY: Modified-site
           (B) LOCATION: 98
           (D) OTHER INFORMATION: /note= "Xaa at position 98 is His,
               Ile, Asn, Leu, Ala, Thr, Arg, Gln, Lys,
               Met, Ser, Tyr, Val, or Pro"

(ix) FEATURE:
           (A) NAME/KEY: Modified-site
           (B) LOCATION: 99
           (D) OTHER INFORMATION: /note= "Xaa at position 99 is Ile,
               Leu, or Val"

(ix) FEATURE:
           (A) NAME/KEY: Modified-site
           (B) LOCATION: 100
           (D) OTHER INFORMATION: /note= "Xaa at position 100 is Lys,
               Arg, Ile, Gln, Pro, or Ser"

-continued (ix) FEATURE:
    (A) NAME/KEY: Modified-site
    (B) LOCATION: 101
    (D) OTHER INFORMATION: /note= "Xaa at position 101 is Asp,
        Pro, Met, Lys, Thr, His, Asn, Ile, Leu, or Tyr"

(ix) FEATURE:
    (A) NAME/KEY: Modified-site
    (B) LOCATION: 104
    (D) OTHER INFORMATION: /note= "Xaa at position 104 is Trp
        or Leu"

(ix) FEATURE:
    (A) NAME/KEY: Modified-site
    (B) LOCATION: 105
    (D) OTHER INFORMATION: /note= "Xaa at position 105 is
        Asn, Pro, Ala, Ser, Trp, Gln, Tyr, Leu, Lys, Ile,
        Asp, or His"

(ix) FEATURE:
    (A) NAME/KEY: Modified-site
    (B) LOCATION: 106
    (D) OTHER INFORMATION: /note= "Xaa at position 106 is Glu
        or Gly"

(ix) FEATURE:
    (A) NAME/KEY: Modified-site
    (B) LOCATION: 108
    (D) OTHER INFORMATION: /note="Xaa at position 108 is Arg,
        Ala, or Ser"

(ix) FEATURE:
    (A) NAME/KEY: Modified-site
    (B) LOCATION: 109
    (D) OTHER INFORMATION: /note= "Xaa at position 109 is Arg,
        Thr, Glu, Leu, or Ser"

(ix) FEATURE:
    (A) NAME/KEY: Modified-site
    (B) LOCATION: 112
    (D) OTHER INFORMATION: /note= "Xaa at position 112 is Thr,
        Val, or Gln"

(ix) FEATURE:
    (A) NAME/KEY: Modified-site
    (B) LOCATION: 114
    (D) OTHER INFORMATION: /note= "Xaa at position 114 is Tyr
        or Trp"

(ix) FEATURE:
    (A) NAME/KEY: Modified-site
    (B) LOCATION: 115
    (D) OTHER INFORMATION: /note= "Xaa at position 115 is Leu
        or Ala"

(ix) FEATURE:
    (A) NAME/KEY: Modified-site
    (B) LOCATION: 116
    (D) OTHER INFORMATION: /note= "Xaa at position 116 is Lys,
        Thr, Val, Trp, Ser, Ala, His, Met, Phe, Tyr, or Ile"

(ix) FEATURE:
    (A) NAME/KEY: Modified-site
    (B) LOCATION: 117
    (D) OTHER INFORMATION: /note= "Xaa at position 117 is Thr
        or Ser"

(ix) FEATURE:
    (A) NAME/KEY: Modified-site
    (B) LOCATION: 120
    (D) OTHER INFORMATION: /note= "Xaa at position 120 is Asn,
        Pro, Leu, His, Val, or Gln"

(ix) FEATURE:
    (A) NAME/KEY: Modified-site
    (B) LOCATION: 121
    (D) OTHER INFORMATION: /note= "Xaa at position 121 is Ala,
        Ser, Ile, Asn, Pro, Asp, or Gly"

```
        (ix) FEATURE:
             (A) NAME/KEY: Modified-site
             (B) LOCATION: 122
             (D) OTHER INFORMATION: /note= "Xaa at position 122 is
                 Gln, Ser, Met, Trp, Arg, Phe, Pro, His, Ile, Tyr,
                 or Cys"

(ix) FEATURE:
             (A) NAME/KEY: Modified-site
             (B) LOCATION: 123
             (D) OTHER INFORMATION: /note= "Xaa at position 123 is Ala,
                 Met, Glu, His, Ser, Pro, Tyr, or Leu"

(xi) SEQUENCE DESCRIPTION: SEQ ID NO:2:

Ala Pro Met Thr Gln Thr Thr Ser Leu Lys Thr Ser Trp Val Asn Cys
1               5                   10                  15

Xaa Xaa Xaa Ile Xaa Glu Xaa Xaa Xaa Leu Lys Xaa Xaa Xaa Xaa
            20              25                  30

Xaa Xaa Xaa Asp Xaa Xaa Asn Leu Asn Xaa Glu Xaa Xaa Xaa Ile Leu
            35              40                  45

Met Xaa Xaa Asn Leu Xaa Xaa Xaa Asn Leu Glu Xaa Phe Xaa Xaa Xaa
        50              55                  60

Xaa Xaa Xaa Xaa Xaa Asn Xaa Xaa Ile Glu Xaa Xaa Leu Xaa Xaa
65              70              75                  80

Leu Xaa Xaa Cys Xaa Pro Xaa Xaa Thr Ala Xaa Pro Xaa Arg Xaa Xaa
            85              90              95

Xaa Xaa Xaa Xaa Xaa Gly Asp Xaa Xaa Xaa Phe Xaa Xaa Lys Leu Xaa
            100             105             110

Phe Xaa Xaa Xaa Xaa Leu Glu Xaa Xaa Xaa Xaa Gln Gln Thr Thr Leu
        115             120             125

Ser Leu Ala Ile Phe
        130

(2) INFORMATION FOR SEQ ID NO:3:

(i) SEQUENCE CHARACTERISTICS:
            (A) LENGTH: 133 amino acids
            (B) TYPE: amino acid
            (D) TOPOLOGY: linear (ii) MOLECULE TYPE: peptide (ix) FEATURE:
             (A) NAME/KEY: Modified-site
             (B) LOCATION: 1
             (D) OTHER INFORMATION: /note= "Met- may or may not precede
                 the amino acid in position 1"

(ix) FEATURE:
             (A) NAME/KEY: Modified-site
             (B) LOCATION: 17
             (D) OTHER INFORMATION: /note= "Xaa at position 17 is Ser,
                 Gly, Asp, or Gln"

(ix) FEATURE:
             (A) NAME/KEY: Modified-site
             (B) LOCATION: 18
             (D) OTHER INFORMATION: /note= "Xaa at position 18 is Asn,
                 His, or Ile"

(ix) FEATURE:
             (A) NAME/KEY: Modified-site
             (B) LOCATION: 23
             (D) OTHER INFORMATION: /note= "Xaa at position 23 is Ile,
                 Ala, Leu, or Gly"

(ix) FEATURE:
             (A) NAME/KEY: Modified-site
             (B) LOCATION: 25
```

(D) OTHER INFORMATION: /note= "Xaa at position 25 is Thr,
                His, or Gln"

(ix) FEATURE:
            (A) NAME/KEY: Modified-site
            (B) LOCATION: 26
            (D) OTHER INFORMATION: /note= "Xaa at position 26 is His
                or Ala"

(ix) FEATURE:
            (A) NAME/KEY: Modified-site
            (B) LOCATION: 29
            (D) OTHER INFORMATION: /note="Xaa at position 29 is Gln
                or Asn"

(ix) FEATURE:
            (A) NAME/KEY: Modified-site
            (B) LOCATION: 30
            (D) OTHER INFORMATION: /note= "Xaa at position 30 is Pro
                or Gly"

(ix) FEATURE:
            (A) NAME/KEY: Modified-site
            (B) LOCATION: 32
            (D) OTHER INFORMATION: /note= "Xaa at position 32 is Leu,
                Arg, Asn, or Ala"

(ix) FEATURE:
            (A) NAME/KEY: Modified-site
            (B) LOCATION: 34
            (D) OTHER INFORMATION: /note= "Xaa at position 34 is Leu,
                Val, Ser, Ala, Arg, Gln, Glu, Ile, Phe, Thr, or Met"

(ix) FEATURE:
            (A) NAME/KEY: Modified-site
            (B) LOCATION: 35
            (D) OTHER INFORMATION: /note= "Xaa at position 35 is Leu,
                Ala, Asn, or Pro"

(ix) FEATURE:
            (A) NAME/KEY: Modified-site
            (B) LOCATION: 38
            (D) OTHER INFORMATION: /note= "Xaa at position 38 is Asn
                or Ala"

(ix) FEATURE:
            (A) NAME/KEY: Modified-site
            (B) LOCATION: 42
            (D) OTHER INFORMATION: /note= "Xaa at position 42 is Gly,
                Asp, Ser, Ala, Asn, Ile, Leu, Met, Tyr, or Arg"

(ix) FEATURE:
            (A) NAME/KEY: Modified-site
            (B) LOCATION: 45
            (D) OTHER INFORMATION: /note= "Xaa at position 45 is Gln,
                Val, Met, Leu, Ala, Asn, Glu, or Lys"

(ix) FEATURE:
            (A) NAME/KEY: Modified-site
            (B) LOCATION: 46
            (D) OTHER INFORMATION: /note= "Xaa at position 46 is Asp,
                Phe, Ser, Gln, Glu, His, Val, or Thr"

(ix) FEATURE:
            (A) NAME/KEY: Modified-site
            (B) LOCATION: 50
            (D) OTHER INFORMATION: /note= "Xaa at position 50 is Glu,
                Asn, Ser, or Asp"

(ix) FEATURE:
            (A) NAME/KEY: Modified-site
            (B) LOCATION: 51
            (D) OTHER INFORMATION: /note= "Xaa at position 51 is Asn,
                Arg, Pro, Thr, or His"

(ix) FEATURE:
            (A) NAME/KEY: Modified-site
            (B) LOCATION: 55
            (D) OTHER INFORMATION: /note= "Xaa at position 55 is Arg,

```
              Leu, or Gly"

(ix) FEATURE:
    (A) NAME/KEY: Modified-site
    (B) LOCATION: 56
    (D) OTHER INFORMATION: /note= "Xaa at position 56 is Pro,
        Gly, Ser, Ala, Asn, Val, Leu, or Gln"

(ix) FEATURE:
    (A) NAME/KEY: Modified-site
    (B) LOCATION: 62
    (D) OTHER INFORMATION: /note= "Xaa at position 62 is Asn,
        Pro, or Thr"

(ix) FEATURE:
    (A) NAME/KEY: Modified-site
    (B) LOCATION: 64
    (D) OTHER INFORMATION: /note= "Xaa at position 64 is Ala
        or Asn"

(ix) FEATURE:
    (A) NAME/KEY: Modified-site
    (B) LOCATION: 65
    (D) OTHER INFORMATION: /note= "Xaa at position 65 is Val
        or Thr"

(ix) FEATURE:
    (A) NAME/KEY: Modified-site
    (B) LOCATION: 67
    (D) OTHER INFORMATION: /note= "Xaa at position 67 is Ser
        or Phe"

(ix) FEATURE:
    (A) NAME/KEY: Modified-site
    (B) LOCATION: 68
    (D) OTHER INFORMATION: /note= "Xaa at position 68 is Leu
        or Phe"

(ix) FEATURE:
    (A) NAME/KEY: Modified-site
    (B) LOCATION: 69
    (D) OTHER INFORMATION: /note= "Xaa at position 69 is Gln,
        Ala, Glu, or Arg"

(ix) FEATURE:
    (A) NAME/KEY: Modified-site
    (B) LOCATION: 76
    (D) OTHER INFORMATION: /note= "Xaa at position 76 is Ser,
        Val, Asn, Pro, or Gly"

(ix) FEATURE:
    (A) NAME/KEY: Modified-site
    (B) LOCATION: 77
    (D) OTHER INFORMATION: /note= "Xaa at position 77 is Ile
        or Leu"

(ix) FEATURE:
    (A) NAME/KEY: Modified-site
    (B) LOCATION: 79
    (D) OTHER INFORMATION: /note= "Xaa at position 79 is Lys,
        Asn, Met, Arg, Ile, or Gly"

(ix) FEATURE:
    (A) NAME/KEY: Modified-site
    (B) LOCATION: 80
    (D) OTHER INFORMATION: /note= "Xaa at position 80 is Asn,
        Gly, Glu, or Arg"

(ix) FEATURE:
    (A) NAME/KEY: Modified-site
    (B) LOCATION: 82
    (D) OTHER INFORMATION: /note= "Xaa at position 82 is Leu,
        Gln, Trp, Arg, Asp, Asn, Glu, His, Met, Phe, Ser,
        Thr, Tyr, or Val"

(ix) FEATURE:
    (A) NAME/KEY: Modified-site
    (B) LOCATION: 87
    (D) OTHER INFORMATION: /note= "Xaa at position 87 is Leu
``` or Ser"

(ix) FEATURE:
    (A) NAME/KEY: Modified-site
    (B) LOCATION: 88
    (D) OTHER INFORMATION: /note= "Xaa at position 88 is Ala
        or Trp"

(ix) FEATURE:
    (A) NAME/KEY: Modified-site
    (B) LOCATION: 91
    (D) OTHER INFORMATION: /note= "Xaa at position 91 is Ala
        or Pro"

(ix) FEATURE:
    (A) NAME/KEY: Modified-site
    (B) LOCATION: 93
    (D) OTHER INFORMATION: /note= "Xaa at position 93 is Thr,
        Asp, or Ala"

(ix) FEATURE:
    (A) NAME/KEY: Modified-site
    (B) LOCATION: 95
    (D) OTHER INFORMATION: /note= "Xaa at position 95 is His,
        Pro, Arg, Val, Gly, Asn, Ser, or Thr"

(ix) FEATURE:
    (A) NAME/KEY: Modified-site
    (B) LOCATION: 98
    (D) OTHER INFORMATION: /note= "Xaa at position 98 is His,
        Ile, Asn, Ala, Thr, Gln, Glu, Lys, Met, Ser, Tyr,
        Val, or Leu"

(ix) FEATURE:
    (A) NAME/KEY: Modified-site
    (B) LOCATION: 99
    (D) OTHER INFORMATION: /note= "Xaa at position 99 is Ile
        or Leu"

(ix) FEATURE:
    (A) NAME/KEY: Modified-site
    (B) LOCATION: 100
    (D) OTHER INFORMATION: /note= "Xaa at position 100 is Lys
        or Arg"

(ix) FEATURE:
    (A) NAME/KEY: Modified-site
    (B) LOCATION: 101
    (D) OTHER INFORMATION: /note= "Xaa at position 101 is Asp,
        Pro, Met, Lys, Thr, His, Asn, Ile, Leu, or Tyr"

(ix) FEATURE:
    (A) NAME/KEY: Modified-site
    (B) LOCATION: 105
    (D) OTHER INFORMATION: /note= "Xaa at position 105 is Asn,
        Pro, Ser, Ile, or Asp"

(ix) FEATURE:
    (A) NAME/KEY:  Modified-site
    (B) LOCATION:  108
    (D) OTHER INFORMATION:  /note= "Xaa at position 108 is Arg, Ala,
        or Ser"

(ix) FEATURE:
    (A) NAME/KEY: Modified-site
    (B) LOCATION: 109
    (D) OTHER INFORMATION: /note= "Xaa at position 109 is Arg,
        Thr, Glu, Leu, or Ser"

(ix) FEATURE:
    (A) NAME/KEY: Modified-site
    (B) LOCATION: 112
    (D) OTHER INFORMATION: /note= "Xaa at position 112 is Thr
        or Gln"

(ix) FEATURE:
    (A) NAME/KEY: Modified-site
    (B) LOCATION: 116
    (D) OTHER INFORMATION: /note= "Xaa at position 116 is Lys, Val, Trp, Ala, His, Phe, Tyr, or Ile"

(ix) FEATURE:
        (A) NAME/KEY: Modified-site
        (B) LOCATION: 117
        (D) OTHER INFORMATION: /note= "Xaa at position 117 is Thr
            or Ser"

(ix) FEATURE:
        (A) NAME/KEY: Modified-site
        (B) LOCATION: 120
        (D) OTHER INFORMATION: /note= "Xaa at position 120 is Asn,
            Pro, Leu, His, Val, or Gln"

(ix) FEATURE:
        (A) NAME/KEY: Modified-site
        (B) LOCATION: 121
        (D) OTHER INFORMATION: /note= "Xaa at position 121 is Ala,
            Ser, Ile, Pro, or Asp"

(ix) FEATURE:
        (A) NAME/KEY: Modified-site
        (B) LOCATION: 122
        (D) OTHER INFORMATION: /note= "Xaa at position 122 is Gln,
            Met, Trp, Phe, Pro, His, Ile, or Tyr"

(ix) FEATURE:
        (A) NAME/KEY: Modified-site
        (B) LOCATION: 123
        (D) OTHER INFORMATION: /note= "Xaa at position 123 is Ala,
            Met, Glu, Ser, or Leu"

(xi) SEQUENCE DESCRIPTION: SEQ ID NO:3:

Ala Pro Met Thr Gln Thr Thr Ser Leu Lys Thr Ser Trp Val Asn Cys
1               5                  10                  15

Xaa Xaa Met Ile Asp Glu Xaa Ile Xaa Xaa Leu Lys Xaa Xaa Pro Xaa
            20                  25                  30

Pro Xaa Xaa Asp Phe Xaa Asn Leu Asn Xaa Glu Asp Xaa Xaa Ile Leu
        35                  40                  45

Met Xaa Xaa Asn Leu Arg Xaa Xaa Asn Leu Glu Ala Phe Xaa Arg Xaa
    50                  55                  60

Xaa Lys Xaa Xaa Xaa Asn Ala Ser Ala Ile Glu Xaa Xaa Leu Xaa Xaa
65                  70                  75                  80

Leu Xaa Pro Cys Leu Pro Xaa Xaa Thr Ala Xaa Pro Xaa Arg Xaa Pro
            85                  90                  95

Ile Xaa Xaa Xaa Xaa Gly Asp Trp Xaa Glu Phe Xaa Xaa Lys Leu Xaa
        100                 105                 110

Phe Tyr Leu Xaa Xaa Leu Glu Xaa Xaa Xaa Xaa Gln Gln Thr Thr Leu
        115                 120                 125

Ser Leu Ala Ile Phe
    130

(2) INFORMATION FOR SEQ ID NO:4:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- or Met-Ala- may or may
            not precede the amino acid in position 1"

(ix) FEATURE:
        (A) NAME/KEY: Modified-site

-continued

```
        (B) LOCATION: 3
        (D) OTHER INFORMATION: /note= "Xaa at position 3 is Ser,
            Lys, Gly, Asp, Met, Gln, or Arg"

(ix) FEATURE:
        (A) NAME/KEY: Modified-site
        (B) LOCATION: 4
        (D) OTHER INFORMATION: /note= "Xaa at position 4 is Asn,
            His, Leu, Ile, Phe, Arg, or Gln"

(ix) FEATURE:
        (A) NAME/KEY: Modified-site
        (B) LOCATION: 5
        (D) OTHER INFORMATION: /note= "Xaa at position 5 is Met,
            Phe, Ile, Arg, Gly, Ala, or Cys"

(ix) FEATURE:
        (A) NAME/KEY: Modified-site
        (B) LOCATION: 6
        (D) OTHER INFORMATION: /note= "Xaa at position 6 is Ile,
            Cys, Gln, Glu, Arg, Pro, or Ala"

(ix) FEATURE:
        (A) NAME/KEY: Modified-site
        (B) LOCATION: 7
        (D) OTHER INFORMATION: /note= "Xaa at position 7 is Asp,
            Phe, Lys, Arg, Ala, Gly, Glu, Gln, Asn, Thr, Ser,
            or Val"

(ix) FEATURE:
        (A) NAME/KEY: Modified-site
        (B) LOCATION: 8
        (D) OTHER INFORMATION: /note= "Xaa at position 8 is Glu,
            Trp, Pro, Ser, Ala, His, Asp, Asn, Gln, Leu, Val,
            or Gly"

(ix) FEATURE:
        (A) NAME/KEY: Modified-site
        (B) LOCATION: 9
        (D) OTHER INFORMATION: /note= "Xaa at position 9 is
            Ile, Val, Ala, Leu, Gly, Trp, Lys, Phe, Leu, Ser
            or Arg"

(ix) FEATURE:
        (A) NAME/KEY: Modified-site
        (B) LOCATION: 10
        (D) OTHER INFORMATION: /note= "Xaa at position 10 is Ile,
            Gly, Val, Arg, Ser, Phe, or Leu"

(ix) FEATURE:
        (A) NAME/KEY: Modified-site
        (B) LOCATION: 11
        (D) OTHER INFORMATION: /note= "Xaa at position 11 is Thr,
            His, Gly, Gln, Arg, Pro, or Ala"

(ix) FEATURE:
        (A) NAME/KEY: Modified-site
        (B) LOCATION: 12
        (D) OTHER INFORMATION: /note= "Xaa at position 12 is His,
            Thr, Phe, Gly, Arg, Ala, or Trp"

(ix) FEATURE:
        (A) NAME/KEY: Modified-site
        (B) LOCATION: 13
        (D) OTHER INFORMATION: /note= "Xaa at position 13 is Leu,
            Gly, Arg, Thr, Ser, or Ala"

(ix) FEATURE:
        (A) NAME/KEY: Modified-site
        (B) LOCATION: 14
        (D) OTHER INFORMATION: /note= "Xaa at position 14 is Lys,
            Arg, Leu, Gln, Gly, Pro, Val, or Trp"

(ix) FEATURE:
        (A) NAME/KEY: Modified-site
        (B) LOCATION: 15
        (D) OTHER INFORMATION: /note= "Xaa at position 15 is Gln,
            Asn, Leu, Pro, Arg, or Val"
```

6,093,395

-continued

```
(ix) FEATURE:
    (A) NAME/KEY: Modified-site
    (B) LOCATION: 16
    (D) OTHER INFORMATION: /note= "Xaa at position 16 is Pro,
        His, Thr, Gly, Asp, Gln, Ser, Leu, or Lys"

(ix) FEATURE:
    (A) NAME/KEY: Modified-site
    (B) LOCATION: 17
    (D) OTHER INFORMATION: /note= "Xaa at position 17 is Pro,
        Asp, Gly, Ala, Arg, Leu, or Gln"

(ix) FEATURE:
    (A) NAME/KEY: Modified-site
    (B) LOCATION: 18
    (D) OTHER INFORMATION: /note= "Xaa at position 18 is Leu,
        Val, Arg, Gln, Asn, Gly, Ala, or Glu"

(ix) FEATURE:
    (A) NAME/KEY: Modified-site
    (B) LOCATION: 19
    (D) OTHER INFORMATION: /note= "Xaa at position 19 is Pro,
        Leu, Gln, Ala, Thr, or Glu"

(ix) FEATURE:
    (A) NAME/KEY: Modified-site
    (B) LOCATION: 20
    (D) OTHER INFORMATION: /note= "Xaa at position 20 is Leu,
        Val, Gly, Ser, Lys, Glu, Gln, Thr, Arg, Ala, Phe,
        Ile, or Met"

(ix) FEATURE:
    (A) NAME/KEY: Modified-site
    (B) LOCATION: 21
    (D) OTHER INFORMATION: /note= "Xaa at position 21 is Leu,
        Ala, Gly, Asn, Pro, Gln, or Val"

(ix) FEATURE:
    (A) NAME/KEY: Modified-site
    (B) LOCATION: 22
    (D) OTHER INFORMATION: /note= "Xaa at position 22 is Asp,
        Leu, or Val"

(ix) FEATURE:
    (A) NAME/KEY: Modified-site
    (B) LOCATION: 23
    (D) OTHER INFORMATION: /note= "Xaa at position 23 is Phe,
        Ser, Pro, Trp, or Ile"

(ix) FEATURE:
    (A) NAME/KEY: Modified-site
    (B) LOCATION: 24
    (D) OTHER INFORMATION: /note= "Xaa at position 24 is Asn
        or Ala"

(ix) FEATURE:
    (A) NAME/KEY: Modified-site
    (B) LOCATION: 26
    (D) OTHER INFORMATION: /note= "Xaa at position 26 is Leu,
        Trp, or Arg"

(ix) FEATURE:
    (A) NAME/KEY: Modified-site
    (B) LOCATION: 27
    (D) OTHER INFORMATION: /note= "Xaa at position 27 is Asn,
        Cys, Arg, Leu, His, Met, or Pro"

(ix) FEATURE:
    (A) NAME/KEY: Modified-site
    (B) LOCATION: 28
    (D) OTHER INFORMATION: /note= "Xaa at position 28 is Gly,
        Asp, Ser, Cys, Ala, Lys, Asn, Thr, Leu, Val, Glu,
        Phe, Tyr, Ile, or Met"

(ix) FEATURE:
    (A) NAME/KEY: Modified-site
    (B) LOCATION: 29
    (D) OTHER INFORMATION: /note= "Xaa at position 29 is Glu,
        Asn, Tyr, Leu, Phe, Asp, Ala, Cys, Gln, Arg, Thr,
```

-continued

```
            Gly, or Ser"

(ix) FEATURE:
     (A) NAME/KEY: Modified-site
     (B) LOCATION: 30
     (D) OTHER INFORMATION: /note= "Xaa at position 30 is Asp,
         Ser, Leu, Arg, Lys, Thr, Met, Trp, Glu, Asn, Gln,
         Ala, or Pro"

(ix) FEATURE:
     (A) NAME/KEY: Modified-site
     (B) LOCATION: 31
     (D) OTHER INFORMATION: /note= "Xaa at position 31 is Gln,
         Pro, Phe, Val, Met, Leu, Thr, Lys, Asp, Asn, Arg,
         Ser, Ala, Ile, Glu, His, or Trp"

(ix) FEATURE:
     (A) NAME/KEY: Modified-site
     (B) LOCATION: 32
     (D) OTHER INFORMATION: /note= "Xaa at position 32 is Asp,
         Phe, Ser, Thr, Cys, Glu, Asn, Gln, Lys, His, Ala,
         Tyr, Ile, Val, or Gly"

(ix) FEATURE:
     (A) NAME/KEY: Modified-site
     (B) LOCATION: 33
     (D) OTHER INFORMATION: /note= "Xaa at position 33 is Ile,
         Gly, Val, Ser, Arg, Pro, or His"

(ix) FEATURE:
     (A) NAME/KEY: Modified-site
     (B) LOCATION: 34
     (D) OTHER INFORMATION: /note= "Xaa at position 34 is Leu,
         Ser, Cys, Arg, Ile, His, Phe, Glu, Lys, Thr, Ala,
         Met, Val, or Asn"

(ix) FEATURE:
     (A) NAME/KEY: Modified-site
     (B) LOCATION: 35
     (D) OTHER INFORMATION: /note= "Xaa at position 35 is Met,
         Arg, Ala, Gly, Pro, Asn, His, or Asp"

(ix) FEATURE:
     (A) NAME/KEY: Modified-site
     (B) LOCATION: 36
     (D) OTHER INFORMATION: /note= "Xaa at position 36 is Glu,
         Leu, Thr, Asp, Tyr, Lys, Asn, Ser, Ala, Ile, Val,
         His, Phe, Met, or Gln"

(ix) FEATURE:
     (A) NAME/KEY: Modified-site
     (B) LOCATION: 37
     (D) OTHER INFORMATION: /note= "Xaa at position 37 is Asn,
         Arg, Met, Pro, Ser, Thr, or His"

(ix) FEATURE:
     (A) NAME/KEY: Modified-site
     (B) LOCATION: 38
     (D) OTHER INFORMATION: /note= "Xaa at position 38 is Asn,
         His, Arg, Leu, Gly, Ser, or Thr"

(ix) FEATURE:
     (A) NAME/KEY: Modified-site
     (B) LOCATION: 39
     (D) OTHER INFORMATION: /note= "Xaa at position 39 is
         Leu, Thr, Ala, Gly, Glu, Pro, Lys, Ser, or Met"

(ix) FEATURE:
     (A) NAME/KEY: Modified-site
     (B) LOCATION: 40
     (D) OTHER INFORMATION: /note= "Xaa at position 40 is Arg,
         Asp, Ile, Ser, Val, Thr, Gln, Asn, Lys, His,
         Ala, or Leu"

(ix) FEATURE:
     (A) NAME/KEY: Modified-site
     (B) LOCATION: 41
     (D) OTHER INFORMATION: /note= "Xaa at position 41 is Arg,
         Thr, Val, Ser, Leu, or Gly"
```

```
(ix) FEATURE:
    (A) NAME/KEY: Modified-site
    (B) LOCATION: 42
    (D) OTHER INFORMATION: /note= "Xaa at position 42 is Pro,
        Gly, Cys, Ser, Gln, Glu, Arg, His, Thr, Ala, Tyr,
        Phe, Leu, Val, or Lys"

(ix) FEATURE:
    (A) NAME/KEY: Modified-site
    (B) LOCATION: 43
    (D) OTHER INFORMATION: /note= "Xaa at position 43 is Asn
        or Gly"

(ix) FEATURE:
    (A) NAME/KEY: Modified-site
    (B) LOCATION: 44
    (D) OTHER INFORMATION: /note= "Xaa at position 44 is Leu,
        Ser, Asp, Arg, Gln, Val, or Cys"

(ix) FEATURE:
    (A) NAME/KEY: Modified-site
    (B) LOCATION: 45
    (D) OTHER INFORMATION: /note= "Xaa at position 45 is Glu,
        Tyr, His, Leu, Pro, or Arg"

(ix) FEATURE:
    (A) NAME/KEY: Modified-site
    (B) LOCATION: 46
    (D) OTHER INFORMATION: /note= "Xaa at position 46 is Ala,
        Ser, Pro, Tyr, Asn, or Thr"

(ix) FEATURE:
    (A) NAME/KEY: Modified-site
    (B) LOCATION: 47
    (D) OTHER INFORMATION: /note= "Xaa at position 47 is Phe,
        Asn, Glu, Pro, Lys, Arg, or Ser"

(ix) FEATURE:
    (A) NAME/KEY: Modified-site
    (B) LOCATION: 48
    (D) OTHER INFORMATION: /note= "Xaa at position 48 is Asn,
        His, Val, Arg, Pro, Thr, Asp, or Ile"

(ix) FEATURE:
    (A) NAME/KEY: Modified-site
    (B) LOCATION: 49
    (D) OTHER INFORMATION: /note= "Xaa at position 49 is Arg,
        Tyr, Trp, Lys, Ser, His, Pro, or Val"

(ix) FEATURE:
    (A) NAME/KEY: Modified-site
    (B) LOCATION: 50
    (D) OTHER INFORMATION: /note= "Xaa at position 50 is Ala,
        Asn, Pro, Ser, or Lys"

(ix) FEATURE:
    (A) NAME/KEY: Modified-site
    (B) LOCATION: 51
    (D) OTHER INFORMATION: /note= "Xaa at position 51 is Val,
        Thr, Pro, His, Leu, Phe, or Ser"

(ix) FEATURE:
    (A) NAME/KEY: Modified-site
    (B) LOCATION: 52
    (D) OTHER INFORMATION: /note= "Xaa at position 52 is Lys,
        Ile, Arg, Val, Asn, Glu, or Ser"

(ix) FEATURE:
    (A) NAME/KEY: Modified-site
    (B) LOCATION: 53
    (D) OTHER INFORMATION: /note= "Xaa at position 53 is Ser,
        Ala, Phe, Val, Gly, Asn, Ile, Pro, or His"

(ix) FEATURE:
    (A) NAME/KEY: Modified-site
    (B) LOCATION: 54
    (D) OTHER INFORMATION: /note= "Xaa at position 54 is Leu,
        Val, Trp, Ser, Ile, Phe, Thr, or His"
```

(ix) FEATURE:
      (A) NAME/KEY: Modified-site
      (B) LOCATION: 55
      (D) OTHER INFORMATION: /note= "Xaa at position 55 is Gln,
          Ala, Pro, Thr, Glu, Arg, Trp, Gly, or Leu"

(ix) FEATURE:
      (A) NAME/KEY: Modified-site
      (B) LOCATION: 56
      (D) OTHER INFORMATION: /note= "Xaa at position 56 is Asn,
          Leu, Val, Trp, Pro, or Ala"

(ix) FEATURE:
      (A) NAME/KEY: Modified-site
      (B) LOCATION: 57
      (D) OTHER INFORMATION: /note= "Xaa at position 57 is Ala,
          Met, Leu, Pro, Arg, Glu, Thr, Gln, Trp, or Asn"

(ix) FEATURE:
      (A) NAME/KEY: Modified-site
      (B) LOCATION: 58
      (D) OTHER INFORMATION: /note= "Xaa at position 58 is Ser,
          Glu, Met, Ala, His, Asn, Arg, or Asp"

(ix) FEATURE:
      (A) NAME/KEY: Modified-site
      (B) LOCATION: 59
      (D) OTHER INFORMATION: /note= "Xaa at position 59 is Ala,
          Glu, Asp, Leu, Ser, Gly, Thr, or Arg"

(ix) FEATURE:
      (A) NAME/KEY: Modified-site
      (B) LOCATION: 60
      (D) OTHER INFORMATION: /note= "Xaa at position 60 is Ile,
          Met, Thr, Pro, Arg, Gly, Ala"

(ix) FEATURE:
      (A) NAME/KEY: Modified-site
      (B) LOCATION: 61
      (D) OTHER INFORMATION: /note= "Xaa at position 61 is
          Glu, Lys, Gly, Asp, Pro, Trp, Arg, Ser, Gln,
          or Leu"

(ix) FEATURE:
      (A) NAME/KEY: Modified-site
      (B) LOCATION: 62
      (D) OTHER INFORMATION: /note= "Xaa at position 62 is Ser,
          Val, Ala, Asn, Trp, Glu, Pro, Gly, or Asp"

(ix) FEATURE:
      (A) NAME/KEY: Modified-site
      (B) LOCATION: 63
      (D) OTHER INFORMATION: /note= "Xaa at position 63 is Ile,
          Ser, Arg, Thr, or Leu"

(ix) FEATURE:
      (A) NAME/KEY: Modified-site
      (B) LOCATION: 64
      (D) OTHER INFORMATION: /note= "Xaa at position 64 is Leu,
          Ala, Ser, Glu, Phe, Gly, or Arg"

(ix) FEATURE:
      (A) NAME/KEY: Modified-site
      (B) LOCATION: 65
      (D) OTHER INFORMATION: /note= "Xaa at position 65 is Lys,
          Thr, Gly, Asn, Met, Arg, Ile, or Asp"

(ix) FEATURE:
      (A) NAME/KEY: Modified-site
      (B) LOCATION: 66
      (D) OTHER INFORMATION: /note= "Xaa at position 66 is Asn,
          Trp, Val, Gly, Thr, Leu, Glu, or Arg"

(ix) FEATURE:
      (A) NAME/KEY: Modified-site
      (B) LOCATION: 67
      (D) OTHER INFORMATION: /note= "Xaa at position 67 is Leu,
          Gln, Gly, Ala, Trp, Arg, Val, or Lys"

```
(ix) FEATURE:
      (A) NAME/KEY: Modified-site
      (B) LOCATION: 68
      (D) OTHER INFORMATION: /note= "Xaa at position 68 is Leu,
            Gln, Lys, Trp, Arg, Asp, Glu, Asn, His, Thr, Ser, Ala,
            Tyr, Phe, Ile, Met, or Val"

(ix) FEATURE:
      (A) NAME/KEY: Modified-site
      (B) LOCATION: 69
      (D) OTHER INFORMATION: /note= "Xaa at position 69 is Pro,
            Ala, Thr, Trp, Arg, or Met"

(ix) FEATURE:
      (A) NAME/KEY: Modified-site
      (B) LOCATION: 70
      (D) OTHER INFORMATION: /note= "Xaa at position 70 is Cys,
            Glu, Gly, Arg, Met, or Val"

(ix) FEATURE:
      (A) NAME/KEY: Modified-site
      (B) LOCATION: 71
      (D) OTHER INFORMATION: /note= "Xaa at position 71 is Leu,
            Asn, Val, or Gln"

(ix) FEATURE:
      (A) NAME/KEY: Modified-site
      (B) LOCATION: 72
      (D) OTHER INFORMATION: /note= "Xaa at position 72 is Pro,
            Cys, Arg, Ala, or Lys"

(ix) FEATURE:
      (A) NAME/KEY: Modified-site
      (B) LOCATION: 73
      (D) OTHER INFORMATION: /note= "Xaa at position 73 is Leu,
            Ser, Trp, or Gly"

(ix) FEATURE:
      (A) NAME/KEY: Modified-site
      (B) LOCATION: 74
      (D) OTHER INFORMATION: /note= "Xaa at position 74 is Ala,
            Lys, Arg, Val, or Trp"

(ix) FEATURE:
      (A) NAME/KEY: Modified-site
      (B) LOCATION: 75
      (D) OTHER INFORMATION: /note= "Xaa at position 75 is Thr,
            Asp, Cys, Leu, Val, Glu, His, Asn, or Ser"

(ix) FEATURE:
      (A) NAME/KEY: Modified-site
      (B) LOCATION: 76
      (D) OTHER INFORMATION: /note= "Xaa at position 76 is Ala,
            Pro, Ser, Thr, Gly, Asp, Ile, or Met"

(ix) FEATURE:
      (A) NAME/KEY: Modified-site
      (B) LOCATION: 77
      (D) OTHER INFORMATION: /note= "Xaa at position 77 is Ala,
            Pro, Ser, Thr, Phe, Leu, Asp, or His"

(ix) FEATURE:
      (A) NAME/KEY: Modified-site
      (B) LOCATION: 78
      (D) OTHER INFORMATION: /note= "Xaa at position 78 is Pro,
            Phe, Arg, Ser, Lys, His, Ala, Gly, Ile, or Leu"

(ix) FEATURE:
      (A) NAME/KEY: Modified-site
      (B) LOCATION: 79
      (D) OTHER INFORMATION: /note= "Xaa at position 79 is Thr,
            Asp, Ser, Asn, Pro, Ala, Leu, or Arg"

(ix) FEATURE:
      (A) NAME/KEY: Modified-site
      (B) LOCATION: 80
      (D) OTHER INFORMATION: /note= "Xaa at position 80 is Arg,
            Ile, Ser, Glu, Leu, Val, Gln, Lys, His, Ala, or Pro"
```

```
(ix) FEATURE:
    (A) NAME/KEY: Modified-site
    (B) LOCATION: 81
    (D) OTHER INFORMATION: /note= "Xaa at position 81 is His,
        Gln, Pro, Arg, Val, Leu, Gly, Thr, Asn, Lys, Ser,
        Ala, Trp, Phe, Ile, or Tyr"

(ix) FEATURE:
    (A) NAME/KEY: Modified-site
    (B) LOCATION: 82
    (D) OTHER INFORMATION: /note= "Xaa at position 82 is Pro,
        Lys, Tyr, Gly, Ile, or Thr"

(ix) FEATURE:
    (A) NAME/KEY: Modified-site
    (B) LOCATION: 83
    (D) OTHER INFORMATION: /note= "Xaa at position 83 is Ile,
        Val, Lys, Ala, or Asn"

(ix) FEATURE:
    (A) NAME/KEY: Modified-site
    (B) LOCATION: 84
    (D) OTHER INFORMATION: /note= "Xaa at position 84 is His,
        Ile, Asn, Leu, Asp, Ala, Thr, Glu, Gln, Ser,
        Phe, Met, Val, Lys, Arg, Tyr, or Pro"

(ix) FEATURE:
    (A) NAME/KEY: Modified-site
    (B) LOCATION: 85
    (D) OTHER INFORMATION: /note= "Xaa at position 85 is
        Ile, Leu, Arg, Asp, Val, Pro, Gln, Gly, Ser,
        Phe, or His"

(ix) FEATURE:
    (A) NAME/KEY: Modified-site
    (B) LOCATION: 86
    (D) OTHER INFORMATION: /note= "Xaa at position 86 is
        Lys, Tyr, Leu, His, Arg, Ile, Ser, Gln, or Pro"

(ix) FEATURE:
    (A) NAME/KEY: Modified-site
    (B) LOCATION: 87
    (D) OTHER INFORMATION: /note= "Xaa at position 87 is
        Asp, Pro, Met, Lys, His, Thr, Val, Tyr, Glu, Asn,
        Ser, Ala, Gly, Ile, Leu, or Gln"

(ix) FEATURE:
    (A) NAME/KEY: Modified-site
    (B) LOCATION: 88
    (D) OTHER INFORMATION: /note= "Xaa at position 88 Gly,
        Leu, Glu, Lys, Ser, Tyr, or Pro"

(ix) FEATURE:
    (A) NAME/KEY: Modified-site
    (B) LOCATION: 89
    (D) OTHER INFORMATION: /note= "Xaa at position 89 is Asp
        or Ser"

(ix) FEATURE:
    (A) NAME/KEY: Modified-site
    (B) LOCATION: 90
    (D) OTHER INFORMATION: /note= "Xaa at position 90 is
        Trp, Val, Cys, Tyr, Thr, Met, Pro, Leu, Gln, Lys,
        Ala, Phe, or Gly"

(ix) FEATURE:
    (A) NAME/KEY: Modified-site
    (B) LOCATION: 91
    (D) OTHER INFORMATION: /note= "Xaa at position 91 is
        Asn, Pro, Ala, Phe, Ser, Trp, Gln, Tyr, Leu, Lys,
        Ile, Asp, or His"

(ix) FEATURE:
    (A) NAME/KEY: Modified-site
    (B) LOCATION: 92
    (D) OTHER INFORMATION: /note= "Xaa at position 92 is Glu,
        Ser, Ala, Lys, Thr, Ile, Gly, or Pro"
```

```
(ix) FEATURE:
    (A) NAME/KEY: Modified-site
    (B) LOCATION: 94
    (D) OTHER INFORMATION: /note= "Xaa at position 94 is Arg,
         Lys, Asp, Leu, Thr, Ile, Gln, His, Ser, Ala, or Pro"

(ix) FEATURE:
    (A) NAME/KEY: Modified-site
    (B) LOCATION: 95
    (D) OTHER INFORMATION: /note= "Xaa at position 95 is Arg,
         Thr, Pro, Glu, Tyr, Leu, Ser, or Gly"

(ix) FEATURE:
    (A) NAME/KEY: Modified-site
    (B) LOCATION: 96
    (D) OTHER INFORMATION: /note= "Xaa at position 96 is Lys,
         Asn, Thr, Leu, Gln, Arg, His, Glu, Ser, Ala,
         or Trp"

(ix) FEATURE:
    (A) NAME/KEY: Modified-site
    (B) LOCATION: 97
    (D) OTHER INFORMATION: /note= "Xaa at position 97 is Leu,
         Ile, Arg, Asp, or Met"

(ix) FEATURE:
    (A) NAME/KEY: Modified-site
    (B) LOCATION: 98
    (D) OTHER INFORMATION: /note= "Xaa at position 98 is Thr,
         Val, Gln, Tyr, Glu, His, Ser, or Phe"

(ix) FEATURE:
    (A) NAME/KEY: Modified-site
    (B) LOCATION: 99
    (D) OTHER INFORMATION: /note= "Xaa at position 99 is Phe,
         Ser, Cys, His, Gly, Trp, Tyr, Asp, Lys, Leu, Ile,
         Val, or Asn"

(ix) FEATURE:
    (A) NAME/KEY: Modified-site
    (B) LOCATION: 100
    (D) OTHER INFORMATION: /note= "Xaa at position 100 is Tyr,
         Cys, His, Ser, Trp, Arg, or Leu"

(ix) FEATURE:
    (A) NAME/KEY: Modified-site
    (B) LOCATION: 101
    (D) OTHER INFORMATION: /note= "Xaa at position 101 is Leu,
         Asn, Val, Pro, Arg, Ala, His, Thr, Trp, or Met"

(ix) FEATURE:
    (A) NAME/KEY: Modified-site
    (B) LOCATION: 102
    (D) OTHER INFORMATION: /note= "Xaa at position 102 is
         Lys, Leu, Pro, Thr, Met, Asp, Val, Glu, Arg, Trp,
         Ser, Asn, His, Ala, Tyr, Phe, Gln, or Ile"

(ix) FEATURE:
    (A) NAME/KEY: Modified-site
    (B) LOCATION: 103
    (D) OTHER INFORMATION: /note= "Xaa at position 103 is Thr,
         Ser, Asn, Ile, Trp, Lys, or Pro"

(ix) FEATURE:
    (A) NAME/KEY: Modified-site
    (B) LOCATION: 104
    (D) OTHER INFORMATION: /note= "Xaa at position 104 is Leu,
         Ser, Pro, Ala, Glu, Cys, Asp, or Tyr"

(ix) FEATURE:
    (A) NAME/KEY: Modified-site
    (B) LOCATION: 105
    (D) OTHER INFORMATION: /note= "Xaa at position 105 is Glu,
         Ser, Lys, Pro, Leu, Thr, Tyr, or Arg"

(ix) FEATURE:
    (A) NAME/KEY: Modified-site
    (B) LOCATION: 106
    (D) OTHER INFORMATION: /note= "Xaa at position 106 is Asn,
```

Ala, Pro, Leu, His, Val or Gln"

(ix) FEATURE:
(A) NAME/KEY: Modified-site
(B) LOCATION: 107
(D) OTHER INFORMATION: /note= "Xaa at position 107 is Ala,
Ser, Ile, Asn, Pro, Lys, Asp, or Gly"

(ix) FEATURE:
(A) NAME/KEY: Modified-site
(B) LOCATION: 108
(D) OTHER INFORMATION: /note= "Xaa at position 108 is
Gln, Ser, Met, Trp, Arg, Phe, Pro, His, Ile, Tyr,
or Cys"

(ix) FEATURE:
(A) NAME/KEY: Modified-site
(B) LOCATION: 109
(D) OTHER INFORMATION: /note= "Xaa at position 109 is Ala,
Met, Glu, His, Ser, Pro, Tyr, or Leu"

(xi) SEQUENCE DESCRIPTION: SEQ ID NO:4:

Asn Cys Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Asn Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65              70                  75                  80

Xaa Xaa Xaa Xaa Xaa Xaa Xaa Xaa Xaa Xaa Xaa Xaa Phe Xaa Xaa Xaa
            85                  90                  95

Xaa Xaa Xaa Xaa Xaa Xaa Xaa Xaa Xaa Xaa Xaa Xaa Xaa Gln Gln
        100                 105                 110

(2) INFORMATION FOR SEQ ID NO:5:

(i) SEQUENCE CHARACTERISTICS:
(A) LENGTH: 111 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Met- or Met-Ala- may or may
not precede the amino acid in position 1"

(ix) FEATURE:
(A) NAME/KEY: Modified-site
(B) LOCATION: 3
(D) OTHER INFORMATION: /note= "Xaa at position 3 is Ser,
Gly, Asp, Met, or Gln"

(ix) FEATURE:
(A) NAME/KEY: Modified-site
(B) LOCATION: 4
(D) OTHER INFORMATION: /note= "Xaa at position 4 is Asn,
His, or Ile"

(ix) FEATURE:
(A) NAME/KEY: Modified-site
(B) LOCATION: 5
(D) OTHER INFORMATION: /note= "Xaa at position 5 is Met
or Ile"

(ix) FEATURE:

```
          (A) NAME/KEY: Modified-site
          (B) LOCATION: 7
          (C) OTHER INFORMATION: /note= "Xaa at position 7 is Asp or Glu"

(ix) FEATURE:
          (A) NAME/KEY: Modified-site
          (B) LOCATION: 9
          (D) OTHER INFORMATION: /note= "Xaa at position 9 is Ile,
              Ala, Leu, or Gly"

(ix) FEATURE:
          (A) NAME/KEY: Modified-site
          (B) LOCATION: 10
          (D) OTHER INFORMATION: /note= "Xaa at position 10 is Ile,
              Val, or Leu"

(ix) FEATURE:
          (A) NAME/KEY: Modified-site
          (B) LOCATION: 11
          (D) OTHER INFORMATION: /note= "Xaa at position 11 is Thr,
              His, Gln, or Ala"

(ix) FEATURE:
          (A) NAME/KEY: Modified-site
          (B) LOCATION: 12
          (D) OTHER INFORMATION: /note= "Xaa at position 12 is His
              or Ala"

(ix) FEATURE:
          (A) NAME/KEY: Modified-site
          (B) LOCATION: 15
          (D) OTHER INFORMATION: /note= "Xaa at position 15 is Gln,
              Asn, or Val"

(ix) FEATURE:
          (A) NAME/KEY: Modified-site
          (B) LOCATION: 16
          (D) OTHER INFORMATION: /note= "Xaa at position 16 is Pro,
              Gly, or Gln"

(ix) FEATURE:
          (A) NAME/KEY: Modified-site
          (B) LOCATION: 17
          (D) OTHER INFORMATION: /note= "Xaa at position 17 is Pro,
              Asp, Gly, or Gln"

(ix) FEATURE:
          (A) NAME/KEY: Modified-site
          (B) LOCATION: 18
          (D) OTHER INFORMATION: /note= "Xaa at position 18 is Leu,
              Arg, Gln, Asn, Gly, Ala, or Glu"

(ix) FEATURE:
          (A) NAME/KEY: Modified-site
          (B) LOCATION: 19
          (D) OTHER INFORMATION: /note= "Xaa at position 19 is Pro
              or Glu"

(ix) FEATURE:
          (A) NAME/KEY: Modified-site
          (B) LOCATION: 20
          (D) OTHER INFORMATION: /note= "Xaa at position 20 is Leu,
              Val, Gly, Ser, Lys, Ala, Arg, Gln, Glu, Ile, Phe,
              Thr, or Met"

(ix) FEATURE:
          (A) NAME/KEY: Modified-site
          (B) LOCATION: 21
          (D) OTHER INFORMATION: /note= "Xaa at position 21 is Leu,
              Ala, Asn, Pro, Gln, or Val"

(ix) FEATURE:
          (A) NAME/KEY: Modified-site
          (B) LOCATION: 23
          (D) OTHER INFORMATION: /note= "Xaa at position 23 is Phe,
              Ser, Pro, or Trp"

(ix) FEATURE:
          (A) NAME/KEY: Modified-site
```

```
          (B) LOCATION: 24
          (D) OTHER INFORMATION: /note= "Xaa at position 24 is Asn
              or Ala"

(ix) FEATURE:
          (A) NAME/KEY: Modified-site
          (B) LOCATION: 28
          (D) OTHER INFORMATION: /note= "Xaa at position 28 is Gly,
              Asp, Ser, Cys, Ala, Asn, Ile, Leu, Met, Tyr, or Arg"

(ix) FEATURE:
          (A) NAME/KEY: Modified-site
          (B) LOCATION: 30
          (D) OTHER INFORMATION: /note= "Xaa at position 30 is Asp
              or Glu"

(ix) FEATURE:
          (A) NAME/KEY: Modified-site
          (B) LOCATION: 31
          (D) OTHER INFORMATION: /note= "Xaa at position 31 is Gln,
              Val, Met, Leu, Thr, Ala, Asn, Glu, Ser, or Lys"

(ix) FEATURE:
          (A) NAME/KEY: Modified-site
          (B) LOCATION: 32
          (D) OTHER INFORMATION: /note= "Xaa at position 32 is Asp,
              Phe, Ser, Thr, Ala, Asn, Gln, Glu, His, Ile, Lys,
              Tyr, Val, or Cys"

(ix) FEATURE:
          (A) NAME/KEY: Modified-site
          (B) LOCATION: 36
          (D) OTHER INFORMATION: /note= "Xaa at position 36 is Glu,
              Ala, Asn, Ser, or Asp"

(ix) FEATURE:
          (A) NAME/KEY: Modified-site
          (B) LOCATION: 37
          (D) OTHER INFORMATION: /note= "Xaa at position 37 is Asn,
              Arg, Met, Pro, Ser, Thr, or His"

(ix) FEATURE:
          (A) NAME/KEY: Modified-site
          (B) LOCATION: 40
          (D) OTHER INFORMATION: /note= "Xaa at position 40 is Arg
              or Ala"

(ix) FEATURE:
          (A) NAME/KEY: Modified-site
          (B) LOCATION: 41
          (D) OTHER INFORMATION: /note= "Xaa at position 41 is Arg,
              Thr, Val, Leu, or Gly"

(ix) FEATURE:
          (A) NAME/KEY: Modified-site
          (B) LOCATION: 42
          (D) OTHER INFORMATION: /note= "Xaa at position 42 is Pro,
              Gly, Ser, Gln, Ala, Arg, Asn, Glu, Leu, Thr, Val,
              or Lys"

(ix) FEATURE:
          (A) NAME/KEY: Modified-site
          (B) LOCATION: 46
          (D) OTHER INFORMATION: /note= "Xaa at position 46 is Ala
              or Ser"

(ix) FEATURE:
          (A) NAME/KEY: Modified-site
          (B) LOCATION: 48
          (D) OTHER INFORMATION: /note= "Xaa at position 48 is Asn,
              Pro, Thr, or Ile"

(ix) FEATURE:
          (A) NAME/KEY: Modified-site
          (B) LOCATION: 49
          (D) OTHER INFORMATION: /note= "Xaa at position 49 is Arg
              or Lys"

(ix) FEATURE:
```

(A) NAME/KEY: Modified-site
        (B) LOCATION: 50
        (D) OTHER INFORMATION: /note= "Xaa at position 50 is Ala
            or Asn"

(ix) FEATURE:
        (A) NAME/KEY: Modified-site
        (B) LOCATION: 51
        (D) OTHER INFORMATION: /note= "Xaa at position 51 is Val
            or Thr"

(ix) FEATURE:
        (A) NAME/KEY: Modified-site
        (B) LOCATION: 52
        (D) OTHER INFORMATION: /note= "Xaa at position 52 is Lys
            or Arg"

(ix) FEATURE:
        (A) NAME/KEY: Modified-site
        (B) LOCATION: 53
        (D) OTHER INFORMATION: /note= "Xaa at position 53 is Ser,
            Phe, or His"

(ix) FEATURE:
        (A) NAME/KEY: Modified-site
        (B) LOCATION: 54
        (D) OTHER INFORMATION: /note= "Xaa at position 54 is Leu,
            Ile, Phe, or His"

(ix) FEATURE:
        (A) NAME/KEY: Modified-site
        (B) LOCATION: 55
        (D) OTHER INFORMATION: /note= "Xaa at position 55 is Gln,
            Ala, Pro, Thr, Glu, Arg, or Gly"

(ix) FEATURE:
        (A) NAME/KEY: Modified-site
        (B) LOCATION: 57
        (D) OTHER INFORMATION: /note= "Xaa at position 57 is Ala,
            Pro, or Arg"

(ix) FEATURE:
        (A) NAME/KEY: Modified-site
        (B) LOCATION: 58
        (D) OTHER INFORMATION: /note= "Xaa at position 58 is Ser,
            Glu, Arg, or Asp"

(ix) FEATURE:
        (A) NAME/KEY: Modified-site
        (B) LOCATION: 59
        (D) OTHER INFORMATION: /note= "Xaa at position 59 is Ala
            or Leu"

(ix) FEATURE:
        (A) NAME/KEY: Modified-site
        (B) LOCATION: 62
        (D) OTHER INFORMATION: /note= "Xaa at position 62 is Ser,
            Val, Ala, Asn, Glu, Pro, or Gly"

(ix) FEATURE:
        (A) NAME/KEY: Modified-site
        (B) LOCATION: 63
        (D) OTHER INFORMATION: /note= "Xaa at position 63 is Ile
            or Leu"

(ix) FEATURE:
        (A) NAME/KEY: Modified-site
        (B) LOCATION: 65
        (D) OTHER INFORMATION: /note= "Xaa at position 65 is Lys,
            Thr, Gly, Asn, Met, Arg, Ile, Gly, or Asp"

(ix) FEATURE:
        (A) NAME/KEY: Modified-site
        (B) LOCATION: 66
        (D) OTHER INFORMATION: /note= "Xaa at position 66 is Asn,
            Gly, Glu, or Arg"

(ix) FEATURE:
        (A) NAME/KEY: Modified-site

```
        (B) LOCATION: 68
        (D) OTHER INFORMATION: /note= "Xaa at position 68 is Leu,
            Gln, Trp, Arg, Asp, Ala, Asn, Glu, His, Ile, Met,
            Phe, Ser, Thr, Tyr, or Val"

(ix) FEATURE:
        (A) NAME/KEY: Modified-site
        (B) LOCATION: 69
        (D) OTHER INFORMATION: /note= "Xaa at position 69 is Pro
            or Thr"

(ix) FEATURE:
        (A) NAME/KEY: Modified-site
        (B) LOCATION: 71
        (D) OTHER INFORMATION: /note= "Xaa at position 71 is Leu
            or Val"

(ix) FEATURE:
        (A) NAME/KEY: Modified-site
        (B) LOCATION: 73
        (D) OTHER INFORMATION: /note= "Xaa at position 73 is Leu
            or Ser"

(ix) FEATURE:
        (A) NAME/KEY: Modified-site
        (B) LOCATION: 74
        (D) OTHER INFORMATION: /note= "Xaa at position 74 is Ala
            or Trp"

(ix) FEATURE:
        (A) NAME/KEY: Modified-site
        (B) LOCATION: 77
        (D) OTHER INFORMATION: /note= "Xaa at position 77 is Ala
            or Pro"

(ix) FEATURE:
        (A) NAME/KEY: Modified-site
        (B) LOCATION: 79
        (D) OTHER INFORMATION: /note= "Xaa at position 79 is Thr,
            Asp, Ser, Pro, Ala, Leu, or Arg"

(ix) FEATURE:
        (A) NAME/KEY: Modified-site
        (B) LOCATION: 81
        (D) OTHER INFORMATION: /note= "Xaa at position 81 is His,
            Pro, Arg, Val, Leu, Gly, Asn, Phe, Ser, or Thr"

(ix) FEATURE:
        (A) NAME/KEY: Modified-site
        (B) LOCATION: 82
        (D) OTHER INFORMATION: /note= "Xaa at position 82 is Pro
            or Tyr"

(ix) FEATURE:
        (A) NAME/KEY: Modified-site
        (B) LOCATION: 83
        (D) OTHER INFORMATION: /note= "Xaa at position 83 is Ile
            or Val"

(ix) FEATURE:
        (A) NAME/KEY: Modified-site
        (B) LOCATION: 84
        (D) OTHER INFORMATION: /note= "Xaa at position 84 is His,
            Ile, Asn, Leu, Ala, Thr, Arg, Gln, Lys,
            Met, Ser, Tyr, Val, or Pro"

(ix) FEATURE:
        (A) NAME/KEY: Modified-site
        (B) LOCATION: 85
        (D) OTHER INFORMATION: /note= "Xaa at position 85 is Ile,
            Leu, or Val"

(ix) FEATURE:
        (A) NAME/KEY: Modified-site
        (B) LOCATION: 86
        (D) OTHER INFORMATION: /note= "Xaa at position 86 is Lys,
            Arg, Ile, Gln, Pro, or Ser"

(ix) FEATURE:
```

```
          (A) NAME/KEY: Modified-site
          (B) LOCATION: 87
          (D) OTHER INFORMATION: /note= "Xaa at position 87 is Asp,
              Pro, Met, Lys, His, Thr, Asn, Ile, Leu, or Tyr"

(ix) FEATURE:
          (A) NAME/KEY: Modified-site
          (B) LOCATION: 90
          (D) OTHER INFORMATION: /note= "Xaa at position 90 is Trp
              or Leu"

(ix) FEATURE:
          (A) NAME/KEY: Modified-site
          (B) LOCATION: 91
          (D) OTHER INFORMATION: /note="Xaa at position 91 is Asn,
              Pro, Ala, Ser, Trp, Gln, Tyr, Leu, Lys, Ile, Asp,
              or His"

(ix) FEATURE:
          (A) NAME/KEY: Modified-site
          (B) LOCATION: 92
          (D) OTHER INFORMATION: /note= "Xaa at position 92 is Glu
              or Gly"

(ix) FEATURE:
          (A) NAME/KEY: Modified-site
          (B) LOCATION: 94
          (C) OTHER INFORMATION: /note= "Xaa at position 94 is Arg,
              Ala, or Ser"

(ix) FEATURE:
          (A) NAME/KEY: Modified-site
          (B) LOCATION: 95
          (D) OTHER INFORMATION: /note= "Xaa at position 95 is Arg,
              Thr, Glu, Leu, or Ser"

(ix) FEATURE:
          (A) NAME/KEY: Modified-site
          (B) LOCATION: 98
          (D) OTHER INFORMATION: /note= "Xaa at position 98 is Thr,
              Val, or Gln"

(ix) FEATURE:
          (A) NAME/KEY: Modified-site
          (B) LOCATION: 100
          (D) OTHER INFORMATION: /note= "Xaa at position 100 is Tyr
              or Trp"

(ix) FEATURE:
          (A) NAME/KEY: Modified-site
          (B) LOCATION: 101
          (D) OTHER INFORMATION: /note= "Xaa at position 101 is Leu
              or Ala"

(ix) FEATURE:
          (A) NAME/KEY: Modified-site
          (B) LOCATION: 102
          (D) OTHER INFORMATION: /note= "Xaa at position 102 is Lys,
              Thr, Val, Trp, Ser, Ala, His, Met, Phe, Tyr, or Ile"

(ix) FEATURE:
          (A) NAME/KEY: Modified-site
          (B) LOCATION: 103
          (D) OTHER INFORMATION: /note= "Xaa at position 103 is Thr
              or Ser"

(ix) FEATURE:
          (A) NAME/KEY: Modified-site
          (B) LOCATION: 106
          (D) OTHER INFORMATION: /note= "Xaa at position 106 is Asn,
              Pro, Leu, His, Val, or Gln"

(ix) FEATURE:
          (A) NAME/KEY: Modified-site
          (B) LOCATION: 107
          (D) OTHER INFORMATION: /note= "Xaa at position 107 is Ala,
              Ser, Ile, Asn, Pro, Asp, or Gly"

(ix) FEATURE:
```

(A) NAME/KEY: Modified-site
        (B) LOCATION: 108
        (D) OTHER INFORMATION: /note= "Xaa at position 108 is Gln,
            Ser, Met, Trp, Arg, Phe, Pro, His, Ile, Tyr, or Cys"

(ix) FEATURE:
        (A) NAME/KEY: Modified-site
        (B) LOCATION: 109
        (D) OTHER INFORMATION: /note= "Xaa at position 109 is Ala,
            Met, Glu, His, Ser, Pro, Tyr, or Leu"

(xi) SEQUENCE DESCRIPTION: SEQ ID NO:5:

Asn Cys Xaa Xaa Xaa Ile Xaa Glu Xaa Xaa Xaa Xaa Leu Lys Xaa Xaa
1               5                   10                  15

Xaa Xaa Xaa Xaa Xaa Asp Xaa Xaa Asn Leu Asn Xaa Glu Xaa Xaa Xaa
            20                  25                  30

Ile Leu Met Xaa Xaa Asn Leu Xaa Xaa Xaa Asn Leu Glu Xaa Phe Xaa
        35                  40                  45

Xaa Xaa Xaa Xaa Xaa Xaa Asn Xaa Xaa Xaa Ile Glu Xaa Xaa Leu
    50                  55                  60

Xaa Xaa Leu Xaa Xaa Cys Xaa Pro Xaa Xaa Thr Ala Xaa Pro Xaa Arg
65              70                  75                  80

Xaa Xaa Xaa Xaa Xaa Xaa Xaa Gly Asp Xaa Xaa Xaa Phe Xaa Xaa Lys
            85                  90                  95

Leu Xaa Phe Xaa Xaa Xaa Xaa Leu Glu Xaa Xaa Xaa Xaa Gln Gln
        100                 105                 110

(2) INFORMATION FOR SEQ ID NO:6:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- or Met-Ala- may or may
            not precede the amino acid in position 1"

(ix) FEATURE:
        (A) NAME/KEY: Modified-site
        (B) LOCATION: 3
        (D) OTHER INFORMATION: /note= "Xaa at position 3 is Ser,
            Gly, Asp, or Gln"

(ix) FEATURE:
        (A) NAME/KEY: Modified-site
        (B) LOCATION: 4
        (D) OTHER INFORMATION: /note= "Xaa at position 4 is Asn,
            His, or Ile"

(ix) FEATURE:
        (A) NAME/KEY: Modified-site
        (B) LOCATION: 9
        (D) OTHER INFORMATION: /note= "Xaa at position 9 is Ile,
            Ala, Leu, or Gly"

(ix) FEATURE:
        (A) NAME/KEY: Modified-site
        (B) LOCATION: 11
        (D) OTHER INFORMATION: /note= "Xaa at position 11 is Thr,
            His, or Gln"

(ix) FEATURE:
        (A) NAME/KEY: Modified-site
        (B) LOCATION: 12
        (D) OTHER INFORMATION: /note= "Xaa at position 12 is His
            or Ala"

```
(ix) FEATURE:
    (A) NAME/KEY: Modified-site
    (B) LOCATION: 15
    (D) OTHER INFORMATION: /note= "Xaa at position 15 is Gln
        or Asn"

(ix) FEATURE:
    (A) NAME/KEY: Modified-site
    (B) LOCATION: 16
    (D) OTHER INFORMATION: /note= "Xaa at position 16 is Pro
        or Gly"

(ix) FEATURE:
    (A) NAME/KEY: Modified-site
    (B) LOCATION: 18
    (D) OTHER INFORMATION: /note= "Xaa at position 18 is Leu,
        Arg, Asn, or Ala"

(ix) FEATURE:
    (A) NAME/KEY: Modified-site
    (B) LOCATION: 20
    (D) OTHER INFORMATION: /note= "Xaa at position 20 is Leu,
        Val, Ser, Ala, Arg, Gln, Glu, Ile, Phe, Thr, or Met"

(ix) FEATURE:
    (A) NAME/KEY: Modified-site
    (B) LOCATION: 21
    (D) OTHER INFORMATION: /note= "Xaa at position 21 is Leu,
        Ala, Asn, or Pro"

(ix) FEATURE:
    (A) NAME/KEY: Modified-site
    (B) LOCATION: 24
    (D) OTHER INFORMATION: /note= "Xaa at position 24 is Asn
        or Ala"

(ix) FEATURE:
    (A) NAME/KEY: Modified-site
    (B) LOCATION: 28
    (D) OTHER INFORMATION: /note= "Xaa at position 28 is Gly,
        Asp, Ser, Ala, Asn, Ile, Leu, Met, Tyr, or Arg"

(ix) FEATURE:
    (A) NAME/KEY: Modified-site
    (B) LOCATION: 31
    (D) OTHER INFORMATION: /note= "Xaa at position 31 is Gln,
        Val, Met, Leu, Ala, Asn, Glu, or Lys"

(ix) FEATURE:
    (A) NAME/KEY: Modified-site
    (B) LOCATION: 32
    (D) OTHER INFORMATION: /note= "Xaa at position 32 is Asp,
        Phe, Ser, Ala, Gln, Glu, His, Val, or Thr"

(ix) FEATURE:
    (A) NAME/KEY: Modified-site
    (B) LOCATION: 36
    (D) OTHER INFORMATION: /note= "Xaa at position 36 is Glu,
        Asn, Ser, or Asp"

(ix) FEATURE:
    (A) NAME/KEY: Modified-site
    (B) LOCATION: 37
    (D) OTHER INFORMATION: /note= "Xaa at position 37 is Asn,
        Arg, Pro, Thr, or His"

(ix) FEATURE:
    (A) NAME/KEY: Modified-site
    (B) LOCATION: 41
    (D) OTHER INFORMATION: /note= "Xaa at position 41 is Arg,
        Leu, or Gly"

(ix) FEATURE:
    (A) NAME/KEY: Modified-site
    (B) LOCATION: 42
    (D) OTHER INFORMATION: /note= "Xaa at position 42 is Pro,
        Gly, Ser, Ala, Asn, Val, Leu, or Gln"
```

```
  (ix) FEATURE:
       (A) NAME/KEY: Modified-site
       (B) LOCATION: 48
       (D) OTHER INFORMATION: /note= "Xaa at position 48 is Asn,
           Pro, or Thr"

(ix) FEATURE:
       (A) NAME/KEY: Modified-site
       (B) LOCATION: 50
       (D) OTHER INFORMATION: /note= "Xaa at position 50 is Ala
           or Asn"

(ix) FEATURE:
       (A) NAME/KEY: Modified-site
       (B) LOCATION: 51
       (D) OTHER INFORMATION: /note= "Xaa at position 51 is Val
           or Thr"

(ix) FEATURE:
       (A) NAME/KEY: Modified-site
       (B) LOCATION: 53
       (D) OTHER INFORMATION: /note= "Xaa at position 53 is Ser
           or Phe"

(ix) FEATURE:
       (A) NAME/KEY: Modified-site
       (B) LOCATION: 54
       (D) OTHER INFORMATION: /note= "Xaa at position 54 is Leu
           or Phe"

(ix) FEATURE:
       (A) NAME/KEY: Modified-site
       (B) LOCATION: 55
       (D) OTHER INFORMATION: /note= "Xaa at position 55 is Gln,
           Ala, Glu, or Arg"

(ix) FEATURE:
       (A) NAME/KEY: Modified-site
       (B) LOCATION: 62
       (D) OTHER INFORMATION: /note= "Xaa at position 62 is Ser,
           Val, Asn, Pro, or Gly"

(ix) FEATURE:
       (A) NAME/KEY: Modified-site
       (B) LOCATION: 63
       (D) OTHER INFORMATION: /note= "Xaa at position 63 is Ile
           or Leu"

(ix) FEATURE:
       (A) NAME/KEY: Modified-site
       (B) LOCATION: 65
       (D) OTHER INFORMATION: /note= "Xaa at position 65 is Lys,
           Asn, Met, Arg, Ile, or Gly"

(ix) FEATURE:
       (A) NAME/KEY: Modified-site
       (B) LOCATION: 66
       (D) OTHER INFORMATION: /note= "Xaa at position 66 is Asn,
           Gly, Glu, or Arg"

(ix) FEATURE:
       (A) NAME/KEY: Modified-site
       (B) LOCATION: 68
       (D) OTHER INFORMATION: /note= "Xaa at position 68 is Leu,
           Gln, Trp, Arg, Asp, Asn, Glu, His, Met, Phe, Ser,
           Thr, Tyr, or Val"

(ix) FEATURE:
       (A) NAME/KEY: Modified-site
       (B) LOCATION: 73
       (D) OTHER INFORMATION: /note= "Xaa at position 73 is Leu
           or Ser"

(ix) FEATURE:
       (A) NAME/KEY: Modified-site
       (B) LOCATION: 74
       (D) OTHER INFORMATION: /note= "Xaa at position 74 is Ala
           or Trp"
```

```
    (ix) FEATURE:
          (A) NAME/KEY: Modified-site
          (B) LOCATION: 77
          (D) OTHER INFORMATION: /note= "Xaa at position 77 is Ala
              or Pro"

(ix) FEATURE:
          (A) NAME/KEY: Modified-site
          (B) LOCATION: 79
          (D) OTHER INFORMATION: /note= "Xaa at position 79 is Thr,
              Asp, or Ala"

(ix) FEATURE:
          (A) NAME/KEY: Modified-site
          (B) LOCATION: 81
          (D) OTHER INFORMATION: /note= "Xaa at position 81 is His,
              Pro, Arg, Val, Gly, Asn, Ser, or Thr"

(ix) FEATURE:
          (A) NAME/KEY: Modified-site
          (B) LOCATION: 84
          (D) OTHER INFORMATION: /note= "Xaa at position 84 is His,
              Ile, Asn, Leu, Ala, Thr, Arg, Gln, Glu, Lys, Met,
              Ser, Tyr, Val, or Leu"

(ix) FEATURE:
          (A) NAME/KEY: Modified-site
          (B) LOCATION: 85
          (D) OTHER INFORMATION: /note= "Xaa at position 85 is Ile
              or Leu"

(ix) FEATURE:
          (A) NAME/KEY: Modified-site
          (B) LOCATION: 86
          (D) OTHER INFORMATION: /note= "Xaa at position 86 is Lys
              or Arg"

(ix) FEATURE:
          (A) NAME/KEY: Modified-site
          (B) LOCATION: 87
          (D) OTHER INFORMATION: /note= "Xaa at position 87 is Asp,
              Pro, Met, Lys, His, Pro, Asn, Ile, Leu, or Tyr"

(ix) FEATURE:
          (A) NAME/KEY: Modified-site
          (B) LOCATION: 91
          (D) OTHER INFORMATION: /note= "Xaa at position 91 is Asn,
              Pro, Ser, Ile, or Asp"

(ix) FEATURE:
          (A) NAME/KEY: Modified-site
          (B) LOCATION: 94
          (D) OTHER INFORMATION: /note="Xaa at position 94 is Arg,
              Ala, or Ser"

(ix) FEATURE:
          (A) NAME/KEY: Modified-site
          (B) LOCATION: 95
          (D) OTHER INFORMATION: /note= "Xaa at position 95 is Arg,
              Thr, Glu, Leu, or Ser"

(ix) FEATURE:
          (A) NAME/KEY: Modified-site
          (B) LOCATION: 98
          (D) OTHER INFORMATION: /note= "Xaa at position 98 is Thr
              or Gln"

(ix) FEATURE:
          (A) NAME/KEY: Modified-site
          (B) LOCATION: 102
          (D) OTHER INFORMATION: /note= "Xaa at position 102 is Lys,
              Val, Trp, or Ile"

(ix) FEATURE:
          (A) NAME/KEY: Modified-site
          (B) LOCATION: 103
          (D) OTHER INFORMATION: /note= "Xaa at position 103 is Thr,
              Ala, His, Phe, Tyr, or Ser"
```

```
    (ix) FEATURE:
          (A) NAME/KEY: Modified-site
          (B) LOCATION: 106
          (D) OTHER INFORMATION: /note= "Xaa at position 106 is Asn,
              Pro, Leu, His, Val, or Gln"

(ix) FEATURE:
          (A) NAME/KEY: Modified-site
          (B) LOCATION: 107
          (D) OTHER INFORMATION: /note= "Xaa at position 107 is Ala,
              Ser, Ile, Pro, or Asp"

(ix) FEATURE:
          (A) NAME/KEY: Modified-site
          (B) LOCATION: 108
          (D) OTHER INFORMATION: /note= "Xaa at position 108 is Gln,
              Met, Trp, Phe, Pro, His, Ile, or Tyr"

(ix) FEATURE:
          (A) NAME/KEY: Modified-site
          (B) LOCATION: 109
          (D) OTHER INFORMATION: /note= "Xaa at position 109 is Ala,
              Met, Glu, Ser, or Leu"

(xi) SEQUENCE DESCRIPTION: SEQ ID NO:6:

Asn Cys Xaa Xaa Met Ile Asp Glu Xaa Ile Xaa Xaa Leu Lys Xaa Xaa
1               5                   10                  15

Pro Xaa Pro Xaa Xaa Asp Phe Xaa Asn Leu Asn Xaa Glu Asp Xaa Xaa
            20                  25                  30

Ile Leu Met Xaa Xaa Asn Leu Arg Xaa Xaa Asn Leu Glu Ala Phe Xaa
            35                  40                  45

Arg Xaa Xaa Lys Xaa Xaa Xaa Asn Ala Ser Ala Ile Glu Xaa Xaa Leu
50                  55                  60

Xaa Xaa Leu Xaa Pro Cys Leu Pro Xaa Xaa Thr Ala Xaa Pro Xaa Arg
65                  70                  75                  80

Xaa Pro Ile Xaa Xaa Xaa Xaa Gly Asp Trp Xaa Glu Phe Xaa Xaa Lys
            85                  90                  95

Leu Xaa Phe Tyr Leu Xaa Xaa Leu Glu Xaa Xaa Xaa Xaa Gln Gln
            100                 105                 110

(2) INFORMATION FOR SEQ ID NO:7:

(i) SEQUENCE CHARACTERISTICS:
          (A) LENGTH: 133 amino acids
          (B) TYPE: amino acid
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /note= "Met- may or may not precede
              the amino acid in position 1"

(ix) FEATURE:
          (A) NAME/KEY: Modified-site
          (B) LOCATION: 18
          (D) OTHER INFORMATION: /note= "Xaa at position 18 is Asn
              or Ile"

(ix) FEATURE:
          (A) NAME/KEY: Modified-site
          (B) LOCATION: 19
          (D) OTHER INFORMATION: /note= "Xaa at position 19 is Met,
              Ala, or Ile"

(ix) FEATURE:
          (A) NAME/KEY: Modified-site
          (B) LOCATION: 20
          (D) OTHER INFORMATION: /note= "Xaa at position 20 is Ile,
```

Pro, or Leu"

(ix) FEATURE:
    (A) NAME/KEY: Modified-site
    (B) LOCATION: 23
    (D) OTHER INFORMATION: /note= "Xaa at position 23 is Ile,
        Ala, or Leu"

(ix) FEATURE:
    (A) NAME/KEY: Modified-site
    (B) LOCATION: 25
    (D) OTHER INFORMATION: /note= "Xaa at position 25 is Thr
        or His"

(ix) FEATURE:
    (A) NAME/KEY: Modified-site
    (B) LOCATION: 29
    (D) OTHER INFORMATION: /note= "Xaa at position 29 is Gln,
        Arg, Val, or Ile"

(ix) FEATURE:
    (A) NAME/KEY: Modified-site
    (B) LOCATION: 32
    (D) OTHER INFORMATION: /note= "Xaa at position 32 is Leu,
        Ala, Asn, or Arg"

(ix) FEATURE:
    (A) NAME/KEY: Modified-site
    (B) LOCATION: 34
    (D) OTHER INFORMATION: /note= "Xaa at position 34 is Leu
        or Ser"

(ix) FEATURE:
    (A) NAME/KEY: Modified-site
    (B) LOCATION: 37
    (D) OTHER INFORMATION: /note= "Xaa at position 37 is Phe,
        Pro, or Ser"

(ix) FEATURE:
    (A) NAME/KEY: Modified-site
    (B) LOCATION:; 38
    (D) OTHER INFORMATION: /note= "Xaa at position 38 is Asn
        or Ala"

(ix) FEATURE:
    (A) NAME/KEY: Modified-site
    (B) LOCATION: 42
    (D) OTHER INFORMATION: /note= "Xaa at position 42 is Gly,
        Ala, Ser, Asp, or Asn"

(ix) FEATURE:
    (A) NAME/KEY: Modified-site
    (B) LOCATION: 45
    (D) OTHER INFORMATION: /note= "Xaa at position 45 is Gln,
        Val, or Met"

(ix) FEATURE:
    (A) NAME/KEY: Modified-site
    (B) LOCATION: 46
    (D) OTHER INFORMATION: /note= "Xaa at position 46 is Asp
        or Ser"

(ix) FEATURE:
    (A) NAME/KEY: Modified-site
    (B) LOCATION: 49
    (D) OTHER INFORMATION: /note= "Xaa at position 49 is Met,
        Ile, Leu, or Asp"

(ix) FEATURE:
    (A) NAME/KEY: Modified-site
    (B) LOCATION: 50
    (D) OTHER INFORMATION: /note= "Xaa at position 50 is Glu
        or Asp"

(ix) FEATURE:
    (A) NAME/KEY: Modified-site
    (B) LOCATION: 51
    (D) OTHER INFORMATION: /note= "Xaa at position 51 is Asn,
        Arg, or Ser"

```
(ix) FEATURE:
    (A) NAME/KEY: Modified-site
    (B) LOCATION: 55
    (D) OTHER INFORMATION: /note= "Xaa at position 55 is Arg,
        Leu, or Thr"

(ix) FEATURE:
    (A) NAME/KEY: Modified-site
    (B) LOCATION: 56
    (D) OTHER INFORMATION: /note= "Xaa at position 56 is Pro
        or Ser"

(ix) FEATURE:
    (A) NAME/KEY: Modified-site
    (B) LOCATION: 59
    (D) OTHER INFORMATION: /note= "Xaa at position 59 is Glu
        or Leu"

(ix) FEATURE:
    (A) NAME/KEY: Modified-site
    (B) LOCATION: 60
    (D) OTHER INFORMATION: /note= "Xaa at position 60 is Ala
        or Ser"

(ix) FEATURE:
    (A) NAME/KEY: Modified-site
    (B) LOCATION: 62
    (D) OTHER INFORMATION: /note= "Xaa at position 62 is Asn
        Val, or Pro"

(ix) FEATURE:
    (A) NAME/KEY: Modified-site
    (B) LOCATION: 63
    (D) OTHER INFORMATION: /note= "Xaa at position 63 is Arg
        or His"

(ix) FEATURE:
    (A) NAME/KEY: Modified-site
    (B) LOCATION: 65
    (D) OTHER INFORMATION: /note= "Xaa at position 65 is Val
        or Ser"

(ix) FEATURE:
    (A) NAME/KEY: Modified-site
    (B) LOCATION: 67
    (D) OTHER INFORMATION: /note= "Xaa at position 67 is Ser,
        Asn, His, or Gln"

(ix) FEATURE:
    (A) NAME/KEY: Modified-site
    (B) LOCATION: 69
    (D) OTHER INFORMATION: /note= "Xaa at position 69 is Gln
        or Glu"

(ix) FEATURE:
    (A) NAME/KEY: Modified-site
    (B) LOCATION: 73
    (D) OTHER INFORMATION: /note= "Xaa at position 73 is Ala
        or Gly"

(ix) FEATURE:
    (A) NAME/KEY: Modified-site
    (B) LOCATION: 76
    (D) OTHER INFORMATION: /note= "Xaa at position 76 is Ser,
        Ala, or Pro"

(ix) FEATURE:
    (A) NAME/KEY: Modified-site
    (B) LOCATION: 79
    (D) OTHER INFORMATION: /note= "Xaa at position 79 is Lys,
        Arg, or Ser"

(ix) FEATURE:
    (A) NAME/KEY: Modified-site
    (B) LOCATION: 82
    (D) OTHER INFORMATION: /note= "Xaa at position 82 is Leu,
        Glu, Val, or Trp"
```

```
  (ix) FEATURE:
        (A) NAME/KEY: Modified-site
        (B) LOCATION: 85
        (D) OTHER INFORMATION: /note= "Xaa at position 85 is Leu
            or Val"

(ix) FEATURE:
        (A) NAME/KEY: Modified-site
        (B) LOCATION: 87
        (D) OTHER INFORMATION: /note= "Xaa at position 87 is Leu,
            Ser, or Tyr"

(ix) FEATURE:
        (A) NAME/KEY: Modified-site
        (B) LOCATION: 88
        (D) OTHER INFORMATION: /note= "Xaa at position 88 is Ala
            or Trp"

(ix) FEATURE:
        (A) NAME/KEY: Modified-site
        (B) LOCATION: 91
        (D) OTHER INFORMATION: /note= "Xaa at position 91 is Ala
            or Pro"

(ix) FEATURE:
        (A) NAME/KEY: Modified-site
        (B) LOCATION: 93
        (D) OTHER INFORMATION: /note= "Xaa at position 93 is Pro
            or Ser"

(ix) FEATURE:
        (A) NAME/KEY: Modified-site
        (B) LOCATION: 95
        (D) OTHER INFORMATION: /note= "Xaa at position 95 is His
            or Thr"

(ix) FEATURE:
        (A) NAME/KEY: Modified-site
        (B) LOCATION: 98
        (D) OTHER INFORMATION: /note= "Xaa at position 98 is His,
            Ile, or Thr"

(ix) FEATURE:
        (A) NAME/KEY: Modified-site
        (B) LOCATION: 100
        (D) OTHER INFORMATION: /note= "Xaa at position 100 is Lys
            or Arg"

(ix) FEATURE:
        (A) NAME/KEY: Modified-site
        (B) LOCATION: 101
        (D) OTHER INFORMATION: /note= "Xaa at position 101 is Asp,
            Ala, or Met"

(ix) FEATURE:
        (A) NAME/KEY: Modified-site
        (B) LOCATION: 105
        (D) OTHER INFORMATION: /note= "Xaa at position 105 is Asn
            or Glu"

(ix) FEATURE:
        (A) NAME/KEY: Modified-site
        (B) LOCATION: 109
        (D) OTHER INFORMATION: /note= "Xaa at position 109 is Arg,
            Glu, or Leu"

(ix) FEATURE:
        (A) NAME/KEY: Modified-site
        (B) LOCATION: 112
        (D) OTHER INFORMATION: /note= "Xaa at position 112 is Thr
            or Gln"

(ix) FEATURE:
        (A) NAME/KEY: Modified-site
        (B) LOCATION: 116
        (D) OTHER INFORMATION: /note= "Xaa at position 116 is Lys,
            Val, Trp, or Ser"

(ix) FEATURE:
```

(A) NAME/KEY: Modified-site
            (B) LOCATION: 117
            (D) OTHER INFORMATION: /note= "Xaa at position 117 is Thr
                or Ser"

(ix) FEATURE:
            (A) NAME/KEY: Modified-site
            (B) LOCATION: 120
            (D) OTHER INFORMATION: /note= "Xaa at position 120 is Asn,
                Gln, or His"

(ix) FEATURE:
            (A) NAME/KEY: Modified-site
            (B) LOCATION: 123
            (D) OTHER INFORMATION: /note= "Xaa at position 123 is Ala
                or Glu"

(xi) SEQUENCE DESCRIPTION: SEQ ID NO:7:

Ala Pro Met Thr Gln Thr Thr Ser Leu Lys Thr Ser Trp Val Asn Cys
1               5                   10                  15

Ser Xaa Xaa Xaa Asp Glu Xaa Ile Xaa His Leu Lys Xaa Pro Pro Xaa
            20                  25                  30

Pro Xaa Leu Asp Xaa Xaa Asn Leu Asn Xaa Glu Asp Xaa Xaa Ile Leu
        35                  40                  45

Xaa Xaa Xaa Asn Leu Arg Xaa Xaa Asn Leu Xaa Xaa Phe Xaa Xaa Ala
50                  55                  60

Xaa Lys Xaa Leu Xaa Asn Ala Ser Xaa Ile Glu Xaa Ile Leu Xaa Asn
65                  70                  75                  80

Leu Xaa Pro Cys Xaa Pro Xaa Xaa Thr Ala Xaa Pro Xaa Arg Xaa Pro
        85                  90                  95

Ile Xaa Ile Xaa Xaa Gly Asp Trp Xaa Glu Phe Arg Xaa Lys Leu Xaa
        100                 105                 110

Phe Tyr Leu Xaa Xaa Leu Glu Xaa Ala Gln Xaa Gln Gln Thr Thr Leu
        115                 120                 125

Ser Leu Ala Ile Phe
        130

(2) INFORMATION FOR SEQ ID NO:8:

(i) SEQUENCE CHARACTERISTICS:
            (A) LENGTH: 111 amino acids
            (B) TYPE: amino acid
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "Met- or Met-Ala may or may
                not precede the amino acid in position 1"

(ix) FEATURE:
            (A) NAME/KEY: Modified-site
            (B) LOCATION: 4
            (D) OTHER INFORMATION: /note= "Xaa at position 4 is Asn or
                Ile"

(ix) FEATURE:
            (A) NAME/KEY: Modified-site
            (B) LOCATION: 5
            (D) OTHER INFORMATION: /note= "Xaa at position 5 is Met,
                Ala, or Ile"

(ix) FEATURE:
            (A) NAME/KEY: Modified-site
            (B) LOCATION: 6
            (D) OTHER INFORMATION: /note= "Xaa at position 6 is Ile,
                Pro, or Leu"

-continued

```
(ix) FEATURE:
    (A) NAME/KEY: Modified-site
    (B) LOCATION: 9
    (D) OTHER INFORMATION: /note= "Xaa at position 9 is Ile,
        Ala, or Leu"

(ix) FEATURE:
    (A) NAME/KEY: Modified-site
    (B) LOCATION: 11
    (D) OTHER INFORMATION: /note= "Xaa at position 11 is Thr
        or His"

(ix) FEATURE:
    (A) NAME/KEY: Modified-site
    (B) LOCATION: 15
    (D) OTHER INFORMATION: /note= "Xaa at position 15 is Gln,
        Arg, Val, or Ile"

(ix) FEATURE:
    (A) NAME/KEY: Modified-site
    (B) LOCATION: 18
    (D) OTHER INFORMATION: /note= "Xaa at position 18 is Leu,
        Ala, Asn, or Arg"

(ix) FEATURE:
    (A) NAME/KEY: Modified-site
    (B) LOCATION: 20
    (D) OTHER INFORMATION: /note= "Xaa at position 20 is Leu
        or Ser"

(ix) FEATURE:
    (A) NAME/KEY: Modified-site
    (B) LOCATION: 23
    (D) OTHER INFORMATION: /note= "Xaa at position 23 is Phe,
        Pro, or Ser"

(ix) FEATURE:
    (A) NAME/KEY: Modified-site
    (B) LOCATION: 24
    (D) OTHER INFORMATION: /note= "Xaa at position 24 is Asn
        or Ala"

(ix) FEATURE:
    (A) NAME/KEY: Modified-site
    (B) LOCATION: 28
    (D) OTHER INFORMATION: /note= "Xaa at position 28 is Gly,
        Ala, Ser, Asp, or Asn"

(ix) FEATURE:
    (A) NAME/KEY: Modified-site
    (B) LOCATION: 31
    (D) OTHER INFORMATION: /note= "Xaa at position 31 is Gln,
        Val, or Met"

(ix) FEATURE:
    (A) NAME/KEY: Modified-site
    (B) LOCATION: 32
    (D) OTHER INFORMATION: /note= "Xaa at position 32 is Asp
        or Ser"

(ix) FEATURE:
    (A) NAME/KEY: Modified-site
    (B) LOCATION: 35
    (D) OTHER INFORMATION: /note= "Xaa at position 35 is Met,
        Ile, or Asp"

(ix) FEATURE:
    (A) NAME/KEY: Modified-site
    (B) LOCATION: 36
    (D) OTHER INFORMATION: /note= "Xaa at position 36 is Glu
        or Asp"

(ix) FEATURE:
    (A) NAME/KEY: Modified-site
    (B) LOCATION: 37
    (D) OTHER INFORMATION: /note= "Xaa at position 37 is Asn,
        Arg, or Ser"
```

(ix) FEATURE:
       (A) NAME/KEY: Modified-site
       (B) LOCATION: 41
       (D) OTHER INFORMATION: /note= "Xaa at position 41 is Arg,
            Leu, or Thr"

(ix) FEATURE:
       (A) NAME/KEY: Modified-site
       (B) LOCATION: 42
       (D) OTHER INFORMATION: /note= "Xaa at position 42 is Pro
            or Ser"

(ix) FEATURE:
       (A) NAME/KEY: Modified-site
       (B) LOCATION: 45
       (D) OTHER INFORMATION: /note= "Xaa at position 45 is Glu
            or Leu"

(ix) FEATURE:
       (A) NAME/KEY: Modified-site
       (B) LOCATION: 46
       (D) OTHER INFORMATION: /note= "Xaa at position 46 is Ala
            or Ser"

(ix) FEATURE:
       (A) NAME/KEY: Modified-site
       (B) LOCATION: 48
       (D) OTHER INFORMATION: /note= "Xaa at position 48 is Asn,
            Val, or Pro"

(ix) FEATURE:
       (A) NAME/KEY: Modified-site
       (B) LOCATION: 49
       (D) OTHER INFORMATION: /note= "Xaa at position 49 is Arg
            or His"

(ix) FEATURE:
       (A) NAME/KEY: Modified-site
       (B) LOCATION: 51
       (D) OTHER INFORMATION: /note= "Xaa at position 51 is Val
            or Ser"

(ix) FEATURE:
       (A) NAME/KEY: Modified-site
       (B) LOCATION: 53
       (D) OTHER INFORMATION: /note= "Xaa at position 53 is Ser,
            Asn, His, or Gln"

(ix) FEATURE:
       (A) NAME/KEY: Modified-site
       (B) LOCATION: 55
       (D) OTHER INFORMATION: /note= "Xaa at position 55 is Gln
            or Glu"

(ix) FEATURE:
       (A) NAME/KEY: Modified-site
       (B) LOCATION: 59
       (D) OTHER INFORMATION: /note= "Xaa at position 59 is Ala
            or Gly"

(ix) FEATURE:
       (A) NAME/KEY: Modified-site
       (B) LOCATION: 62
       (D) OTHER INFORMATION: /note= "Xaa at position 62 is Ser,
            Ala, or Pro"

(ix) FEATURE:
       (A) NAME/KEY: Modified-site
       (B) LOCATION: 65
       (D) OTHER INFORMATION: /note= "Xaa at position 65 is Lys,
            Arg, or Ser"

(ix) FEATURE:
       (A) NAME/KEY: Modified-site
       (B) LOCATION: 67
       (D) OTHER INFORMATION: /note= "Xaa at position 67 is Leu,
            Glu, or Val"

(ix) FEATURE:

(A) NAME/KEY: Modified-site
              (B) LOCATION: 68
              (D) OTHER INFORMATION: /note= "Xaa at position 68 is Leu,
                  Glu, Val, or Trp"

(ix) FEATURE:
              (A) NAME/KEY: Modified-site
              (B) LOCATION: 71
              (D) OTHER INFORMATION: /note= "Xaa at position 71 is Leu
                  or Val"

(ix) FEATURE:
              (A) NAME/KEY: Modified-site
              (B) LOCATION: 73
              (D) OTHER INFORMATION: /note= "Xaa at position 73 is Leu,
                  Ser, or Tyr"

(ix) FEATURE:
              (A) NAME/KEY: Modified-site
              (B) LOCATION: 74
              (D) OTHER INFORMATION: /note= "Xaa at position 74 is Ala
                  or Trp"

(ix) FEATURE:
              (A) NAME/KEY: Modified-site
              (B) LOCATION: 77
              (D) OTHER INFORMATION: /note= "Xaa at position 77 is Ala
                  or Pro"

(ix) FEATURE:
              (A) NAME/KEY: Modified-site
              (B) LOCATION: 79
              (D) OTHER INFORMATION: /note= "Xaa at position 79 is Pro
                  or Ser"

(ix) FEATURE:
              (A) NAME/KEY: Modified-site
              (B) LOCATION: 81
              (D) OTHER INFORMATION: /note= "Xaa at position 81 is His
                  or Thr"

(ix) FEATURE:
              (A) NAME/KEY: Modified-site
              (B) LOCATION: 84
              (D) OTHER INFORMATION: /note= "Xaa at position 84 is His,
                  Ile, or Thr"

(ix) FEATURE:
              (A) NAME/KEY: Modified-site
              (B) LOCATION: 86
              (D) OTHER INFORMATION: /note= "Xaa at position 86 is Lys
                  or Arg"

(ix) FEATURE:
              (A) NAME/KEY: Modified-site
              (B) LOCATION: 87
              (D) OTHER INFORMATION: /note= "Xaa at position 87 is Asp,
                  Ala, or Met"

(ix) FEATURE:
              (A) NAME/KEY: Modified-site
              (B) LOCATION: 91
              (D) OTHER INFORMATION: /note= "Xaa at position 91 is Asn
                  or Glu"

(ix) FEATURE:
              (A) NAME/KEY: Modified-site
              (B) LOCATION: 95
              (D) OTHER INFORMATION: /note= "Xaa at position 95 is Arg,
                  Glu, or Leu"

(ix) FEATURE:
              (A) NAME/KEY: Modified-site
              (B) LOCATION: 98
              (D) OTHER INFORMATION: /note= "Xaa at position 98 is Thr
                  or Gln"

(ix) FEATURE:
              (A) NAME/KEY: Modified-site (B) LOCATION: 102
        (D) OTHER INFORMATION: /note= "Xaa at position 102 is Lys,
            Val, Trp, or Ser"

(ix) FEATURE:
        (A) NAME/KEY: Modified-site
        (B) LOCATION: 103
        (D) OTHER INFORMATION: /note= "Xaa at position 103 is Thr
            or Ser"

(ix) FEATURE:
        (A) NAME/KEY: Modified-site
        (B) LOCATION: 106
        (D) OTHER INFORMATION: /note= "Xaa at position 106 is Asn,
            Gln, or His"

(ix) FEATURE:
        (A) NAME/KEY: Modified-site
        (B) LOCATION: 109
        (D) OTHER INFORMATION: /note= "Xaa at position 109 is Ala
            or Glu"

(xi) SEQUENCE DESCRIPTION: SEQ ID NO:8:

Asn Cys Ser Xaa Xaa Xaa Asp Glu Xaa Ile Xaa His Leu Lys Xaa Pro
1               5                   10                  15

Pro Xaa Pro Xaa Leu Asp Xaa Xaa Asn Leu Asn Xaa Glu Asp Xaa Xaa
            20                  25                  30

Ile Leu Xaa Xaa Xaa Asn Leu Arg Xaa Xaa Asn Leu Xaa Xaa Phe Xaa
            35                  40                  45

Xaa Ala Xaa Lys Xaa Leu Xaa Asn Ala Ser Xaa Ile Glu Xaa Ile Leu
50                  55                  60

Xaa Asn Xaa Xaa Pro Cys Xaa Pro Xaa Xaa Thr Ala Xaa Pro Xaa Arg
65                  70                  75                  80

Xaa Pro Ile Xaa Ile Xaa Xaa Gly Asp Trp Xaa Glu Phe Arg Xaa Lys
                85                  90                  95

Leu Xaa Phe Tyr Leu Xaa Xaa Leu Glu Xaa Ala Gln Xaa Gln Gln
            100                 105                 110

(2) INFORMATION FOR SEQ ID NO:9:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:9:

Asn Cys Ser Ile Met Ile Asp Glu Ile Ile His His Leu Lys Arg Pro
1               5                   10                  15

Pro Ala Pro Leu Leu Asp Pro Asn Asn Leu Asn Ala Glu Asp Val Asp
            20                  25                  30

Ile Leu Met Glu Asn Asn Leu Arg Arg Pro Asn Leu Glu Ala Phe Asn
            35                  40                  45

Arg Ala Val Lys Ser Leu Gln Asn Ala Ser Ala Ile Glu Ser Ile Leu
50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
            100                 105                 110

(2) INFORMATION FOR SEQ ID NO:10:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:10:

```
Asn Cys Ser Ile Met Ile Asp Glu Ile Ile His His Leu Lys Arg Pro
1               5                   10                  15

Pro Asn Pro Leu Leu Asp Pro Asn Asn Leu Asn Ser Glu Asp Met Asp
            20                  25                  30

Ile Leu Met Glu Asn Asn Leu Arg Arg Pro Asn Leu Glu Ala Phe Asn
            35                  40                  45

Arg Ala Val Lys Ser Leu Gln Asn Ala Ser Ala Ile Glu Ser Ile Leu
        50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
                100                 105                 110
```

(2) INFORMATION FOR SEQ ID NO:11:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:11:

```
Asn Cys Ser Ile Met Ile Asp Glu Ile Ile His His Leu Lys Val Pro
1               5                   10                  15

Pro Ala Pro Leu Leu Asp Ser Asn Asn Leu Asn Ser Glu Asp Met Asp
            20                  25                  30

Ile Leu Met Glu Asn Asn Leu Arg Arg Pro Asn Leu Glu Ala Phe Asn
            35                  40                  45

Arg Ala Val Lys Ser Leu Gln Asn Ala Ser Ala Ile Glu Ser Ile Leu
        50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
                100                 105                 110
```

(2) INFORMATION FOR SEQ ID NO:12:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:12:

```
Asn Cys Ser Asn Met Ile Asp Glu Ile Ile Thr His Leu Lys Gln Pro
1               5                   10                  15
```

Pro Leu Pro Leu Leu Asp Phe Asn Asn Leu Asn Gly Glu Asp Gln Asp
            20                  25                  30

Ile Leu Met Glu Arg Asn Leu Arg Leu Pro Asn Leu Leu Ala Phe Val
            35                  40                  45

Arg Ala Val Lys Asn Leu Glu Asn Ala Ser Ala Ile Glu Ser Ile Leu
 50                  55                  60

Lys Asn Leu Leu Pro Cys Leu Pro Leu Ala Thr Ala Ala Pro Thr Arg
 65                  70                  75                  80

His Pro Ile His Ile Lys Asp Gly Asp Trp Asn Glu Phe Arg Arg Lys
                 85                  90                  95

Leu Thr Phe Tyr Leu Lys Thr Leu Glu Asn Ala Gln Ala Gln Gln
                100                 105                 110

(2) INFORMATION FOR SEQ ID NO:13:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:13:

Asn Cys Ser Asn Met Ile Asp Glu Ile Ile Thr His Leu Lys Gln Pro
 1                   5                  10                  15

Pro Leu Pro Leu Leu Asp Phe Asn Asn Leu Asn Gly Glu Asp Gln Asp
            20                  25                  30

Ile Leu Met Glu Arg Asn Leu Arg Leu Pro Asn Leu Glu Ser Phe Val
            35                  40                  45

Arg Ala Val Lys Asn Leu Glu Asn Ala Ser Ala Ile Glu Ser Ile Leu
 50                  55                  60

Lys Asn Leu Leu Pro Cys Leu Pro Leu Ala Thr Ala Ala Pro Thr Arg
 65                  70                  75                  80

His Pro Ile His Ile Lys Asp Gly Asp Trp Asn Glu Phe Arg Arg Lys
                 85                  90                  95

Leu Thr Phe Tyr Leu Lys Thr Leu Glu Asn Ala Gln Ala Gln Gln
                100                 105                 110

(2) INFORMATION FOR SEQ ID NO:14:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:14:

Asn Cys Ser Asn Met Ile Asp Glu Ile Ile Thr His Leu Lys Gln Pro
 1                   5                  10                  15

Pro Leu Pro Leu Leu Asp Phe Asn Asn Leu Asn Gly Glu Asp Gln Asp
            20                  25                  30

Ile Leu Met Glu Arg Asn Leu Arg Thr Pro Asn Leu Leu Ala Phe Val
            35                  40                  45

Arg Ala Val Lys His Leu Glu Asn Ala Ser Ala Ile Glu Ser Ile Leu
 50                  55                  60

Lys Asn Leu Leu Pro Cys Leu Pro Leu Ala Thr Ala Ala Pro Thr Arg
 65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
                100                 105                 110

(2) INFORMATION FOR SEQ ID NO:15:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:15:

Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
                20                  25                  30

Ile Leu Met Glu Asn Asn Leu Arg Arg Pro Asn Leu Glu Ala Phe Asn
                35                  40                  45

Arg Ala Val Lys Ser Leu Gln Asn Ala Ser Gly Ile Glu Ala Ile Leu
        50                  55                  60

Arg Asn Leu Gln Pro Cys Leu Pro Ser Ala Thr Ala Ala Pro Ser Arg
65                  70                  75                  80

His Pro Ile Ile Ile Lys Ala Gly Asp Trp Gln Glu Phe Arg Arg Lys
                85                  90                  95

Leu Thr Phe Tyr Leu Lys Thr Leu Glu Asn Ala Gln Ala Gln Gln
                100                 105                 110

(2) INFORMATION FOR SEQ ID NO:16:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:16:

Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
                20                  25                  30

Ile Leu Met Glu Asn Asn Leu Arg Arg Pro Asn Leu Glu Ala Phe Asn
                35                  40                  45

Arg Ala Val Lys Ser Leu Gln Asn Ala Ser Gly Ile Glu Ala Ile Leu
        50                  55                  60

Arg Asn Leu Val Pro Cys Leu Pro Ser Ala Thr Ala Ala Pro Ser Arg
65                  70                  75                  80

His Pro Ile Thr Ile Lys Ala Gly Asp Trp Gln Glu Phe Arg Arg Lys
                85                  90                  95

Leu Thr Phe Tyr Leu Lys Thr Leu Glu Asn Ala Gln Ala Gln Gln
                100                 105                 110

(2) INFORMATION FOR SEQ ID NO:17:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:17:

```
Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

Ile Leu Met Glu Asn Asn Leu Arg Arg Pro Asn Leu Glu Ala Phe Asn
            35                  40                  45

Arg Ala Val Lys Ser Leu Gln Asn Ala Ser Ala Ile Glu Ser Ile Leu
        50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Glu Lys
                85                  90                  95

Leu Thr Phe Tyr Leu Val Thr Leu Glu Gln Ala Gln Glu Gln Gln
                100                 105                 110
```

(2) INFORMATION FOR SEQ ID NO:18:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:18:

```
Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

Ile Leu Met Glu Asn Asn Leu Arg Arg Pro Asn Leu Glu Ala Phe Asn
            35                  40                  45

Arg Ala Val Lys Ser Leu Gln Asn Ala Ser Ala Ile Glu Ser Ile Leu
        50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Glu Lys
                85                  90                  95

Leu Thr Phe Tyr Leu Val Ser Leu Glu His Ala Gln Glu Gln Gln
                100                 105                 110
```

(2) INFORMATION FOR SEQ ID NO:19:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:19:

```
Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

Ile Leu Met Glu Asn Asn Leu Arg Arg Pro Asn Leu Glu Ala Phe Asn
            35                  40                  45
```

```
Arg Ala Val Lys Ser Leu Gln Asn Ala Ser Gly Ile Glu Ala Ile Leu
    50                  55                  60

Arg Asn Leu Gln Pro Cys Leu Pro Ser Ala Thr Ala Ala Pro Ser Arg
65                  70                  75                  80

His Pro Ile Ile Ile Lys Ala Gly Asp Trp Gln Glu Phe Arg Glu Lys
                85                  90                  95

Leu Thr Phe Tyr Leu Val Thr Leu Glu Gln Ala Gln Glu Gln Gln
                100                 105                 110
```

(2) INFORMATION FOR SEQ ID NO:20:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:20:

```
Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
                20                  25                  30

Ile Leu Met Glu Asn Asn Leu Arg Arg Pro Asn Leu Glu Ala Phe Asn
                35                  40                  45

Arg Ala Val Lys Ser Leu Gln Asn Ala Ser Gly Ile Glu Ala Ile Leu
    50                  55                  60

Arg Asn Leu Val Pro Cys Leu Pro Ser Ala Thr Ala Ala Pro Ser Arg
65                  70                  75                  80

His Pro Ile Thr Ile Lys Ala Gly Asp Trp Gln Glu Phe Arg Glu Lys
                85                  90                  95

Leu Thr Phe Tyr Leu Val Thr Leu Glu Gln Ala Gln Glu Gln Gln
                100                 105                 110
```

(2) INFORMATION FOR SEQ ID NO:21:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:21:

```
Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
                20                  25                  30

Ile Leu Met Glu Asn Asn Leu Arg Arg Pro Asn Leu Glu Ala Phe Asn
                35                  40                  45

Arg Ala Val Lys Ser Leu Gln Asn Ala Ser Gly Ile Glu Ala Ile Leu
    50                  55                  60

Arg Asn Leu Val Pro Cys Leu Pro Ser Ala Thr Ala Ala Pro Ser Arg
65                  70                  75                  80

His Pro Ile Thr Ile Lys Ala Gly Asp Trp Gln Glu Phe Arg Glu Lys
                85                  90                  95

Leu Thr Phe Tyr Leu Val Ser Leu Glu His Ala Gln Glu Gln Gln
                100                 105                 110
```

(2) INFORMATION FOR SEQ ID NO:22:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:22:

Asn Cys Ser Ile Met Ile Asp Glu Ile Ile His His Leu Lys Arg Pro
1               5                   10                  15

Pro Ala Pro Leu Leu Asp Pro Asn Asn Leu Asn Ala Glu Asp Val Asp
            20                  25                  30

Ile Leu Met Glu Arg Asn Leu Arg Leu Pro Asn Leu Glu Ser Phe Val
        35                  40                  45

Arg Ala Val Lys Asn Leu Glu Asn Ala Ser Ala Ile Glu Ser Ile Leu
    50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
            100                 105                 110

(2) INFORMATION FOR SEQ ID NO:23:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:23:

Asn Cys Ser Ile Met Ile Asp Glu Ile Ile His His Leu Lys Arg Pro
1               5                   10                  15

Pro Asn Pro Leu Leu Asp Pro Asn Asn Leu Asn Ser Glu Asp Met Asp
            20                  25                  30

Ile Leu Met Glu Arg Asn Leu Arg Thr Pro Asn Leu Leu Ala Phe Val
        35                  40                  45

Arg Ala Val Lys His Leu Glu Asn Ala Ser Ala Ile Glu Ser Ile Leu
    50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
            100                 105                 110

(2) INFORMATION FOR SEQ ID NO:24:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:24:

Asn Cys Ser Ile Met Ile Asp Glu Ile Ile His His Leu Lys Val Pro

-continued

```
1               5                    10                   15
Pro Ala Pro Leu Leu Asp Ser Asn Asn Leu Asn Ser Glu Asp Met Asp
                20                  25                  30

Ile Leu Met Glu Arg Asn Leu Arg Leu Pro Asn Leu Leu Ala Phe Val
            35                  40                  45

Arg Ala Val Lys Asn Leu Glu Asn Ala Ser Ala Ile Glu Ser Ile Leu
50                      55                  60

Lys Asn Leu Leu Pro Cys Leu Pro Leu Ala Thr Ala Ala Pro Thr Arg
65                      70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
                100                 105                 110
```

(2) INFORMATION FOR SEQ ID NO:25:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:25:

```
Met Ala Asn Cys Ser Asn Met Ile Asp Glu Ile Ile Thr His Leu Lys
1               5                   10                  15

Gln Pro Pro Leu Pro Leu Leu Asp Phe Asn Asn Leu Asn Gly Glu Asp
                20                  25                  30

Gln Asp Ile Leu Met Glu Asn Asn Leu Arg Arg Pro Asn Leu Glu Ala
            35                  40                  45

Phe Asn Arg Ala Val Lys Ser Leu Gln Asn Ala Ser Gly Ile Glu Ala
50                  55                      60

Ile Leu Arg Asn Leu Gln Pro Cys Leu Pro Ser Ala Thr Ala Ala Pro
65                  70                  75                      80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln
```

(2) INFORMATION FOR SEQ ID NO:26:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:26:

```
Met Ala Asn Cys Ser Asn Met Ile Asp Glu Ile Ile Thr His Leu Lys
1               5                   10                  15

Gln Pro Pro Leu Pro Leu Leu Asp Phe Asn Asn Leu Asn Gly Glu Asp
                20                  25                  30

Gln Asp Ile Leu Met Glu Asn Asn Leu Arg Arg Pro Asn Leu Glu Ala
            35                  40                  45

Phe Asn Arg Ala Val Lys Ser Leu Gln Asn Ala Ser Gly Ile Glu Ala
50                  55                      60
```

-continued

```
Ile Leu Arg Asn Leu Val Pro Cys Leu Pro Ser Ala Thr Ala Ala Pro
 65                  70                  75                  80

Ser Arg His Pro Ile Thr Ile Lys Ala Gly Asp Trp Gln Glu Phe Arg
                 85                  90                  95

Glu Lys Leu Thr Phe Tyr Leu Val Thr Leu Glu Gln Ala Gln Glu Gln
                100                 105                 110

Gln
```

(2) INFORMATION FOR SEQ ID NO:27:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:27:

```
Met Ala Asn Cys Ser Asn Met Ile Asp Glu Ile Ile Thr His Leu Lys
 1               5                  10                  15

Gln Pro Pro Leu Pro Leu Leu Asp Phe Asn Asn Leu Asn Gly Glu Asp
                 20                  25                  30

Gln Asp Ile Leu Met Glu Asn Asn Leu Arg Arg Pro Asn Leu Glu Ala
                 35                  40                  45

Phe Asn Arg Ala Val Lys Ser Leu Gln Asn Ala Ser Gly Ile Glu Ala
 50                  55                  60

Ile Leu Arg Asn Leu Val Pro Cys Leu Pro Ser Ala Thr Ala Ala Pro
 65                  70                  75                  80

Ser Arg His Pro Ile Thr Ile Lys Ala Gly Asp Trp Gln Glu Phe Arg
                 85                  90                  95

Glu Lys Leu Thr Phe Tyr Leu Val Ser Leu Glu His Ala Gln Glu Gln
                100                 105                 110

Gln
```

(2) INFORMATION FOR SEQ ID NO:28:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:28:

```
Met Ala Asn Cys Ser Ile Met Ile Asp Glu Ile Ile His His Leu Lys
 1               5                  10                  15

Arg Pro Pro Ala Pro Leu Leu Asp Pro Asn Asn Leu Asn Ala Glu Asp
                 20                  25                  30

Val Asp Ile Leu Met Glu Arg Asn Leu Arg Leu Pro Asn Leu Glu Ser
                 35                  40                  45

Phe Val Arg Ala Val Lys Asn Leu Glu Asn Ala Ser Ala Ile Glu Ser
 50                  55                  60

Ile Leu Lys Asn Leu Leu Pro Cys Leu Pro Leu Ala Thr Ala Ala Pro
 65                  70                  75                  80

Thr Arg His Pro Ile His Ile Lys Asp Gly Asp Trp Asn Glu Phe Arg
                 85                  90                  95

Arg Lys Leu Thr Phe Tyr Leu Lys Thr Leu Glu Asn Ala Gln Ala Gln
                100                 105                 110
```

Gln (2) INFORMATION FOR SEQ ID NO:29:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:29:

```
Met Ala Asn Cys Ser Ile Met Ile Asp Glu Ile Ile His His Leu Lys
 1               5                  10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
        35                  40                  45

Phe Val Arg Ala Val Lys His Leu Glu Asn Ala Ser Ala Ile Glu Ser
    50                  55                  60

Ile Leu Lys Asn Leu Leu Pro Cys Leu Pro Leu Ala Thr Ala Ala Pro
65                  70                  75                  80

Thr Arg His Pro Ile His Ile Lys Asp Gly Asp Trp Asn Glu Phe Arg
                85                  90                  95

Arg Lys Leu Thr Phe Tyr Leu Lys Thr Leu Glu Asn Ala Gln Ala Gln
            100                 105                 110

Gln
```

(2) INFORMATION FOR SEQ ID NO:30:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:30:

```
Met Ala Asn Cys Ser Ile Met Ile Asp Glu Ile Ile His His Leu Lys
 1               5                  10                  15

Val Pro Pro Ala Pro Leu Leu Asp Ser Asn Asn Leu Asn Ser Glu Asp
            20                  25                  30

Met Asp Ile Leu Met Glu Arg Asn Leu Arg Leu Pro Asn Leu Leu Ala
        35                  40                  45

Phe Val Arg Ala Val Lys Asn Leu Glu Asn Ala Ser Ala Ile Glu Ser
    50                  55                  60

Ile Leu Lys Asn Leu Leu Pro Cys Leu Pro Leu Ala Thr Ala Ala Pro
65                  70                  75                  80

Thr Arg His Pro Ile His Ile Lys Asp Gly Asp Trp Asn Glu Phe Arg
                85                  90                  95

Arg Lys Leu Thr Phe Tyr Leu Lys Thr Leu Glu Asn Ala Gln Ala Gln
            100                 105                 110

Gln
```

(2) INFORMATION FOR SEQ ID NO:31:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:31:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
            20                  25                  30

Val Asp Ile Leu Met Glu Arg Asn Leu Arg Leu Pro Asn Leu Glu Ser
        35                  40                  45

Phe Val Arg Ala Val Lys Asn Leu Glu Asn Ala Ser Gly Ile Glu Ala
50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln (2) INFORMATION FOR SEQ ID NO:32:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:32:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
        35                  40                  45

Phe Val Arg Ala Val Lys His Leu Glu Asn Ala Ser Gly Ile Glu Ala
50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln (2) INFORMATION FOR SEQ ID NO:33:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:33:

Met Ala Asn Cys Ser Ile Met Ile Asp Glu Ile Ile His His Leu Lys
1               5                   10                  15

Val Pro Pro Ala Pro Leu Leu Asp Ser Asn Asn Leu Asn Ser Glu Asp 20                  25                  30

Met Asp Ile Leu Met Glu Arg Asn Leu Arg Leu Pro Asn Leu Leu Ala
            35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln (2) INFORMATION FOR SEQ ID NO:34:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:34:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
                20                  25                  30

Val Asp Ile Leu Met Glu Arg Asn Leu Arg Leu Pro Asn Leu Glu Ser
            35                  40                  45

Phe Val Arg Ala Val Lys Asn Leu Glu Asn Ala Ser Gly Ile Glu Ala
    50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln (2) INFORMATION FOR SEQ ID NO:35:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:35:

Met Ala Asn Cys Ser Ile Met Ile Asp Glu Ile Ile His His Leu Lys
1               5                   10                  15

Val Pro Pro Ala Pro Leu Leu Asp Ser Asn Asn Leu Asn Ser Glu Asp
                20                  25                  30

Met Asp Ile Leu Met Glu Arg Asn Leu Arg Leu Pro Asn Leu Leu Ala
            35                  40                  45

Phe Val Arg Ala Val Lys Asn Leu Glu Asn Ala Ser Gly Ile Glu Ala
    50                  55                  60

Ile Leu Arg Asn Leu Val Pro Cys Leu Pro Ser Ala Thr Ala Ala Pro

-continued

```
65                  70                  75                  80
Ser Arg His Pro Ile Thr Ile Lys Ala Gly Asp Trp Gln Glu Phe Arg
                85                  90                  95
Glu Lys Leu Thr Phe Tyr Leu Val Thr Leu Glu Gln Ala Gln Glu Gln
            100                 105                 110
Gln
```

(2) INFORMATION FOR SEQ ID NO:36:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:36:

```
Met Ala Asn Cys Ser Ile Met Ile Asp Glu Ile Ile His His Leu Lys
1               5                   10                  15
Arg Pro Asn Pro Leu Leu Asp Pro Asn Asn Leu Asn Ser Glu Asp
                20                  25                  30
Met Asp Ile Leu Met Glu Arg Asn Leu Arg Thr Pro Asn Leu Leu Ala
            35                  40                  45
Phe Val Arg Ala Val Lys His Leu Glu Asn Ala Ser Gly Ile Glu Ala
        50                  55                  60
Ile Leu Arg Asn Leu Val Pro Cys Leu Pro Ser Ala Thr Ala Ala Pro
65                  70                  75                  80
Ser Arg His Pro Ile Thr Ile Lys Ala Gly Asp Trp Gln Glu Phe Arg
                85                  90                  95
Glu Lys Leu Thr Phe Tyr Leu Val Ser Leu Glu His Ala Gln Glu Gln
            100                 105                 110
Gln
```

(2) INFORMATION FOR SEQ ID NO:37:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:37:

```
Met Ala Asn Cys Ser Ile Met Ile Asp Glu Ile Ile His His Leu Lys
1               5                   10                  15
Val Pro Pro Ala Pro Leu Leu Asp Ser Asn Asn Leu Asn Ser Glu Asp
                20                  25                  30
Met Asp Ile Leu Met Glu Arg Asn Leu Arg Leu Pro Asn Leu Leu Ala
            35                  40                  45
Phe Val Arg Ala Val Lys Asn Leu Glu Asn Ala Ser Gly Ile Glu Ala
        50                  55                  60
Ile Leu Arg Asn Leu Val Pro Cys Leu Pro Ser Ala Thr Ala Ala Pro
65                  70                  75                  80
Ser Arg His Pro Ile Thr Ile Lys Ala Gly Asp Trp Gln Glu Phe Arg
                85                  90                  95
Glu Lys Leu Thr Phe Tyr Leu Val Ser Leu Glu His Ala Gln Glu Gln
            100                 105                 110
Gln
```

(2) INFORMATION FOR SEQ ID NO:38:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:38:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
        35                  40                  45

Phe Val Arg Ala Val Lys His Leu Glu Asn Ala Ser Gly Ile Glu Ala
    50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:39:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:39:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
            20                  25                  30

Val Asp Ile Leu Met Glu Arg Asn Leu Arg Leu Pro Asn Leu Glu Ser
        35                  40                  45

Phe Val Arg Ala Val Lys Asn Leu Glu Asn Ala Ser Gly Ile Glu Ala
    50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Ser Leu Glu His Ala Gln Glu Gln
            100                 105                 110

Gln
```

(2) INFORMATION FOR SEQ ID NO:40:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:40:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
                20                  25                  30

Val Asp Ile Leu Met Asp Arg Asn Leu Arg Leu Ser Asn Leu Glu Ser
            35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln
```

(2) INFORMATION FOR SEQ ID NO:41:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:41:

```
Met Ala Asn Cys Ser Ile Met Ile Asp Glu Ala Ile His His Leu Lys
1               5                   10                  15

Arg Pro Pro Ala Pro Ser Leu Asp Pro Asn Asn Leu Asn Asp Glu Asp
                20                  25                  30

Met Ser Ile Leu Met Glu Arg Asn Leu Arg Leu Pro Asn Leu Glu Ser
            35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln
```

(2) INFORMATION FOR SEQ ID NO:42:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:42:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
                20                  25                  30
```

```
Met Ser Ile Leu Met Glu Arg Asn Leu Arg Leu Pro Asn Leu Glu Ser
            35                  40                  45
Phe Val Arg Ala Val Lys Asn Leu Glu Asn Ala Ser Gly Ile Glu Ala
        50                  55                  60
Ile Leu Arg Asn Leu Gln Pro Cys Leu Pro Ser Ala Thr Ala Ala Pro
 65                  70                  75                  80
Ser Arg His Pro Ile Ile Ile Lys Ala Gly Asp Trp Gln Glu Phe Arg
                    85                  90                  95
Glu Lys Leu Thr Phe Tyr Leu Val Thr Leu Glu Gln Ala Gln Glu Gln
                100                 105                 110
Gln
```

(2) INFORMATION FOR SEQ ID NO:43:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:43:

```
Met Ala Asn Cys Ser Ile Met Ile Asp Glu Ile Ile His His Leu Lys
  1               5                  10                  15
Arg Pro Pro Ala Pro Leu Leu Asp Pro Asn Asn Leu Asn Ala Glu Asp
                20                  25                  30
Val Asp Ile Leu Met Asp Arg Asn Leu Arg Leu Pro Asn Leu Glu Ser
            35                  40                  45
Phe Val Arg Ala Val Lys Asn Leu Glu Asn Ala Ser Gly Ile Glu Ala
        50                  55                  60
Ile Leu Arg Asn Leu Gln Pro Cys Leu Pro Ser Ala Thr Ala Ala Pro
 65                  70                  75                  80
Ser Arg His Pro Ile Ile Ile Lys Ala Gly Asp Trp Gln Glu Phe Arg
                    85                  90                  95
Glu Lys Leu Thr Phe Tyr Leu Val Thr Leu Glu Gln Ala Gln Glu Gln
                100                 105                 110
Gln
```

(2) INFORMATION FOR SEQ ID NO:44:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:44:

```
Met Ala Asn Cys Ser Ile Met Ile Asp Glu Ile Ile His His Leu Lys
  1               5                  10                  15
Arg Pro Pro Ala Pro Leu Leu Asp Pro Asn Asn Leu Asn Asp Glu Asp
                20                  25                  30
Val Ser Ile Leu Met Glu Arg Asn Leu Arg Leu Pro Asn Leu Glu Ser
            35                  40                  45
Phe Val Arg Ala Val Lys Asn Leu Glu Asn Ala Ser Gly Ile Glu Ala
        50                  55                  60
Ile Leu Arg Asn Leu Gln Pro Cys Leu Pro Ser Ala Thr Ala Ala Pro
 65                  70                  75                  80
```

-continued

```
Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:45:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:45:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
                20                  25                  30

Met Ser Ile Leu Met Glu Arg Asn Leu Arg Leu Pro Asn Leu Glu Ser
            35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:46:

(i) SEQUENCE CHARACTERISTICS:
        (A) LENGTH: 125 amino acids
        (B) TYPE: amino acid
        (D) TOPOLOGY: linear (ii) MOLECULE TYPE: peptide (xi) SEQUENCE DESCRIPTION: SEQ ID NO:46:

```
Met Ala Tyr Pro Glu Thr Asp Tyr Lys Asp Asp Asp Lys Asn Cys
1               5                   10                  15

Ser Ile Met Ile Asp Glu Ile Ile His His Leu Lys Arg Pro Pro Ala
                20                  25                  30

Pro Leu Leu Asp Pro Asn Asn Leu Asn Ala Glu Asp Val Asp Ile Leu
            35                  40                  45

Met Glu Arg Asn Leu Arg Leu Pro Asn Leu Glu Ser Phe Val Arg Ala
    50                  55                  60

Val Lys Asn Leu Glu Asn Ala Ser Gly Ile Glu Ala Ile Leu Arg Asn
65                  70                  75                  80

Leu Gln Pro Cys Leu Pro Ser Ala Thr Ala Ala Pro Ser Arg His Pro
                85                  90                  95

Ile Ile Ile Lys Ala Gly Asp Trp Gln Glu Phe Arg Glu Lys Leu Thr
            100                 105                 110

Phe Tyr Leu Val Thr Leu Glu Gln Ala Gln Glu Gln Gln
    115                 120                 125
```

(2) INFORMATION FOR SEQ ID NO:47:

(i) SEQUENCE CHARACTERISTICS:
        (A) LENGTH: 125 amino acids
        (B) TYPE: amino acid
        (D) TOPOLOGY: linear (ii) MOLECULE TYPE: peptide (xi) SEQUENCE DESCRIPTION: SEQ ID NO:47:

```
Met Ala Tyr Pro Glu Thr Asp Tyr Lys Asp Asp Asp Lys Asn Cys
1               5                   10                  15

Ser Ile Met Ile Asp Glu Ile Ile His His Leu Lys Arg Pro Pro Asn
            20                  25                  30

Pro Leu Leu Asp Pro Asn Asn Leu Asn Ser Glu Asp Met Asp Ile Leu
                35                  40                  45

Met Glu Arg Asn Leu Arg Thr Pro Asn Leu Leu Ala Phe Val Arg Ala
        50                  55                  60

Val Lys His Leu Glu Asn Ala Ser Gly Ile Glu Ala Ile Leu Arg Asn
65                  70                  75                  80

Leu Gln Pro Cys Leu Pro Ser Ala Thr Ala Ala Pro Ser Arg His Pro
                85                  90                  95

Ile Ile Ile Lys Ala Gly Asp Trp Gln Glu Phe Arg Glu Lys Leu Thr
            100                 105                 110

Phe Tyr Leu Val Thr Leu Glu Gln Ala Gln Glu Gln Gln
        115                 120                 125
```

(2) INFORMATION FOR SEQ ID NO:48:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:48:

```
Met Ala Asn Cys Ser Ile Met Ile Asp Glu Leu Ile His His Leu Lys
1               5                   10                  15

Ile Pro Pro Asn Pro Ser Leu Asp Ser Ala Asn Leu Asn Ser Glu Asp
            20                  25                  30

Val Ser Ile Leu Met Glu Arg Asn Leu Arg Thr Pro Asn Leu Leu Ala
        35                  40                  45

Phe Val Arg Ala Val Lys His Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:49:

(i) SEQUENCE CHARACTERISTICS:
        (A) LENGTH: 134 amino acids
        (B) TYPE: amino acid
        (D) TOPOLOGY: linear (ii) MOLECULE TYPE: peptide (xi) SEQUENCE DESCRIPTION: SEQ ID NO:49:

```
Met Ala Pro Met Thr Gln Thr Thr Ser Leu Lys Thr Ser Trp Val Asn
1               5                   10                  15

Cys Ser Asn Met Ile Asp Glu Ile Ile Thr His Leu Lys Gln Pro Pro
            20                  25                  30

Leu Pro Leu Leu Asp Phe Asn Asn Leu Asn Gly Glu Asp Gln Asp Ile
            35                  40                  45

Leu Met Glu Asn Asn Leu Arg Arg Pro Asn Leu Glu Ala Phe Asn Arg
    50                  55                  60

Ala Val Lys Ser Leu Gln Asn Ala Ser Ala Ile Glu Ser Ile Leu Lys
65                  70                  75                  80

Asn Leu Leu Pro Cys Leu Pro Leu Ala Thr Ala Ala Pro Thr Arg His
                85                  90                  95

Pro Ile His Ile Lys Asp Gly Asp Trp Asn Glu Phe Arg Arg Lys Leu
            100                 105                 110

Thr Phe Tyr Leu Lys Thr Leu Glu Asn Ala Gln Ala Gln Gln Thr Thr
            115                 120                 125

Leu Ser Leu Ala Ile Phe
    130
```

(2) INFORMATION FOR SEQ ID NO:50:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:50:

CATGGCAAGA TCTCCGGCCA GAATGGAGCT GACTGA                          36

(2) INFORMATION FOR SEQ ID NO:51:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:51:

AATAGCTGAA TTCTTACCCT TCCTGAGACA GATT                            34

(2) INFORMATION FOR SEQ ID NO:52:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:52:

ACGTCCATGG CNTCNCCNGC NCCNCCTGCT TGTGACCTCC GAGTC                45

(2) INFORMATION FOR SEQ ID NO:53:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:53:

| | |
|---|---|
| TGACAAGCTT ACCTGACGCA GAGGGTGGAC CCT | 33 |

(2) INFORMATION FOR SEQ ID NO:54:

(i) SEQUENCE CHARACTERISTICS:
        (A) LENGTH: 465 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:54:

| | |
|---|---|
| ATGGCGTCTC CGGCGCCGCC TGCTTGTGAC CTCCGAGTCC TCAGTAAACT GCTTCGTGAC | 60 |
| TCCCATGTCC TTCACAGCAG ACTGAGCCAG TGCCCAGAGG TTCACCCTTT GCCTACACCT | 120 |
| GTCCTGCTGC CTGCTGTGGA CTTTAGCTTG GGAGAATGGA AAACCCAGAT GGAGGAGACC | 180 |
| AAGGCACAGG ACATTCTGGG AGCAGTGACC CTTCTGCTGG AGGGAGTGAT GGCAGCACGG | 240 |
| GGACAACTGG GACCCACTTG CCTCTCATCC CTCCTGGGGC AGCTTTCTGG ACAGGTCCGT | 300 |
| CTCCTCCTTG GGGCCCTGCA GAGCCTCCTT GGAACCCAGC TTCCTCCACA GGGCAGGACC | 360 |
| ACAGCTCACA AGGATCCCAA TGCCATCTTC CTGAGCTTCC AACACCTGCT CCGAGGAAAG | 420 |
| GTGCGTTTCC TGATGCTTGT AGGAGGGTCC ACCCTCTGCG TCAGG | 465 |

(2) INFORMATION FOR SEQ ID NO:55:

(i) SEQUENCE CHARACTERISTICS:
        (A) LENGTH: 353 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:55:

```
Met Glu Leu Thr Glu Leu Leu Val Val Met Leu Leu Thr Ala
1               5                   10                  15

Arg Leu Thr Leu Ser Ser Pro Ala Pro Pro Ala Cys Asp Leu Arg Val
            20                  25                  30

Leu Ser Lys Leu Leu Arg Asp Ser His Val Leu His Ser Arg Leu Ser
        35                  40                  45

Gln Cys Pro Glu Val His Pro Leu Pro Thr Pro Val Leu Leu Pro Ala
    50                  55                  60

Val Asp Phe Ser Leu Gly Glu Trp Lys Thr Gln Met Glu Glu Thr Lys
65                  70                  75                  80

Ala Gln Asp Ile Leu Gly Ala Val Thr Leu Leu Leu Glu Gly Val Met
                85                  90                  95

Ala Ala Arg Gly Gln Leu Gly Pro Thr Cys Leu Ser Ser Leu Leu Gly
            100                 105                 110
```

-continued

```
Gln Leu Ser Gly Gln Val Arg Leu Leu Gly Ala Leu Gln Ser Leu
        115                 120                 125
Leu Gly Thr Gln Leu Pro Pro Gln Gly Arg Thr Thr Ala His Lys Asp
130                 135                 140
Pro Asn Ala Ile Phe Leu Ser Phe Gln His Leu Leu Arg Gly Lys Val
145                 150                 155                 160
Arg Phe Leu Met Leu Val Gly Gly Ser Thr Leu Cys Val Arg Arg Ala
                165                 170                 175
Pro Pro Thr Thr Ala Val Pro Ser Arg Thr Ser Leu Val Leu Thr Leu
                180                 185                 190
Asn Glu Leu Pro Asn Arg Thr Ser Gly Leu Leu Glu Thr Asn Phe Thr
                195                 200                 205
Ala Ser Ala Arg Thr Thr Gly Ser Gly Leu Leu Lys Trp Gln Gln Gly
                210                 215                 220
Phe Arg Ala Lys Ile Pro Gly Leu Leu Asn Gln Thr Ser Arg Ser Leu
225                 230                 235                 240
Asp Gln Ile Pro Gly Tyr Leu Asn Arg Ile His Glu Leu Leu Asn Gly
                245                 250                 255
Thr Arg Gly Leu Phe Pro Gly Pro Ser Arg Arg Thr Leu Gly Ala Pro
                260                 265                 270
Asp Ile Ser Ser Gly Thr Ser Asp Thr Gly Ser Leu Pro Pro Asn Leu
                275                 280                 285
Gln Pro Gly Tyr Ser Pro Ser Pro Thr His Pro Pro Thr Gly Gln Tyr
                290                 295                 300
Thr Leu Phe Pro Leu Pro Pro Thr Leu Pro Thr Pro Val Val Gln Leu
305                 310                 315                 320
His Pro Leu Leu Pro Asp Pro Ser Ala Pro Thr Pro Thr Pro Thr Ser
                325                 330                 335
Pro Leu Leu Asn Thr Ser Tyr Thr His Ser Gln Asn Leu Ser Gln Glu
                340                 345                 350
Gly
```

(2) INFORMATION FOR SEQ ID NO:56:

(i) SEQUENCE CHARACTERISTICS:
        (A) LENGTH: 174 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:56:

```
Met Glu Leu Thr Glu Leu Leu Val Val Met Leu Leu Leu Thr Ala
1               5                   10                  15
Arg Leu Thr Leu Ser Ser Pro Ala Pro Ala Cys Asp Leu Arg Val
                20                  25                  30
Leu Ser Lys Leu Leu Arg Asp Ser His Val Leu His Ser Arg Leu Ser
            35                  40                  45
Gln Cys Pro Glu Val His Pro Leu Pro Thr Pro Val Leu Leu Pro Ala
50                  55                  60
Val Asp Phe Ser Leu Gly Glu Trp Lys Thr Gln Met Glu Glu Thr Lys
65                  70                  75                  80
Ala Gln Asp Ile Leu Gly Ala Val Thr Leu Leu Leu Glu Gly Val Met
                85                  90                  95
```

```
Ala Ala Arg Gly Gln Leu Gly Pro Thr Cys Leu Ser Ser Leu Leu Gly
            100                 105                 110

Gln Leu Ser Gly Gln Val Arg Leu Leu Leu Gly Ala Leu Gln Ser Leu
        115                 120                 125

Leu Gly Thr Gln Leu Pro Pro Gln Gly Arg Thr Thr Ala His Lys Asp
    130                 135                 140

Pro Asn Ala Ile Phe Leu Ser Phe Gln His Leu Leu Arg Gly Lys Val
145                 150                 155                 160

Arg Phe Leu Met Leu Val Gly Gly Ser Thr Leu Cys Val Arg
                165                 170
```

(2) INFORMATION FOR SEQ ID NO:57:

(i) SEQUENCE CHARACTERISTICS:
        (A) LENGTH: 1059 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:57:

```
ATGGAGCTGA CTGAATTGCT CCTCGTGGTC ATGCTTCTCC TAACTGCAAG GCTAACGCTG      60

TCCAGCCCGG CTCCTCCTGC TTGTGACCTC CGAGTCCTCA GTAAACTGCT TCGTGACTCC     120

CATGTCCTTC ACAGCAGACT GAGCCAGTGC CCAGAGGTTC ACCCTTTGCC TACACCTGTC     180

CTGCTGCCTG CTGTGGACTT TAGCTTGGGA GAATGGAAAA CCCAGATGGA GGAGACCAAG     240

GCACAGGACA TTCTGGGAGC AGTGACCCTT CTGCTGGAGG GAGTGATGGC AGCACGGGGA     300

CAACTGGGAC CCACTTGCCT CTCATCCCTC CTGGGGCAGC TTTCTGGACA GGTCCGTCTC     360

CTCCTTGGGG CCCTGCAGAG CCTCCTTGGA ACCCAGCTTC CTCCACAGGG CAGGACCACA     420

GCTCACAAGG ATCCCAATGC CATCTTCCTG AGCTTCCAAC ACCTGCTCCG AGGAAAGGTG     480

CGTTTCCTGA TGCTTGTAGG AGGGTCCACC CTCTGCGTCA GGCGGGCCCC ACCCACCACA     540

GCTGTCCCCA GCAGAACCTC TCTAGTCCTC ACACTGAACG AGCTCCCAAA CAGGACTTCT     600

GGATTGTTGG AGACAAACTT CACTGCCTCA GCCAGAACTA CTGGCTCTGG GCTTCTGAAG     660

TGGCAGCAGG GATTCAGAGC CAAGATTCCT GGTCTGCTGA ACCAAACCTC CAGGTCCCTG     720

GACCAAATCC CCGGATACCT GAACAGGATA CACGAACTCT TGAATGGAAC TCGTGGACTC     780

TTTCCTGGAC CCTCACGCAG GACCCTAGGA GCCCCGGACA TTTCCTCAGG AACATCAGAC     840

ACAGGCTCCC TGCCACCCAA CCTCCAGCCT GGATATTCTC CTTCCCCAAC CCATCCTCCT     900

ACTGGACAGT ATACGCTCTT CCCTCTTCCA CCCACCTTGC CCACCCCTGT GGTCCAGCTC     960

CACCCCCTGC TTCCTGACCC TTCTGCTCCA ACGCCCACCC CTACCAGCCC TCTTCTAAAC    1020

ACATCCTACA CCCACTCCCA GAATCTGTCT CAGGAAGGG                           1059
```

(2) INFORMATION FOR SEQ ID NO:58:

(i) SEQUENCE CHARACTERISTICS:
        (A) LENGTH: 408 base pairs
        (B) TYPE: nucleic acid
        (C) STRANDEDNESS: double
        (D) TOPOLOGY: linear (ii) MOLECULE TYPE: DNA other nucleic acid
        (A) DESCRIPTION: /desc = "synthetic DNA"

(xi) SEQUENCE DESCRIPTION: SEQ ID NO:58:

```
ATGGCTCCAA TGACTCAGAC TACTTCTCTT AAGACTTCTT GGGTTAACTG CTCTAACATG      60
```

-continued

```
ATCGATGAAA TTATAACACA CTTAAAGCAG CCACCTTTGC CTTTGCTGGA CTTCAACAAC      120

CTCAATGGGG AAGACCAAGA CATTCTGATG GAAAATAACC TTCGAAGGCC AAACCTGGAG      180

GCATTCAACA GGGCTGTCAA GAGTTTACAG AATGCATCAG CAATTGAGAG CATTCTTAAA      240

AATCTCCTGC CATGTCTGCC CCTGGCCACG GCCGCACCCA CGCGACATCC AATCCATATC      300

AAGGACGGTG ACTGGAATGA ATTCCGTCGT AAACTGACCT TCTATCTGAA AACCTTGGAG      360

AACGCGCAGG CTCAACAGAC CACTCTGTCG CTAGCGATCT TTTAATAA                   408
```